United States Patent
Obrecht et al.

(10) Patent No.: US 10,829,520 B2
(45) Date of Patent: Nov. 10, 2020

(54) BETA-HAIRPIN PEPTIDOMIMETICS

(71) Applicant: POLYPHOR AG, Allschwil (CH)

(72) Inventors: Daniel Obrecht, Bättwil (CH); Anatol Luther, Binzen (DE); Francesca Bernardini, Hésingue (FR); Peter Zbinden, Magden (CH); Alexander Lederer, Basel (CH)

(73) Assignee: POLYPHOR AG, Allschwil (CH)

( * ) Notice: Subject to any disclaimer, the term of this patent is extended or adjusted under 35 U.S.C. 154(b) by 0 days.

(21) Appl. No.: 15/560,200

(22) PCT Filed: Mar. 23, 2016

(86) PCT No.: PCT/EP2016/025027
§ 371 (c)(1),
(2) Date: Sep. 21, 2017

(87) PCT Pub. No.: WO2016/150576
PCT Pub. Date: Sep. 29, 2016

(65) Prior Publication Data
US 2018/0072775 A1    Mar. 15, 2018

(30) Foreign Application Priority Data

Mar. 23, 2015 (EP) .................................... 15000843

(51) Int. Cl.
| | | |
|---|---|---|
| *A61K 38/00* | (2006.01) | |
| *C07K 7/64* | (2006.01) | |
| *C07K 7/62* | (2006.01) | |
| *C07K 7/08* | (2006.01) | |

(52) U.S. Cl.
CPC .................. *C07K 7/64* (2013.01); *C07K 7/08* (2013.01); *C07K 7/62* (2013.01); *A61K 38/00* (2013.01); *C07K 2319/00* (2013.01)

(58) Field of Classification Search
None
See application file for complete search history.

(56) References Cited

U.S. PATENT DOCUMENTS 9,938,322 B2 *  4/2018  Obrecht .................. C07K 7/08

FOREIGN PATENT DOCUMENTS

| WO | WO 2014/161781 A1 | 10/2014 |
| WO | WO 2014/161782 A1 | 10/2014 |

OTHER PUBLICATIONS

Weinstein et al. (Selective chemical modifications of polymyxin B. Bioorganic & Medicinal Chemistry Letters. vol. 8, Issue 23, Dec. 1, 1998, pp. 3391-3396).*
Milner-White, Biochem. J. (1986) 240, 289-292.*
International Search Report for PCT/EP2016/025027, dated Jun. 2, 2016.
Velkov et al., "Teaching 'Old' Polymyxins New Tricks: New Generation Lipopeptides Targeting Gram-Negative 'Superbugs'," ACS Chemical Biology 9(5):1172-1177 (2014).

* cited by examiner

*Primary Examiner* — Jeanette M Lieb
(74) *Attorney, Agent, or Firm* — Medler Ferro Woodhouse & Mills PLLC

(57) ABSTRACT

Beta-hairpin peptidomimetics of the general formula (I), and pharmaceutically acceptable salts thereof, with P, T, Q, and optionally L being elements as defined in the description and the claims, have Gram-negative antimicrobial activity to e.g. inhibit the growth or to kill microorganisms such as *Klebsiella pneumoniae* and/or *Acinetobacter baumannii* and/or *Escherichia coli* and/or *Pseudomonas aeruginosa*.

They can be used as medicaments to treat or prevent infections or as disinfectants for foodstuffs, cosmetics, medicaments or other nutrient-containing materials.

These peptidomimetics can be manufactured by a process which is based on a mixed solid- and solution phase synthetic strategy.

10 Claims, No Drawings

BETA-HAIRPIN PEPTIDOMIMETICS

The present invention provides β-hairpin peptidomimetics having Gram-negative antimicrobial activity.

The β-hairpin peptidomimetics of the invention are compounds of the general formula (I), as depicted below, and pharmaceutically acceptable salts thereof, with P, T, Q, and optionally L being elements as described herein below.

In addition, the present invention provides an efficient synthetic process by which these compounds can, if desired, be made in parallel library-format. Moreover, the β-hairpin peptidomimetics of the invention show improved efficacy, reduced hemolysis of red blood cells and reduced or no cytotoxicity.

A major cause of death worldwide and a leading cause of mortality in developed countries are infectious diseases. They result from the presence of pathogenic microbial agents including pathogenic viruses and pathogenic bacteria. The problem of bacterial resistance to established antibiotics has stimulated intense interest in developing novel antimicrobial agents with new modes of action (D. Obrecht, J. A. Robinson, F. Bernadini, C. Bisang, S. J. DeMarco, K. Moehle, F. O. Gombert, Curr. Med. Chem. 2009, 16, 42-65; H. Breithaupt, Nat. Biotechnol. 1999, 17, 1165-1169).

A growing unmet medical need is represented by Gram-negative bacteria causing 60% of nosocomial pneumonias (R. Frechette, Ann. Rep. Med. Chem., Elsevier, 2007, 349-64). Extended spectrum beta lactamase (ESBL)-producing Gram-negative bacteria have also compromised the utility of many front-line beta-lactam drugs (S. J. Projan, P. A. Bradford, Curr. Opin. Microbiol., 2007, 10, 441). The lack of suitable new compounds is forcing clinicians to use previously discarded antibiotics like colistin, despite well-known toxicity problems (M. E. Falagas, S. K. Kasiakou, Crit. Care, 2006, 10, R 27). Therefore, novel approaches are needed to treat inter alia resistant strains of Klebsiella pneumoniae, Acinetobacter baumannii, Escherichia coli (H. W. Boucher, G. H. Talbot, J. S. Bradley, J. E. Edwards Jr, D. Gilbert, L. B. Rice, M. Scheld, B. Spellberg, J. Bartlett, IDSA Report on Development Pipeline, CID 2009, 48, 1), as well as Pseudomonas aeruginosa.

Antibiotic drug discovery in the last 20 years focused on the development of novel antibiotics against Gram-positive bacteria, while the discovery of novel agents against Gram-negative pathogens has been particularly sparse. There is an urgent need for novel classes of antibiotics with novel mechanisms of action, in particular against Gram-negative MDR ESKAPE pathogens (D. Obrecht, F. Bernardini, G. Dale, K. Dembowsky, Ann. Reps Med. Chem. 2011, 46, 245), due to emergence of resistance against the last resort antibiotics, colistin and polymyxin B (M. Vaara, Curr. Opin. Microbiol. 2010, 13, 574). Gram-negative ESKAPE pathogens encompass Klebsiella pneumoniae, Acinetobacter baumannii, Pseudomonas aeruginosa, and Enterobacter species (L. B. Rice, J. Infect. Dis. 2008, 197, 1079). Gram-negative organisms are particularly hard to kill due to the highly negatively charged outer membrane which is composed of up to 75% with lipopolysaccharides forming a formidable shield to prevent entry of antibacterials (C. Alexander, E. T. Rietschel, J. Endotox. Res. 2001, 7, 167; D. S. Kabanov, I. R. Prokhorenko, Biochemistry (Moscow), 2010, 75, 383).

One emerging class of antibiotics is based on naturally occurring cationic peptides (T. Ganz, R. I. Lehrer, Mol. Medicine Today 1999, 5, 292-297; R. M. Epand, H. J. Vogel, Biochim. Biophys. Acta 1999, 1462, 11-28). These include disulfide-bridged β-hairpin and β-sheet peptides (such as the protegrins [V. N. Kokryakov, S. S. L. Harwig, E. A. Panyutich, A. A. Shevchenko, G. M. Aleshina, O. V. Shamova, H. A. Korneva, R. I. Lehrer, FEBS Lett. 1993, 327, 231-236], tachyplesins [T. Nakamura, H. Furunaka, T. Miyata, F. Tokunaga, T. Muta, S. Iwanaga, M. Niwa, T. Takao, Y. Shimonishi, J. Biol. Chem. 1988, 263, 16709-16713], and the defensins [R. I. Lehrer, A. K. Lichtenstein, T. Ganz, Annu. Rev. Immunol. 1993, 11, 105-128]), amphipathic α-helical peptides (e.g. cecropins, dermaseptins, magainins, and mellitins [A. Tossi, L. Sandri, A. Giangaspero, Biopolymers 2000, 55, 4-30]), as well as other linear and loop-structured peptides. Although the mechanisms of action of antimicrobial cationic peptides are not yet fully understood, their primary site of interaction is the microbial cell membrane (H. W. Huang, Biochemistry 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, Biochemistry 1999, 38, 7235-7242).

The compounds of the invention, comprising a module A and a module B, being linked directly or via linker L, as described below, exhibit Gram-negative antimicrobial activity, in particular against Gram-negative pathogens of the so-called ESKAPE pathogens (L. B. Rice, J. Infect. Dis. 2008, 197, 1079).

In module A a strategy is adopted to stabilize β-hairpin conformations in cationic peptide mimetics by the introduction into the hairpin sequence of a template, $T^6$-$T^7$, whose function is to restrain the peptide loop backbone into a hairpin geometry. The rigidity of the hairpin of module A is further enhanced by backbone cyclization and/or introduction of additional interstrand (β-strand) linkages.

In addition, a module B, being a cyclic heptapeptide derived from the polymyxin family (T. Velkov, P. E. Thompson, R. L. Nation, J. Li, J. Med. Chem. 2010, 53, 1898; T. Velkov, K. D. Roberts, R. L. Nation, J. Wang, P. E. Thompson, J. Li, ACS Chem. Biol. 2014, 9, 1172), is covalently linked to module A, either directly or via a peptide linker L, as described below.

Template-bound hairpin mimetic peptides have been described in the literature (D. Obrecht, M. Altorfer, J. A. Robinson, Adv. Med. Chem. 1999, 4, 1-68; J. A. Robinson, Syn. Lett. 2000, 4, 429-441) and the ability to generate β-hairpin peptidomimetics using combinatorial and parallel synthesis methods has been established (L. Jiang, K. Moehle, B. Dhanapal, D. Obrecht, J. A. Robinson, Helv. Chim. Acta. 2000, 83, 3097-3112). Antibacterial template-fixed peptidomimetics and methods for their synthesis have been described in international patent applications WO02/070547 A1, WO2004/018503 A1, WO2007/079605 A2, WO2012/016595 A1, WO2014/161781 A1 and WO2014/161782 A1. The molecules described in the latter two patent applications show Gram-negative antimicrobial activity having high potency against Klebsiella pneumoniae and/or Acinetobacter baumannii and/or Escherichia coli.

In a first embodiment (1) the present invention relates to novel β-hairpin peptidomimetics of formula (I),

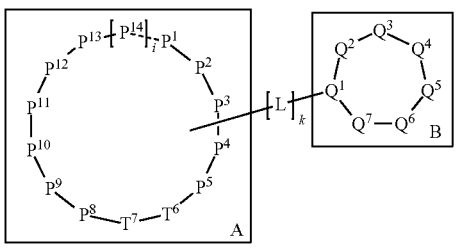

comprising a module A consisting of single elements P or T being connected in either direction from the carbonyl (C=O) point of attachment to the nitrogen (N) of the next element with the proviso that, if i=1, $P^{13}$ and $P^{14}$; or $P^{14}$ and $P^1$ may not be connected as aforementioned; if i=0, $P^{13}$ and $P^1$ are not connected as aforementioned; and wherein,
if i=1, and
$P^2$ and $P^{11}$ taken together and/or $P^4$ and $P^9$ taken together and/or $P^{13}$ and $P^{14}$ taken together may form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ and/or $P^{13}$ and $P^{14}$ by covalent interaction (inter-strand linkage); then $P^1$ is a naturally or non-naturally occurring aromatic L α-amino acid containing 1 to 25 carbon- and/or heteroatoms in a single side-chain; or a naturally or non-naturally occurring aliphatic L α-amino acid containing in total 1 to 25 carbon- and/or heteroatoms in a single side-chain;

$P^2$ is a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one amide function; or a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

$P^3$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^4$ is Gly; Sar; or a naturally or non-naturally occurring aliphatic α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function; or a naturally or non-naturally occurring aromatic L α-amino acid containing 1 to 25 carbon- and/or heteroatoms in a single side-chain;

$P^5$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring aromatic L α-amino acid containing 1 to 25 carbon- and/or heteroatoms in a single side-chain;

$T^6$ is a naturally or non-naturally occurring D α-amino acid containing an optionally substituted side-chain which forms a four-, five- or six-membered hetero-cycle or a bicyclic system comprising the α-carbon and the α-amino atom; or a naturally or non-naturally occurring aliphatic D α-amino acid containing in total 1 to 25 carbon- and/or heteroatoms in a single side-chain; or a naturally or non-naturally occurring basic D α-amino acid containing in total 1 to 25 carbon- and/or heteroatoms in a single side-chain comprising at least one amino function; or a naturally or non-naturally occurring aromatic D α-amino acid containing 1 to 25 carbon- and/or heteroatoms in a single side-chain; or a naturally or non-naturally occurring alcoholic D α-amino acid containing in total 1 to 25 carbon- and/or heteroatoms in a single side-chain;

$T^7$ is a naturally or non-naturally occurring L α-amino acid containing an optionally substituted side-chain which forms a five- or six-membered heterocycle or a bicyclic system comprising the α-carbon and the α-amino atom; or a naturally or non-naturally occurring aliphatic L α-amino acid containing in total 1 to 25 carbon- and/or heteroatoms in a single side-chain; or a naturally or non-naturally occurring aromatic L α-amino acid containing 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain;

$P^8$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$P^9$ is Gly; Sar; or a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function; or a naturally or non-naturally occurring aromatic L α-amino acid containing 1 to 25 carbon- and/or heteroatoms in a single side-chain; or a naturally or non-naturally occurring L α-amino acid containing in total 1 to 25 carbon- and/or heteroatoms in a single side-chain comprising at least one urea function, carboxylic acid function, amide function, ester function, sulfone function or ether function;

$P^{10}$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^{11}$ is Gly; Sar; or a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one amide function; or a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$P^{12}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain; or a naturally or non-naturally occurring aromatic α-amino acid containing in total 1 to 25 carbon- and/or heteroatoms in a single side-chain; or a naturally or non-naturally occurring α-amino acid containing in total 1 to 25 carbon- and/or heteroatoms in a single side-chain comprising at least one urea function, carboxylic acid function, amide function, ester function, sulfone function or ether function;

$P^{13}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain; or a naturally or non-naturally occurring aromatic α-amino acid containing 1 to 25 carbon- and/or heteroatoms in a single side-chain; or a naturally or non-naturally occurring α-amino acid containing in total 1 to 25 carbon- and/or heteroatoms in a single side-chain comprising at least one amide function;

$P^{14}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring α-amino acid containing in total 1 to 25 carbon- and/or heteroatoms in a single side-chain comprising at least one urea function, carboxylic acid function, amide function, ester function, sulfone function or ether function; or a naturally or non-naturally occurring alcoholic α-amino acid containing in total 1 to 25 carbon- and/or heteroatoms in a single side-chain;

with the proviso that,
  if no interstrand linkage is formed, then $P^{13}$ and $P^{14}$, and $P^{14}$ and $P^1$ are connected as aforementioned;
  if $P^{13}$ and $P^{14}$ taken together form an interstrand linkage, as defined above, then $P^{13}$ and $P^{14}$ are not additionally connected as aforementioned;

with the further proviso that,
  if linker L, as defined below, is connected with module A by a carbonyl (C=O) point of attachment of $P^2$; $P^5$; or $P^{12}$; then
    $P^2$; $P^5$; or $P^{12}$; is a naturally or non-naturally occurring α-amino acid containing in total 1 to 25 carbon- and/or heteroatoms in a single side-chain comprising at least one carboxyl function;
  if linker L, as defined below, is connected with module A by a carbonyl (C=O) point of attachment of $P^{13}$ and
    $P^{13}$ and $P^{14}$, and $P^{14}$ and $P^1$ are connected as aforementioned; or
    $P^{14}$ and $P^1$ are not connected as aforementioned; then
    $P^{13}$ is a naturally or non-naturally occurring α-amino acid containing in total 1 to 25 carbon- and/or heteroatoms in a single side-chain comprising at least one carboxyl function;
  if linker L, as defined below, is connected with module A by a carbonyl (C=O) point of attachment of $P^{14}$ and
    $P^{13}$ and $P^{14}$, and $P^{14}$ and $P^1$ are connected as aforementioned; or
    $P^{13}$ and $P^{14}$ are not connected as aforementioned; then
    $P^{14}$ is a naturally or non-naturally occurring α-amino acid containing in total 1 to 25 carbon- and/or heteroatoms in a single side-chain comprising at least one carboxyl function;

if i=0, and
$P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage); then
$P^1$ to $P^5$; $T^6$; $T^7$; $P^8$ to $P^{13}$ are naturally or non-naturally occurring α-amino acids as defined above;
with the proviso that,
  if linker L, as defined below, is connected with module A by a carbonyl (C=O) point of attachment of $P^5$; or $P^{12}$; then
    $P^5$; or $P^{12}$; is a naturally or non-naturally occurring α-amino acid containing in total 1 to 25 carbon- and/or heteroatoms in a single side-chain comprising at least one carboxyl function;

and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein $Q^1$ is a naturally or non-naturally occurring basic α-amino acid containing in total 1 to 25 carbon- and/or heteroatoms in a single side-chain comprising at least one amino function;

$Q^2$, $Q^5$, and $Q^6$ are independently
  a naturally or non-naturally occurring basic L α-amino acid containing in total 1 to 25 carbon- and/or heteroatoms in a single side-chain comprising at least one amino function;

$Q^3$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain;

$Q^4$ is a naturally or non-naturally occurring aliphatic L α-amino acid containing in total 1 to 25 carbon- and/or heteroatoms in a single side-chain;

$Q^7$ is a naturally or non-naturally occurring alcoholic α-amino acid containing in total 1 to 25 carbon- and/or heteroatoms in a single side-chain; or a naturally or non-naturally occurring α-amino acid containing in total 1 to 25 carbon- and/or heteroatoms in a single side-chain comprising at least one amide function; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function;

and a linker L consisting of k=0-3 single elements L being connected in either direction from the carbonyl (C=O) point of attachment to the nitrogen (N) of the next element, and wherein, if k=1, $L^1$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain; or a naturally or non-naturally occurring aromatic α-amino acid containing 1 to 25 carbon- and/or heteroatoms in a single side-chain; or a naturally or non-naturally occurring α-amino acid containing in total 1 to 25 carbon- and/or heteroatoms in a single side-chain comprising at least one amide function;

if k=2, the additional element $L^2$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;

if k=3, the additional element $L^3$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;

said linker L being connected with module B from the carbonyl (C=O) point of attachment of $L^k$ to the α-nitrogen (N) of $Q^1$ and, if k=1-3 and i=1, being connected with module A from the carbonyl (C=O) point of attachment of $P^2$; $P^5$; $P^{12}$; $P^{13}$; or $P^{14}$; to the nitrogen (N) of $L^1$; or, if k=1-3 and i=0, being connected with module A from the carbonyl (C=O) point of attachment of $P^5$; $P^{12}$; or $P^{13}$; to the nitrogen (N) of $L^1$; or if k=0 and i=1, then $Q^1$ being directly connected with module A from the carbonyl (C=O) point of attachment of $P^2$; $P^5$; $P^{12}$; $P^{13}$; or $P^{14}$; to the α-nitrogen (N) of $Q^1$; or if k=0 and i=0, then $Q^1$ being directly connected with module A from the carbonyl (C=O) point of attachment of $P^5$; $P^{12}$; or $P^{13}$; to the α-nitrogen (N) of $Q^1$;

the carbonyl (C=O) point of attachment of $P^{13}$; or $P^{14}$; and/or nitrogen (N) of $P^1$; or $P^{14}$; not connected as aforementioned being appropriately saturated to form the corresponding naturally or non-naturally occurring terminal α-amino acids optionally having modified carbonyl (C=O) functional groups and/or nitrogen (N) functional groups;

or a tautomer or rotamer thereof; or a salt; or a pharmaceutically acceptable salt; or a hydrate; or a solvate thereof.

A further embodiment (2) of the invention relates to compounds of formula (I) according to embodiment (1) with the proviso that $P^4$ and $P^9$ taken together form naturally or non-naturally cross-linking α-amino acids containing each in total 1 to 12 carbon- and/or heteroatoms in a single side-chain which together are connecting or $P^4$ and $P^9$; and/or $P^1$ is a naturally or non-naturally occurring aliphatic L α-amino acid containing in total 1 to 25 carbon- and/or heteroatoms in a single side-chain; and/or $P^2$ is a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain; and/or $P^4$ is Gly; or Sar; or a naturally or non-naturally occurring aliphatic D α-amino acid containing in total 1 to 25 carbon- and/or heteroatoms in a single side-chain; or a naturally or non-naturally occurring aromatic L α-amino acid containing 1 to 25 carbon- and/or heteroatoms in a single side-chain; and/or $P^5$ is a naturally or non-naturally occurring aromatic L α-amino acid containing 1 to 25 carbon- and/or heteroatoms in a single side-chain; and/or $T^6$ is a six-membered heterocycle or a bicyclic system comprising the α-carbon and the α-amino atom; or a naturally or non-naturally occurring aromatic D α-amino acid containing 1 to 25 carbon- and/or heteroatoms in a single side-chain; or a naturally or non-naturally occurring alcoholic D α-amino acid containing in total 1 to 25 carbon- and/or heteroatoms in a single side-chain; and/or $T^7$ is a naturally or non-naturally occurring aliphatic L α-amino acid containing in total 1 to 25 carbon- and/or heteroatoms in a single side-chain; or a naturally or non-naturally occurring aromatic L α-amino acid containing 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; and/or $P^8$ is a naturally or non-naturally occurring alcoholic L α-amino acid containing in total 1 to 25 carbon- and/or heteroatoms in a single side-chain; and/or $P^9$ is a naturally or non-naturally occurring aromatic L α-amino acid containing 1 to 25 carbon- and/or heteroatoms in a single side-chain; or a naturally or non-naturally occurring L α-amino acid containing in total 1 to 25 carbon- and/or heteroatoms in a single side-chain comprising at least one urea function, carboxylic acid function, amide function, ester function, sulfone function or ether function; and/or $P^{11}$ is Gly; Sar; or a naturally or non-naturally occurring aliphatic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one urea function, carboxylic acid function, amide function, ester function, sulfone function or ether function; a naturally or non-naturally occurring alcoholic L α-amino acid containing in total 1 to 25 carbon- and/or heteroatoms in a single side-chain; and/or $P^{12}$ is a naturally or non-naturally occurring aromatic α-amino acid containing in total 1 to 25 carbon- and/or heteroatoms in a single side-chain; or a naturally or non-naturally occurring α-amino acid containing in total 1 to 25 carbon- and/or heteroatoms in a single side-chain comprising at least one urea function, carboxylic acid function, amide function, ester function, sulfone function or ether function; and/or $P^{13}$ is or a naturally or non-naturally occurring aromatic α-amino acid containing 1 to 25 carbon- and/or heteroatoms in a single side-chain; or a naturally or non-naturally occurring L α-amino acid containing in total 1 to 25 carbon- and/or heteroatoms in a single side-chain comprising at least one amide function; and/or if k=1, then $L^1$ is a naturally or non-naturally occurring aromatic α-amino acid containing 1 to 25 carbon- and/or heteroatoms in a single side-chain; or a naturally or non-naturally occurring α-amino acid containing in total 1 to 25 carbon- and/or heteroatoms in a single side-chain comprising at least one amide function; and/or $Q^7$ is a naturally or non-naturally occurring alcoholic D α-amino acid containing in total 1 to 25 carbon- and/or heteroatoms in a single side-chain; or a naturally or non-naturally occurring D α-amino acid containing in total 1 to 25 carbon- and/or heteroatoms in a single side-chain comprising at least one amide function; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function;

or a tautomer or rotamer thereof; or a salt; or a pharmaceutically acceptable salt; or a hydrate; or a solvate thereof.

A further embodiment (3) of the invention relates to compounds of formula (I) comprising a module A consisting of single elements P or T being connected in either direction from the carbonyl (C=O) point of attachment to the nitrogen (N) of the next element with the proviso that, if i=1, $P^{13}$ and $P^{14}$; or $P^{14}$ and $P^1$ may not be connected as aforementioned; if i=0, $P^{13}$ and $P^1$ are not connected as aforementioned; and wherein, if i=1, and $P^2$ and $P^{11}$ taken together and/or $P^{13}$ and $P^{14}$ taken together may form naturally or non-naturally cross-linking α-amino acids containing each in total 1 to 12 carbon- and/or heteroatoms in a single side-chain which together are connecting $P^2$ and $P^{11}$ and/or $P^{13}$ and $P^{14}$ by covalent interaction (interstrand linkage); then $P^1$ is a naturally or non-naturally occurring aromatic L α-amino acid containing 1 to 25 carbon- and/or heteroatoms in a single side-chain;

$P^2$ is a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one amide function;

$P^3$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25

$P^4$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function;

$P^5$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function;

$T^6$ is a naturally or non-naturally occurring D α-amino acid containing an optionally substituted side-chain which forms a four- or five-membered heterocycle or a bicyclic system comprising the α-carbon and the α-amino atom; or a naturally or non-naturally occurring aliphatic D α-amino acid containing in total 1 to 25 carbon- and/or heteroatoms in a single side-chain; or a naturally or non-naturally occurring basic D α-amino acid containing in total 1 to 25 carbon- and/or heteroatoms in a single side-chain comprising at least one amino function;

$T^7$ is a naturally or non-naturally occurring L α-amino acid containing an optionally substituted side-chain which forms a five- or six-membered heterocycle or a bicyclic system comprising the α-carbon and the α-amino atom;

$P^8$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain $P^9$ is Gly; Sar; or a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function;

$P^{10}$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^{11}$ is a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one amide function;

$P^{12}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;

$P^{13}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;

$P^{14}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring α-amino acid containing in total 1 to 25 carbon- and/or heteroatoms in a single side-chain comprising at least one urea function, carboxylic acid function, amide function, ester function, sulfone function or ether function; or a naturally or non-naturally occurring alcoholic α-amino acid containing in total 1 to 25 carbon- and/or heteroatoms in a single side-chain;

with the proviso that,
  if no interstrand linkage is formed, then $P^{13}$ and $P^{14}$, and $P^{14}$ and $P^1$ are connected as aforementioned;
  if $P^{13}$ and $P^{14}$ taken together form an interstrand linkage, as defined above, then $P^{13}$ and $P^{14}$ are not additionally connected as aforementioned;

with the further proviso that,
  if linker L, as defined below, is connected with module A by a carbonyl (C=O) point of attachment of $P^2$; $P^5$; or $P^{12}$; then
  $P^2$; $P^5$; or $P^{12}$; is a naturally or non-naturally occurring α-amino acid containing in total 1 to 25 carbon- and/or heteroatoms in a single side-chain comprising at least one carboxyl function;
  if linker L, as defined below, is connected with module A by a carbonyl (C=O) point of attachment of $P^{13}$ and $P^{13}$ and $P^{14}$, and $P^{14}$ and $P^1$ are connected as aforementioned; or
  $P^{14}$ and $P^1$ are not connected as aforementioned; then
  $P^{13}$ is a naturally or non-naturally occurring α-amino acid containing in total 1 to 25 carbon- and/or heteroatoms in a single side-chain comprising at least one carboxyl function;
  if linker L, as defined below, is connected with module A by a carbonyl (C=O) point of attachment of $P^{14}$ and $P^{13}$ and $P^{14}$, and $P^{14}$ and $P^1$ are connected as aforementioned; or
  $P^{13}$ and $P^{14}$ are not connected as aforementioned; then
  $P^{14}$ is a naturally or non-naturally occurring α-amino acid containing in total 1 to 25 carbon- and/or heteroatoms in a single side-chain comprising at least one carboxyl function;

if i=0, and
$P^2$ and $P^{11}$ taken together form naturally or non-naturally cross-linking α-amino acids containing each in total 1 to 12 carbon- and/or heteroatoms in a single side-chain which together are connecting $P^2$ and $P^{11}$ by covalent interaction (interstrand linkage); then
$P^1$; $P^3$ to $P^5$; $P^6$; $P^7$; $P^8$ to $P^{10}$; $P^{12}$; and $P^{13}$ are naturally or non-naturally occurring α-amino acids as defined above;
with the proviso that,
  if linker L, as defined below, is connected with module A by a carbonyl (C=O) point of attachment of $P^5$; or $P^{12}$; then
  $P^5$; or $P^{12}$; is a naturally or non-naturally occurring α-amino acid containing in total 1 to 25 carbon- and/or heteroatoms in a single side-chain comprising at least one carboxyl function;

and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein $Q^1$ is a naturally or non-naturally occurring α-amino acid containing in total 1 to 25 carbon- and/or heteroatoms in a single side-chain comprising at least one amino function;

$Q^2$, $Q^5$, and $Q^6$ are independently
  a naturally or non-naturally occurring basic L α-amino acid containing in total 1 to 25 carbon- and/or heteroatoms in a single side-chain comprising at least one amino function;

$Q^3$ is a naturally or non-naturally occurring aliphatic D α-amino acid containing in total 1 to 25 carbon- and/or heteroatoms in a single side-chain; or a naturally or non-naturally occurring aromatic D α-amino acid containing in total 1 to 25 carbon- and/or heteroatoms in a single side-chain;

$Q^4$ is a naturally or non-naturally occurring aliphatic L α-amino acid containing in total 1 to 25 carbon- and/or heteroatoms in a single side-chain;

$Q^7$ is a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function;

and a linker L consisting of k=0-3 single elements L being connected in either direction from the carbonyl (C=O) point of attachment to the nitrogen (N) of the next element, and wherein,
if k=1,
$L^1$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;
if k=2, the additional element
L² is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;
if k=3, the additional element
L³ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;
said linker L being connected with module B from the carbonyl (C=O) point of attachment of $L^k$ to the α-nitrogen (N) of $Q^1$ and,
if k=1-3 and i=1, being connected with module A from the carbonyl (C=O) point of attachment of $P^2$; $P^5$; $P^{12}$; $P^{13}$; or $P^{14}$; to the nitrogen (N) of $L^1$; or,
if k=1-3 and i=0, being connected with module A from the carbonyl (C=O) point of attachment of $P^5$; $P^{12}$; or $P^{13}$; to the nitrogen (N) of $L^1$; or
if k=0 and i=1, then
$Q^1$ being directly connected with module A from the carbonyl (C=O) point of attachment of $P^2$; $P^5$; $P^{12}$; $P^{13}$; or $P^{14}$; to the α-nitrogen (N) of $Q^1$; or
if k=0 and i=0, then
$Q^1$ being directly connected with module A from the carbonyl (C=O) point of attachment of $P^5$; $P^{12}$; or $P^{13}$; to the α-nitrogen (N) of $Q^1$;
carbonyl (C=O) point of attachment of $P^{13}$; or $P^{14}$; and/or nitrogen (N) of $P^1$; or $P^{14}$; not connected as aforementioned being appropriately saturated to form the corresponding naturally or non-naturally occurring terminal α-amino acids optionally having modified carbonyl (C=O) functional groups and/or nitrogen (N) functional groups;
or a tautomer or rotamer thereof; or a salt; or a pharmaceutically acceptable salt; or a hydrate; or a solvate thereof.
A particular embodiment (4) of the present invention relates to compounds according to general formula (I), wherein,
if i=1, and
$P^2$ and $P^{11}$ taken together and/or $P^4$ and $P^9$ taken together may form an interstrand linking bis(amino acid)-structure of one of the formulae

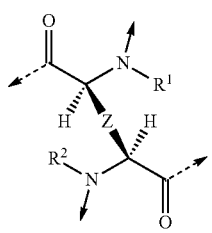
AA13

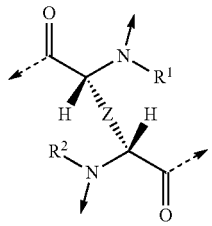
AA13$^D$ based on the linkage of two α-amino acid residues; and/or $P^{13}$ and $P^{14}$ taken together may form an interstrand linking bis(amino acid)-structure of one of the formulae

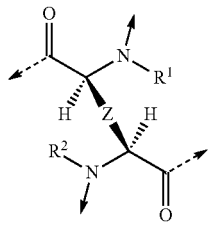
AA13

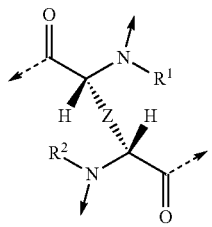
AA13$^D$

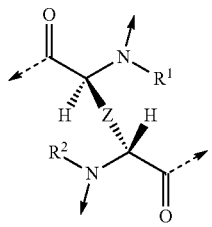
AA13$^{LD}$

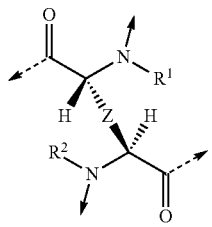
AA13$^{DL}$ based on the linkage of two α-amino acid residues;
$P^1$ is an L α-amino acid residue of one of the formulae

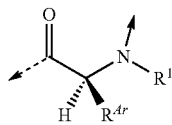
AA8

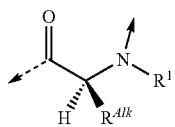
AA7
P² is an L α-amino acid residue of one of the formulae
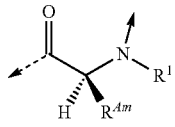
AA10
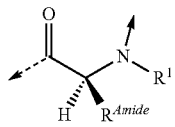
AA16
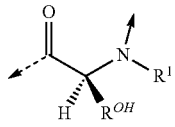
AA11
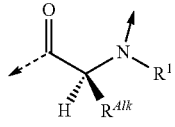
AA7
P³ is an L α-amino acid residue of one of the formulae
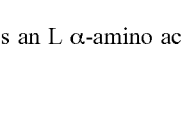
AA7
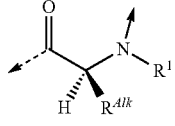
AA8
P⁴ is Gly; Sar; or an α-amino acid residue of one of the formulae
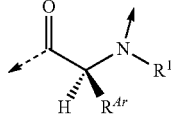
AA7
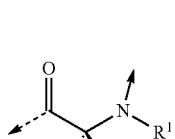
AA7$^D$
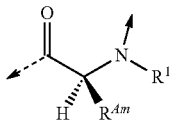
AA10
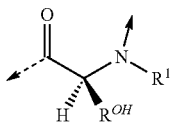
AA11
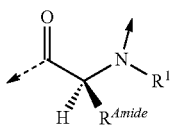
AA16
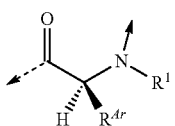
AA8
P⁵ is an L α-amino acid residue of one of the formulae
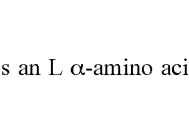
AA7
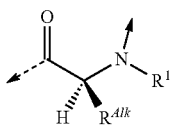
AA11
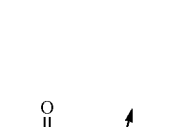
AA10
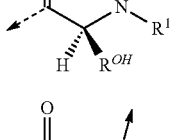
AA8
T⁶ is an D α-amino acid residue of one of the formulae
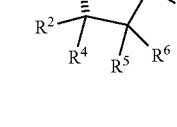
AA1$^D$ -continued
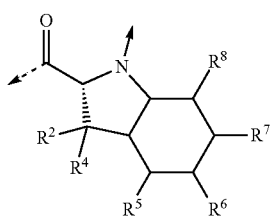
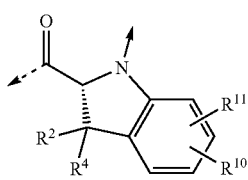
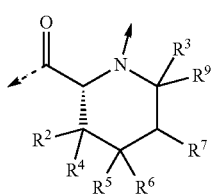
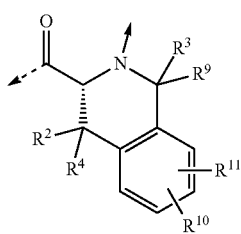
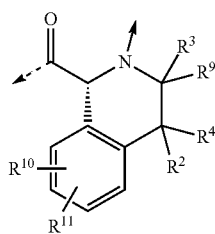
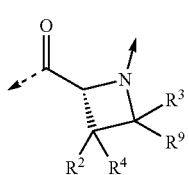
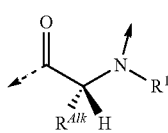
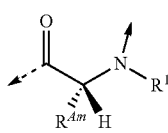
AA2$^D$
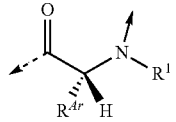
AA3$^D$
AA11$^D$
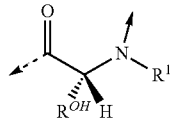
$T^7$ is an L α-amino acid residue of one of the formulae
AA4$^D$
AA1
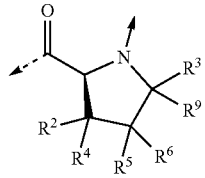
AA5$^D$
AA2
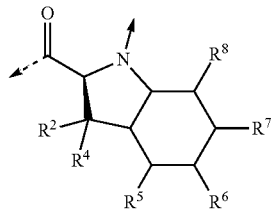
AA6$^D$
AA3
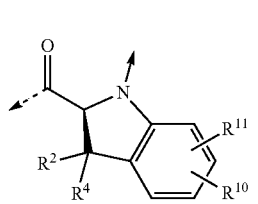
AA12$^D$
AA4
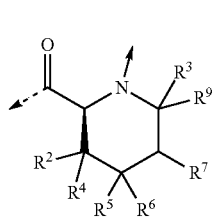
AA7$^D$
AA5
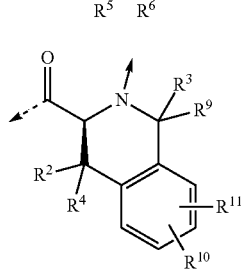
AA10$^D$

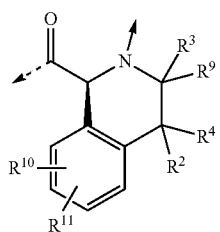
AA6
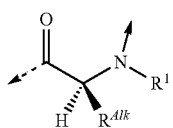
AA7
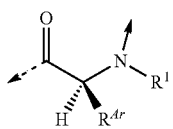
AA8
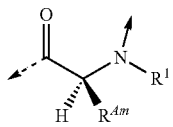
AA10
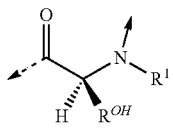
AA11
$P^8$ is an L α-amino acid residue of one of the formulae
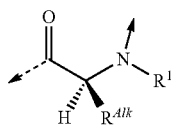
AA7
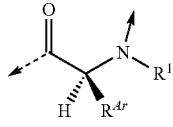
AA8
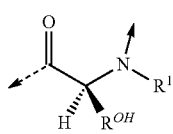
AA11
$P^9$ is Gly; Sar; or an L α-amino acid residue of one of the formulae
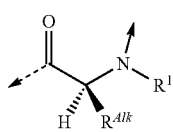
AA7
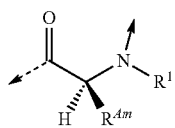
AA10
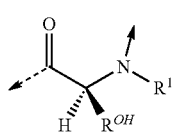
AA11
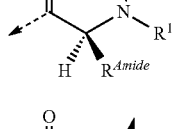
AA16
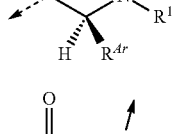
AA8
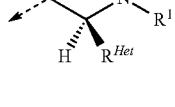
AA9
$P^{10}$ is an L α-amino acid residue of one of the formulae
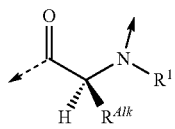
AA7
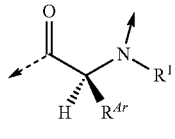
AA8
$P^{11}$ is Gly; Sar; or an L α-amino acid residue of one of the formulae
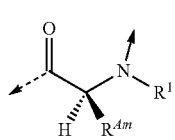
AA10
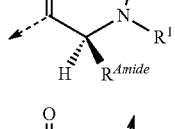
AA16
AA7

-continued
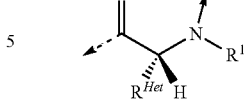
AA11
P$^{12}$ is Gly; Sar; Aib; or an α-amino acid residue of one of the formulae
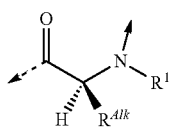
AA7
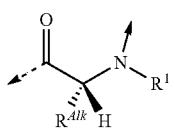
AA7$^D$
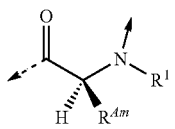
AA10
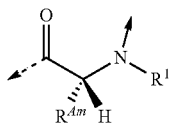
AA10$^D$
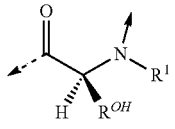
AA11
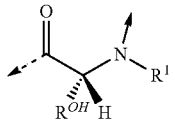
AA11$^D$
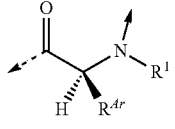
AA8
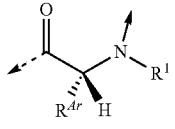
AA8$^D$
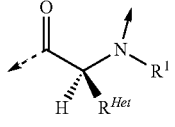
AA9
-continued
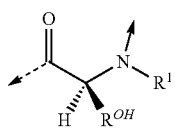
AA9$^D$
P$^{13}$ is Gly; Sar; Aib; or an α-amino acid residue of one of the formulae
AA7
AA7$^D$
AA10
AA10$^D$
AA11
AA11$^D$
AA8
AA8$^D$
AA16

-continued

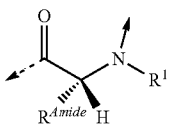
AA16$^D$ $P^{14}$ is Gly; Sar; Aib; or an α-amino acid residue of one of the formulae

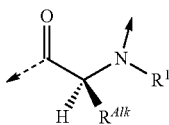
AA7

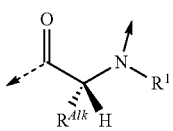
AA7$^D$

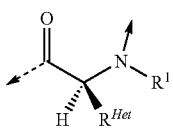
AA9

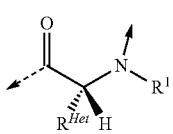
AA9$^D$

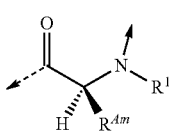
AA10

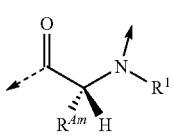
AA10$^D$

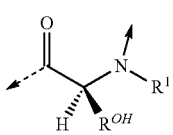
AA11

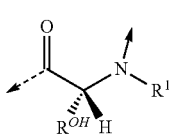
AA11$^D$ with the proviso that,
if no interstrand linkage is formed, then
$P^{13}$ and $P^{14}$, and $P^{14}$ and $P^1$ are connected as aforementioned;
if $P^{13}$ and $P^{14}$ taken together form an interstrand linkage, as defined above, then $P^{13}$ and $P^{14}$ are not additionally connected as aforementioned;

with the further proviso that,
if linker L, as defined below, is connected with module A by a carbonyl (C=O) point of attachment of $P^2$; $P^5$; or $P^{12}$; then
$P^2$; $P^5$; or $P^{12}$; is an α-amino acid residue of one of the formulae

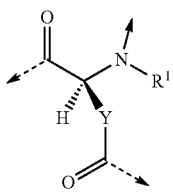
AA14

AA14$^D$ if linker L, as defined below, is connected with module A by a carbonyl (C=O) point of attachment of $P^{13}$ and
$P^{13}$ and $P^{14}$, and $P^{14}$ and $P^1$ are connected as aforementioned; or
$P^{14}$ and $P^1$ are not connected as aforementioned; then
$P^{13}$ is an α-amino acid residue of one of the formulae AA14; or AA14$^D$, as depicted above;
if linker L, as defined below, is connected with module A by a carbonyl (C=O) point of attachment of $P^{14}$; and
$P^{13}$ and $P^{14}$, and $P^{14}$ and $P^1$ are connected as aforementioned; or
$P^{13}$ and $P^{14}$ are not connected as aforementioned; then
$P^{14}$ is an α-amino acid residue of one of the formulae AA14; or AA14$^D$, as depicted above;
if i=0, and
$P^2$ and $P^{11}$ taken together and/or $P^4$ and $P^9$ taken together form naturally or non-naturally cross-linking α-amino acids, as defined above, then
$P^1$ to $P^5$; $T^6$; $T^7$; $P^8$ to $P^{13}$ are naturally or non-naturally occurring α-amino acids, as defined in this embodiment;
with the proviso that,
if linker L, as defined below, is connected with module A by a carbonyl (C=O) point of attachment of $P^5$; or $P^{12}$, then
$P^5$; or $P^{12}$; is an α-amino acid residue of one of the formulae AA14; or AA14$^D$, as depicted above;
and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein $Q^1$ is an α-amino acid residue of one of the formulae

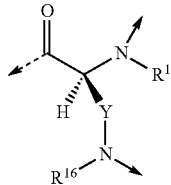
AA15

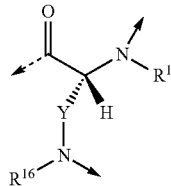
AA15$^D$ $Q^2$, $Q^5$, and $Q^6$ are independently an L α-amino acid residue of formula

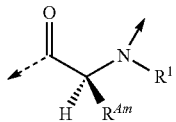
AA10

$Q^3$ is an D α-amino acid residue of one of the formulae

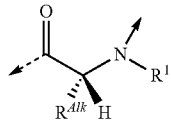
AA7$^D$

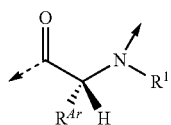
AA8$^D$ $Q^4$ is an L α-amino acid residue of formula

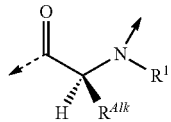
AA7

$Q^7$ is an L α-amino acid residue of one of the formulae

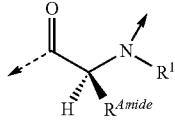
AA16

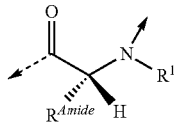
AA16$^D$

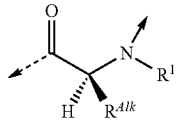
AA7

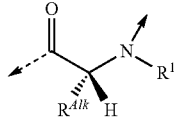
AA7$^D$

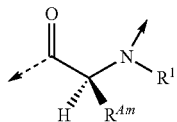
AA10

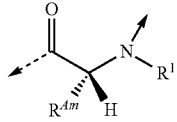
AA10$^D$

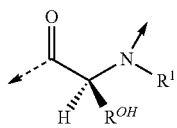
AA11

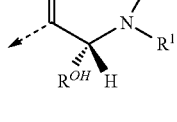
AA11$^D$ and a linker L consisting of k=0-3 single elements L being connected in either direction from the carbonyl (C=O) point of attachment to the nitrogen (N) of the next element, and wherein,
if k=1,
$L^1$ is Gly; Sar; Aib; or an α-amino acid residue of one of the formulae

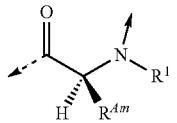
AA10

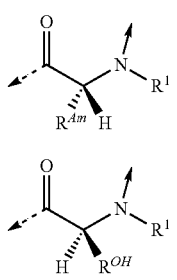
AA10$^D$

AA11

-continued

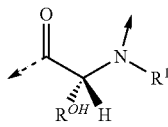
AA11$^D$

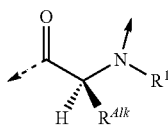
AA7

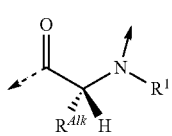
AA7$^D$

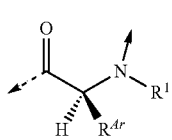
AA8

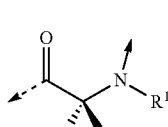
AA8$^D$

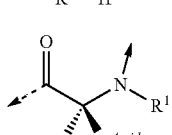
AA16

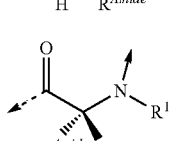
AA16$^D$ if k=2, the additional element
L$^2$ is Gly; Sar; Aib; or an α-amino acid residue of one of the formulae
AA10; AA10$^D$; AA11; AA11$^D$; AA7; or AA7$^D$, as depicted above;
if k=3, the additional element
L$^3$ is Gly; Sar; Aib; or an α-amino acid residue of one of the formulae
AA10; AA10$^D$; AA11; AA11$^D$; AA7; or AA7$^D$, as depicted above;
said linker L being connected with module B from the carbonyl (C=O) point of attachment of L$^k$ to the α-nitrogen (N) of Q$^1$ and,
if k=1-3 and i=1, being connected with module A from the carbonyl (C=O) point of attachment of P$^2$; P$^5$; P$^{12}$; P$^{13}$; or P$^{14}$; to the nitrogen (N) of L$^1$; or,
if k=1-3 and i=0, being connected with module A from the carbonyl (C=O) point of attachment of P$^5$; P$^{12}$; or P$^{13}$; to the nitrogen (N) of L$^1$; or
if k=0 and i=1, then
Q$^1$ being directly connected with module A from the carbonyl (C=O) point of attachment of P$^2$; P$^5$; P$^{12}$; P$^{13}$; or P$^{14}$; to the α-nitrogen (N) of Q$^1$; or
if k=0 and i=0, then
Q$^1$ being directly connected with module A from the carbonyl (C=O) point of attachment of P$^5$; P$^{12}$; or P$^{13}$; to the α-nitrogen (N) of Q$^1$;

P$^{13}$; or P$^{14}$; having a carbonyl (C=O) point of attachment not connected as aforementioned, being appropriately saturated by linkage with R$^{30}$ to form the corresponding naturally or non-naturally occurring terminal α-amino acid residue; optionally having a modified carbonyl (C=O) functional group;

P$^1$; or P$^{14}$; having a nitrogen (N) not connected as aforementioned, being appropriately saturated by linkages with R$^1$, as already depicted above, and R$^{31}$ to form the corresponding naturally or non-naturally occurring terminal α-amino acid residue; optionally having a modified nitrogen (N) functional group;

R$^{Alk}$ is, with the proviso of containing less than 26 carbon- and/or heteroatoms,
C$_{1-12}$-alkyl; C$_{2-12}$-alkenyl; cycloalkyl; cycloalkyl-C$_{1-6}$-alkyl; or C$_{1-6}$-alkoxy-C$_{1-6}$-alkyl;

R$^{Ar}$ is, with the proviso of containing less than 26 carbon- and/or heteroatoms,
—(CR$^1$R$^4$)$_n$R$^{19}$; —(CH$_2$)$_n$O(CH$_2$)$_m$R$^{19}$; —(CH$_2$)$_n$S(CH$_2$)$_m$R$^{19}$; or —(CH$_2$)$_n$NR$^{14}$(CH$_2$)$_m$R$^{19}$;

R$^{Am}$ is, with the proviso of containing less than 26 carbon- and/or heteroatoms,
—(CR$^1$R$^{13}$)$_q$NR$^{15}$R$^{16}$; —(CH$_2$)$_q$C(=NR$^{13}$)NR$^{15}$R$^{16}$;
—(CH$_2$)$_q$C(=NOR$^{17}$)NR$^{15}$R$^{16}$;
—(CH$_2$)$_q$C(=NNR$^{15}$R$^{16}$)NR$^{17}$R$^{18}$; —(CR$^1$R$^{13}$)$_q$NR$^2$C(=NR$^{17}$)NR$^{15}$R$^{16}$;
—(CR$^1$R$^{13}$)$_q$N=C(NR$^{15}$R$^{16}$)NR$^{17}$R$^{18}$; —(CH$_2$)$_n$O(CH$_2$)$_m$ NR$^{15}$R$^{16}$;
—(CH$_2$)$_n$O(CH$_2$)$_m$C(=NR$^{17}$)NR$^{15}$R$^{16}$; —(CH$_2$)$_n$O(CH$_2$)$_m$C(=NOR$^{17}$)NR$^{15}$R$^{16}$;
—(CH$_2$)$_n$O(CH$_2$)$_m$C(=NNR$^{15}$R$^{16}$)NR$^{17}$R$^{18}$; —(CH$_2$)$_n$O(CH$_2$)$_m$NR$^1$C(=NR$^{17}$)NR$^{15}$R$^{16}$;
—(CH$_2$)$_n$O(CH$_2$)$_m$N=C(NR$^{15}$R$^{16}$)NR$^{17}$R$^{18}$; —(CH$_2$)$_n$S(CH$_2$)$_m$NR$^{15}$R$^{16}$;
—(CH$_2$)$_n$S(CH$_2$)$_m$C(=NR$^{17}$)NR$^{15}$R$^{16}$; —(CH$_2$)$_n$S(CH$_2$)$_m$ C(=NOR$^{17}$)NR$^{15}$R$^{16}$;
—(CH$_2$)$_n$S(CH$_2$)$_m$C(=NNR$^{15}$R$^{16}$)NR$^{17}$R$^{18}$; —(CH$_2$)$_n$S(CH$_2$)$_m$NR$^1$C(=NR$^{17}$)NR$^{15}$R$^{16}$;
—(CH$_2$)$_n$S(CH$_2$)$_m$N=C(NR$^{15}$R$^{16}$)NR$^{17}$R$^{18}$; or —(CR$^1$R$^{13}$)$_q$NR$^{14}$R$^{27}$;

R$^{Het}$ is, with the proviso of containing less than 26 carbon- and/or heteroatoms,
—(CR$^1$R$^{13}$)$_q$OR$^{14}$; —(CR$^1$R$^{13}$)$_q$SR$^{15}$; —(CR$^1$R$^{13}$)$_q$SO$_2$R$^{15}$; —(CR$^1$R$^{13}$)$_q$SO$_2$NR$^1$R$^{14}$;
—(CR$^1$R$^{13}$)$_q$SO$_2$NR$^{15}$R$^{16}$; —(CR$^1$R$^{13}$)$_q$NR$^{14}$SO$_2$R$^{15}$;
—(CR$^1$R$^{13}$)$_q$NR$^{14}$SO$_2$NR$^{15}$R$^{16}$;
—(CH$_2$)$_n$O(CH$_2$)$_m$OR$^{14}$; —(CH$_2$)$_n$O(CH$_2$)$_m$SR$^{15}$;
—(CR$^1$R$^{13}$)$_q$COOR$^{15}$;
—(CR$^1$R$^{13}$)$_q$CONR$^{15}$R$^{16}$; or —(CR$^1$R$^{13}$)$_q$NR$^2$CONR$^{15}$R$^{16}$;

R$^{OH}$ is, with the proviso of containing less than 26 carbon- and/or heteroatoms, —(CR$^1$R$^{13}$)$_q$OH; —(CR$^1$R$^{13}$)$_q$SH;
—(CH$_2$)$_n$O(CH$_2$)$_m$OH; —(CH$_2$)$_n$S(CH$_2$)$_m$OH; —(CH$_2$)$_n$NR$^1$(CH$_2$)$_m$OH; hydroxy-C$_{1-8}$-alkyl; hydroxy-C$_{2-8}$-alkenyl; hydroxy-cycloalkyl; or hydroxy-heterocycloalkyl;

R$^{Amide}$ is, with the proviso of containing less than 26 carbon- and/or heteroatoms, —(CR$^1$R$^{13}$)$_q$CONR$^{15}$R$^{16}$;

Y is, with the proviso of containing less than 25 carbon- and/or heteroatoms, —(CR$^1$R$^{13}$)$_q$—;

Z is, with the proviso of containing less than 25 carbon- and/or heteroatoms,
—(CH$_2$)$_n$—S—S—(CH$_2$)$_m$—; —(CR$^{28}$R$^{29}$)$_n$—S—S—(CR$^{28}$R$^{29}$)$_m$—; —(CH$_2$)$_n$CH=CH(CH$_2$)$_m$—;
—(CR$^{28}$R$^{29}$)$_n$CH=CH(CR$^{28}$R$^{29}$)$_m$—; —(CH$_2$)$_n$-heteroaryl-(CH$_2$)$_m$—;
—(CR$^{28}$R$^{29}$)$_n$-heteroaryl-(CR$^{28}$R$^{29}$)$_m$—; —(CH$_2$)$_n$CONR$^1$(CH$_2$)$_m$—; —(CH$_2$)$_n$NR$^1$CO(CH$_2$)$_m$—

$-(CR^{28}R^{29})_nCONR^1(CR^{28}R^{29})_m-$; $-(CR^{28}R^{29})_nNR^1CO(CR^{28}R^{29})_m-$;

$-(CH_2)_nNR^1CONR^2(CH_2)_m-$; or $-(CR^{28}R^{29})_nNR^1CONR^2(CR^{28}R^{29})_m-$;

$R^1$, $R^2$ and $R^3$ are independently

H; $CF_3$; $C_{1-8}$-alkyl; $C_{2-8}$-alkenyl; or aryl-$C_{1-6}$-alkyl;

$R^4$, $R^5$, $R^6$, $R^7$ and $R^8$ are independently

H; F; $CF_3$; $C_{1-8}$-alkyl; $C_{2-8}$-alkenyl; cycloalkyl; heterocycloalkyl; aryl; heteroaryl;

aryl-$C_{1-6}$-alkyl; heteroaryl-$C_{1-6}$-alkyl; $-(CHR^{13})_oOR^{15}$; $-O(CO)R^{15}$; $-(CHR^{13})_oSR^{15}$;

$-(CHR^{13})_oNR^{15}R^{16}$; $-(CHR^{13})_oOCONR^{15}R^{16}$;

$-(CHR^{13})_oNR^1CONR^{15}R^{16}$;

$-(CHR^{13})_oNR^1COR^{15}$; $-(CHR^{13})_oOCOR^{15}$;

$-(CHR^{13})_oCONR^{15}R^{16}$; $-(CHR^{13})_oPO(OR^1)_2$;

$-(CHR^{13})_oSO_2R^{15}$; $-(CHR^{13})_oNR^1SO_2R^{15}$; $-(CHR^{13})_oSO_2NR^{15}R^{16}$; $-(CR^1R^{13})_oR^{19}$; or $-(CHR^1)_nO(CHR^2)_mR^{23}$; or $R^4$ and $R^2$; or $R^5$ and $R^6$ taken together can form:

=O; =$NR^1$; =$NOR^1$; =$NOCF_3$; or $-(CHR^1)_p-$;

$R^4$ and $R^5$; $R^6$ and $R^7$; $R^7$ and $R^8$; or $R^6$ and $R^9$ taken together can form:

$-(CHR^1)_p-$; $-(CH_2)_nO(CH_2)_m-$; $-(CH_2)_nS(CH_2)_m-$; or $-(CH_2)_nNR^1(CH_2)_m-$;

$R^9$ is H; F; $CF_3$; $C_{1-8}$-alkyl; $C_{2-8}$-alkenyl; cycloalkyl; heterocycloalkyl; aryl; heteroaryl;

aryl-$C_{1-6}$-alkyl; heteroaryl-$C_{1-6}$-alkyl; $-(CHR^{13})_rOR^{15}$; $-O(CO)R^{15}$; $-(CHR^{13})_rSR^{15}$;

$-(CHR^{10})_rNR^{15}R^{16}$; $-(CHR^{13})_rOCONR^{15}R^{16}$;

$-(CHR^{13})_rNR^1CONR^{15}R^{16}$;

$-(CHR^{13})_rNR^1COR^{15}$; $-(CHR^{13})_oCOOR^{15}$;

$-(CHR^{13})_oCONR^{15}R^{16}$; $-(CHR^{13})_rPO(OR^1)_2$;

$-(CHR^{13})_rSO_2R^{15}$; $-(CHR^{13})_rNR^1SO_2R^{15}$;

$-(CHR^{13})_rSO_2NR^{15}R^{16}$; $-(CR^1R^{13})_oR^{19}$; or $-(CHR^1)_rO(CHR^1)_oR^{23}$;

$R^{10}$ and $R^{11}$ are independently

H; F; Cl; Br; I; $CF_3$; $OCF_3$; $OCHF_2$; CN; $NO_2$; $C_{1-8}$-alkyl; $C_{2-8}$-alkenyl; aryl; heteroaryl;

aryl-$C_{1-6}$-alkyl; heteroaryl-$C_{1-6}$-alkyl; $-(CHR^{13})_oOR^{15}$; $-O(CO)R^{15}$;

$-(CHR^{13})_oSR^{15}$;

$-(CHR^{13})_oNR^{15}R^{16}$; $-(CHR^{13})_oCONR^{15}R^{16}$;

$-(CHR^{13})_oNR^1CONR^{15}R^{16}$;

$-(CHR^{13})_oNR^1COR^{15}$; $-(CHR^{13})_oCOOR^{15}$;

$-(CHR^{13})_oCONR^{15}R^{16}$; $-(CHR^{13})_oPO(OR^1)_2$;

$-(CHR^{13})_oSO_2R^{15}$; $-(CHR^{13})_oNR^1SO_2R^{15}$;

$-(CHR^{13})_oSO_2NR^{15}R^{16}$; or $-(CR^1R^{13})_oR^{19}$;

$R^{13}$ is H; F; $CF_3$; $C_{1-8}$-alkyl; $C_{2-8}$-alkenyl; cycloalkyl; heterocycloalkyl;

cycloalkyl-$C_{1-6}$-alkyl; heterocycloalkyl-$C_{1-6}$-alkyl; aryl; heteroaryl;

aryl-$C_{1-6}$-alkyl; heteroaryl-$C_{1-6}$-alkyl; $-(CR^1R^{13})_oOR^{15}$; $-OCOR^1$; $-(CR^1R^{13})_oNR^{15}R^{16}$;

$-(CR^1R^{13})_qNR^2C(=NR^{17})NR^{15}R^{16}$; $-(CR^1R^{13})_qNR^2CONR^{15}R^{16}$; $-COOR^{15}$; $-CONR^{15}R^{16}$;

or $-SO_2R^{15}$; or $-SO_2NR^{15}R^{16}$;

$R^{14}$ is H; $CF_3$; $C_{1-8}$-alkyl; $C_{2-8}$-alkenyl; cycloalkyl; heterocycloalkyl;

cycloalkyl-$C_{1-6}$-alkyl; heterocycloalkyl-$C_{1-6}$-alkyl; aryl; heteroaryl;

aryl-$C_{1-6}$-alkyl; heteroaryl-$C_{1-6}$-alkyl; cycloalkyl-aryl; heterocycloalkyl-aryl;

cycloalkyl-heteroaryl; heterocycloalkyl-heteroaryl; aryl-cycloalkyl;

aryl-heterocycloalkyl; heteroaryl-cycloalkyl; heteroaryl-heterocycloalkyl;

$-(CHR^1)_oOR^{15}$; $-(CHR^1)_oSR^{15}$; $-(CHR^1)_oNR^{15}R^{16}$; $-(CHR^1)_oCOOR^{15}$;

$-(CHR^1)_oCONR^{15}R^{16}$; or $-(CHR^1)_oSO_2R^{15}$;

$R^{15}$, $R^{16}$, $R^{17}$ and $R^{18}$ are independently

H; $C_{1-8}$-alkyl; $C_{2-8}$-alkenyl; $C_{1-6}$-alkoxy; cycloalkyl; heterocycloalkyl;

cycloalkyl-$C_{1-6}$-alkyl; heterocycloalkyl-$C_{1-6}$-alkyl; aryl; heteroaryl;

aryl-$C_{1-6}$-alkyl; heteroaryl-$C_{1-6}$-alkyl; cycloalkyl-aryl; heterocycloalkyl-aryl;

cycloalkyl-heteroaryl; heterocycloalkyl-heteroaryl; aryl-cycloalkyl;

aryl-heterocycloalkyl; heteroaryl-cycloalkyl; or heteroaryl-heterocycloalkyl;

or the structural elements $-NR^{15}R^{16}$ and $-NR^{17}R^{18}$ can independently form:

heterocycloalkyl; aryl-heterocycloalkyl; or heteroaryl-heterocycloalkyl;

$R^{19}$ is an aryl group of one of the formulae

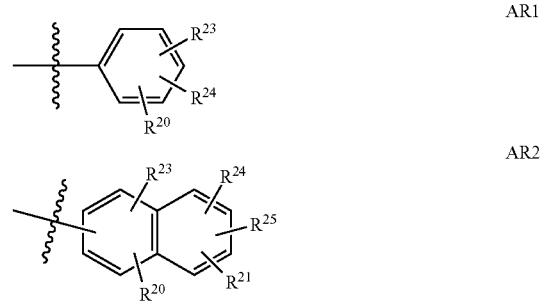

AR1

AR2 or a group of one of the formulae

H1

H2

H3

H4

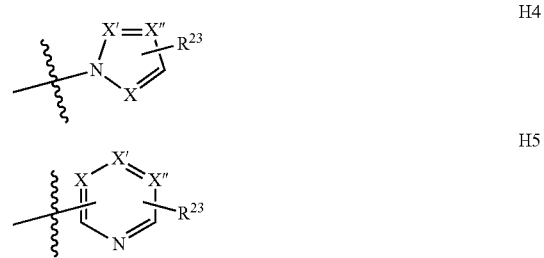

H5

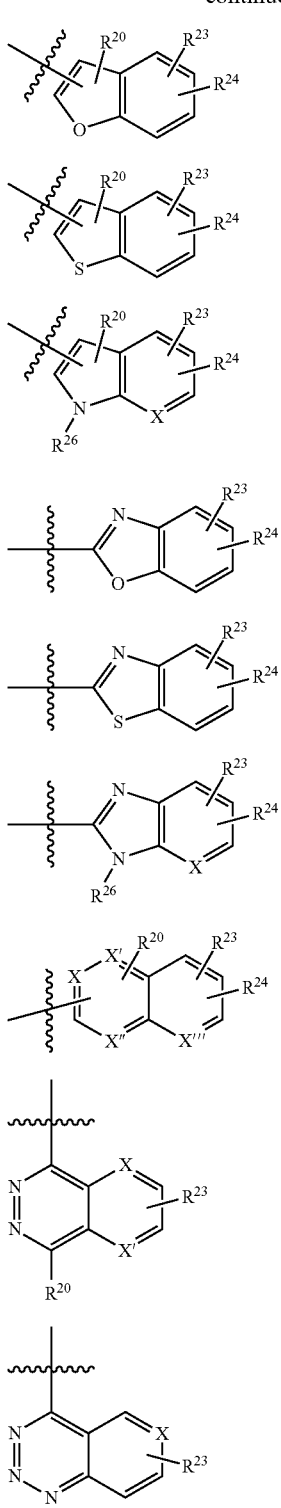

X, X', X" and X''' are independently
—CR²⁰; or N;
R²⁰ and R²¹ are independently
H; F; Cl; Br; I; OH; NH₂; NO₂; CN; CF₃; OCHF₂; OCF₃; $C_{1-8}$-alkyl; $C_{2-8}$-alkenyl; aryl;
heteroaryl; aryl-$C_{1-6}$-alkyl; heteroaryl-$C_{1-6}$-alkyl;
—(CH₂)ₒR²²; —(CH₂)ₒOR¹⁵; —O(CO)R¹⁵;
—O(CH₂)ₒR²²; —(CH₂)ₒSR¹⁵; —(CH₂)ₒNR¹⁵R¹⁶;
—(CH₂)ₒCONR¹⁵R¹⁶;
—(CH₂)ₒNR¹CONR¹⁵R¹⁶; —(CH₂)ₒNR¹COR¹⁵;
—(CH₂)ₒCOOR¹⁵; —(CH₂)ₒCONR¹⁵R¹⁶;
—(CH₂)ₒPO(OR¹)₂; —(CH₂)ₒSO₂R¹⁵; or —(CH₂)ₒCOR¹⁵;

R²² is an aryl group of the formula

AR3

R²³, R²⁴ and R²⁵ are independently
H; F; Cl; Br; I; OH; NH₂; NO₂; CN; CF₃; OCHF₂; OCF₃; $C_{1-8}$-alkyl; $C_{2-8}$-alkenyl;
—(CH₂)ₒOR¹⁵; —O(CO)R¹⁵; —(CH₂)ₒNR¹R¹⁵;
—(CH₂)ₒCOOR¹⁵; —(CH₂)ₒCONR¹R¹⁵;
R²⁶ is H; Ac; $C_{1-8}$-alkyl; or aryl-$C_{1-6}$-alkyl;
R²⁷ is —CO(CR¹R¹³)ᵩR¹⁵;
R²⁸ and R²⁹ are independently
H; CF₃; $C_{1-8}$-alkyl; $C_{2-8}$-alkenyl; or aryl-$C_{1-6}$-alkyl; cycloalkyl-$C_{1-6}$-alkyl; or heterocycloalkyl-$C_{1-6}$-alkyl;
R³⁰ is —OR¹⁴; —SR¹⁴; or —NR¹⁵R¹⁶;
R³¹ is H; $C_{1-8}$-alkyl; $C_{2-8}$-alkenyl; $C_{1-6}$-alkoxy; cycloalkyl; heterocycloalkyl;
cycloalkyl-$C_{1-6}$-alkyl; heterocycloalkyl-$C_{1-6}$-alkyl; aryl; heteroaryl;
aryl-$C_{1-6}$-alkyl; heteroaryl-$C_{1-6}$-alkyl; cycloalkyl-aryl; heterocycloalkyl-aryl;
cycloalkyl-heteroaryl; heterocycloalkyl-heteroaryl; aryl-cycloalkyl;
aryl-heterocycloalkyl; heteroaryl-cycloalkyl; heteroaryl-heterocycloalkyl;
—COR¹⁵; —CONR¹⁵R¹⁶; —C(=NR¹³)NR¹⁵R¹⁶; or the structural element —NR¹R³¹ can form: —N=C(NR¹⁵R¹⁶)₂; heterocycloalkyl; aryl-heterocycloalkyl; or heteroaryl-heterocycloalkyl;
n and m are independently an integer of 0-5 with the proviso that n+m≤6;
o is 0-4; p is 2-6; q is 1-6; and r is 1-3;
or a tautomer or rotamer thereof; or a salt; or a pharmaceutically acceptable salt; or a hydrate; or a solvate thereof.

A further particular embodiment (5) of the invention relates to compounds of general formula (I) according to particular embodiment (4)
with the proviso that
P⁴ and P⁹ taken together form an interstrand linking bis(amino acid)-structure of one of the formulae AA13; or AA13ᴰ; based on the linkage of two α-amino acid residues; and/or
P¹ is AA7; and/or
P² is AA11; or AA7; and/or
P⁴ is Gly; Sar; AA7ᴰ; or AA8; and/or
P⁵ is AA8; and/or
T⁶ is AA4ᴰ; AA5ᴰ; AA6ᴰ; AA8ᴰ; or AA11ᴰ; and/or
T⁷ is AA7; AA8; AA10; or AA11; and/or
P⁸ is AA11; and/or
P⁹ is AA8; or AA9; and/or
P¹¹ is Gly; Sar; AA7; or AA11; and/or
P¹² is AA8; AA8ᴰ; AA9; or AA9ᴰ; and/or
P¹³ is AA8; AA8ᴰ; AA16; or AA16ᴰ; and/or
if k=1-3, then $L^1$ is AA8; AA8$^D$; AA16; AA16$^D$; and/or
$Q^7$ is AA11$^D$; AA16$^D$; AA7; AA7$^D$; AA10; or AA10$^D$;
or a tautomer or rotamer thereof; or a salt; or a pharmaceutically acceptable salt; or a hydrate; or a solvate thereof.

A further particular embodiment (6) of the invention relates to compounds of general formula (I), wherein
if i=1, and
$P^2$ and $P^{11}$ taken together may form an interstrand linking bis(amino acid)-structure of one of the formulae AA13; or AA13$^D$; based on the linkage of two α-amino acid residues; and/or
$P^{13}$ and $P^{14}$ taken together may form an interstrand linking bis(amino acid)-structure of one of the formulae AA13; AA13$^D$; AA13$^{LD}$; or AA13$^{DL}$; based on the linkage of two α-amino acid residues;
$P^1$ is an L α-amino acid residue of formula
   AA8;
$P^2$ is an L α-amino acid residue of one of the formulae
   AA10; or AA16;
$P^3$ is an L α-amino acid residue of one of the formulae
   AA7; or AA8;
$P^4$ is an L α-amino acid residue of one of the formulae
   AA7; AA10; AA11; or AA16;
$P^5$ is an L α-amino acid residue of one of the formulae
   AA7; AA11; or AA10;
$T^6$ is an D α-amino acid residue of one of the formulae
   AA1$^D$; AA2$^D$; AA3$^D$; AA12$^D$; AA7$^D$; or AA10$^D$;
$T^7$ is an L α-amino acid residue of one of the formulae
   AA1; AA2; AA3; AA4; AA5; or AA6;
$P^8$ is an L α-amino acid residue of one of the formulae
   AA7; or AA8;
$P^9$ is Gly; Sar; or an L α-amino acid residue of one of the formulae
   AA7; AA10; AA11; or AA16;
$P^{10}$ is an L α-amino acid residue of one of the formulae
   AA7; or AA8;
$P^{11}$ is an L α-amino acid residue of one of the formulae
   AA10; or AA16;
$P^{12}$ is Gly; Sar; Aib; or an α-amino acid residue of one of the formulae
   AA7; AA7$^D$; AA10; AA10$^D$; AA11; or AA11$^D$;
$P^{13}$ is Gly; Sar; Aib; or an α-amino acid residue of one of the formulae
   AA7; AA7$^D$; AA10; AA10$^D$; AA11; or AA11$^D$;
$P^{14}$ is Gly; Sar; Aib; or an α-amino acid residue of one of the formulae
   AA7; AA7$^D$; AA9; AA9$^D$; AA10; AA10$^D$; AA11; or AA11$^D$;
with the proviso that,
   if no interstrand linkage is formed, then
      $P^{13}$ and $P^{14}$, and $P^{14}$ and $P^1$ are connected as aforementioned;
   if $P^{13}$ and $P^{14}$ taken together form an interstrand linkage, as defined above, then
      $P^{13}$ and $P^{14}$ are not additionally connected as aforementioned;
with the further proviso that,
   if linker L, as defined below, is connected with module A by a carbonyl (C=O) point of attachment of $P^2$; $P^5$; or $P^{12}$; then
      $P^2$; $P^5$; or $P^{12}$; is an α-amino acid residue of one of the formulae AA14; or AA14$^D$;
   if linker L, as defined below, is connected with module A by a carbonyl (C=O) point of attachment of $P^{13}$ and $P^{13}$ and $P^{14}$, and $P^{14}$ and $P^1$ are connected as aforementioned; or
      $P^{14}$ and $P^1$ are not connected as aforementioned; then
         $P^{13}$ is an α-amino acid residue of one of the formulae AA14; or AA14$^D$, as depicted above;
   if linker L, as defined below, is connected with module A by a carbonyl (C=O) point of attachment of $P^{14}$; and
      $P^{13}$ and $P^{14}$, and $P^{14}$ and $P^1$ are connected as aforementioned; or
      $P^{13}$ and $P^{14}$ are not connected as aforementioned; then
         $P^{14}$ is an α-amino acid residue of one of the formulae AA14; or AA14$^D$, as depicted above;
if i=0, and
$P^2$ and $P^{11}$ taken together form naturally or non-naturally cross-linking α-amino acids, as defined above, then
   $P^1$; $P^3$ to $P^5$; $T^6$, $T^7$; $P^8$ to $P^{10}$; $P^{12}$ and $P^{13}$ are naturally or non-naturally occurring α-amino acids, as defined in this embodiment;
with the proviso that,
   if linker L, as defined below, is connected with module A by a carbonyl (C=O) point of attachment of $P^5$; or $P^{12}$, then
      $P^5$; or $P^{12}$; is an α-amino acid residue of one of the formulae AA14; or AA14$^D$, as depicted above;
and a module B consisting of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$, and wherein
$Q^1$ is an α-amino acid residue of one of the formulae
   AA15; or AA15$^D$;
$Q^2$, $Q^5$, and $Q^6$ are independently an L α-amino acid residue of formula
   AA10;
$Q^3$ is an D α-amino acid residue of one of the formulae
   AA7$^D$; or AA8$^D$;
$Q^4$ is an L α-amino acid residue of formula
   AA7;
$Q^7$ is an L α-amino acid residue of one of the formulae
   AA11; or AA16;
and a linker L consisting of k=0-3 single elements L being connected in either direction from the carbonyl (C=O) point of attachment to the nitrogen (N) of the next element, and wherein,
if k=1,
$L^1$ is Gly; Sar; Aib; or an α-amino acid residue of one of the formulae
   AA10; AA10$^D$; AA11; AA11$^D$; AA7; AA7$^D$;
if k=2, the additional element
$L^2$ is Gly; Sar; Aib; or an α-amino acid residue of one of the formulae
   AA10; AA10$^D$; AA11; AA11$^D$; AA7; or AA7$^D$;
if k=3, the additional element
$L^3$ is Gly; Sar; Aib; or an α-amino acid residue of one of the formulae
   AA10; AA10$^D$; AA11; AA11$^D$; AA7; or AA7$^D$;
said linker L being connected with module B from the carbonyl (C=O) point of attachment of $L^k$ to the α-nitrogen (N) of $Q^1$ and,
if k=1-3 and i=1, being connected with module A from the carbonyl (C=O) point of attachment of $P^2$; $P^5$; $P^{12}$; $P^{13}$; or $P^{14}$; to the nitrogen (N) of $L^1$; or,
if k=1-3 and i=0, being connected with module A from the carbonyl (C=O) point of attachment of $P^5$; $P^{12}$; or $P^{13}$; to the nitrogen (N) of $L^1$; or
if k=0 and i=1, then
$Q^1$ being directly connected with module A from the carbonyl (C=O) point of attachment of $P^2$; $P^5$; $P^{12}$; $P^{13}$; or $P^{14}$; to the α-nitrogen (N) of $Q^1$; or if k=0 and i=0, then Q$^1$ being directly connected with module A from the carbonyl (C=O) point of attachment of P$^5$; P$^{12}$; or P$^{13}$; to the α-nitrogen (N) of Q$^1$;

P$^{13}$; or P$^{14}$; having a carbonyl (C=O) point of attachment not connected as aforementioned, being appropriately saturated by linkage with R$^{30}$ to form the corresponding naturally or non-naturally occurring terminal α-amino acid residue; optionally having a modified carbonyl (C=O) functional group;

P$^1$; or P$^{14}$; having a nitrogen (N) not connected as aforementioned, being appropriately saturated by linkages with R$^1$, as already depicted above, and R$^{31}$ to form the corresponding naturally or non-naturally occurring terminal α-amino acid residue; optionally having a modified nitrogen (N) functional group;

R$^{Alk}$ is, with the proviso of containing less than 26 carbon- and/or heteroatoms, C$_{1-12}$-alkyl; C$_{2-12}$-alkenyl; cycloalkyl; cycloalkyl-C$_{1-6}$-alkyl; or C$_{1-6}$-alkoxy-C$_{1-6}$-alkyl;

R$^{Ar}$ is, with the proviso of containing less than 26 carbon- and/or heteroatoms, —(CR$^1$R$^4$)$_n$R$^{19}$; —(CH$_2$)$_n$O(CH$_2$)$_m$R$^{19}$; —(CH$_2$)$_n$S(CH$_2$)$_m$R$^{19}$; or —(CH$_2$)$_n$NR$^{14}$(CH$_2$)$_m$R$^{19}$;

R$^{Am}$ is, with the proviso of containing less than 26 carbon- and/or heteroatoms,
—(CR$^1$R$^{13}$)$_q$NR$^{15}$R$^{16}$; —(CH$_2$)$_q$C(=NR$^{13}$)NR$^{15}$R$^{16}$;
—(CH$_2$)$_q$C(=NOR$^{17}$)NR$^{15}$R$^{16}$;
—(CH$_2$)$_q$C(=NNR$^{15}$R$^{16}$)NR$^{17}$R$^{18}$; —(CR$^1$R$^{13}$)$_q$NR$^2$C(=NR$^{17}$)NR$^{15}$R$^{16}$;
—(CR$^1$R$^{13}$)$_q$N=C(NR$^{15}$R$^{16}$)NR$^{17}$R$^{18}$; —(CH$_2$)$_n$O(CH$_2$)$_m$NR$^{15}$R$^{16}$;
—(CH$_2$)$_n$O(CH$_2$)$_m$C(=NR$^{17}$)NR$^{15}$R$^{16}$; —(CH$_2$)$_n$O(CH$_2$)$_m$C(=NOR$^{17}$)NR$^{15}$R$^{16}$;
—(CH$_2$)$_n$O(CH$_2$)$_m$C(=NNR$^{15}$R$^{16}$)NR$^{17}$R$^{18}$; —(CH$_2$)$_n$O(CH$_2$)$_m$NR$^1$C(=NR$^{17}$)NR$^{15}$R$^{16}$;
—(CH$_2$)$_n$O(CH$_2$)$_m$N=C(NR$^{15}$R$^{16}$)NR$^{17}$R$^{18}$; —(CH$_2$)$_n$S(CH$_2$)$_m$NR$^{15}$R$^{16}$;
—(CH$_2$)$_n$S(CH$_2$)$_m$C(=NR$^{17}$)NR$^{15}$R$^{16}$; —(CH$_2$)$_n$S(CH$_2$)$_m$C(=NOR$^{17}$)NR$^{15}$R$^{16}$;
—(CH$_2$)$_n$S(CH$_2$)$_m$C(=NNR$^{15}$R$^{16}$)NR$^{17}$R$^{18}$; —(CH$_2$)$_n$S(CH$_2$)$_m$NR$^1$C(=NR$^{17}$)NR$^{15}$R$^{16}$;
—(CH$_2$)$_n$S(CH$_2$)$_m$N=C(NR$^{15}$R$^{16}$)NR$^{17}$R$^{18}$; or
—(CR$^1$R$^{13}$)$_q$NR$^{14}$R$^{27}$;

R$^{Het}$ is, with the proviso of containing less than 26 carbon- and/or heteroatoms,
—(CR$^1$R$^{13}$)$_q$OR$^{14}$; —(CR$^1$R$^{13}$)$_q$SR$^{15}$; —(CR$^1$R$^{13}$)$_q$SO$_2$R$^{15}$; —(CR$^1$R$^{13}$)$_q$SO$_2$NR$^1$R$^{14}$;
—(CR$^1$R$^{13}$)$_q$SO$_2$NR$^{15}$R$^{16}$; —(CR$^1$R$^{13}$)$_q$NR$^{14}$SO$_2$R$^{15}$;
—(CR$^1$R$^{13}$)$_q$NR$^{14}$SO$_2$NR$^{15}$R$^{16}$;
—(CH$_2$)$_n$O(CH$_2$)$_m$OR$^{14}$; —(CH$_2$)$_n$O(CH$_2$)$_m$SR$^{15}$;
—(CR$^1$R$^{13}$)$_q$COOR$^{15}$;
—(CR$^1$R$^{13}$)$_q$CONR$^{15}$R$^{16}$; or —(CR$^1$R$^{13}$)$_q$NR$^2$CONR$^{15}$R$^{16}$;

R$^{OH}$ is, with the proviso of containing less than 26 carbon- and/or heteroatoms,
—(CR$^1$R$^{13}$)$_q$OH; —(CR$^1$R$^{13}$)$_q$SH; —(CH$_2$)$_n$O(CH$_2$)$_m$OH; —(CH$_2$)$_n$S(CH$_2$)$_m$OH;
—(CH$_2$)$_n$NR$^1$(CH$_2$)$_m$OH; hydroxy-C$_{1-8}$-alkyl; hydroxy-C$_{2-8}$-alkenyl; hydroxy-cycloalkyl; or hydroxy-heterocycloalkyl;

R$^{Amide}$ is, with the proviso of containing less than 26 carbon- and/or heteroatoms, —(CR$^1$R$^{13}$)$_q$CONR$^{15}$R$^{16}$;

Y is, with the proviso of containing less than 25 carbon- and/or heteroatoms,
—(CR$^1$R$^{13}$)$_q$—;

Z is, with the proviso of containing less than 25 carbon- and/or heteroatoms,
—(CH$_2$)$_n$—S—S—(CH$_2$)$_m$—; —(CR$^{28}$R$^{29}$)$_n$—S—S—(CR$^{28}$R$^{29}$)$_m$—; —(CH$_2$)$_n$CH=CH(CH$_2$)$_m$—;
—(CR$^{28}$R$^{29}$)$_n$CH=CH(CR$^{28}$R$^{29}$)$_m$—; —(CH$_2$)$_n$-heteroaryl-(CH$_2$)$_m$—;
—(CR$^{28}$R$^{29}$)$_n$-heteroaryl-(CR$^{28}$R$^{29}$)$_m$—; —(CH$_2$)$_n$CONR$^1$(CH$_2$)$_m$—; —(CH$_2$)$_n$NR$^1$CO(CH$_2$)$_m$—
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
—(CH$_2$)$_n$NR$^1$CONR$^2$(CH$_2$)$_m$—; or —(CR$^{28}$R$^{29}$)$_n$NR$^1$CONR$^2$(CR$^{28}$R$^{29}$)$_m$—;

R$^1$, R$^2$ and R$^3$ are independently
H; CF$_3$; C$_{1-8}$-alkyl; C$_{2-8}$-alkenyl; or aryl-C$_{1-6}$-alkyl;

R$^4$, R$^5$, R$^6$, R$^7$ and R$^8$ are independently
H; F; CF$_3$; C$_{1-6}$-alkyl; C$_{2-8}$-alkenyl; cycloalkyl; heterocycloalkyl; aryl; heteroaryl;
aryl-C$_{1-6}$-alkyl; heteroaryl-C$_{1-6}$-alkyl; —(CHR$^{13}$)$_o$OR$^{16}$;
—O(CO)R$^{16}$; —(CHR$^{13}$)$_o$SR$^{15}$;
—(CHR$^{13}$)$_o$NR$^{15}$R$^{16}$; —(CHR$^{13}$)$_o$CONR$^{15}$R$^{16}$;
—(CHR$^{13}$)$_o$NR$^1$CONR$^{16}$R$^{16}$;
—(CHR$^{13}$)$_o$NR$^1$COR$^{16}$; —(CHR$^{13}$)$_o$COOR$^{16}$;
—(CHR$^{13}$)$_o$CONR$^{16}$R$^{16}$; —(CHR$^{13}$)$_o$PO(OR$^1$)$_2$;
—(CHR$^{13}$)$_o$SO$_2$R$^{16}$; —(CHR$^{13}$)$_o$NR$^1$SO$_2$R$^{16}$;
—(CHR$^{13}$)$_o$SO$_2$NR$^{16}$R$^{16}$; —(CR$^1$R$^{13}$)$_o$OR$^{19}$; or
—(CHR$^1$)$_n$O(CHR$^2$)$_m$R$^{23}$; or R$^4$ and R$^2$; or R$^5$ and R$^6$ taken together can form:
=O; =NR$^1$; =NOR$^1$; =NOCF$_3$; or —(CHR$^1$)$_p$—;

R$^4$ and R$^5$; R$^6$ and R$^7$; R$^7$ and R$^8$; or R$^8$ and R$^9$ taken together can form:
—(CHR$^1$)$_p$—; —(CH$_2$)$_n$O(CH$_2$)$_m$—; —(CH$_2$)$_n$S(CH$_2$)$_m$—; or —(CH$_2$)$_n$NR$^1$(CH$_2$)$_m$—;

R$^9$ is H; F; CF$_3$; C$_{1-8}$-alkyl; C$_{2-8}$-alkenyl; cycloalkyl; heterocycloalkyl; aryl; heteroaryl;
aryl-C$_{1-6}$-alkyl; heteroaryl-C$_{1-6}$-alkyl; —(CHR$^{13}$)$_r$OR$^{15}$;
—O(CO)R$^{15}$; —(CHR$^{13}$)$_r$SR$^{15}$;
—(CHR$^{10}$)$_r$NR$^{15}$R$^{16}$; —(CHR$^{13}$)$_r$OCONR$^{15}$R$^{16}$; —(CHR$^{13}$)$_r$NR$^1$CONR$^{15}$R$^{16}$;
—(CHR$^{13}$)$_r$NR$^1$COR$^{15}$; —(CHR$^{13}$)$_o$COOR$^{16}$;
—(CHR$^{13}$)$_o$CONR$^{15}$R$^{16}$; —(CHR$^{13}$)$_r$PO(OR$^1$)$_2$;
—(CHR$^{13}$)$_o$SO$_2$R$^{16}$; —(CHR$^{13}$)$_r$NR$^1$SO$_2$R$^{16}$;
—(CHR$^{13}$)$_r$SO$_2$NR$^{16}$R$^{16}$; —(CR$^1$R$^{13}$)$_o$R$^{19}$; or
—(CHR$^1$)$_o$O(CHR$^1$)$_o$R$^{23}$;

R$^{10}$ and R$^{11}$ are independently
H; F; Cl; Br; I; CF$_3$; OCF$_3$; OCHF$_2$; CN; NO$_2$; C$_{1-8}$-alkyl; C$_{2-8}$-alkenyl; aryl; heteroaryl;
aryl-C$_{1-6}$-alkyl; heteroaryl-C$_{1-6}$-alkyl; —(CHR$^{13}$)$_o$OR$^{15}$;
—O(CO)R$^{15}$;
—(CHR$^{13}$)$_o$SR$^{15}$;
—(CHR$^{13}$)$_o$NR$^{15}$R$^{16}$; —(CHR$^{13}$)$_o$CONR$^{15}$R$^{16}$;
—(CHR$^{13}$)$_o$NR$^1$CONR$^{15}$R$^{16}$;
—(CHR$^{13}$)$_o$NR$^1$COR$^{15}$; —(CHR$^{13}$)$_o$COOR$^{15}$;
—(CHR$^{13}$)$_o$CONR$^{15}$R$^{16}$; —(CHR$^{13}$)$_o$PO(OR$^1$)$_2$;
—(CHR$^{13}$)$_o$SO$_2$R$^{15}$; —(CHR$^{13}$)$_o$NR$^1$SO$_2$R$^{15}$;
—(CHR$^{13}$)$_o$SO$_2$NR$^{15}$R$^{16}$; or —(CR$^1$R$^{13}$)$_o$R$^{19}$;

R$^{13}$ is H; F; CF$_3$; C$_{1-8}$-alkyl; C$_{2-8}$-alkenyl; cycloalkyl; heterocycloalkyl;
cycloalkyl-C$_{1-6}$-alkyl; heterocycloalkyl-C$_{1-6}$-alkyl; aryl; heteroaryl;
aryl-C$_{1-6}$-alkyl; heteroaryl-C$_{1-6}$-alkyl; —(CR$^1$R$^{13}$)$_o$OR$^{15}$;
—OCOR$^1$; —(CR$^1$R$^{13}$)$_o$NR$^{15}$R$^{16}$;
—(CR$^1$R$^{13}$)$_q$NR$^2$C(=NR$^{17}$)NR$^{15}$R$^{16}$; —(CR$^1$R$^{13}$)$_q$NR$^2$CONR$^{15}$R$^{16}$; —COOR$^{15}$; —CONR$^{15}$R$^{16}$;
or —SO$_2$R$^{15}$; or —SO$_2$NR$^{15}$R$^{16}$;

R$^{14}$ is H; CF$_3$; C$_{1-8}$-alkyl; C$_{2-8}$-alkenyl; cycloalkyl; heterocycloalkyl;

cycloalkyl-C$_{1-6}$-alkyl; heterocycloalkyl-C$_{1-6}$-alkyl; aryl; heteroaryl;
aryl-C$_{1-6}$-alkyl; heteroaryl-C$_{1-6}$-alkyl; cycloalkyl-aryl; heterocycloalkyl-aryl;
cycloalkyl-heteroaryl; heterocycloalkyl-heteroaryl; aryl-cycloalkyl;
aryl-heterocycloalkyl; heteroaryl-cycloalkyl; heteroaryl-heterocycloalkyl;
—(CHR$^1$)$_o$OR$^{15}$; —(CHR$^1$)$_o$SR$^{15}$; —(CHR$^1$)$_o$NR$^{15}$R$^{16}$; —(CHR$^1$)$_o$COOR$^{15}$;
—(CHR$^1$)$_o$CONR$^{15}$R$^{16}$; or —(CHR$^1$)$_o$SO$_2$R$^{15}$;

R$^{15}$, R$^{16}$, R$^{17}$ and R$^{18}$ are independently

H; C$_{1-8}$-alkyl; C$_{2-8}$-alkenyl; C$_{1-6}$-alkoxy; cycloalkyl; heterocycloalkyl;
cycloalkyl-C$_{1-6}$-alkyl; heterocycloalkyl-C$_{1-6}$-alkyl; aryl; heteroaryl;
aryl-C$_{1-6}$-alkyl; heteroaryl-C$_{1-6}$-alkyl; cycloalkyl-aryl; heterocycloalkyl-aryl;
cycloalkyl-heteroaryl; heterocycloalkyl-heteroaryl; aryl-cycloalkyl;
aryl-heterocycloalkyl; heteroaryl-cycloalkyl; or heteroaryl-heterocycloalkyl;

or the structural elements —NR$^{15}$R$^{16}$ and —NR$^{17}$R$^{18}$ can independently form:
heterocycloalkyl; aryl-heterocycloalkyl; or heteroaryl-heterocycloalkyl;

R$^{19}$ is an aryl group of one of the formulae

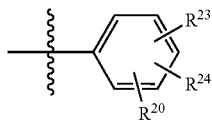  AR1

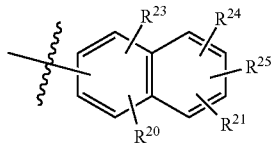  AR2 or a group of one of the formulae

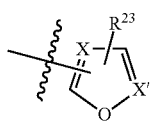  H1

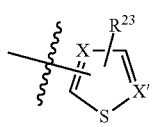  H2

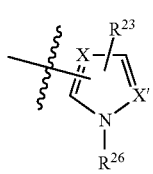  H3

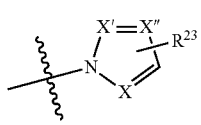  H4

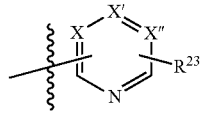  H5

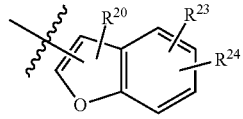  H6

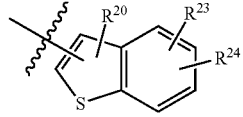  H7

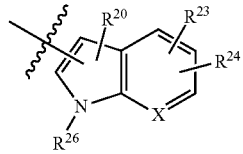  H8

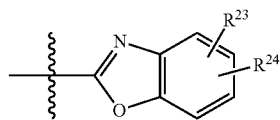  H9

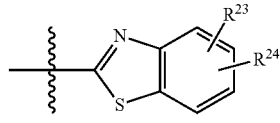  H10

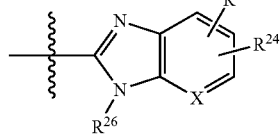  H11

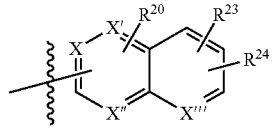  H12

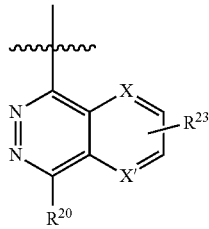  H13

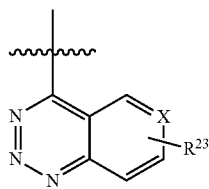  H14

X, X', X" and X'" are independently
—CR$^{20}$; or N;

R$^{20}$ and R$^{21}$ are independently
H; F; Cl; Br; I; OH; NH$_2$; NO$_2$; CN; CF$_3$; OCHF$_2$; OCF$_3$;
C$_{1-8}$-alkyl; C$_{2-8}$-alkenyl; aryl;
heteroaryl; aryl-C$_{1-6}$-alkyl; heteroaryl-C$_{1-6}$-alkyl;
—(CH$_2$)$_o$R$^{22}$; —(CH$_2$)$_o$OR$^{15}$; —O(CO)R$^{15}$;
—O(CH$_2$)$_o$R$^{22}$; —(CH$_2$)$_o$SR$^{15}$; —(CH$_2$)$_o$NR$^{15}$R$^{16}$;
—(CH$_2$)$_o$CONR$^{15}$R$^{16}$;
—(CH$_2$)$_o$NR$^1$CONR$^{15}$R$^{16}$; —(CH$_2$)$_o$NR$^1$COR$^{15}$;
—(CH$_2$)$_o$COOR$^{15}$; —(CH$_2$)$_o$CONR$^{15}$R$^{16}$;
—(CH$_2$)$_o$PO(OR$^1$)$_2$; —(CH$_2$)$_o$SO$_2$R$^{15}$; or —(CH$_2$)$_o$COR$^{15}$;

R$^{22}$ is an aryl group of the formula

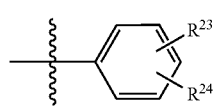

AR3

R$^{23}$, R$^{24}$ and R$^{25}$ are independently
H; F; Cl; Br; I; OH; NH$_2$; NO$_2$; CN; CF$_3$; OCHF$_2$; OCF$_3$;
C$_{1-8}$-alkyl; C$_{2-8}$-alkenyl;
—(CH$_2$)$_o$OR$^{15}$; —O(CO)R$^{15}$; —(CH$_2$)$_o$NR$^1$R$^{15}$;
—(CH$_2$)$_o$COOR$^{15}$; —(CH$_2$)$_o$CONR$^1$R$^{15}$;

R$^{26}$ is H; Ac; C$_{1-8}$-alkyl; or aryl-C$_{1-6}$-alkyl;
R$^{27}$ is —CO(CR$^1$R$^{13}$)$_q$R$^{15}$;
R$^{28}$ and R$^{29}$ are independently
H; CF$_3$; C$_{1-8}$-alkyl; C$_{2-8}$-alkenyl; or aryl-C$_{1-6}$-alkyl;
cycloalkyl-C$_{1-6}$-alkyl; or heterocycloalkyl-C$_{1-6}$-alkyl;
R$^{30}$ is —OR$^{14}$; —SR$^{14}$; or —NR$^{15}$R$^{16}$;
R$^{31}$ is H; C$_{1-8}$-alkyl; C$_{2-8}$-alkenyl; C$_{1-6}$-alkoxy; cycloalkyl;
heterocycloalkyl;
cycloalkyl-C$_{1-6}$-alkyl; heterocycloalkyl-C$_{1-6}$-alkyl; aryl;
heteroaryl;
aryl-C$_{1-6}$-alkyl; heteroaryl-C$_{1-6}$-alkyl; cycloalkyl-aryl;
heterocycloalkyl-aryl;
cycloalkyl-heteroaryl; heterocycloalkyl-heteroaryl; aryl-cycloalkyl;
aryl-heterocycloalkyl; heteroaryl-cycloalkyl; heteroaryl-heterocycloalkyl;
—COR$^{15}$; —CONR$^{15}$R$^{16}$; or the structural element
—NR$^1$R$^{31}$ can form:
heterocycloalkyl; aryl-heterocycloalkyl; or heteroaryl-heterocycloalkyl;

n and m are independently an integer of 0-5 with the proviso that n+m 6;
o is 0-4; p is 2-6; q is 1-6; and r is 1-3;
or a tautomer or rotamer thereof; or a salt; or a pharmaceutically acceptable salt; or a hydrate; or a solvate thereof.

Each single group "Fix" with the same index-number x for x=1-31 is independently selected on each occurrence in a specific formula and, therefore, they can be the same or different.

As used in this description, the term "alkyl", taken alone or in combinations (i.e. as part of another group, such as "aryl-C$_{1-6}$-alkyl") designates saturated, straight-chain or branched hydrocarbon radicals and may be optionally substituted. The term "C$_{x-y}$-alkyl" (x and y each being an integer) refers to an alkyl group as defined before containing x to y carbon atoms. For example a C$_{1-6}$-alkyl group contains one to six carbon atoms. Representative examples of alkyl groups include methyl, ethyl, n-propyl, iso-propyl, n-butyl, iso-butyl, sec-butyl, tert-butyl, n-pentyl, n-hexyl and the like.

The term "alkenyl", taken alone or in combinations, designates straight chain or branched hydrocarbon radicals containing at least one or, depending on the chain length, up to four olefinic double bonds. Such alkenyl moieties are optionally substituted and can independently exist as E or Z configurations per double bond, which are all part of the invention. The term "C$_{x-y}$-alkenyl" (x and y each being an integer) refers to an alkenyl group as defined before containing x to y carbon atoms.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbornyl, decalinyl and the like.

The term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4]nonyl and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, CF$_3$, OH, OCF$_3$, OCHF$_2$, NH$_2$, N(CH$_3$)$_2$, NO$_2$, CN, C$_{1-6}$-alkyl, C$_{2-6}$-alkenyl, phenyl or phenoxy.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "aryl-C$_{x-y}$-alkyl", as used herein, refers to an C$_{x-y}$-alkyl group as defined above, substituted by an aryl group, as defined above. Representative examples of aryl-C$_{x-y}$-alkyl moieties include, but are not limited to, benzyl, 1-phenylethyl, 2-phenylethyl, 3-phenylpropyl, 2-phenylpropyl and the like.

The term "heteroaryl-C$_{x-y}$-alkyl", as used herein, refers to an C$_{x-y}$-alkyl group as defined above, substituted by a heteroaryl group, as defined above. Examples of heteroaryl-C$_{x-y}$-alkyl groups include pyridin-3-ylmethyl, (1H-pyrrol-2-yl)ethyl and the like.

The term "aryl-cycloalkyl", as used herein, refers to a cycloalkyl group as defined above, substituted or annelated by an aryl group, as defined above. Examples of aryl-cycloalkyl moieties include, but are not limited to, phenyl-cyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydroquinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analogously to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "hydroxy", "alkoxy" and "aryloxy", taken alone or in combinations, refer to the groups of —OH, —O-alkyl and —O-aryl respectively, wherein an alkyl group or an aryl group is as defined above. The term "$C_{x-y}$-alkoxy" (x and y each being an integer) refers to an —O-alkyl group as defined before containing x to y carbon atoms attached to an oxygen atom. Representative examples of alkoxy groups include methoxy, ethoxy, n-propoxy, iso-propoxy, n-butoxy, tert-butoxy and the like. Examples of aryloxy include e.g. phenoxy. For avoidance of doubt e.g. the term "hydroxy-$C_{1-8}$-alkyl" represents, among others, groups like e.g. hydroxymethyl, 1-hydroxypropyl, 2-hydroxypropyl or 3-hydroxy-2,3-dimethylbutyl.

The term "optionally substituted" is in general intended to mean that a group, such as, but not limited to $C_{x-y}$-alkyl, $C_{x-y}$-alkenyl, cycloalkyl, aryl, heteroaryl, heterocycloalkyl, $C_{x-y}$-alkoxy and aryloxy may be substituted with one or more substituents independently selected from amino (—NH$_2$), dimethylamino, nitro (—NO$_2$), halogen (F, Cl, Br, I), CF$_3$, cyano (—CN), hydroxy, methoxy, ethoxy, phenyloxy, benzyloxy, acetoxy, oxo (=O), carboxy, carboxamido, methyl, ethyl, phenyl, benzyl, sulfonic acid, sulfate, phosphonic acid, phosphate, or phosphonate.

In the context of this invention the term "naturally or non-naturally occurring α-amino acid" typically comprises any natural α-amino acid, such as the proteogenic amino acids (examples listed below), their natural or semi-synthetic derivatives as well as α-amino acids of purely synthetic origin. This term includes as well α-amino acids which are optionally substituted at the α-nitrogen of the amino acid such as, but not limited to, acetylation or alkylation, e.g. methylation, or benzylation.

The term "aliphatic α-amino acid" refers to α-amino acids with an aliphatic side-chain, such as, but not limited to, alanine, valine, leucine, isoleucine, n-octylglycine etc.

The term "aromatic α-amino acid" refer to α-amino acids with a side-chain comprising an aromatic or heteroaromatic group, such as, but not limited to, phenylalanine, tryptophan, histidine, O-methyl-tyrosine, 4-trifluormethyl-phenylalanine, 3,4-dichloro-homophenylalanine etc.

The term "basic α-amino acid" refers to α-amino acids with a side-chain comprising at least one amino group, such as, but not limited to, lysine, ornithine etc. and further substituted derivatives thereof. The aforesaid amino group can be substituted by amidino groups to form α-amino acids, such as, but not limited to, arginine, homoarginine etc. and further substituted derivatives thereof, or by diamino methylidine groups.

The term "alcoholic α-amino acid" refers to α-amino acids with a side-chain comprising an alcoholic or thioalcoholic group, i.e. a hydroxy or sulfhydryl function, such as, but not limited to, serine, threonine etc.

The term "α-amino acids with a side-chain comprising at least one urea function, carboxylic acid function, amide function, ester function, sulfone function or ether function" encompasses, but is not limited to, citrulline, aspartic acid, glutamic acid, asparagine, glutamine etc.

The term "α-amino acids with a side-chain comprising at least one amide function" encompasses, but is not limited to, asparagine, glutamine etc.

The term "cross-linking α-amino acid" refers to α-amino acids with a side-chain comprising a function able to cross-link to a second α-amino acid by a covalent bond, such as, but not limited to, cysteine, homocysteine etc.

For the avoidance of doubt the term "single side-chain" in the context of an α-amino acid refers to a structure where the α-carbon of the amino acid is covalently connected to the (in-chain) groups of the carbonyl (C=O) and nitrogen (N) as well as to one hydrogen (H) and one variable side-chain, e.g. as defined above. A "single side-chain" may include as well a heterocyclic structure comprising the α-amino atom, such as but not limited to, proline, pipecolic acid etc.

For the avoidance of doubt the term "heteroatom" refers to any atom that is not carbon or hydrogen.

The descriptors L respectively D refer to the stereochemistry at the α-position of an α-amino acid and are used according the Fischer-Rosanoff convention of the IUPAC. The peptidomimetics of the present invention can also be diastereomers (e.g. epimers) of compounds of formula (I) if no specific stereochemistry of the chiral center is determined in the description. These stereoisomers can be prepared by a modification of the process described below in which the appropriate isomers (e.g. epimers/enantiomers) of chiral starting materials are used. In case of ambiguous stereochemistry in the above description each single epimer is part of the present invention as well as a mixture of both.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in $^2$H (D), $^3$H, $^{11}$C, $^{14}$C, $^{127}$I etc. These isotopic analogs and their pharmaceutical salts and formulations are considered useful agents in the therapy and/or diagnostic, for example, but not limited to, where a fine-tuning of in vivo half-life time could lead to an optimized dosage regimen.

A further particular embodiment (7) of the invention relates to derivatives of general formula (I), wherein specifically
for module A,
T$^6$ is an D α-amino acid residue or one of the formulae AA1$^D$; AA12$^D$; AA7$^D$; or AA10$^D$;
T$^7$ is an L α-amino acid residue of one of the formulae AA1; or AA2;
or a pharmaceutically acceptable salt thereof.

Another alternative particular embodiment (8) of the invention relates to derivatives of general formula (I), wherein specifically
for module A,
if i=1, and P$^{13}$ and P$^{14}$, and P$^{14}$ and P$^1$ are connected as aforementioned, and
P$^2$ and P$^{11}$ taken together and/or P$^4$ and P$^9$ taken together may form an interstrand linking bis(amino acid) structure of one of the formulae AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;

P¹ is an L α-amino acid of one of the formulae
  AA8; or AA7;
P² is an L α-amino acid of one of the formulae
  AA10; AA16; AA11; or AA7;
P³ is an L α-amino acid of one of the formulae
  AA7; or AA8;
P⁴ is Gly; Sar; or an α-amino acid of one of the formulae
  AA7; AA10; AA11; AA16; AA7$^D$; or AA8;
P⁵ is an L α-amino acid of one of the formulae
  AA7; AA10; AA11; or AA8;
T⁶ is an D α-amino acid of one of the formulae
  AA1$^D$; AA2$^D$; AA3$^D$; AA7$^D$; AA10$^D$; AA12$^D$; AA4$^D$; AA5$^D$; AA6$^D$; AA8$^D$; or AA11$^D$;
T⁷ is an L α-amino acid of one of the formulae
  AA1; AA2; AA3; AA4; AA5; AA6; AA7; AA8; AA10; or AA11;
P⁸ is an L α-amino acid of one of the formulae
  AA7; AA8; or AA11;
P⁹ is Gly; Sar; or an L α-amino acid of one of the formulae
  AA7; AA10; AA11; AA16; AA8; or AA9;
P¹⁰ is an L α-amino acid of one of the formulae
  AA7; or AA8;
P¹¹ is Gly; Sar; or an L α-amino acid of one of the formulae
  AA10; AA16; AA7; or AA11;
P¹² is Gly; Sar; or an L α-amino acid of one of the formulae
  AA7; AA10; AA11; AA8; or AA9;
P¹³ is Gly; Sar; or an α-amino acid of one of the formulae
  AA10; AA10$^D$; AA7; AA7$^D$; AA11; or AA11$^D$;
P¹⁴ is Gly; Sar; or an L α-amino acid of formula
  AA10; AA11; AA7; or AA9;
with the proviso that,
  if linker L is connected with module A by a carbonyl
    (C=O) point of attachment of P²; P⁵; P¹²; P¹³; or P¹⁴;
    then
  P²; P⁵; P¹²; P¹³; or P¹⁴; is an α-amino acid residue of one of the formulae
    AA14; or AA14$^D$;
or a pharmaceutically acceptable salt thereof.

Another alternative particular embodiment (9) of the invention relates to derivatives of general formula (I) according to alternative particular embodiment (8) with the proviso that
P⁴ and P⁹ taken together form an interstrand linking bis(amino acid)-structure of one of the formulae AA13; or AA13$^D$; based on the linkage of two α-amino acid residues; and/or
P¹ is AA7; and/or
P² is AA11; or AA7; and/or
P⁴ is Gly; Sar; AA7$^D$; or AA8; and/or
P⁵ is AA8; and/or
T⁶ is AA4$^D$; AA5$^D$; AA6$^D$; AA8$^D$; or AA11$^D$; and/or T⁷ is AA7; AA8; AA10; or AA11; and/or
P⁸ is AA11; and/or
P⁹ is AA8; or AA9; and/or
P¹¹ is Gly; Sar; AA7; or AA11; and/or
P¹² is AA8; or AA9;
or a pharmaceutically acceptable salt thereof.

Another alternative particular embodiment (10) of the invention relates to derivatives of general formula (I), wherein specifically
for module A,
if i=1, and P¹³ and P¹⁴, and P¹⁴ and P¹ are connected as aforementioned, and
P² and P¹¹ taken together may form an interstrand linking bis(amino acid) structure of one of the formulae AA13; or AA13$^D$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of formula
  AA8;
P² is an L α-amino acid of one of the formulae
  AA10; or AA16;
P³ is an L α-amino acid of one of the formulae
  AA7; or AA8;
P⁴ is an L α-amino acid of one of the formulae
  AA7; AA10 AA11; or AA16;
P⁵ is an L α-amino acid of one of the formulae
  AA7; AA10; or AA11;
T⁶ is an D α-amino acid of one of the formulae
  AA1$^D$; AA2$^D$; AA3$^D$; AA7$^D$; AA10$^D$; or AA12$^D$;
T⁷ is an L α-amino acid of one of the formulae
  AA1; AA2; AA3; AA4; AA5; or AA6;
P⁸ is an L α-amino acid of one of the formulae
  AA7; or AA8;
P⁹ is Gly; Sar; or an L α-amino acid of one of the formulae
  AA7; AA10; AA11; or AA16;
P¹⁰ is an L α-amino acid of one of the formulae
  AA7; or AA8;
is an L α-amino acid of formula
  AA10;
P¹² is Gly; Sar; or an L α-amino acid of one of the formulae
  AA7; AA10; or AA11;
P¹³ is Gly; Sar; or an α-amino acid of one of the formulae
  AA10; or AA10$^D$;
P¹⁴ is Gly; Sar; or an L α-amino acid of formula
  AA10;
with the proviso that,
  if linker L is connected with module A by a carbonyl
    (C=O) point of attachment of P²; P⁵; P¹²; P¹³; or P¹⁴;
    then
  P²; P⁵; P¹²; P¹³; or P¹⁴; is an α-amino acid residue of one of the formulae
    AA14; or AA14$^D$;
or a pharmaceutically acceptable salt thereof.

Another alternative particular embodiment (11) of the invention relates to derivatives of general formula (I), wherein specifically
for module A,
if i=1, and P¹⁴ and P¹, are not connected as aforementioned, and
P² and P¹¹ taken together and/or P⁴ and P⁹ taken together form an interstrand linking bis(amino acid) structure of one of the formulae AA13; or AA13$^D$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of one of the formulae
  AA8; or AA7;
P² is an L α-amino acid of one of the formulae
  AA10; AA16; AA11; or AA7;
P³ is an L α-amino acid of one of the formulae
  AA7; or AA8;
P⁴ is Gly; Sar; or an α-amino acid of one of the formulae
  AA7; AA10; AA11; AA16; AA7$^D$; or AA8;
P⁵ is an L α-amino acid of one of the formulae
  AA7; AA10; AA11; or AA8;

T⁶ is an D α-amino acid of one of the formulae
  AA1$^D$; AA2$^D$; AA3$^D$; AA4$^D$; AA5$^D$; AA6$^D$; AA7$^D$; AA10$^D$; AA12$^D$; AA8$^D$; or AA11$^D$;
T⁷ is an L α-amino acid of one of the formulae
  AA1; AA2; AA3; AA4; AA5; AA6; AA7; AA8; AA10; or AA11;
P⁸ is an L α-amino acid of one of the formulae
  AA7; AA8; or AA11;
P⁹ is Gly; Sar; or an L α-amino acid of one of the formulae
  AA7; AA10; AA11; AA16; AA8; or AA9;
P¹⁰ is an L α-amino acid of one of the formulae
  AA7; or AA8;
P¹¹ is Gly; Sar; or an L α-amino acid of one of the formulae
  AA10; AA16; AA7; or AA11;
P¹² is Gly; Sar; Aib; or an α-amino acid residue of one of the formulae
  AA7; AA7$^D$; AA10; AA10$^D$; AA11; AA11$^D$; AA8; AA8$^D$; AA9; or AA9$^D$;
P¹³ is Gly; Sar; Aib; or an α-amino acid residue of one of the formulae
  AA7; AA7$^D$; AA10; AA10$^D$; AA11; AA11$^D$; AA8; AA8$^D$; AA16; or AA16$^D$;
P¹⁴ is Gly; Sar; Aib; or an α-amino acid residue of one of the formulae
  AA7; AA7$^D$; AA9; AA9$^D$; AA10; AA10$^D$; AA11; or AA11$^D$;
with the proviso that,
  if linker L is connected with module A by a carbonyl (C=O) point of attachment of P⁵; P¹²; or P¹³; then P⁵; P¹²; or P¹³; is an α-amino acid residue of one of the formulae
    AA14; or AA14$^D$;
or a pharmaceutically acceptable salt thereof.

Another alternative particular embodiment (12) of the invention relates to derivatives of general formula (I) according to alternative particular embodiment (11) with the proviso that
P⁴ and P⁹ taken together form an interstrand linking bis (amino acid)-structure of one of the formulae AA13; or AA13$^D$; based on the linkage of two α-amino acid residues; and/or
P¹ is AA7; and/or
P² is AA11; or AA7; and/or
P⁴ is Gly; Sar; AA7$^D$; or AA8; and/or
P⁵ is AA8; and/or
T⁶ is AA4$^D$; AA5$^D$; AA6$^D$; AA8$^D$; or AA11$^D$; and/or
T⁷ is AA7; AA8; AA10; or AA11; and/or
P⁸ is AA11; and/or
P⁹ is AA8; or AA9; and/or
P¹¹ is Gly; Sar; AA7; or AA11; and/or
P¹² is AA8; AA8$^D$; AA9; or AA9$^D$; and/or
P¹³ is AA8; AA8$^D$; AA16; or AA16$^D$;
or a pharmaceutically acceptable salt thereof.

Another alternative particular embodiment (13) of the invention relates to derivatives of general formula (I), wherein specifically
for module A,
if i=1, and P¹⁴ and P¹, are not connected as aforementioned, and
P² and P¹¹ taken together form an interstrand linking bis (amino acid) structure of one of the formulae AA13; or AA13$^D$; with Z being, with the proviso of containing less than carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of formula
  AA8;
P³ is an L α-amino acid of one of the formulae
  AA7; or AA8;
P⁴ is an L α-amino acid of one of the formulae
  AA7; AA10; AA11; or AA16;
P⁵ is an L α-amino acid of one of the formulae
  AA7; AA10; or AA11;
T⁶ is an D α-amino acid of one of the formulae
  AA1$^D$; AA2$^D$; AA3$^D$; AA7$^D$; AA10$^D$; or AA12$^D$;
T⁷ is an L α-amino acid of one of the formulae
  AA1; AA2; AA3; AA4; AA5; or AA6;
P⁸ is an L α-amino acid of one of the formulae
  AA7; or AA8;
P⁹ is Gly; Sar; or an L α-amino acid of one of the formulae
  AA7; AA10; AA11; or AA16;
P¹⁰ is an L α-amino acid of one of the formulae
  AA7; or AA8;
P¹² is Gly; Sar; Aib; or an α-amino acid residue of one of the formulae
  AA7; AA7$^D$; AA10; AA10$^D$; AA11; or AA11$^D$;
P¹³ is Gly; Sar; Aib; or an α-amino acid residue of one of the formulae
  AA7; AA7$^D$; AA10; AA10$^D$; AA11; or AA11$^D$;
P¹⁴ is Gly; Sar; Aib; or an α-amino acid residue of one of the formulae
  AA7; AA7$^D$; AA9; AA9$^D$; AA10; AA10$^D$; AA11; or AA11$^D$;
with the proviso that,
  if linker L is connected with module A by a carbonyl (C=O) point of attachment of P⁵; P¹²; or P¹³; then P⁵; P¹²; or P¹³; is an α-amino acid residue of one of the formulae
    AA14; or AA14$^D$;
or a pharmaceutically acceptable salt thereof.

Another alternative particular embodiment (14) of the invention relates to derivatives of general formula (I), wherein specifically
for module A,
if i=1, and P¹³ and P¹⁴ are not connected as aforementioned, and
P² and P¹¹ taken together and/or P⁴ and P⁹ taken together form an interstrand linking bis(amino acid) structure of one of the formulae AA13; or AA13$^D$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of one of the formulae
  AA8; or AA7;
P² is an L α-amino acid of one of the formulae
  AA10; AA16; AA11; or AA7;
P³ is an L α-amino acid of one of the formulae
  AA7; or AA8;
P⁴ is Gly; Sar; or an α-amino acid of one of the formulae
  AA7; AA10; AA11; AA16; AA7$^D$; or AA8;
P⁵ is an L α-amino acid of one of the formulae
  AA7; AA10; AA11; or AA8;
T⁶ is an D α-amino acid of one of the formulae
  AA1$^D$; AA2$^D$; AA3$^D$; AA4$^D$; AA5$^D$; AA6$^D$; AA7$^D$; AA10$^D$; AA12$^D$; AA8$^D$; or AA11$^D$;

T⁷ is an L α-amino acid of one of the formulae
  AA1; AA2; AA3; AA4; AA5; AA6; AA7; AA8; AA10; or AA11;
P⁸ is an L α-amino acid of one of the formulae
  AA7; AA8; or AA11;
P⁹ is Gly; Sar; or an L α-amino acid of one of the formulae
  AA7; AA10; AA11; AA16; AA8 or AA9;
P¹⁰ is an L α-amino acid of one of the formulae
  AA7; or AA8;
P¹¹ is Gly; Sar; or an L α-amino acid of one of the formulae
  AA10; AA16; AA7; or AA11;
P¹² is Gly; Sar; Aib; or an α-amino acid residue of one of the formulae
  AA7; AA7$^D$; AA10; AA10$^D$; AA11; AA11$^D$; AA8; AA8$^D$; AA9; or AA9$^D$;
P¹³ is Gly; Sar; Aib; or an α-amino acid residue of one of the formulae
  AA7; AA7$^D$; AA10; AA10$^D$; AA11; AA11$^D$; AA8; AA8$^D$; AA16; or AA16$^D$;
P¹⁴ is Gly; Sar; Aib; or an α-amino acid residue of one of the formulae
  AA7; AA7$^D$; AA9; AA9$^D$; AA10; AA10$^D$; AA11; or AA11$^D$;
with the proviso that,
  if linker L is connected with module A by a carbonyl (C=O) point of attachment of P⁵; P¹²; or P¹⁴; then P⁵; P¹²; or P¹⁴; is an α-amino acid residue of one of the formulae
  AA14; or AA14$^D$;
or a pharmaceutically acceptable salt thereof.

Another alternative particular embodiment (15) of the invention relates to derivatives of general formula (I) according to alternative particular embodiment (14) with the proviso that
P⁴ and P⁹ taken together form an interstrand linking bis(amino acid)-structure of one of the formulae AA13; or AA13$^D$; based on the linkage of two α-amino acid residues; and/or
P¹ is AA7; and/or
P² is AA11; or AA7; and/or
P⁴ is Gly; Sar; AA7$^D$; or AA8; and/or
P⁵ is AA8; and/or
T⁶ is AA4$^D$; AA5$^D$; AA6$^D$; AA8$^D$; or AA11$^D$; and/or
T⁷ is AA7; AA8; AA10; or AA11; and/or
P⁸ is AA11; and/or
P⁹ is AA8; or AA9; and/or
P¹¹ is Gly; Sar; AA7; or AA11; and/or
P¹² is AA8; AA8$^D$; AA9; or AA9$^D$; and/or
P¹³ is AA8; AA8$^D$; AA16; or AA16$^D$;
or a pharmaceutically acceptable salt thereof.

Another alternative particular embodiment (16) of the invention relates to derivatives of general formula (I), wherein specifically
for module A,
if i=1, and P¹³ and P¹⁴ are not connected as aforementioned, and
P² and P¹¹ taken together form an interstrand linking bis(amino acid) structure of one of the formulae AA13; or AA13$^D$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of formula
  AA8;
P³ is an L α-amino acid of one of the formulae
  AA7; or AA8;
P⁴ is an L α-amino acid of one of the formulae
  AA7; AA10; AA11; or AA16;
P⁵ is an L α-amino acid of one of the formulae
  AA7; AA10; or AA11;
T⁶ is an D α-amino acid of one of the formulae
  AA1$^D$; AA2$^D$; AA3$^D$; AA7$^D$; AA10$^D$; or AA12$^D$;
T⁷ is an L α-amino acid of one of the formulae
  AA1; AA2; AA3; AA4; AA5; or AA6;
P⁸ is an L α-amino acid of one of the formulae
  AA7; or AA8;
P⁹ is Gly; Sar; or an L α-amino acid of one of the formulae
  AA7; AA10; AA11; or AA16;
P¹⁰ is an L α-amino acid of one of the formulae
  AA7; or AA8;
P¹² is Gly; Sar; Aib; or an α-amino acid residue of one of the formulae
  AA7; AA7$^D$; AA10; AA10$^D$; AA11; or AA11$^D$;
P¹³ is Gly; Sar; Aib; or an α-amino acid residue of one of the formulae
  AA7; AA7$^D$; AA10; AA10$^D$; AA11; or AA11$^D$;
P¹⁴ is Gly; Sar; Aib; or an α-amino acid residue of one of the formulae
  AA7; AA7$^D$; AA9; AA9$^D$; AA10; AA10$^D$; AA11; AA11$^D$; AA16; or AA16$^D$;
with the proviso that,
  if linker L is connected with module A by a carbonyl (C=O) point of attachment of P⁵; P¹²; or P¹⁴; then P⁵; P¹²; or P¹⁴; is an α-amino acid residue of one of the formulae
  AA14; or AA14$^D$;
or a pharmaceutically acceptable salt thereof.

Another alternative particular embodiment (17) of the invention relates to derivatives of general formula (I), wherein specifically
for module A,
if i=0, and
P² and P¹¹ taken together and/or P⁴ and P⁹ taken together form an interstrand linking bis(amino acid) structure of one of the formulae AA13; or AA13$^D$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of one of the formulae
  AA8; or AA7;
P² is an L α-amino acid of one of the formulae
  AA10; AA16; AA11; or AA7;
P³ is an L α-amino acid of one of the formulae
  AA7; or AA8;
P⁴ is Gly; Sar; or an α-amino acid of one of the formulae
  AA7; AA10; AA11 AA16; AA7$^D$; or AA8;
P⁵ is an L α-amino acid of one of the formulae
  AA7; AA10; AA11; or AA8;
T⁶ is an D α-amino acid of one of the formulae
  AA1$^D$; AA2$^D$; AA3$^D$; AA4$^D$; AA5$^D$; AA6$^D$; AA7$^D$; AA10$^D$; AA12$^D$; AA8$^D$; or AA11$^D$;
T⁷ is an L α-amino acid of one of the formulae
  AA1; AA2; AA3; AA4; AA5; AA6; AA7; AA8; AA10; or AA11;
P⁸ is an L α-amino acid of one of the formulae
  AA7; AA8; or AA11;

P$^9$ is Gly; Sar; or an L α-amino acid of one of the formulae
  AA7; AA10; AA11; AA16; AA8; or AA9;
P$^{10}$ is an L α-amino acid of one of the formulae
  AA7; or AA8;
P$^{11}$ is Gly; Sar; or an L α-amino acid of one of the formulae
  AA10; AA16; AA7; or AA11;
P$^{12}$ is Gly; Sar; Aib; or an α-amino acid residue of one of the
  formulae
  AA7; AA7$^D$; AA10; AA10$^D$; AA11; AA11$^D$; AA8; AA8$^D$;
  AA9; or AA9$^D$;
P$^{13}$ is Gly; Sar; Aib; or an α-amino acid residue of one of the
  formulae
  AA7; AA7$^D$; AA10; AA10$^D$; AA11; AA11$^D$; AA8; AA8$^D$;
  AA16; or AA16$^D$;
with the proviso that,
  if linker L is connected with module A by a carbonyl
    (C=O) point of attachment of P$^5$; or P$^{12}$; then
  P$^5$; or P$^{12}$; is an α-amino acid residue of one of the
    formulae
    AA14; or AA14$^D$;
or a pharmaceutically acceptable salt thereof.

Another alternative particular embodiment (18) of the invention relates to derivatives of general formula (I) according to alternative particular embodiment (17) with the proviso that
P$^4$ and P$^9$ taken together form an interstrand linking bis(amino acid)-structure of one of the formulae AA13; or AA13$^D$; based on the linkage of two α-amino acid residues; and/or
P$^1$ is AA7; and/or
P$^2$ is AA11; or AA7; and/or
P$^4$ is Gly; Sar; AA7$^D$; or AA8; and/or
P$^5$ is AA8; and/or
T$^6$ is AA4$^D$; AA5$^D$; AA6$^D$; AA8$^D$; or AA11$^D$; and/or
T$^7$ is AA7; AA8; AA10; or AA11; and/or
P$^8$ is AA11; and/or
P$^9$ is AA8; or AA9 and/or
P$^{11}$ is Gly; Sar; AA7; or AA11; and/or
P$^{12}$ is AA8; AA8$^D$; AA9; or AA9$^D$; and/or
P$^{13}$ is AA8; AA8$^D$; AA16; or AA16$^D$;
or a pharmaceutically acceptable salt thereof.

Another alternative particular embodiment (19) of the invention relates to derivatives of general formula (I), wherein specifically
for module A,
if i=0, and
P$^2$ and P$^{11}$ taken together form an interstrand linking bis(amino acid) structure of one of the formulae AA13; or AA13$^D$; with Z being, with the proviso of containing less than carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
P$^1$ is an L α-amino acid of formula
  AA8;
P$^3$ is an L α-amino acid of one of the formulae
  AA7; or AA8;
P$^4$ is an L α-amino acid of one of the formulae
  AA7; AA10; AA11; or AA16;
P$^5$ is an L α-amino acid of one of the formulae
  AA7; AA10; or AA11;
T$^6$ is an D α-amino acid of one of the formulae
  AA1$^D$; AA2$^D$; AA3$^D$; AA7$^D$; AA10$^D$; or AA12$^D$;
T$^7$ is an L α-amino acid of one of the formulae
  AA1; AA2; AA3; AA4; AA5; or AA6;
P$^8$ is an L α-amino acid of one of the formulae
  AA7; or AA8;
P$^9$ is Gly; Sar; or an L α-amino acid of one of the formulae
  AA7; AA10; AA11; or AA16;
P$^{10}$ is an L α-amino acid of one of the formulae
  AA7; or AA8;
P$^{12}$ is Gly; Sar; Aib; or an α-amino acid residue of one of the
  formulae
  AA7; AA7$^D$; AA10; AA10$^D$; AA11; or AA11$^D$;
P$^{13}$ is Gly; Sar; Aib; or an α-amino acid residue of one of the
  formulae
  AA7; AA7$^D$; AA10; AA10$^D$; AA11; or AA11$^D$;
with the proviso that,
  if linker L is connected with module A by a carbonyl
    (C=O) point of attachment of P$^5$; or P$^{12}$; then
  P$^5$; or P$^{12}$; is an α-amino acid residue of one of the
    formulae
    AA14; or AA14$^D$;
or a pharmaceutically acceptable salt thereof.

Another alternative particular embodiment (20) of the invention relates to derivatives of general formula (I), wherein specifically
for module A,
if i=1, and P$^{13}$ and P$^{14}$ are not connected as aforementioned,
and
P$^{13}$ and P$^{14}$ taken together form an interstrand linking bis(amino acid) structure of one of the formulae AA13; AA13$^D$; AA13$^{LD}$; or AA13$^{D\ L}$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—; and
P$^2$ and P$^{11}$ taken together and/or P$^4$ and P$^9$ taken together may form an interstrand linking bis(amino acid) structure of one of the formulae AA13; or AA13$^D$; with Z being,
with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
P$^1$ is an L α-amino acid of one of the formulae
  AA8; or AA7;
P$^2$ is an L α-amino acid of one of the formulae
  AA10; AA16; AA11; or AA7;
P$^3$ is an L α-amino acid of one of the formulae
  AA7; or AA8;
P$^4$ is Gly; Sar; or an α-amino acid of one of the formulae
  AA7; AA10; AA11; AA16; AA7$^D$; or AA8;
P$^5$ is an L α-amino acid of one of the formulae
  AA7; AA10; AA11; or AA8;
T$^6$ is an D α-amino acid of one of the formulae
  AA1$^D$AA2$^D$AA3$^D$AA4$^D$AA5$^D$AA6$^D$AA7$^D$AA10$^D$AA12$^D$AA8$^D$ or AA11$^D$;
T$^7$ is an L α-amino acid of one of the formulae
  AA1; AA2; AA3; AA4; AA5; AA6; AA7; AA8; AA10; or AA11;
P$^8$ is an L α-amino acid of one of the formulae
  AA7; AA8; or AA11;
P$^9$ is Gly; Sar; or an L α-amino acid of one of the formulae
  AA7; AA10; AA11; AA16; AA8; or AA9;
P$^{10}$ is an L α-amino acid of one of the formulae
  AA7; or AA8;

$P^{11}$ is Gly; Sar; or an L α-amino acid of one of the formulae
  AA10; AA16; AA7; or AA11;
$P^{12}$ is Gly; Sar; or an α-amino acid residue of one of the formulae
  AA7; AA7$^D$; AA10; AA10$^D$; AA11; AA11$^D$; AA8; AA8$^D$; AA9; or AA9$^D$;
with the proviso that,
  if linker L is connected with module A by a carbonyl (C=O) point of attachment of $P^2$; $P^5$; or $P^{12}$; then
  $P^2$; $P^5$; or $P^{12}$; is an α-amino acid residue of one of the formulae
    AA14; or AA14$^D$;
or a pharmaceutically acceptable salt thereof.

Another alternative particular embodiment (21) of the invention relates to derivatives of general formula (I) according to alternative particular embodiment (20)
  with the proviso that
  $P^4$ and $P^9$ taken together form an interstrand linking bis(amino acid)-structure of one of the formulae AA13; or AA13$^D$; based on the linkage of two α-amino acid residues; and/or
  $P^1$ is AA7; and/or
  $P^2$ is AA11; or AA7; and/or
  $P^4$ is Gly; Sar; AA7$^D$; or AA8; and/or
  $P^5$ is AA8; and/or
  $T^6$ is AA4$^D$; AA5$^D$; AA6$^D$; AA8$^D$; or AA11$^D$; and/or
  $T^2$ is AA7; AA8; AA10; or AA11; and/or
  $P^8$ is AA11; and/or
  $P^9$ is AA8; or AA9; and/or
  $P^{11}$ is Gly; Sar; AA7; or AA11; and/or
  $P^{12}$ is AA8; AA8$^D$; AA9; or AA9$^D$;
or a pharmaceutically acceptable salt thereof.

Another alternative particular embodiment (22) of the invention relates to derivatives of general formula (I), wherein specifically
for module A,
if i=1, and $P^{13}$ and $P^{14}$ are not connected as aforementioned, and
$P^{13}$ and $P^{14}$ taken together form an interstrand linking bis(amino acid) structure of one of the formulae AA13; AA13$^D$; AA13$^{LD}$; or AA13$^{D\ L}$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—; and
$P^2$ and $P^{11}$ taken together may form an interstrand linking bis(amino acid) structure of one of the formulae AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
$P^1$ is an L α-amino acid of formula
  AA8;
$P^2$ is an L α-amino acid of one of the formulae
  AA10; or AA16;
$P^3$ is an L α-amino acid of one of the formulae
  AA7; or AA8;
$P^4$ is an L α-amino acid of one of the formulae
  AA7; AA10; AA11; or AA16;
$P^5$ is an L α-amino acid of one of the formulae
  AA7; AA10; or AA11;
$T^6$ is an D α-amino acid of one of the formulae
  AA1$^D$AA2$^D$AA3$^D$AA7$^D$AA10$^D$ or AA12$^D$;
$T^7$ is an L α-amino acid of one of the formulae
  AA1; AA2; AA3; AA4; AA5; or AA6;
$P^8$ is an L α-amino acid of one of the formulae
  AA7; or AA8;
$P^9$ is Gly; Sar; or an L α-amino acid of one of the formulae
  AA7; AA10; AA11; or AA16;
$P^{10}$ is an L α-amino acid of one of the formulae
  AA7; or AA8;
$P^{11}$ is an L α-amino acid of one of the formulae
  AA10; or AA16;
$P^{12}$ is Gly; Sar; or an α-amino acid residue of one of the formulae
  AA7; AA7$^D$; AA10; AA10$^D$; AA11; or AA11$^D$;
with the proviso that,
  if linker L is connected with module A by a carbonyl (C=O) point of attachment of $P^2$; $P^5$; or $P^{12}$; then
  $P^2$; $P^5$; or $P^{12}$; is an α-amino acid residue of one of the formulae
    AA14; or AA14$^D$;
or a pharmaceutically acceptable salt thereof.

An alternative particular embodiment (23) of the invention relates to derivatives of general formula (I), wherein specifically
for module A,
if i=1, and
$P^2$ and $P^{11}$ taken together and/or $P^4$ and $P^9$ taken together may form an interstrand linking bis(amino acid)-structure of one of the formulae
  AA13; or AA13$^D$; with Z being, with the proviso of containing less than 25 carbon- and/or heteroatoms,
  —(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
  —(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
  or —(CR$^{28}$R$^{29}$)$_n$NR$^1$CONR$^2$(CR$^{28}$R$^{29}$)$_m$—;
and/or
$P^{13}$ and $P^{14}$ taken together may form an interstrand linking bis(amino acid)-structure of one of the formulae
  AA13; AA13$^D$; AA13$^{LD}$; or AA13$^{DL}$; with Z being, with the proviso of containing less than 25 carbon- and/or heteroatoms,
  —(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
  —(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
  or —(CR$^{28}$R$^{29}$)$_n$NR$^1$CONR$^2$(CR$^{28}$R$^{29}$)$_m$—;
$P^1$ is an L α-amino acid of one of the formulae
  AA8; or AA7;
$P^2$ is an L α-amino acid residue of formula
  AA10; AA11; or AA7;
$P^3$ is an L α-amino acid of one of the formulae
  AA7; or AA8;
$P^4$ is Gly; an α-amino acid residue of one of the formulae
  AA7; AA10; AA11; AA7$^D$; or AA8;
$P^5$ is an L α-amino acid residue of one of the formulae
  AA7; AA10; AA11; or AA8;
$T^6$ is an D α-amino acid of one of the formulae
  AA1$^D$; AA2$^D$; AA3$^D$; AA4$^D$; AA5$^D$; AA6$^D$; AA7$^D$; AA10$^D$; AA12$^D$; AA8$^D$; or AA11$^D$;
$T^7$ is an L α-amino acid of one of the formulae
  AA1; AA2; AA3; AA4; AA5; AA6; AA7; AA8; AA10; or AA11;
$P^8$ is an L α-amino acid residue of formula
  AA7; AA8; or AA11;

P$^9$ is Gly; or an L α-amino acid residue of one of the formulae
AA7; AA10; AA11; AA8 or AA9;
P$^{10}$ is an L α-amino acid residue of formula
AA7; or AA8;
P$^{11}$ is Gly; or an L α-amino acid residue of one of the formulae
AA10; AA16; AA11; or AA7;
P$^{12}$ is Gly; Sar; Aib; or an α-amino acid residue of one of the formulae
AA7; AA7$^D$; AA10; AA10$^D$; AA11; AA11$^D$; AA8; AA8$^D$; AA9; or AA9$^D$;
P$^{13}$ is Gly; Aib; or an α-amino acid residue of one of the formulae
AA7; AA7$^D$; AA10; AA10$^D$; AA11; AA11$^D$; AA8; AA8$^D$; AA16; or AA16$^D$;
P$^{14}$ is Gly; Sar; Aib; or an α-amino acid residue of one of the formulae
AA7; AA7$^D$; AA9; AA9$^D$; AA10; AA10$^D$; AA11; or AA11$^D$;
with the proviso that,
if no interstrand linkage is formed, then
P$^{13}$ and P$^{14}$, and P$^{14}$ and P$^1$ are connected as aforementioned;
if P$^{13}$ and P$^{14}$ taken together form an interstrand linkage, as defined above, then
P$^{13}$ and P$^{14}$ are not additionally connected as aforementioned;
with the further proviso that,
if linker L is connected with module A by a carbonyl (C=O) point of attachment of P$^2$; P$^5$; or P$^{12}$; then
P$^2$; P$^5$; or P$^{12}$; is an α-amino acid residue of one of the formulae
AA14; or AA14$^D$;
if linker L is connected with module A by a carbonyl (C=O) point of attachment of P$^{13}$ and
P$^{13}$ and P$^{14}$, and P$^{14}$ and P$^1$ are connected as aforementioned; or
P$^{14}$ and P$^1$ are not connected as aforementioned; then
P$^{13}$ is an α-amino acid residue of one of the formulae
AA14; or AA14$^D$;
if linker L is connected with module A by a carbonyl (C=O) point of attachment of P$^{14}$; and
P$^{13}$ and P$^{14}$, and P$^{14}$ and P$^1$ are connected as aforementioned; or
P$^{13}$ and P$^{14}$ are not connected as aforementioned; then
P$^{14}$ is an α-amino acid residue of one of the formulae
AA14; or AA14$^D$;
if i=0, and
P$^2$ and P$^{11}$ taken together and/or P$^4$ and P$^9$ taken together form naturally or non-naturally cross-linking α-amino acids, as defined above, then
P$^1$ to P$^5$; T$^6$; T$^7$; P$^8$ to P$^{13}$ are naturally or non-naturally occurring α-amino acids,
as defined in this embodiment;
with the proviso that,
if linker L is connected with module A by a carbonyl (C=O) point of attachment of P$^5$; or P$^{12}$; then
P$^5$; or P$^{12}$; is an α-amino acid residue of one of the formulae
AA14; or AA14$^D$;
or a pharmaceutically acceptable salt thereof;
Another alternative particular embodiment (24) of the invention relates to derivatives of general formula (I) according to alternative particular embodiment (23) with the proviso that P$^4$ and P$^9$ taken together form an interstrand linking bis(amino acid)-structure of one of the formulae AA13; or AA13$^D$; based on the linkage of two α-amino acid residues; and/or
P$^1$ is AA7; and/or
P$^2$ is AA11; or AA7; and/or
P$^4$ is Gly; AA7$^D$; or AA8; and/or
P$^5$ is AA8; and/or
T$^6$ is AA4$^D$; AA5$^D$; AA6$^D$; AA8$^D$; or AA11$^D$; and/or
T$^7$ is AA7; AA8; AA10; or AA11; and/or
P$^8$ is AA11; and/or
P$^9$ is AA8; or AA9; and/or
P$^{11}$ is Gly; AA11; or AA7; and/or
P$^{12}$ is AA8; AA8$^D$; AA9; or AA9$^D$; and/or
P$^{13}$ is AA8; AA8$^D$; AA16; or AA16$^D$.
or a pharmaceutically acceptable salt thereof.
Another alternative particular embodiment (25) of the invention relates to derivatives of general formula (I), wherein specifically
for module A,
if i=1, and
P$^2$ and P$^{11}$ taken together may form an interstrand linking bis(amino acid)-structure of one of the formulae
AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
and/or
P$^{13}$ and P$^{14}$ taken together may form an interstrand linking bis(amino acid)-structure of one of the formulae
AA13; AA13$^D$; AA13$^{LD}$; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
P$^2$ is an L α-amino acid residue of formula
AA10;
P$^4$ is an L α-amino acid residue of one of the formulae
AA7; AA10; or AA11;
P$^5$ is an L α-amino acid residue of one of the formulae
AA7; or AA11;
P$^8$ is an L α-amino acid residue of formula
AA7;
P$^9$ is Gly; or an L α-amino acid residue of one of the formulae
AA7; AA10; or AA11;
P$^{10}$ is an L α-amino acid residue of formula
AA8;
P$^{11}$ is an L α-amino acid residue of formula
AA10;
P$^{12}$ is Gly; or an α-amino acid residue of one of the formulae
AA7; AA7$^D$; AA10; or AA10$^D$;
P$^{13}$ is Gly; or an α-amino acid residue of one of the formulae
AA10; AA10$^D$; AA11; or AA11$^D$;
P$^{14}$ is Gly; or an α-amino acid residue of one of the formulae
AA7; AA7$^D$; AA9; AA9$^D$; AA10; AA10$^D$; AA11; or AA11$^D$;
with the proviso that,
if no interstrand linkage is formed, then
P$^{13}$ and P$^{14}$, and P$^{14}$ and P$^1$ are connected as aforementioned;

if $P^{13}$ and $P^{14}$ taken together form an interstrand linkage, as defined above, then
$P^{13}$ and $P^{14}$ are not additionally connected as aforementioned;
with the further proviso that,
if linker L is connected with module A by a carbonyl (C=O) point of attachment of $P^2$; $P^5$; or $P^{12}$; then
$P^2$; $P^5$; or $P^{12}$; is an α-amino acid residue of one of the formulae
AA14; or AA14$^D$;
if linker L is connected with module A by a carbonyl (C=O) point of attachment of $P^{13}$ and
$P^{13}$ and $P^{14}$, and $P^{14}$ and $P^1$ are connected as aforementioned; or
$P^{14}$ and $P^1$ are not connected as aforementioned; then
$P^{13}$ is an α-amino acid residue of one of the formulae
AA14; or AA14$^D$;
if linker L is connected with module A by a carbonyl (C=O) point of attachment of $P^{14}$; and
$P^{13}$ and $P^{14}$, and $P^{14}$ and $P^1$ are connected as aforementioned; or
$P^{13}$ and $P^{14}$ are not connected as aforementioned; then
$P^{14}$ is an α-amino acid residue of one of the formulae
AA14; or AA14$^D$;
if i=0, and
$P^2$ and $P^{11}$ taken together form naturally or non-naturally cross-linking α-amino acids, as defined above, then
$P^1$; $P^3$ to $P^5$; $T^6$; $T^7$; $P^8$ to $P^{10}$; $P^{12}$ and $P^{13}$ are naturally or non-naturally occurring α-amino acids, as defined in this embodiment;
with the proviso that,
if linker L is connected with module A by a carbonyl (C=O) point of attachment of $P^5$; or $P^{12}$; then
$P^5$; or $P^{12}$; is an α-amino acid residue of one of the formulae
AA14; or AA14$^D$;
or a pharmaceutically acceptable salt thereof.

Another alternative particular embodiment (26) of the invention relates to derivatives of general formula (I), wherein specifically
for module A,
if i=1, and $P^{13}$ and $P^{14}$, and $P^{14}$ and $P^1$ are connected as aforementioned, and
$P^2$ and $P^{11}$ taken together and/or $P^4$ and $P^9$ taken together may form an interstrand linking bis(amino acid) structure of one of the formulae AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—; —(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—; or —(CR$^{28}$R$^{29}$)$_n$NR$^1$CONR$^2$(CR$^{28}$R$^{29}$)$_m$—;
$P^1$ is an L α-amino acid of one of the formulae
AA8; or AA7;
$P^2$ is an L α-amino acid of one of the formulae
AA10; or AA11;
$P^3$ is an L α-amino acid of one of the formulae
AA7; or AA8;
$P^4$ is an L α-amino acid of one of the formulae
AA7; AA10; AA11; or AA8;
$P^5$ is an L α-amino acid of one of the formulae
AA7; AA11; or AA8;
$T^6$ is an D α-amino acid of one of the formulae
AA1$^D$; AA12$^D$; AA7$^D$; or AA10$^D$;
$T^7$ is an L α-amino acid of one of the formulae
AA1; or AA10;
$P^8$ is an L α-amino acid of formula
AA7;
$P^9$ is an L α-amino acid of one of the formulae
AA11; or AA10;
$P^{10}$ is an L α-amino acid of formula
AA8;
$P^{11}$ is Gly; or an L α-amino acid of one of the formulae
AA11; or AA10;
$P^{12}$ is Gly; or an L α-amino acid of formula
AA10;
$P^{13}$ is Gly; or an α-amino acid of one of the formulae
AA10; AA10$^D$; AA11; or AA11$^D$;
$P^{14}$ is an L α-amino acid of one of the formulae
AA10; or AA11;
with the proviso that,
if linker L is connected with module A by a carbonyl (C=O) point of attachment of $P^2$; $P^5$; $P^{12}$; $P^{13}$; or $P^{14}$; then
$P^2$; $P^5$; $P^{12}$; $P^{13}$; or $P^{14}$; is an α-amino acid residue of one of the formulae
AA14; or AA14$^D$;
or a pharmaceutically acceptable salt thereof.

Another alternative particular embodiment (27) of the invention relates to derivatives of general formula (I) according to alternative particular embodiment (26) with the proviso that
$P^4$ and $P^9$ taken together form an interstrand linking bis (amino acid)-structure of one of the formulae AA13; or AA13$^D$; based on the linkage of two α-amino acid residues; and/or
$P^1$ is AA7; and/or
$P^2$ is AA11; and/or
$P^4$ is AA8; and/or
$P^5$ is AA8; and/or
$T^2$ is AA10; and/or
$P^{11}$ is Gly; or AA11;
or a pharmaceutically acceptable salt thereof.

Another alternative particular embodiment (28) of the invention relates to derivatives of general formula (I), wherein specifically
for module A,
if i=1, and $P^{13}$ and $P^{14}$, and $P^{14}$ and $P^1$ are connected as aforementioned, and
$P^2$ and $P^{11}$ taken together may form an interstrand linking bis(amino acid) structure of one of the formulae AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
$P^2$, $P^{11}$, $P^{12}$ and $P^{14}$ are independently an L α-amino acid of formula
AA10;
$P^3$, $P^4$ and $P^8$ are independently an L α-amino acid of formula
AA7;
$P^5$ and $P^9$ are independently an L α-amino acid of formula
AA11;
$T^6$ is an D α-amino acid of formula
AA1$^D$;
$T^7$ is an L α-amino acid of formula
AA1;
$P^{10}$ is an L α-amino acid of formula
AA8;

$P^{13}$ is an α-amino acid of one of the formulae
AA10; or AA10$^D$;
with the proviso that,
if linker L is connected with module A by a carbonyl (C=O) point of attachment of $P^2$; $P^5$; $P^{12}$; $P^{13}$; or $P^{14}$; then
$P^2$; $P^5$; $P^{12}$; $P^{13}$; or $P^{14}$; is an α-amino acid residue of one of the formulae
AA14; or AA14$^D$;
or a pharmaceutically acceptable salt thereof.

Another alternative particular embodiment (29) of the invention relates to derivatives of general formula (I), wherein specifically
for module A,
if i=1, and $P^{14}$ and $P^1$, are not connected as aforementioned, and
$P^2$ and $P^{11}$ taken together and/or $P^4$ and $P^9$ taken together form an interstrand linking bis(amino acid) structure of one of the formulae AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_q$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
$P^1$ is an L α-amino acid of one of the formulae
AA8; or AA7;
$P^2$ is an L α-amino acid residue of one of the formulae
AA10; AA11; or AA7;
$P^3$ is an L α-amino acid of one of the formulae
AA7; or AA8;
$P^4$ is Gly; an α-amino acid residue of one of the formulae
AA7; AA10; AA11; AA7$^D$; or AA8;
$P^5$ is an L α-amino acid residue of one of the formulae
AA7; AA10; AA11; or AA8;
$T^6$ is an D α-amino acid of one of the formulae
AA1$^D$; AA4$^D$; AA7$^D$; AA10$^D$; AA12$^D$; AA8$^D$; or AA11$^D$;
$T^7$ is an L α-amino acid of one of the formulae
AA1; AA7; AA8; AA10; or AA11;
$P^8$ is an L α-amino acid residue of one of the formulae
AA7; AA8; or AA11;
$P^9$ is Gly; or an L α-amino acid residue of one of the formulae
AA7; AA10; AA11; AA8; or AA9;
$P^{10}$ is an L α-amino acid residue of one of the formulae
AA7; or AA8;
$P^{11}$ is an L α-amino acid residue of one of the formulae
AA10; AA16; or AA7;
$P^{12}$ is Gly; Sar; Aib; or an α-amino acid residue of one of the formulae
AA7; AA7$^D$; AA10; AA10$^D$; AA11; AA11$^D$; AA8; AA8$^D$; AA9; or AA9$^D$;
$P^{13}$ is Gly; Aib; or an α-amino acid residue of one of the formulae
AA10; AA10$^D$; AA11; AA8; AA8$^D$; AA7; or AA7$^D$;
$P^{14}$ is an α-amino acid residue of one of the formulae
AA7; AA7$^D$; AA10; AA10$^D$; AA11; or AA11$^D$;
with the proviso that,
if linker L is connected with module A by a carbonyl (C=O) point of attachment of $P^5$; $P^{12}$; or $P^{13}$; then
$P^5$; $P^{12}$; or $P^{13}$; is an α-amino acid residue of one of the formulae
AA14; or AA14$^D$;
or a pharmaceutically acceptable salt thereof.

Another alternative particular embodiment (30) of the invention relates to derivatives of general formula (I) according to alternative particular embodiment (29) with the proviso that
$P^4$ and $P^9$ taken together form an interstrand linking bis(amino acid)-structure of one of the formulae AA13; or AA13$^D$; based on the linkage of two α-amino acid residues; and/or
$P^1$ is AA7; and/or
$P^2$ is AA11; or AA7; and/or
$P^4$ is Gly; AA7$^D$; or AA8; and/or
$P^5$ is AA8; and/or
$T^6$ is AA4$^D$; AA8$^D$; or AA11$^D$; and/or
$T^7$ is AA7; AA8; AA10; or AA11; and/or
$P^8$ is AA11; and/or
$P^9$ is AA8; or AA9; and/or
$P^{11}$ is AA7; and/or
$P^{12}$ is AA8; AA8$^D$; AA9; or AA9$^D$; and/or
$P^{13}$ is AA8; or AA8$^D$;
or a pharmaceutically acceptable salt thereof.

Another alternative particular embodiment (31) of the invention relates to derivatives of general formula (I), wherein specifically
for module A,
if i=1, and $P^{14}$ and $P^1$, are not connected as aforementioned, and
$P^2$ and $P^{11}$ taken together form an interstrand linking bis(amino acid) structure of one of the formulae AA13; or AA13$^D$; with Z being, with the proviso of containing less than carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
$P^3$ and $P^8$ are independently an L α-amino acid of formula
AA7;
$P^4$ is an L α-amino acid of one of the formulae
AA7; AA10; or AA11;
$P^5$ is an L α-amino acid of formula
AA11;
$T^6$ is an D α-amino acid of one of the formulae
AA1$^D$; or AA7$^D$;
$T^7$ is an L α-amino acid of formula
AA1;
$P^9$ is Gly; or an L α-amino acid of one of the formulae
AA7; or AA11;
$P^{10}$ is an L α-amino acid of formula
AA8;
$P^{12}$ is Gly; Aib; or an L α-amino acid of one of the formulae
AA7; or AA10;
or an D α-amino acid of formula
AA7$^D$;
$P^{13}$ and $P^{14}$ are independently Gly; Aib; or an L α-amino acid of one of the formulae
AA7; AA10; or AA11;
or an D α-amino acid of formula
AA7$^D$;
with the proviso that,
if linker L is connected with module A by a carbonyl (C=O) point of attachment of $P^5$; $P^{12}$; or $P^{13}$; then
$P^5$; $P^{12}$; or $P^{13}$; is an α-amino acid residue of one of the formulae
AA14; or AA14$^D$;
or a pharmaceutically acceptable salt thereof.

Another alternative particular embodiment (32) of the invention relates to derivatives of general formula (I), wherein specifically
for module A,
if i=1, and $P^{13}$ and $P^{14}$ are not connected as aforementioned, and
$P^2$ and $P^{11}$ taken together and/or $P^4$ and $P^9$ taken together form an interstrand linking bis(amino acid) structure of one of the formulae AA13; or AA13$^D$; with Z being, with the proviso of containing less than 25 carbon- and/or heteroatoms,
—$(CR^{28}R^{29})_n$—S—S—$(CR^{28}R^{29})_m$—; —$(CR^{28}R^{29})_n$-heteroaryl-$(CR^{28}R^{29})_m$—;
—$(CR^{28}R^{29})_n$CONR$^1(CR^{28}R^{29})_m$—; —$(CR^{28}R^{29})_n$NR$^1$CO$(CR^{28}R^{29})_m$—;
or —$(CR^{28}R^{29})_n$NR$^1$CONR$^2(CR^{28}R^{29})_m$—;
$P^1$ is an L α-amino acid of one of the formulae
  AA8; or AA7;
$P^2$ is an L α-amino acid residue of one of the formulae
  AA10; AA16; AA11; or AA7;
$P^3$, $P^4$ and $P^8$ are independently an L α-amino acid of formula
  AA7;
$P^5$ is an L α-amino acid residue of one of the formulae
  AA7; AA10; AA11; or AA8;
$T^6$ is an D α-amino acid of one of the formulae
  AA1$^D$; or AA12$^D$;
$T^7$ is an L α-amino acid of formula
  AA1;
$P^9$ is an L α-amino acid residue of formula
  AA11;
$P^{10}$ is an L α-amino acid of formula
  AA8;
$P^{11}$ is Gly; Sar; or an L α-amino acid residue of one of the formulae
  AA7; AA10; or AA16;
$P^{12}$ is Sar; or an L α-amino acid of formula
  AA10;
$P^{13}$ is an L α-amino acid of one of the formulae
  AA10; or AA11;
$P^{14}$ is Gly; Sar; Aib; or an L α-amino acid of one of the formulae
  AA7; AA10; AA11; or AA9;
with the proviso that,
  if linker L is connected with module A by a carbonyl (C═O) point of attachment of $P^5$; $P^{12}$; or $P^{14}$; then
  $P^5$; $P^{12}$; or $P^{14}$; r is an α-amino acid residue of one of the formulae
    AA14; or AA14$^D$;
or a pharmaceutically acceptable salt thereof.

Another alternative particular embodiment (33) of the invention relates to derivatives of general formula (I) according to alternative particular embodiment (32) with the proviso that
$P^4$ and $P^9$ taken together form an interstrand linking bis (amino acid)-structure of one of the formulae AA13; or AA13$^D$; based on the linkage of two α-amino acid residues; and/or
$P^1$ is AA7; and/or
$P^2$ is AA11; or AA7; and/or
$P^5$ is AA8; and/or
$P^{11}$ is Gly; Sar; or AA7;
or a pharmaceutically acceptable salt thereof.

Another alternative particular embodiment (34) of the invention relates to derivatives of general formula (I), wherein specifically
for module A,
if i=1, and $P^{13}$ and $P^{14}$ are not connected as aforementioned, and
$P^2$ and $P^{11}$ taken together form an interstrand linking bis (amino acid) structure of one of the formulae AA13; or AA13$^D$; with Z being, with the proviso of containing less than carbon- and/or heteroatoms,
—$(CR^{28}R^{29})_n$—S—S—$(CR^{28}R^{29})_m$—; —$(CR^{28}R^{29})_n$-heteroaryl-$(CR^{28}R^{29})_m$—;
—$(CR^{28}R^{29})_n$CONR$^1(CR^{28}R^{29})_m$—; —$(CR^{28}R^{29})_n$NR$^1$CO$(CR^{28}R^{29})_m$—;
or —$(CR^{28}R^{29})_n$NR$^1$CONR$^2(CR^{28}R^{29})_m$—;
$P^3$, $P^4$ and $P^8$ are independently an L α-amino acid of formula
  AA7;
$P^5$ and $P^9$ are independently an L α-amino acid of formula
  AA11;
$T^6$ is an D α-amino acid of formula
  AA1$^D$;
$T^7$ is an L α-amino acid of formula
  AA1;
$P^{10}$ is an L α-amino acid of formula
  AA8;
$P^{12}$ is an L α-amino acid of formula
  AA10;
$P^{13}$ is an L α-amino acid of one of the formulae
  AA10; or AA11;
$P^{14}$ is Gly; Aib; or an L α-amino acid of one of the formulae
  AA7; AA10; or AA11;
  or an D α-amino acid of formula
  AA7$^D$;
with the proviso that,
  if linker L is connected with module A by a carbonyl (C═O) point of attachment of $P^5$; $P^{12}$; or $P^{14}$; then
  $P^5$; $P^{12}$; or $P^{14}$; is an α-amino acid residue of one of the formulae
    AA14; or AA14$^D$;
or a pharmaceutically acceptable salt thereof.

Another alternative particular embodiment (35) of the invention relates to derivatives of general formula (I), wherein specifically
for module A,
if i=0, and
$P^2$ and $P^{11}$ taken together and/or $P^4$ and $P^9$ taken together form an interstrand linking bis(amino acid) structure of one of the formulae AA13; or AA13$^D$; with Z being, with the proviso of containing less than 25 carbon- and/or heteroatoms,
—$(CR^{28}R^{29})_n$—S—S—$(CR^{28}R^{29})_m$—; —$(CR^{28}R^{29})_n$-heteroaryl-$(CR^{28}R^{29})_m$—;
—$(CR^{28}R^{29})_n$CONR$^1(CR^{28}R^{29})_m$—; —$(CR^{28}R^{29})_n$NR$^1$CO$(CR^{28}R^{29})_m$—;
or —$(CR^{28}R^{29})_n$NR$^1$CONR$^2(CR^{28}R^{29})_m$—;
$P^1$ is an L α-amino acid of formula
  AA8;
$P^2$ is an L α-amino acid residue of one of the formulae
  AA10; AA16; AA11; or AA7;
$P^3$ is an L α-amino acid of one of the formulae
  AA7; or AA8;
$P^4$ and $P^5$ are independently an L α-amino acid of one of the formulae
  AA7; or AA11;
$T^6$ is an D α-amino acid of one of the formulae
  AA1$^D$; AA12$^D$; or AA10$^D$;
$T^7$ is an L α-amino acid of formula
  AA1;
$P^8$ is an L α-amino acid of formula
  AA7;

P⁹ is an L α-amino acid of one of the formulae
    AA10; or AA11;
P¹⁰ is an L α-amino acid of one of the formulae
    AA8; or AA7;
P¹¹ is Gly; Sar; or an L α-amino acid residue of one of the formulae
    AA7; AA10; or AA16;
P¹² is an L α-amino acid of formula
    AA10;
P¹³ is an α-amino acid of one of the formulae
    AA10; AA10$^D$; AA16; or AA16$^D$;
with the proviso that,
    if linker L is connected with module A by a carbonyl (C=O) point of attachment of P⁵; or P¹²; then
    P⁵; or P¹²; is an α-amino acid residue of one of the formulae
        AA14; or AA14$^D$;
or a pharmaceutically acceptable salt thereof.

Another alternative particular embodiment (36) of the invention relates to derivatives of general formula (I) according to alternative particular embodiment (35) with the proviso that
    P⁴ and P⁹ taken together form an interstrand linking bis(amino acid)-structure of one of the formulae AA13; or AA13$^D$; based on the linkage of two α-amino acid residues; and/or
    P² is AA11; or AA7; and/or
    P¹¹ is Gly; Sar; or AA7;
or a pharmaceutically acceptable salt thereof.

Another alternative particular embodiment (37) of the invention relates to derivatives of general formula (I), wherein specifically for module A,
if i=0, and
P² and P¹¹ taken together form an interstrand linking bis(amino acid) structure of one of the formulae AA13; or AA13$^D$; with Z being, with the proviso of containing less carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P³ is an L α-amino acid of one of the formulae
    AA7; or AA8;
P⁴ and P⁵ are independently an L α-amino acid of one of the formulae
    AA7; or AA11;
T⁶ is an D α-amino acid of one of the formulae
    AA1$^D$; or AA10$^D$;
T⁷ is an L α-amino acid of formula
    AA1;
P⁸ is an L α-amino acid of formula
    AA7;
P⁹ is an L α-amino acid of one of the formulae
    AA10; or AA11;
P¹⁰ is an L α-amino acid of formula
    AA8;
P¹² is an L α-amino acid of formula
    AA10;
P¹³ is an α-amino acid of one of the formulae
    AA10; or AA10$^D$;
with the proviso that,
    if linker L is connected with module A by a carbonyl (C=O) point of attachment of P⁵; or P¹²; then
    P⁵; or P¹²; is an α-amino acid residue of one of the formulae
        AA14; or AA14$^D$;
or a pharmaceutically acceptable salt thereof.

Another alternative particular embodiment (38) of the invention relates to derivatives of general formula (I), wherein specifically
for module A,
if i=1, and P¹³ and P¹⁴ are not connected as aforementioned, and
P¹³ and P¹⁴ taken together form an interstrand linking bis(amino acid) structure of one of the formulae AA13; AA13$^D$; AA13$^{LD}$; or AA13$^{DL}$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—; and
P² and P¹¹ taken together and/or P⁴ and P⁹ taken together may form an interstrand linking bis(amino acid) structure of one of the formulae AA13; or AA13$^D$; with Z being, with the proviso of containing less than 25 carbon- and/or heteroatoms,
—(CR²⁸R²⁹)$_n$—S—S—(CR²⁸R²⁹)$_m$—; —(CR²⁸R²⁹)$_n$-heteroaryl-(CR²⁸R²⁹)$_m$—;
—(CR²⁸R²⁹)$_n$CONR¹(CR²⁸R²⁹)$_m$—; —(CR²⁸R²⁹)$_n$NR¹CO(CR²⁸R²⁹)$_m$—;
or —(CR²⁸R²⁹)$_n$NR¹CONR²(CR²⁸R²⁹)$_m$—;
P¹ is an L α-amino acid of formula
    AA8;
P² is an L α-amino acid residue of one of the formulae
    AA10; or AA11;
P³ is an L α-amino acid of one of the formulae
    AA7; or AA8;
P⁴ is an L α-amino acid residue of one of the formulae
    AA7; AA11; AA16; or AA8;
P⁵ is an L α-amino acid residue of one of the formulae
    AA7; AA11; or AA8;
T⁶ is an D α-amino acid of one of the formulae
    AA1$^D$; AA12$^D$; or AA10$^D$;
T⁷ is an L α-amino acid of one of the formulae
    AA1; or AA10;
P⁸ is an L α-amino acid of formula
    AA7;
P⁹ is an L α-amino acid residue of one of the formulae
    AA10; or AA11;
P¹⁰ is an L α-amino acid of formula
    AA8;
P¹¹ is an L α-amino acid residue of one of the formulae
    AA10; or AA16;
P¹² is Sar; or an L-α-amino acid residue of formula
    AA10;
with the proviso that,
    if linker L is connected with module A by a carbonyl (C=O) point of attachment of P²; P⁵; or P¹²; then
    P²; P⁵; or P¹²; is an α-amino acid residue of one of the formulae
        AA14; or AA14$^D$;
or a pharmaceutically acceptable salt thereof.

Another alternative particular embodiment (39) of the invention relates to derivatives of general formula (I) according to alternative particular embodiment (38) with the proviso that
    P⁴ and P⁹ taken together form an interstrand linking bis(amino acid)-structure of one of the formulae AA13; or AA13$^D$; based on the linkage of two α-amino acid residues; and/or $P^2$ is AA11; and/or
$P^4$ is AA8; and/or
$P^5$ is AA8; and/or
$T^7$ is AA10;
or a pharmaceutically acceptable salt thereof.

Another alternative particular embodiment (40) of the invention relates to derivatives of general formula (I), wherein specifically
for module A,
if i=1, and $P^{13}$ and $P^{14}$ are not connected as aforementioned, and
$P^{13}$ and $P^{14}$ taken together form an interstrand linking bis(amino acid) structure of one of the formulae AA13; AA13$^D$; AA13$^{LD}$; or AA13$^{DL}$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—; and
$P^2$ and $P^{11}$ taken together may form an interstrand linking bis(amino acid) structure of one of the formulae AA13; or AA13$^D$; with Z being, with the proviso of containing less than 25 carbon- and/or heteroatoms,
—(CR$^{28}$R$^{29}$)$_n$—S—S—(CR$^{28}$R$^{29}$)$_m$—; —(CR$^{28}$R$^{29}$)$_n$-heteroaryl-(CR$^{28}$R$^{29}$)$_m$—;
—(CR$^{28}$R$^{29}$)$_n$CONR$^1$(CR$^{28}$R$^{29}$)$_m$—; —(CR$^{28}$R$^{29}$)$_n$NR$^1$CO(CR$^{28}$R$^{29}$)$_m$—;
or —(CR$^{28}$R$^{29}$)$_n$NR$^1$CONR$^2$(CR$^{28}$R$^{29}$)$_m$—;
$P^2$, $P^{11}$, and $P^{12}$ are independently an L α-amino acid of formula
AA10;
$P^3$, $P^4$ and $P^8$ are independently an L α-amino acid of formula
AA7;
$P^5$ and $P^9$ are independently an L α-amino acid of formula
AA11;
$T^6$ is an D α-amino acid of formula
AA1$^D$;
$T^7$ is an L α-amino acid of formula
AA1;
$P^{10}$ is an L α-amino acid of formula
AA8;
with the proviso that,
if linker L is connected with module A by a carbonyl (C=O) point of attachment of $P^2$; $P^5$; or $P^{12}$; then
$P^2$; $P^5$; or $P^{12}$; is an α-amino acid residue of one of the formulae
AA14; or AA14$^D$;
or a pharmaceutically acceptable salt thereof.

Another alternative particular embodiment (41) of the invention relates to derivatives of general formula (I), wherein specifically
for linker L,
if k=1,
$L^1$ is Gly; Sar; or an α-amino acid residue of one of the formulae
AA10; AA10$^D$; AA7; AA7$^D$; AA11; AA11$^D$; AA8; AA8$^D$; AA16; or AA16$^D$;
if k=2, the additional element
$L^2$ is an L-α-amino acid residue of one of the formulae
AA10; AA10$^D$; AA11; or AA11$^D$;
if k=3, the additional element
$L^3$ is an L-α-amino acid residue of formula
AA10;
or a pharmaceutically acceptable salt thereof.

Another alternative particular embodiment (42) of the invention relates to derivatives of general formula (I) according to alternative particular embodiment (41) with the proviso that,
if k=1-3, then
$L^1$ is AA8; AA8$^D$; AA16; or AA16$^D$;
or a pharmaceutically acceptable salt thereof.

Another alternative particular embodiment (43) of the invention relates to derivatives of general formula (I), wherein specifically
for linker L,
if k=1,
$L^1$ is Gly; or an α-amino acid residue of one of the formulae
AA10; or AA10$^D$;
or an L α-amino acid residue of formula
AA11;
if k=2, the additional element
$L^2$ is an L-α-amino acid residue of one of the formulae
AA10; or AA11;
if k=3, the additional element
$L^3$ is an L-α-amino acid residue of formula
AA10;
or a pharmaceutically acceptable salt thereof.

Another alternative particular embodiment (44) of the invention relates to derivatives of general formula (I), wherein specifically
for linker L,
if k=1,
$L^1$ is an α-amino acid residue of one of the formulae
AA10; or AA10$^1$);
if k=2, the additional element
$L^2$ is an L-α-amino acid residue of one of the formulae
AA10; or AA11;
if k=3, the additional element
$L^3$ is an L-α-amino acid residue of formula
AA10;
or a pharmaceutically acceptable salt thereof.

In another particular embodiment (45) of the invention the elements of general formula (I) are defined as follows,
for module A,
if i=1, and
$P^2$ and $P''$ taken together and/or $P^4$ and $P^9$ taken together may form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage; or
connection of the side chain of Pra with the side chain of Abu(4N$_3$) by a 1,4-disubstituted 1,2,3-triazole-containing linkage;
and/or
$P^{13}$ and $P^{14}$ taken together may form an interstrand linking bis(amino acid)-structure based on the linkage of two L amino acid residues; or two D amino acid residues; or an L amino residue with an D amino acid residue; following
connection of the side chain of Cys; Hcy; or Pen; Cys-NH$_2$; Hcy-NH$_2$; or Pen-NH$_2$; of $P^{13}$ with the side chain of Cys; Hcy; or Pen; NMeCys; NMeHcy; or NMePen; Ac-Cys; Ac-Hcy; or Ac-Pen; Gua-Cys; Gua-Hcy; or Gua-Pen; TMG-Cys; TMG-Hcy; or TMG-Pen; of $P^{14}$ by a disulfide linkage; or connection of the side chain of Dap; Dab; Orn; or Lys; Dap-NH$_2$; Dab-NH$_2$; Orn-NH$_2$; or Lys-NH$_2$; of P$^{13}$ with the side chain of Asp; Glu; or hGlu; NMeAsp; NMeGlu; or NMehGlu; Ac-Asp; Ac-Glu; or Ac-hGlu; Gua-Asp; Gua-Glu; or Gua-hGlu; TMG-Asp; TMG-Glu; or TMG-hGlu; of P$^{14}$ by a lactam linkage; or connection of the side chain of Asp; Glu; or hGlu; Asp-NH$_2$; Glu-NH$_2$; or hGlu-NH$_2$; of P$^{13}$ with the side chain of Dap; Dab; Orn; or Lys; NMeDap; NMeDab; NMeOrn; or NMeLys; Ac-Dap; Ac-Dab; Ac-Orn; or Ac-Lys; Gua-Dap; Gua-Dab; Gua-Orn; or Gua-Lys; TMG-Dap; TMG-Dab; TMG-Orn; or TMG-Lys; of P$^{14}$ by a lactam linkage;

P$^1$ is Trp; Tyr; Phe; Ala; Val; Nva; Abu; Leu; Ile; or Nle;
P$^2$ is Dab; Dap; Orn; Lys; Arg; Asn; Gln; Ser; Thr; alloThr; Hse; Ala; Val; Nva; Abu; Leu; Ile; or Nle;
P$^3$ is tBuGly; Ala; Val; Abu; Leu; Ile; Nle; Nva; Tyr; Phe; Trp; or Phg;
P$^4$ is Gly; Sar; Ala; Val; Abu; Leu; Ile; Nle; Nva; Dap; Dab; Orn; Lys; Arg; Ser; Thr; alloThr; Hse; Asn; Gln; $^D$Ala; $^D$Val; $^D$Abu; $^D$Nva; $^D$Leu; $^D$Ile; $^D$Nle; Tyr; Phe; or Trp;
P$^5$ is Ser; Thr; alloThr; Hse; Val; Leu; Ile; Nle; Nva; Abu; Ala; Dab; Dap; Orn; Lys; Arg; Tyr; Phe; His; or Trp;
T$^6$ is $^D$Pro; $^D$Pro(4S)OH; $^D$Pro(3S)OH; $^D$Azt; $^D$Pic; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; $^D$Arg; $^D$Tyr; $^D$Phe; $^D$Trp; $^D$Ser; $^D$Thr; $^D$alloThr; or $^D$Hse;
T$^7$ is Pro; Hyp; Pro(4S)OH; Pro(3S)OH; Pro(4R)F; Pic; Oic; Tic; Ala; Abu; Leu; Val; Nva; Ile; Nle; Tyr; Phe; Trp; Dab; Dap; Orn; Lys; Arg; Ser; Thr; alloThr; or Hse;
P$^8$ is Nle; Val; Leu; Ile; Nva; Abu; Ala; Cpg; Cpa; Trp; Tyr; Phe; Ser; Thr; alloThr; or Hse;
P$^9$ is Gly; Ala; Abu; Leu; Nle; Ile; Val; Nva; Ser; Thr; alloThr; Hse; Dap; Dap(iPr) Dab; Orn; Lys; Arg; Asn; Gln; Tyr; Phe; His; Trp; Asp; or Glu;
P$^{10}$ is Tyr; Phe; Trp; Phg; tBuGly; Ala; Val; Abu; Leu; Ile; Nle; or Nva;
P$^{11}$ is Gly; Sar; Dab; Dap; Orn; Lys; Arg; Asn; Gln; Nle; Val; Leu; Ile; Nva; Abu; Ala; Ser; Thr; alloThr; or Hse;
P$^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Dap; $^D$Orn; $^D$Lys; $^D$Arg; Ser; Thr; alloThr; Hse; $^D$Ser; $^D$Thr; $^D$alloThr; $^D$Hse; $^D$Tyr; $^D$Phe; $^D$Trp; Tyr; Phe; Trp; $^D$Glu; $^D$Asp Glu; or Asp;
P$^{13}$ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$alloThr; $^D$Ser; $^D$Hse; Ala; Val; Abu; Nva; Leu; Ile; Nle; $^D$Ala; $^D$Abu; $^D$Leu; $^D$Val; $^D$Nva; $^D$Ile; $^D$Nle; $^D$Tyr; $^D$Phe; $^D$Trp; Tyr; Phe; Trp; $^D$Gln; $^D$Asn; Gln; or Asn;
P$^{14}$ is Gly; Sar; Aib; Dab; Dap; Orn; Lys; Arg; $^D$Dab; $^D$Dap; $^D$Orn; $^D$Lys; $^D$Arg; Thr; alloThr; Ser; Hse; $^D$Thr; $^D$alloThr; $^D$Ser; $^D$Hse; $^D$Ala; $^D$Abu; $^D$Leu; $^D$Val; $^D$Nva; $^D$Ile; $^D$Nle; Ala; Abu; Leu; Ile; Nle; Val; Nva; Glu; Asp; Gln; Asn; $^D$Glu; $^D$Asp; $^D$Gln; or $^D$Asn;

with the proviso that,
if no interstrand linkage is formed, then
P$^{13}$ and P$^{14}$, and P$^{14}$ and P$^1$ are connected as aforementioned;
if P$^{13}$ and P$^{14}$ taken together form an interstrand linkage, as defined above, then
P$^{13}$ and P$^{14}$ are not additionally connected as aforementioned;
with the further proviso that,
if linker L is connected with module A by a carbonyl (C=O) point of attachment of P$^2$; P$^5$; or P$^{12}$; then
P$^2$; P$^5$; or P$^{12}$; is an α-amino acid residue of one of the formulae
Asp; Glu; $^D$Asp; or $^D$Glu;
if linker L is connected with module A by a carbonyl (C=O) point of attachment of P$^{13}$ and
P$^{13}$ and P$^{14}$, and P$^{14}$ and P$^1$ are connected as aforementioned; or
P$^{14}$ and P$^1$ are not connected as aforementioned; then
P$^{13}$ is Asp; Glu; $^D$Asp; or $^D$Glu;
if linker L is connected with module A by a carbonyl (C=O) point of attachment of P$^{14}$; and
P$^{13}$ and P$^{14}$, and P$^{14}$ and P$^1$ are connected as aforementioned; or
P$^{13}$ and P$^{14}$ are not connected as aforementioned; then
P$^{14}$ is Asp; Glu; $^D$Asp; or $^D$Glu;
if i=0, and
P$^2$ and P$^{11}$ taken together and/or P$^4$ and P$^9$ taken together form naturally or non-naturally cross-linking α-amino acids, as defined above, then
P$^1$ to P$^5$; T$^6$; T$^7$; P$^8$ to P$^{13}$ are naturally or non-naturally occurring α-amino acids, as defined in this embodiment;
with the proviso that,
if linker L is connected with module A by a carbonyl (C=O) point of attachment of P$^5$; or P$^{12}$; then
P$^5$; or P$^{12}$; is
Asp; Glu; $^D$Asp; or $^D$Glu;

for module B which consists of single elements Q being connected in either direction from the carbonyl (C=O) point of attachment to the nitrogen (N) of the next element with the proviso that Q$^7$ is connected from the α-carbonyl (C=O) point of attachment to the ω-nitrogen (N) of Q$^1$,
Q$^1$ is Dab; Dap; Orn; Lys; Dab(Me); $^D$Dab; $^D$Dap; $^D$Orn; or $^D$Lys;
Q$^2$ is Dab; Dap; Orn; Lys; or Arg;
Q$^3$ is $^D$Leu; $^D$Ile; $^D$Nle; $^D$Val; $^D$Nva; $^D$Ala; $^D$OctGly; $^D$Phe; $^D$Tyr; or $^D$Trp;
Q$^4$ is Leu; Ile; Nle; Val; Nva; Abu; Ala; or OctGly;
Q$^5$ is Dab; Dap; Orn; Lys; Arg; or Dab(Trp);
Q$^6$ is Dab; Dap; Orn; Lys; Arg; Dap(Glu); or Dab(Arg);
Q$^7$ is Thr; alloThr; Ser; Hse; Asn; Gln; Ala; Abu; Leu; Nle; Ile; Val; Nva; Dap; Dab; Orn; Lys; Arg; $^D$Thr; $^D$alloThr; $^D$Ser; $^D$Hse; $^D$Asn; $^D$Gln; $^D$Ala; $^D$Abu; $^D$Leu; $^D$Nle; $^D$Ile; $^D$Val; $^D$Nva; $^D$Dap; $^D$Dab; $^D$Orn; $^D$Lys; or $^D$Arg;

for a linker L consisting of k=0-3 single elements L being connected in either direction from the carbonyl (C=O) point of attachment to the nitrogen (N) of the next element,
if k=1,
L$^1$ is Gly; Sar; Aib; Dab; NMeDab; Dab(Me); Dap; Orn; Lys; $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; $^D$Nle; Gln; Asn; $^D$Gln; $^D$Asn; Tyr; Phe; Trp; $^D$Tyr; $^D$Phe; or $^D$Trp;
if k=2, the additional element
L$^2$ is Gly; Sar; Aib; Dab; Dap; Orn; Lys; Dab(Me); $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; or $^D$Nle;
if k=3, the additional element
L$^3$ is Gly; Sar; Aib; Dab; Dap; Orn; Lys; Dab(Me); $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; or $^D$Nle;
said linker L being connected with module B from the carbonyl (C=O) point of attachment of L$^k$ to the α-nitrogen (N) of Q$^1$ and,
if k=1-3 and i=1, being connected with module A from the carbonyl (C=O) point of attachment of P$^2$; P$^5$; P$^{12}$; P$^{13}$; or P$^{14}$; to the nitrogen (N) of L$^1$; or, if k=1-3 and i=0, being connected with module A from the carbonyl (C=O) point of attachment of $P^5$; $P^{12}$; or $P^{13}$; to the nitrogen (N) of $L^1$; or if k=0 and i=1, then $Q^1$ being directly connected with module A from the carbonyl (C=O) point of attachment of $P^2$; $P^5$; $P^{12}$; $P^{13}$; or $P^{14}$; to the α-nitrogen (N) of $Q^1$; or if k=0 and i=0, then $Q^1$ being directly connected with module A from the carbonyl (C=O) point of attachment of $P^5$; $P^{12}$; or $P^{13}$; to the α-nitrogen (N) of $Q^1$;

$P^{13}$; or $P^{14}$; having a carbonyl (C=O) point of attachment not connected as aforementioned, being appropriately saturated by linkage with $R^{30}$ being —OH; —OCH$_3$; —OCH(CH$_3$)$_2$; —NH$_2$; —NH(CH$_3$); —NH(CH$_3$)$_2$; or NH(CH(CH$_3$)$_2$);

to form the corresponding naturally or non-naturally occurring terminal α-amino acid residue; optionally having a modified carbonyl (C=O) functional group;

$P^1$; or $P^{14}$; having a nitrogen (N) not connected as aforementioned, being appropriately saturated by linkages with $R^1$ being —H; —CH$_3$; or —CH(CH$_3$)$_2$; and $R^{31}$ being —H; —CH$_3$; —COCH$_3$; or —C(=NH)NH$_2$; or $R^1$ and $R^{31}$ taken together being =C(N(CH$_3$)$_2$)$_2$;

to form the corresponding naturally or non-naturally occurring terminal α-amino acid residue;

or a pharmaceutically acceptable salt thereof.

In another particular embodiment (46) of the invention the elements of general formula (I) are defined as in particular embodiment (45), with the further proviso that, $P^4$ and $P^9$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage; or connection of the side chain of Pra with the side chain of Abu(4N$_3$) by a 1,4-disubstituted 1,2,3-triazole-containing linkage;

and/or $P^1$ is Ala; Val; Nva; Abu; Leu; Ile; or Nle; and/or $P^2$ is Ser; Thr; alloThr; Hse; Ala; Val; Nva; Abu; Leu; Ile; or Nle; and/or $P^4$ is Gly; Sar; $^D$Ala; $^D$Val; $^D$Abu; $^D$Nva; $^D$Leu; $^D$Ile; $^D$Nle; Tyr; Phe; or Trp; and/or $P^5$ is Tyr; Phe; His; or Trp; and/or $T^6$ is $^D$Pic; $^D$Tyr; $^D$Phe; $^D$Trp; $^D$Ser; $^D$Thr; $^D$alloThr; or $^D$Hse; and/or $T^7$ is Ala; Abu; Leu; Val; Nva; Ile; Nle; Tyr; Phe; Trp; Dab; Dap; Orn; Lys; Arg; Ser; Thr; alloThr; or Hse; and/or $P^8$ is Ser; Thr; alloThr; or Hse; and/or $P^9$ is Tyr; Phe; His; Trp; Asp; or Glu; and/or $P^{11}$ is Gly; Sar; Ala; Val; Nva; Abu; Leu; Ile; Nle; Ser; Thr; alloThr; or Hse; and/or $P^{12}$ is $^D$Tyr; $^D$Phe; $^D$Trp; Tyr; Phe; Trp; $^D$Glu; $^D$Asp; Glu; or Asp; and/or $P^{13}$ is $^D$Tyr; $^D$Phe; $^D$Trp; Tyr; Phe; Trp; $^D$Gln; $^D$Asn; Gln; or Asn; and/or if k=1-3, then $L^1$ is Tyr; Phe; Trp; $^D$Tyr; $^D$Phe; $^D$Trp; Gln; Asn; or $^D$Gln; or $^D$Asn; and/or $Q^7$ is Ala; Abu; Leu; Nle; Ile; Val; Nva; Dap; Dab; Orn; Lys; Arg; $^D$Thr; $^D$alloThr; $^D$Ser; $^D$Hse; $^D$Asn; $^D$Gln; $^D$Ala; $^D$Abu; $^D$Leu; $^D$Nle; $^D$Ile; $^D$Val; $^D$Nva; $^D$Dap; $^D$Dab; $^D$Orn; $^D$Lys; or $^D$Arg;

or a pharmaceutically acceptable salt thereof.

In another particular embodiment (47) of the invention the elements of general formula (I) are defined as follows, for module A, if i=1, and $P^2$ and $P^{11}$ taken together may form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage; or connection of the side chain of Pra with the side chain of Abu(4N$_3$) by a 1,4-disubstituted 1,2,3-triazole-containing linkage;

and/or $P^{13}$ and $P^{14}$ taken together may form an interstrand linking bis(amino acid)-structure based on the linkage of two L amino acid residues; or two D amino acid residues; or an L amino residue with an D amino acid residue; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage;

$P^1$ is Trp; Tyr; or Phe;

$P^2$ is Dab; Dap; Orn; Lys; Arg; Asn; or Gln;

$P^3$ is tBuGly; Ala; Val; Abu; Leu; Ile; Nle; Nva; Tyr; Phe; Trp; or Phg;

$P^4$ is Ala; Val; Abu; Leu; Ile; Nle; Nva; Dap; Dab; Orn; Lys; Arg; Ser; Thr; alloThr; Hse; Asn; or Gln;

$P^5$ is Ser; Thr; alloThr; Hse; Val; Leu; Ile; Nle; Nva; Abu; Ala; Dab; Dap; Orn; Lys; or Arg;

$T^6$ is $^D$Pro; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; or $^D$Arg;

$T^7$ is Pro; Pic; Oic; or Tic;

$P^8$ is Nle; Val; Leu; Ile; Nva; Abu; Ala; Cpg; Cpa; Trp; Tyr; or Phe;

$P^9$ is Gly; Ala; Abu; Leu; Nle; Ile; Val; Nva; Ser; Thr; alloThr; Hse; Dap; Dab; Orn; Lys; Arg; Asn; or Gln;

$P^{10}$ is Tyr; Phe; Trp; Phg; tBuGly; Ala; Val; Abu; Leu; Ile; Nle; or Nva;

$P^{11}$ is Dab; Dap; Orn; Lys; Arg; Asn; or Gln;

$P^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Dap; $^D$Orn; $^D$Lys; $^D$Arg; Ser; Thr; alloThr; Hse; $^D$Ser; $^D$Thr; $^D$alloThr; or $^D$Hse;

$P^{13}$ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$alloThr; $^D$Ser; $^D$Hse; Ala; Val; Abu; Nva; Leu; Ile; Nle; $^D$Ala; $^D$Abu; $^D$Leu; $^D$Val; $^D$Nva; $^D$Ile; or $^D$Nle;

$P^{14}$ is Gly; Sar; Aib; Dab; Dap; Orn; Lys; Arg; $^D$Dab; $^D$Dap; $^D$Orn; $^D$Lys; $^D$Arg; Thr; alloThr; Ser; Hse; $^D$Thr; $^D$alloThr; $^D$Ser; $^D$Hse; $^D$Ala; $^D$Abu; $^D$Leu; $^D$Val; $^D$Nva; $^D$Ile; $^D$Nle; Ala; Abu; Leu; Ile; Nle; Val; Nva; Glu; Asp; Gln; Asn; $^D$Glu; $^D$Asp; $^D$Gln; or $^D$Asn;

with the proviso that,
  if no interstrand linkage is formed, then
    $P^{13}$ and $P^{14}$, and $P^{14}$ and $P^1$ are connected as aforementioned;
  if $P^{13}$ and $P^{14}$ taken together form an interstrand linkage, as defined above, then
    $P^{13}$ and $P^{14}$ are not additionally connected as aforementioned;
with the further proviso that,
  if linker L is connected with module A by a carbonyl (C=O) point of attachment of $P^2$; $P^5$; or $P^{12}$; then
    $P^2$; $P^5$; or $P^{12}$; is an α-amino acid residue of one of the formulae
    Asp; Glu; $^D$Asp; or $^D$Glu;
  if linker L is connected with module A by a carbonyl (C=O) point of attachment of $P^{13}$ and
    $P^{13}$ and $P^{14}$, and $P^{14}$ and $P^1$ are connected as aforementioned; or
    $P^{14}$ and $P^1$ are not connected as aforementioned; then
    $P^{13}$ is Asp; Glu; $^D$Asp; or $^D$Glu;
  if linker L is connected with module A by a carbonyl (C=O) point of attachment of $P^{14}$; and
    $P^{13}$ and $P^{14}$, and $P^{14}$ and $P^1$ are connected as aforementioned; or
    $P^{13}$ and $P^{14}$ are not connected as aforementioned; then
    $P^{14}$ is Asp; Glu; $^D$Asp; or $^D$Glu;
if i=0, and
$P^2$ and $P^{11}$ taken together form naturally or non-naturally cross-linking α-amino acids, as defined above, then
$P^1$; $P^3$ to $P^5$; $T^6$; $T^7$; $P^8$ to $P^{10}$; $P^{12}$; and $P^{13}$ are naturally or non-naturally occurring α-amino acids, as defined in this embodiment;
with the proviso that,
  if linker L is connected with module A by a carbonyl (C=O) point of attachment of $P^5$; or $P^{12}$; then
    $P^5$; or $P^{12}$; is
    Asp; Glu; $^D$Asp; or $^D$Glu;
for module B which consists of single elements Q being connected in either direction from the carbonyl (C=O) point of attachment to the nitrogen (N) of the next element with the proviso that $Q^7$ is connected from the α-carbonyl (C=O) point of attachment to the ω-nitrogen (N) of $Q^1$,
$Q^1$ is Dab; Dap; Orn; Lys; $^D$Dab; $^D$Dap; $^D$Orn; or $^D$Lys;
$Q^2$; or $Q^5$ is
  Dab; Dap; Orn; Lys; or Arg;
$Q^6$ is Dab; Dap; Orn; Lys; Arg; Dap(Glu); or Dab(Arg);
$Q^3$ is $^D$Leu; $^D$Ile; $^D$Nle; $^D$Val; $^D$Nva; $^D$Ala; $^D$OctGly; $^D$Phe; $^D$Tyr; or $^D$Trp;
$Q^4$ is Leu; Ile; Nle; Val; Nva; Abu; Ala; or OctGly;
$Q^7$ is Thr; alloThr; Ser; Hse; Asn; or Gln;
for a linker L consisting of k=0-3 single elements L being connected in either direction from the carbonyl (C=O) point of attachment to the nitrogen (N) of the next element,
if k=1,
$L^1$ is Gly; Sar; Aib; Dab; Dap; Orn; Lys; $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; or $^D$Nle;
if k=2, the additional element
$L^2$ is Gly; Sar; Aib; Dab; Dap; Orn; Lys; $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; or $^D$Nle;
if k=3, the additional element
$L^3$ is Gly; Sar; Aib; Dab; Dap; Orn; Lys; $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; or $^D$Nle;
said linker L being connected with module B from the carbonyl (C=O) point of attachment of $L^k$ to the α-nitrogen (N) of $Q^1$ and,
if k=1-3 and i=1, being connected with module A from the carbonyl (C=O) point of attachment of $P^2$; $P^5$; $P^{12}$; $P^{13}$; or $P^{14}$; to the nitrogen (N) of $L^1$; or,
if k=1-3 and i=0, being connected with module A from the carbonyl (C=O) point of attachment of $P^5$; $P^{12}$; or $P^{13}$; to the nitrogen (N) of $L^1$; or
if k=0 and i=1, then
$Q^1$ being directly connected with module A from the carbonyl (C=O) point of attachment of $P^2$; $P^5$; $P^{12}$; $P^{13}$; or $P^{14}$; to the α-nitrogen (N) of $Q^1$; or
if k=0 and i=0, then
$Q^1$ being directly connected with module A from the carbonyl (C=O) point of attachment of $P^5$; $P^{12}$; or $P^{13}$; to the α-nitrogen (N) of $Q^1$;
$P^{13}$; or $P^{14}$; having a carbonyl (C=O) point of attachment not connected as aforementioned, being appropriately saturated by linkage with
$R^{39}$ being —OH; —OCH$_3$; —OCH(CH$_3$)$_2$; —NH$_2$; —NH(CH$_3$); —NH(CH$_3$)$_2$; or NH(CH(CH$_3$)$_2$);
to form the corresponding naturally or non-naturally occurring terminal α-amino acid residue; optionally having a modified carbonyl (C=O) functional group;
$P^1$; or $P^{14}$; having a nitrogen (N) not connected as aforementioned, being appropriately saturated by linkages with
$R^1$ being —H; —CH$_3$; or —CH(CH$_3$)$_2$; and
$R^{31}$ being —H; —CH$_3$; or —COCH$_3$;
to form the corresponding naturally or non-naturally occurring terminal α-amino acid residue; optionally having a modified nitrogen (N) functional group;
or a pharmaceutically acceptable salt thereof.
In another particular embodiment (48) of the invention the elements of general formula (I) are defined as follows,
for module A,
if i=1, and $P^{13}$ and $P^{14}$, and $P^{14}$ and $P^1$ are connected as aforementioned, and
$P^2$ and $P^{11}$ taken together and/or $P^4$ and $P^9$ taken together may form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;
$P^1$ is Trp; Tyr; Phe; NMeTrp; NMeTyr; NMePhe; Ala; Val; Nva; Abu; Leu; Ile; Nle; NMeAla; NMeVal; NMeNva; NMeAbu; NMeLeu; NMeIle; or NMeNle;
$P^2$ is Dab; Dap; Orn; Lys; Arg; Asn; Gln; Ser; Thr; alloThr; Hse; Ala; Val; Nva; Abu; Leu; Ile; or Nle;
$P^3$ is tBuGly; Ala; Val; Abu; Leu; Ile; Nle; Nva; Tyr; Phe; Trp; or Phg;
$P^4$ is Ala; Val; Abu; Leu; Ile; Nle; Nva; Dap; Dab; Orn; Lys; Arg; Ser; Thr; alloThr; Hse; Asn; Gln; $^D$Ala; $^D$Val; $^D$Abu; $^D$Nva; $^D$Leu; $^D$Ile; $^D$Nle; Tyr; Phe; or Trp;
$P^5$ is Ser; Thr; alloThr; Hse; Val; Leu; Ile; Nle; Nva; Abu; Ala; Dab; Dap; Orn; Lys; Arg; Tyr; Phe; His; or Trp;

T⁶ is ᴰPro; ᴰPro(4S)OH; ᴰPro(3S)OH; ᴰPic; ᴰAzt; ᴰTic; ᴰAla; ᴰAbu; ᴰLeu; ᴰVal; ᴰNva; ᴰIle; ᴰNle; ᴰDab; ᴰDap; ᴰOrn; ᴰLys; ᴰArg; ᴰTyr; ᴰPhe; ᴰTrp; ᴰSer; ᴰThr; ᴰalloThr; or ᴰHse;

T⁷ is Pro; Hyp; Pro(4S)OH; Pro(3S)OH; Pro(4R)F; Pic; Oic; Tic; Ala; Val; Nva; Abu; Leu; Ile; Nle; Tyr; Phe; Trp; Dab; Dap; Orn; Lys; Arg; Ser; Thr; alloThr; or Hse;

P⁸ is Nle; Val; Leu; Ile; Nva; Abu; Ala; Cpg; Cpa; Trp; Tyr; Phe; Ser; Thr; alloThr; or Hse;

P⁹ is Gly; Sar; Ala; Abu; Leu; Nle; Ile; Val; Nva; Ser; Thr; alloThr; Hse; Dap; Dab; Orn; Lys; Arg; Dap(iPr); Asn; Gln; Tyr; Phe; His; or Trp;

P¹⁰ is Tyr; Phe; Trp; Phg; Cha; tBuGly; Ala; Val; Abu; Leu; Ile; Nle; or Nva;

P¹¹ is Gly; Sar; Dab; Dap; Orn; Lys; Arg; Asn; Gln; Ser; Thr; alloThr; or Hse;

P¹² is Gly; Sar; Ala; Nle; Val; Leu; Ile; Nva; Abu; Dab; Dap; Orn; Lys; Arg; Ser; Thr; alloThr; or Hse;

P¹³ is Gly; Sar; ᴰDab; ᴰDap; ᴰOrn; ᴰLys; ᴰArg; Dab; Dap; Orn; Lys Arg; Ala; Abu; Leu; Nle; Ile; Val; Nva; ᴰAla; ᴰAbu; ᴰLeu; ᴰVal; ᴰNva; ᴰIle; ᴰNle; Ser; Thr; alloThr; Hse; ᴰSer; ᴰThr; ᴰalloThr; or ᴰHse;

P¹⁴ is Gly; Sar; Dab; Dap; Orn; Lys; Arg; Ser; Thr; alloThr; Hse; Ala; Abu; Leu; Nle; Ile; Val; Nva; Asn; or Gln;

with the proviso that,
if linker L is connected with module A by a carbonyl (C=O) point of attachment of P²; P⁶; P¹²; P¹³; or P¹⁴; then
P²; P⁵; P¹²; P¹³; or P¹⁴; is
Asp; Glu; ᴰAsp; or ᴰGlu;
or a pharmaceutically acceptable salt thereof.

In another particular embodiment (49) of the invention the elements of general formula (I) are defined as in particular embodiment (48),
with the proviso that
P⁴ and P⁹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage; and/or P¹ is Ala; Val; Nva; Abu; Leu; Ile; Nle; NMeAla; NMeVal; NMeNva; NMeAbu; NMeLeu; NMeIle; or NMeNle; and/or P² is Ser; Thr; alloThr; Hse; Ala; Val; Nva; Abu; Leu; Ile; or Nle; and/or P⁴ is ᴰAla; ᴰVal; ᴰAbu; ᴰNva; ᴰLeu; ᴰIle; ᴰNle; Tyr; Phe; or Trp; and/or P⁵ is Tyr; Phe; His; or Trp; and/or T⁶ is ᴰPic; ᴰTyr; ᴰPhe; ᴰTrp; ᴰSer; ᴰThr; ᴰalloThr; or ᴰHse; and/or T⁷ is Ala; Abu; Leu; Val; Nva; Ile; Nle; Tyr; Phe; Trp; Dab; Dap; Orn; Lys; Arg; Ser; Thr; alloThr; or Hse; and/or P⁸ is Ser; Thr; alloThr; or Hse; and/or P⁹ is Tyr; Phe; His; or Trp; and/or P¹¹ is Gly; Sar; Ser; Thr; alloThr; or Hse;
or a pharmaceutically acceptable salt thereof.

In another particular embodiment (50) of the invention the elements of general formula (I) are defined as follows, for module A,
if i=1, and P¹³ and P¹⁴, and P¹⁴ and P¹ are connected as aforementioned, and
P² and P¹¹ taken together may form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; to Dab; or Orn; by an urea linkage;

P¹ is Trp; Tyr; or Phe;

P² is Dab; Dap; Orn; Lys; Arg; Asn; or Gln;

P³ is tBuGly; Ala; Val; Abu; Leu; Ile; Nle; Nva; Tyr; Phe; Trp; or Phg;

P⁴ is Ala; Val; Abu; Leu; Ile; Nle; Nva; Dap; Dab; Orn; Lys; Arg; Ser; Thr; alloThr; Hse; Asn; or Gln;

P⁵ is Ser; Thr; alloThr; Hse; Val; Leu; Ile; Nle; Nva; Abu; Ala; Dab; Dap; Orn; Lys; or Arg;

T⁶ is ᴰPro; ᴰAzt; ᴰTic; ᴰAla; ᴰAbu; ᴰLeu; ᴰVal; ᴰNva; ᴰIle; ᴰNle; ᴰDab; ᴰDap; ᴰOrn; ᴰLys; or ᴰArg;

T⁷ is Pro; Pic; Oic; or Tic;

P⁸ is Nle; Val; Leu; Ile; Nva; Abu; Ala; Cpg; Cpa; Trp; Tyr; or Phe;

P⁹ is Gly; Sar; Ala; Abu; Leu; Nle; Ile; Val; Nva; Ser; Thr; alloThr; Hse; Dap; Dab; Orn; Lys; Arg; Asn; or Gln;

P¹⁰ is Tyr; Phe; Trp; Phg; tBuGly; Ala; Val; Abu; Leu; Ile; Nle; or Nva;

P¹¹ is Dab; Dap; Orn; Lys; or Arg;

P¹² is Gly; Sar; Ala; Nle; Val; Leu; Ile; Nva; Abu; Dab; Dap; Orn; Lys; Arg; Ser; Thr; alloThr; or Hse;

P¹³ is Gly; Sar; ᴰDab; ᴰDap; ᴰOrn; ᴰLys; ᴰArg; Dab; Dap; Orn; Lys; or Arg;

P¹⁴ is Gly; Sar; Dab; Dap; Orn; Lys; or Arg;

with the proviso that,
if linker L is connected with module A by a carbonyl (C=O) point of attachment
of P²; P⁵; P¹²; P¹³; or P¹⁴; then
P²; P⁵; P¹²; P¹³; or P¹⁴; is
Asp; Glu; ᴰAsp; or ᴰGlu;
or a pharmaceutically acceptable salt thereof.

In another particular embodiment (51) of the invention the elements of general formula (I) are defined as follows, for module A,
if i=1, and P¹⁴ and P¹, are not connected as aforementioned, and
P² and P¹¹ taken together and/or P⁴ and P⁹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;

P¹ is Trp; Tyr; Phe; NMeTrp; NMeTyr; NMePhe; Ac-Trp; Ac-Tyr; Ac-Phe; Gua-Trp; Gua-Tyr; Gua-Phe; TMG-Trp; TMG-Tyr; TMG-Phe; Ala; Val; Nva; Abu; Leu; Ile; Nle; NMeAla; NMeVal; NMeNva; NMeAbu; NMeLeu; NMeIle; NMeNle; Ac-Ala; Ac-Val; Ac-Nva; Ac-Abu; Ac-Leu; Ac-Ile; Ac-Nle; Gua-Ala; Gua-Val; Gua-Nva;

Gua-Abu; Gua-Leu; Gua-Ile; Gua-Nle; TMG-Ala; TMG-Val; TMG-Nva; TMG-Abu; TMG-Leu; TMG-Ile; or TMG-Nle;

$P^2$ is Dab; Dap; Orn; Lys; Arg; Asn; Gln; Ser; Thr; alloThr; Hse; Ala; Val; Nva; Abu; Leu; Ile; or Nle;

$P^3$ is tBuGly; Ala; Val; Abu; Leu; Ile; Nle; Nva; Tyr; Phe; Trp; or Phg;

$P^4$ is Gly; Sar; Ala; Val; Abu; Leu; Ile; Nle; Nva; Dap; Dab; Orn; Lys; Arg; Ser; Thr; alloThr; Hse; Asn; Gln; $^D$Ala; $^D$Val; $^D$Abu; $^D$Nva; $^D$Leu; $^D$Ile; $^D$Nle; Tyr; Phe; or Trp;

$P^5$ is Ser; Thr; alloThr; Hse; Val; Leu; Ile; Nle; Nva; Abu; Ala; Dab; Dap; Orn; Lys; Arg; Tyr; Phe; His; or Trp;

$T^6$ is $^D$Pro; $^D$Pro(4S)OH; $^D$Pro(3S)OH; $^D$Pic; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; $^D$Arg; $^D$Tyr; $^D$Phe; $^D$Trp; $^D$Ser; $^D$Thr; $^D$alloThr; or $^D$Hse;

$T^7$ is Pro; Hyp; Pro(4S)OH; Pro(3S)OH; Pro(4R)F; Pic; Oic; Tic; Ala; Val; Nva; Abu; Leu; Ile; or Nle; Tyr; Phe; Trp; Dab; Dap; Orn; Lys; Arg; Ser; Thr; alloThr; or Hse;

$P^8$ is Nle; Val; Leu; Ile; Nva; Abu; Ala; Cpg; Cpa; Trp; Tyr; Phe; Ser; Thr; alloThr; or Hse;

$P^9$ is Gly; Sar; Ala; Abu; Leu; Nle; Ile; Val; Nva; Ser; Thr; alloThr; Hse; Dap; Dab; Orn; Lys; Arg; Dap(iPr); Asn; Gln; Tyr; Phe; His; Trp; Asp; or Glu;

$P^{10}$ is Tyr; Phe; Trp; Phg; Cha; tBuGly; Ala; Val; Abu; Leu; Ile; Nle; or Nva;

$P^{11}$ is Gly; Sar; Dab; Dap; Orn; Lys; Arg; Asn; Gln; Ala; Val; Abu; Nva; Leu; Ile; Nle; Ser; Thr; alloThr; or Hse;

$P^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Dap; $^D$Orn; $^D$Lys; $^D$Arg; Ser; Thr; alloThr; Hse; $^D$Ser; $^D$Thr; $^D$alloThr; $^D$Hse; $^D$Tyr; $^D$Phe; $^D$Trp; Tyr; Phe; Trp; $^D$Glu; $^D$Asp; Glu; or Asp;

$P^{13}$ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$alloThr; $^D$Ser; $^D$Hse; Ala; Val; Abu; Nva; Leu; Ile; Nle; $^D$Ala; $^D$Abu; $^D$Leu; $^D$Val; $^D$Nva; $^D$Ile; or $^D$Nle; $^D$Tyr; $^D$Phe; $^D$Trp; Tyr; Phe; Trp; $^D$Gln; $^D$Asn; Gln; or Asn;

$P^{14}$ is Gly; Sar; Aib; Dab; Dap; Orn; Lys; Arg; $^D$Dab; $^D$Dap; $^D$Orn; $^D$Lys; $^D$Arg; Thr; alloThr; Ser; Hse; $^D$Thr; $^D$alloThr; $^D$Ser; $^D$Hse; $^D$Ala; $^D$Abu; $^D$Leu; $^D$Val; $^D$Nva; $^D$Ile; $^D$Nle; Ala; Abu; Leu; Ile; Nle; Val; Nva; Glu; Asp; Gln; Asn; $^D$Glu; $^D$Asp; $^D$Gln; or $^D$Asn;

with the proviso that,
if linker L is connected with module A by a carbonyl (C═O) point of attachment of $P^5$; $P^{12}$; or $P^{13}$; then $P^5$; $P^{12}$; or $P^{13}$; is
Asp; Glu; $^D$Asp; or $^D$Glu;
or a pharmaceutically acceptable salt thereof.

In another particular embodiment (52) of the invention the elements of general formula (I) are defined as in particular embodiment (51),
with the proviso that
$P^4$ and $P^9$ taken together form an interstrand linking bis (amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage; and/or $P^1$ is Ala; Val; Nva; Abu; Leu; Ile; Nle; NMeAla; NMeVal; NMeNva; NMeAbu; NMeLeu; NMeIle; or NMeNle; and/or $P^2$ is Ser; Thr; alloThr; Hse; Ala; Val; Nva; Abu; Leu; Ile; or Nle; and/or $P^4$ is Gly; Sar; $^D$Ala; $^D$Val; $^D$Abu; $^D$Nva; $^D$Leu; $^D$Ile; $^D$Nle; Tyr; Phe; or Trp; and/or $P^5$ is Tyr; Phe; His; or Trp; and/or $T^6$ is $^D$Pic; $^D$Tyr; $^D$Phe; $^D$Trp; $^D$Ser; $^D$Thr; $^D$alloThr; or $^D$Hse; and/or $T^7$ is Ala; Abu; Leu; Val; Nva; Ile; Nle; Tyr; Phe; Trp; Dab; Dap; Orn; Lys; Arg; Ser; Thr; alloThr; or Hse; and/or $P^8$ is Ser; Thr; alloThr; or Hse; and/or $P^9$ is Tyr; Phe; His; Trp; Asp; or Glu; and/or $P^{11}$ is Gly; Sar; Ala; Val; Abu; Nva; Leu; Ile; Nle; Ser; Thr; alloThr; or Hse; and/or $P^{12}$ is $^D$Tyr; $^D$Phe; $^D$Trp; Tyr; Phe; Trp; $^D$Glu; $^D$Asp; Glu; or Asp; and/or $P^{13}$ is $^D$Tyr; $^D$Phe; $^D$Trp; Tyr; Phe; Trp; $^D$Gln; $^D$Asn; Gln; or Asn;
or a pharmaceutically acceptable salt thereof.

In another particular embodiment (53) of the invention the elements of general formula (I) are defined as follows, for module A,
if i=1, and $P^{14}$ and $P^1$, are not connected as aforementioned, and
$P^2$ and $P^{11}$ taken together form an interstrand linking bis (amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;

$P^1$ is Trp; Tyr; Phe; Ac-Trp; Ac-Tyr; or Ac-Phe;

$P^3$ is tBuGly; Ala; Val; Abu; Leu; Ile; Nle; Nva; Tyr; Phe; Trp; or Phg;

$P^4$ is Ala; Val; Abu; Leu; Ile; Nle; Nva; Dap; Dab; Orn; Lys; Arg; Ser; Thr; alloThr; Hse; Asn; or Gln;

$P^5$ is Ser; Thr; alloThr; Hse; Val; Leu; Ile; Nle; Nva; Abu; Ala; Dab; Dap; Orn; Lys; or Arg;

$T^6$ is $^D$Pro; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; or $^D$Arg;

$T^7$ is Pro; Pic; Oic; or Tic;

$P^8$ is Nle; Val; Leu; Ile; Nva; Abu; Ala; Cpg; Cpa; Trp; Tyr; or Phe;

$P^9$ is Gly; Sar; Ala; Abu; Leu; Nle; Ile; Val; Nva; Ser; Thr; alloThr; Hse; Dap; Dab; Orn; Lys; Arg; Asn; or Gln;

$P^{10}$ is Tyr; Phe; Trp; Phg; tBuGly; Ala; Val; Abu; Leu; Ile; Nle; or Nva;

$P^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Dap; $^D$Orn; $^D$Lys; $^D$Arg; Ser; Thr; alloThr; Hse; $^D$Ser; $^D$Thr; $^D$alloThr; or $^D$Hse;

$P^{13}$ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$alloThr; $^D$Ser; $^D$Hse; Ala; Val; Abu; Nva; Leu; Ile; Nle; $^D$Ala; $^D$Abu; $^D$Leu; $^D$Val; $^D$Nva; $^D$Ile; or $^D$Nle;

$P^{14}$ is Gly; Sar; Aib; Dab; Dap; Orn; Lys; Arg; $^D$Dab; $^D$Dap; $^D$Orn; $^D$Lys; $^D$Arg; Thr; alloThr; Ser Hse; $^D$Thr; $^D$alloThr; $^D$Ser; $^D$Hse; $^D$Ala; $^D$Abu; $^D$Leu; $^D$Val; $^D$Nva; $^D$Ile; $^D$Nle;

Ala; Abu; Leu; Ile; Nle; Val; Nva; Glu; Asp; Gln; Asn; $^D$Glu; $^D$Asp; $^D$Gln; or $^D$Asn;

with the proviso that,
if linker L is connected with module A by a carbonyl (C=O) point of attachment of P$^5$; P$^{12}$; or P$^{13}$; then P$^5$; P$^{12}$; or P$^{13}$; is
Asp; Glu; $^D$Asp; or $^D$Glu;

or a pharmaceutically acceptable salt thereof.

In another particular embodiment (54) of the invention the elements of general formula (I) are defined as follows, for module A,
if i=1, and P$^{13}$ and P$^{14}$ are not connected as aforementioned, and
P$^2$ and P$^{11}$ taken together and/or P$^4$ and P$^9$ taken together form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;
P$^1$ is Trp; Tyr; Phe; NMeTrp; NMeTyr; NMePhe; Ala; Val; Nva; Abu; Leu; Ile; Nle; NMeAla; NMeVal; NMeNva; NMeAbu; NMeLeu; NMeIle; or NMeNle;
P$^2$ is Dab; Dap; Orn; Lys; Arg; Asn; Gln; Ser; Thr; alloThr; Hse; Ala; Val; Nva; Abu; Leu; Ile; or Nle;
P$^3$ is tBuGly; Ala; Val; Abu; Leu; Ile; Nle; Nva; Tyr; Phe; Trp; or Phg;
P$^4$ is Gly; Sar; Ala; Val; Abu; Leu; Ile; Nle; Nva; Dap; Dab; Orn; Lys; Arg; Ser; Thr; alloThr; Hse; Asn; Gln; $^D$Ala; $^D$Val; $^D$Abu; $^D$Nva; $^D$Leu; $^D$Ile; $^D$Nle; Tyr; Phe; or Trp;
P$^5$ is Ser; Thr; alloThr; Hse; Val; Leu; Ile; Nle; Nva; Abu; Ala; Dab; Dap; Orn; Lys; Arg; Tyr; Phe; His; or Trp;
T$^6$ is $^D$Pro; $^D$Pro(4S)OH; $^D$Pro(3S)OH; $^D$Pic; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; $^D$Arg; $^D$Tyr; $^D$Phe; $^D$Trp; $^D$Ser; $^D$Thr; $^D$alloThr; or $^D$Hse;
T$^7$ is Pro; Hyp; Pro(4S)OH; Pro(3S)OH; Pro(4R)F; Pic; Oic; Tic; Ala; Val; Nva; Abu; Leu; Ile; or Nle; Tyr; Phe; Trp; Dab; Dap; Orn; Lys; Arg; Ser; Thr; alloThr; or Hse;
P$^8$ is Nle; Val; Leu; Ile; Nva; Abu; Ala; Cpg; Cpa; Trp; Tyr; Phe; Ser; Thr; alloThr; or Hse;
P$^9$ is Gly; Sar; Ala; Abu; Leu; Nle; Ile; Val; Nva; Ser; Thr; alloThr; Hse; Dap; Dab; Orn; Lys; Arg; Dap(iPr); Asn; or Gln; Tyr; Phe; His; Trp; Glu; or Asp;
P$^{10}$ is Tyr; Phe; Trp; Phg; Cha; tBuGly; Ala; Val; Abu; Leu; Ile; Nle; or Nva;
P$^{11}$ is Gly; Sar; Dab; Dap; Orn; Lys; Arg; Asn; or Gln; Ala; Val; Nva; Abu; Leu; Ile; Nle; Ser; Thr; alloThr; or Hse;
P$^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Dap; $^D$Orn; $^D$Lys; $^D$Arg; Ser; Thr; alloThr; Hse; $^D$Ser; $^D$Thr; $^D$alloThr; or $^D$Hse; $^D$Tyr; $^D$Phe; $^D$Trp; Tyr; Phe; Trp; $^D$Glu; $^D$Asp; Glu; or Asp;
P$^{13}$ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$alloThr; $^D$Ser; $^D$Hse; Ala; Val; Abu; Nva; Leu; Ile; Nle; $^D$Ala; $^D$Abu; $^D$Leu; $^D$Val; $^D$Nva; $^D$Ile; $^D$Nle; $^D$Tyr; $^D$Phe; $^D$Trp; Tyr; Phe; Trp; $^D$Gln; $^D$Asn; Gln; or Asn;
P$^{14}$ is Gly; Sar; Aib; Dab; Dap; Orn; Lys; Arg; $^D$Dab; $^D$Dap; $^D$Orn; $^D$Lys; $^D$Arg; Thr; alloThr; Ser; Hse; $^D$Thr; $^D$alloThr; $^D$Ser; $^D$Hse; $^D$Ala; $^D$Abu; $^D$Leu; $^D$Val; $^D$Nva; $^D$Ile;

$^D$Nle; Ala; Abu; Leu; Ile; Nle; Val; Nva; Glu; Asp; Gln; Asn; $^D$Glu; $^D$Asp; $^D$Gln; $^D$Asn; Ac-Gly; Ac-Sar; Ac-Aib; Ac-Dab; Ac-Dap; Ac-Orn; Ac-Lys; Ac-Arg; Ac-$^D$Dab; Ac-$^D$Dap; Ac-$^D$Orn; Ac-$^D$Lys; Ac-$^D$Arg; Ac-Thr; Ac-alloThr; Ac-Ser; Ac-Hse; Ac-$^D$Thr; Ac-$^D$alloThr; Ac-$^D$Ser; Ac-$^D$Hse; Ac-$^D$Ala; Ac-$^D$Abu; Ac-$^D$Leu; Ac-$^D$Val; Ac-$^D$Nva; Ac-$^D$Ile; Ac-$^D$Nle; Ac-Ala; Ac-Abu; Ac-Leu; Ac-Ile; Ac-Nle; Ac-Val; Ac-Nva; Ac-Glu; Ac-Asp; Ac-Gln; Ac-Asn; Ac-$^D$Glu; Ac-$^D$Asp; Ac-$^D$Gln; or Ac-$^D$Asn; Gua-Gly; Gua-Sar; Gua-Aib; Gua-Dab; Gua-Dap; Gua-Orn; Gua-Lys; Gua-Arg; Gua-$^D$Dab; Gua-$^D$Dap; Gua-$^D$Orn; Gua-$^D$Lys; Gua-$^D$Arg; Gua-Thr; Gua-alloThr; Gua-Ser; Gua-Hse; Gua-$^D$Thr; Gua-$^D$alloThr; Gua-$^D$Ser; Gua-$^D$Hse; Gua-$^D$Ala; Gua-$^D$Abu; Gua-$^D$Leu; Gua-$^D$Val; Gua-$^D$Nva; Gua-$^D$Ile; Gua-$^D$Nle; Gua-Ala; Gua-Abu; Gua-Leu; Gua-Ile; Gua-Nle; Gua-Val; Gua-Nva; Gua-Glu; Gua-Asp; Gua-Gln; Gua-Asn; Gua-$^D$Glu; Gua-$^D$Asp; Gua-$^D$Gln; or Gua-$^D$Asn;

with the proviso that,
if linker L is connected with module A by a carbonyl (C=O) point of attachment of P$^5$; P$^{12}$; or P$^{14}$; then P$^5$; P$^{12}$; or P$^{14}$; is
Asp; Glu; $^D$Asp; or $^D$Glu;

or a pharmaceutically acceptable salt thereof.

In another particular embodiment (55) of the invention the elements of general formula (I) are defined as in particular embodiment (54),
with the proviso that
P$^4$ and P$^9$ taken together form an interstrand linking bis (amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage; and/or
P$^1$ is Ala; Val; Nva; Abu; Leu; Ile; Nle; NMeAla; NMeVal; NMeNva; NMeAbu; NMeLeu; NMeIle; or NMeNle; and/or
P$^2$ is Ser; Thr; alloThr; Hse; Ala; Val; Nva; Abu; Leu; Ile; or Nle; and/or
P$^4$ is Gly; Sar; $^D$Ala; $^D$Val; $^D$Abu; $^D$Nva; $^D$Leu; $^D$Ile; $^D$Nle; Tyr; Phe; or Trp; and/or
P$^5$ is Tyr; Phe; His; or Trp; and/or
T$^6$ is $^D$Pic; $^D$Tyr; $^D$Phe; $^D$Trp; $^D$Ser; $^D$Thr; $^D$alloThr; or $^D$Hse; and/or
T$^7$ is Ala; Abu; Leu; Val; Nva; Ile; Nle; Tyr; Phe; Trp; Dab; Dap; Orn; Lys; Arg; Ser; Thr; alloThr; or Hse; and/or
P$^8$ is Ser; Thr; alloThr; or Hse; and/or
P$^9$ is Tyr; Phe; His; or Trp; and/or
P$^{11}$ is Gly; Sar; Ala; Val; Nva; Abu; Leu; Ile; Nle; Thr; alloThr; or Hse; and/or
P$^{12}$ is $^D$Tyr; $^D$Phe; $^D$Trp; Tyr; Phe; Trp; $^D$Glu; $^D$Asp; Glu; or Asp; and/or
P$^{13}$ is $^D$Tyr; $^D$Phe; $^D$Trp; Tyr; Phe; Trp; $^D$Gln; $^D$Asn; Gln; or Asn;

or a pharmaceutically acceptable salt thereof.

In another particular embodiment (56) of the invention the elements of general formula (I) are defined as follows, for module A,
if i=1, and P$^{13}$ and P$^{14}$ are not connected as aforementioned, and P² and P¹¹ taken together form an interstrand linking bis (amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

P¹ is Trp; Tyr; or Phe;

P³ is tBuGly; Ala; Val; Abu; Leu; Ile; Nle; Nva; Tyr; Phe; Trp; or Phg;

P⁴ is Ala; Val; Abu; Leu; Ile; Nle; Nva; Dap; Dab; Orn; Lys; Arg; Ser; Thr; alloThr; Hse; Asn; or Gln;

P⁵ is Ser; Thr; alloThr; Hse; Val; Leu; Ile; Nle; Nva; Abu; Ala; Dab; Dap; Orn; Lys; or Arg;

T⁶ is ᴰPro; ᴰAzt; ᴰTic; ᴰAla; ᴰAbu; ᴰLeu; ᴰVal; ᴰNva; ᴰIle; ᴰNle; ᴰDab; ᴰDap; ᴰOrn; ᴰLys; or ᴰArg;

T⁷ is Pro; Pic; Oic; or Tic;

P⁸ is Nle; Val; Leu; Ile; Nva; Abu; Ala; Cpg; Cpa; Trp; Tyr; or Phe;

P⁹ is Gly; Sar; Ala; Abu; Leu; Nle; Ile; Val; Nva; Ser; Thr; alloThr; Hse; Dap; Dab; Orn; Lys; Arg; Asn; or Gln;

P¹⁰ is Tyr; Phe; Trp; Phg; tBuGly; Ala; Val; Abu; Leu; Ile; Nle; or Nva;

P¹² is Gly; Sar; Aib; Ala; Val; Abu; Nva; Leu; Ile; Nle; Dab; Dap; Orn; Lys; Arg; Dap(Glu); Dab(Arg); ᴰAla; ᴰVal; ᴰAbu; ᴰNva; ᴰLeu; ᴰIle; ᴰNle; ᴰDab; ᴰDap; ᴰOrn; ᴰLys; ᴰArg; Ser; Thr; alloThr; Hse; ᴰSer; ᴰThr; ᴰalloThr; or ᴰHse;

P¹³ is Gly; Sar; Aib; ᴰDab; ᴰDap; ᴰOrn; ᴰLys; ᴰArg; Dab; Dap; Orn; Lys; Arg; Thr; alloThr; Ser; Hse; ᴰThr; ᴰalloThr; ᴰSer; ᴰHse; Ala; Val; Abu; Nva; Leu; Ile; Nle; ᴰAla; ᴰAbu; ᴰLeu; ᴰVal; ᴰNva; ᴰIle; or ᴰNle;

P¹⁴ is Gly; Sar; Aib; Dab; Dap; Orn; Lys; Arg; ᴰDab; ᴰDap; ᴰOrn; ᴰLys; ᴰArg; Thr; alloThr; Ser; Hse; ᴰThr; ᴰalloThr; ᴰSer; ᴰHse; ᴰAla; ᴰAbu; ᴰLeu; ᴰVal; ᴰNva; ᴰIle; ᴰNle; Ala; Abu; Leu; Ile; Nle; Val; Nva; Glu; Asp; Gln; Asn; ᴰGlu; ᴰAsp; ᴰGln; ᴰAsn; Ac-Gly; Ac-Sar; Ac-Dab; Ac-Dab; Ac-Dap; Ac-Orn; Ac-Lys; Ac-Arg; Ac-ᴰDab; Ac-ᴰDap; Ac-ᴰOrn; Ac-ᴰLys; Ac-ᴰArg; Ac-Thr; Ac-alloThr; Ac-Ser; Ac-Hse; Ac-ᴰThr; Ac-ᴰalloThr; Ac-ᴰSer; Ac-ᴰHse; Ac-ᴰAla; Ac-ᴰAbu; Ac-ᴰLeu; Ac-ᴰVal; Ac-ᴰNva; Ac-ᴰIle; Ac-ᴰNle; Ac-Ala; Ac-Abu; Ac-Leu; Ac-Ile; Ac-Nle; Ac-Val; Ac-Nva; Ac-Glu; Ac-Asp; Ac-Gln; Ac-Asn; Ac-ᴰGlu; Ac-ᴰAsp; Ac-ᴰGln; or Ac-ᴰAsn;

with the proviso that, if linker L is connected with module A by a carbonyl (C=O) point of attachment of P⁵; P¹²; or P¹⁴; then P⁶; P¹²; or P¹⁴; is Asp; Glu; ᴰAsp; or ᴰGlu;

or a pharmaceutically acceptable salt thereof.

In another particular embodiment (57) of the invention the elements of general formula (I) are defined as follows, for module A, if i=0, and P² and P¹¹ taken together and/or P⁴ and P⁹ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

P¹ is Trp; Tyr; Phe; NMeTrp; NMeTyr; NMePhe; Ac-Trp; Ac-Tyr; Ac-Phe; Gua-Trp; Gua-Tyr; Gua-Phe; TMG-Trp; TMG-Tyr; TMG-Phe; Ala; Val; Nva; Abu; Leu; Ile; Nle; NMeAla; NMeVal; NMeNva; NMeAbu; NMeLeu; NMeIle; or NMeNle; Ac-Ala; Ac-Val; Ac-Nva; Ac-Abu; Ac-Leu; Ac-Ile; Ac-Nle; Gua-Ala; Gua-Val; Gua-Nva; Gua-Abu; Gua-Leu; Gua-Ile; Gua-Nle; TMG-Ala; TMG-Val; TMG-Nva; TMG-Abu; TMG-Leu; TMG-Ile; or TMG-Nle;

P² is Dab; Dap; Orn; Lys; Arg; Asn; Gln; Ser; Thr; alloThr; Hse; Ala; Val; Nva; Abu; Leu; Ile; or Nle;

P³ is tBuGly; Ala; Val; Abu; Leu; Ile; Nle; Nva; Tyr; Phe; Trp; or Phg;

P⁴ is Gly; Sar; Ala; Val; Abu; Leu; Ile; Nle; Nva; Dap; Dab; Orn; Lys; Arg; Ser; Thr; alloThr; Hse; Asn; Gln; ᴰAla; ᴰVal; ᴰAbu; ᴰNva; ᴰLeu; ᴰIle; ᴰNle; Tyr; Phe; or Trp;

P⁵ is Ser; Thr; alloThr; Hse; Val; Leu; Ile; Nle; Nva; Abu; Ala; Dab; Dap; Orn; Lys; Arg; Tyr; Phe; His; or Trp;

T⁶ is ᴰPro; ᴰPro(4S)OH; ᴰPro(3S)OH; ᴰPic; ᴰAzt; ᴰTic; ᴰAla; ᴰAbu; ᴰLeu; ᴰVal; ᴰNva; ᴰIle; ᴰNle; ᴰDab; ᴰDap; ᴰOrn; ᴰLys; ᴰArg; ᴰTyr; ᴰPhe; ᴰTrp; ᴰSer; ᴰThr; ᴰalloThr; or ᴰHse;

T⁷ is Pro; Hyp; Pro(4S)OH; Pro(3S)OH; Pro(4R)F; Pic; Oic; Tic; Ala; Val; Nva; Abu; Leu; Ile; or Nle; Tyr; Phe; Trp; Dab; Dap; Orn; Lys; Arg; Ser; Thr; alloThr; or Hse;

P⁸ is Nle; Val; Leu; Ile; Nva; Abu; Ala; Cpg; Cpa; Trp; Tyr; Phe; Ser; Thr; alloThr; or Hse;

P⁹ is Gly; Sar; Ala; Abu; Leu; Nle; Ile; Val; Nva; Ser; Thr; alloThr; Hse; Dap; Dab; Orn; Lys; Arg; Dap(iPr); Asn; Gln; Tyr; Phe; His; Trp; Glu; or Asp;

P¹⁰ is Tyr; Phe; Trp; Phg; Cha; tBuGly; Ala; Val; Abu; Leu; Ile; Nle; or Nva;

P¹¹ is Gly; Sar; Dab; Dap; Orn; Lys; Arg; Asn; Gln; Ala; Val; Nva; Abu; Leu; Ile; Nle; Ser; Thr; alloThr; or Hse;

P¹² is Gly; Sar; Aib; Ala; Val; Abu; Nva; Leu; Ile; Nle; Dab; Dap; Orn; Lys; Arg; Dap(Glu); Dab(Arg); ᴰAla; ᴰVal; ᴰAbu; ᴰNva; ᴰLeu; ᴰIle; ᴰNle; ᴰDab; ᴰDap; ᴰOrn; ᴰLys; ᴰArg; Ser; Thr; alloThr; Hse; ᴰSer; ᴰThr; ᴰalloThr; or ᴰHse; ᴰTyr; ᴰPhe; ᴰTrp; Tyr; Phe; Trp; ᴰGlu; ᴰAsp; Glu; or Asp;

P¹³ is Gly; Sar; Aib; ᴰDab; ᴰDap; ᴰOrn; ᴰLys; ᴰArg; Dab; Dap; Orn; Lys; Arg; Thr; alloThr; Ser; Hse; ᴰThr; ᴰalloThr; ᴰSer; ᴰHse; Ala; Val; Abu; Nva; Leu; Ile; Nle; ᴰAla; ᴰAbu; ᴰLeu; ᴰVal; ᴰNva; ᴰIle; or ᴰNle; ᴰTyr; ᴰPhe; ᴰTrp; Tyr; Phe; Trp; ᴰGln; ᴰAsn; Gln; or Asn;

with the proviso that, if linker L is connected with module A by a carbonyl (C=O) point of attachment of P⁵; or P¹²; then P⁵; or P¹²; is Asp; Glu; ᴰAsp; or ᴰGlu;

or a pharmaceutically acceptable salt thereof.

In another particular embodiment (58) of the invention the elements of general formula (I) are defined as in particular embodiment (57), with the proviso that P⁴ and P⁹ taken together form an interstrand linking bis (amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage; and/or $P^1$ is Ala; Val; Nva; Abu; Leu; Ile; Nle; NMeAla; NMeVal; NMeNva; NMeAbu; NMeLeu; NMeIle; or NMeNle; and/or $P^2$ is Ser; Thr; alloThr; Hse; Ala; Val; Nva; Abu; Leu; Ile; or Nle; and/or $P^4$ is Gly; Sar; $^D$Ala; $^D$Val; $^D$Abu; $^D$Nva; $^D$Leu; $^D$Ile; $^D$Nle; Tyr; Phe; or Trp; and/or $P^5$ is Tyr; Phe; His; or Trp; and/or $T^6$ is $^D$Pic; $^D$Tyr; $^D$Phe; $^D$Trp; $^D$Ser; $^D$Thr; $^D$alloThr; or $^D$Hse; and/or $T^7$ is Ala; Abu; Leu; Val; Nva; Ile; Nle; Tyr; Phe; Trp; Dab; Dap; Orn; Lys; Arg; Ser; Thr; alloThr; or Hse; and/or $P^8$ is Ser; Thr; alloThr; or Hse; and/or $P^9$ is Tyr; Phe; His; Trp; Glu; or Asp; and/or $P^{11}$ is Gly; Sar; Ala; Val; Nva; Abu; Leu; Ile; Nle; Ser; Thr; alloThr; or Hse; and/or $P^{12}$ is $^D$Tyr; $^D$Phe; $^D$Trp; Tyr; Phe; Trp; $^D$Glu; $^D$Asp; Glu; or Asp; and/or $P^{13}$ is $^D$Tyr; $^D$Phe; $^D$Trp; Tyr; Phe; Trp; $^D$Gln; $^D$Asn; Gln; or Asn;

or a pharmaceutically acceptable salt thereof.

In another particular embodiment (59) of the invention the elements of general formula (I) are defined as follows, for module A, if i=0, and $P^2$ and $P^{11}$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; Phe; Ac-Trp; Ac-Tyr; or Ac-Phe;

$P^3$ is tBuGly; Ala; Val; Abu; Leu; Ile; Nle; Nva; Tyr; Phe; Trp; or Phg;

$P^4$ is Ala; Val; Abu; Leu; Ile; Nle; Nva; Dap; Dab; Orn; Lys; Arg; Ser; Thr; alloThr; Hse; Asn; or Gln;

$P^5$ is Ser; Thr; alloThr; Hse; Val; Leu; Ile; Nle; Nva; Abu; Ala; Dab; Dap; Orn; Lys; or Arg;

$T^6$ is $^D$Pro; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; or $^D$Arg;

$T^7$ is Pro; Pic; Oic; or Tic;

$P^8$ is Nle; Val; Leu; Ile; Nva; Abu; Ala; Cpg; Cpa; Trp; Tyr; or Phe;

$P^9$ is Gly; Sar; Ala; Abu; Leu; Nle; Ile; Val; Nva; Ser; Thr; alloThr; Hse; Dap; Dab; Orn; Lys; Arg; Asn; or Gln;

$P^{10}$ is Tyr; Phe; Trp; Phg; tBuGly; Ala; Val; Abu; Leu; Ile; Nle; or Nva;

$P^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Dap; $^D$Orn; $^D$Lys; $^D$Arg; Ser; Thr; alloThr; Hse; $^D$Ser; $^D$Thr; $^D$alloThr; or $^D$Hse;

$P^{13}$ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$allo-Thr; $^D$Ser; $^D$Hse; Ala; Val; Abu; Nva; Leu; Ile; Nle; $^D$Ala; $^D$Abu; $^D$Leu; $^D$Val; $^D$Nva; $^D$Ile; or $^D$Nle;

with the proviso that, if linker L is connected with module A by a carbonyl (C=O) point of attachment of $P^5$; or $P^{12}$; then $P^5$; or $P^{12}$; is Asp; Glu; $^D$Asp; or $^D$Glu;

or a pharmaceutically acceptable salt thereof.

In another particular embodiment (60) of the invention the elements of general formula (I) are defined as follows, for module A, if i=1, and $P^{13}$ and $P^{14}$ are not connected as aforementioned, and $P^{13}$ and $P^{14}$ taken together form an interstrand linking bis(amino acid)-structure based on the linkage of two L amino acid residues; or two D amino acid residues; or an L amino acid residue with an D amino acid residue; following connection of the side chain of Cys; Hcy; or Pen; Cys-NH$_2$; Hcy-NH$_2$; or Pen-NH$_2$; of $P^{13}$ with the side chain of Cys; Hcy; or Pen; NMeCys; NMeHcy; or NMePen; Ac-Cys; Ac-Hcy; or Ac-Pen; Gua-Cys; Gua-Hcy; or Gua-Pen; TMG-Cys; TMG-Hcy; or TMG-Pen; of $P^{14}$ by a disulfide linkage; or connection of the side chain of Dap; Dab; Orn; or Lys; Dap-NH$_2$; Dab-NH$_2$; Orn-NH$_2$; or Lys-NH$_2$; of $P^{13}$ with the side chain of Asp; Glu; or hGlu; NMeAsp; NMeGlu; or NMehGlu; Ac-Asp; Ac-Glu; or Ac-hGlu; Gua-Asp; Gua-Glu; or Gua-hGlu; TMG-Asp; TMG-Glu; or TMG-hGlu; of $P^{14}$ by a lactam linkage; or connection of the side chain of Asp; Glu; or hGlu; Asp-NH$_2$; Glu-NH$_2$; or hGlu-NH$_2$; of $P^{13}$ with the side chain of Dap; Dab; Orn; or Lys; NMeDap; NMeDab; NMeOrn; or NMeLys; Ac-Dap; Ac-Dab; Ac-Orn; or Ac-Lys; Gua-Dap; Gua-Dab; Gua-Orn; or Gua-Lys; TMG-Dap; TMG-Dab; TMG-Orn; or TMG-Lys; of $P^{14}$ by a lactam linkage; and $P^2$ and $P^{11}$ taken together and/or $P^4$ and $P^9$ taken together may form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; Phe; NMeTrp; NMeTyr; NMePhe; Ala; Val; Nva; Abu; Leu; Ile; Nle; NMeAla; NMeVal; NMeNva; NMeAbu; NMeLeu; NMeIle; or NMeNle;

$P^2$ is Dab; Dap; Orn; Lys; Arg; Asn; or Gln; Ser; Thr; alloThr; Hse; Ala; Val; Nva; Abu; Leu; Ile; or Nle;

$P^3$ is tBuGly; Ala; Val; Abu; Leu; Ile; Nle; Nva; Tyr; Phe; Trp; or Phg;

$P^4$ is Gly; Sar; Ala; Val; Abu; Leu; Ile; Nle; Nva; Dap; Dab; Orn; Lys; Arg; Ser; Thr; alloThr; Hse; Asn; Gln; $^D$Ala; $^D$Val; $^D$Abu; $^D$Nva; $^D$Leu; $^D$Ile; $^D$Nle; Tyr; Phe; or Trp;

$P^5$ is Ser; Thr; alloThr; Hse; Val; Leu; Ile; Nle; Nva; Abu; Ala; Dab; Dap; Orn; Lys; Arg; Tyr; Phe; His; or Trp;

$T^6$ is $^D$Pro; $^D$Pro(4S)OH; $^D$Pro(3S)OH; $^D$Pic; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; $^D$Arg; $^D$Tyr; $^D$Phe; $^D$Trp; $^D$Ser; $^D$Thr; $^D$alloThr; or $^D$Hse;

T$^7$ is Pro; Hyp; Pro(4S)OH; Pro(3S)OH; Pro(4R)F; Pic; Oic; Tic; Ala; Val; Nva; Abu; Leu; Ile; or Nle; Tyr; Phe; Trp; Dab; Dap; Orn; Lys; Arg; Ser; Thr; alloThr; or Hse;

P$^8$ is Nle; Val; Leu; Ile; Nva; Abu; Ala; Cpg; Cpa; Trp; Tyr; Phe; Ser; Thr; alloThr; or Hse;

P$^9$ is Gly; Sar; Ala; Abu; Leu; Nle; Ile; Val; Nva; Ser; Thr; alloThr; Hse; Dap; Dab; Orn; Lys; Arg; Dap(iPr); Asn; Gln; Tyr; Phe; His; Trp; Glu; or Asp;

P$^{10}$ is Tyr; Phe; Trp; Phg; Cha; tBuGly; Ala; Val; Abu; Leu; Ile; Nle; or Nva;

P$^{11}$ is Gly; Sar; Dab; Dap; Orn; Lys; Arg; Asn; Gln; Ala; Abu; Leu; Val; Nva; Ile; Nle; Ser; Thr; alloThr; or Hse;

P$^{12}$ is Gly; Sar; Dab; Dap; Orn; Lys; Arg; $^D$Dab; $^D$Dap; $^D$Orn; $^D$Lys; $^D$Arg; Val; Leu; Ile; Nle; Nva; Abu; Ala; $^D$Val; $^D$Leu; $^D$Ile; $^D$Nle; $^D$Nva; $^D$Abu; $^D$Ala; Ser; Thr; alloThr; Hse; $^D$Ser; $^D$Thr; $^D$alloThr; $^D$Hse; $^D$Tyr; $^D$Phe; $^D$Trp; Tyr; Phe; Trp; $^D$Glu; $^D$Asp; Glu; or Asp;

with the proviso that, if linker L is connected with module A by a carbonyl (C=O) point of attachment of P$^2$; P$^5$; or P$^{12}$; then P$^2$; P$^5$; or P$^{12}$; is Asp; Glu; $^D$Asp; or $^D$Glu;

or a pharmaceutically acceptable salt thereof.

In another particular embodiment (61) of the invention the elements of general formula (I) are defined as in particular embodiment (60), with the proviso that P$^4$ and P$^9$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage; and/or P$^1$ is Ala; Val; Nva; Abu; Leu; Ile; Nle; NMeAla; NMeVal; NMeNva; NMeAbu; NMeLeu; NMeIle; or NMeNle; and/or P$^2$ is Ser; Thr; alloThr; Hse; Ala; Val; Nva; Abu; Leu; Ile; or Nle; and/or P$^4$ is Gly; Sar; $^D$Ala; $^D$Val; $^D$Abu; $^D$Nva; $^D$Leu; $^D$Ile; $^D$Nle; Tyr; Phe; or Trp; and/or P$^5$ is Tyr; Phe; His; or Trp; and/or T$^6$ is $^D$Pic; $^D$Tyr; $^D$Phe; $^D$Trp; $^D$Ser; $^D$Thr; $^D$alloThr; or $^D$Hse; and/or T$^7$ is Ala; Abu; Leu; Val; Nva; Ile; Nle; Tyr; Phe; Trp; Dab; Dap; Orn; Lys; Arg; Ser; Thr; alloThr; or Hse; and/or P$^8$ is Ser; Thr; alloThr; or Hse; and/or P$^9$ is Tyr; Phe; His; Trp; Glu; or Asp; and/or P$^{11}$ is Gly; Sar; Ala; Abu; Leu; Val; Nva; Ile; Nle; Ser; Thr; alloThr; or Hse; and/or P$^{12}$ is $^D$Tyr; $_D$Phe; $^D$Trp; Tyr; Phe; Trp; $^D$Glu; $^D$Asp; Glu; or Asp;

or a pharmaceutically acceptable salt thereof.

In another particular embodiment (62) of the invention the elements of general formula (I) are defined as follows, for module A, if i=1, and P$^{13}$ and P$^{14}$ are not connected as aforementioned, and P$^{13}$ and P$^{14}$ taken together form an interstrand linking bis(amino acid)-structure based on the linkage of two L amino acid residues; or two D amino acid residues; or an L amino acid residue with an D amino acid residue; following connection of the side chain of Cys; Hcy; or Pen; of P$^{13}$ with the side chain of Cys; Hcy; or Pen; Ac-Cys; Ac-Hcy; or Ac-Pen; of P$^{14}$ by a disulfide linkage; or connection of the side chain of Dap; Dab; Orn; or Lys; of P$^{13}$ with the side chain of Asp; Glu; hGlu; Ac-Asp; Ac-Glu; or Ac-hGlu; of P$^{14}$ by a lactam linkage; or connection of the side chain of Asp; Glu; or hGlu; of P$^{13}$ with the side chain of Dap; Dab; Orn; Lys; or Ac-Dap; Ac-Dab; Ac-Orn; or Ac-Lys; of P$^{14}$ by a lactam linkage; and P$^2$ and P$^{11}$ taken together may form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

P$^1$ is Trp; Tyr; or Phe;

P$^2$ is Dab; Dap; Orn; Lys; Arg; Asn; or Gln;

P$^3$ is tBuGly; Ala; Val; Abu; Leu; Ile; Nle; Nva; Tyr; Phe; Trp; or Phg;

P$^4$ is Ala; Val; Abu; Leu; Ile; Nle; Nva; Dap; Dab; Orn; Lys; Arg; Ser; Thr; alloThr; Hse; Asn; or Gln;

P$^5$ is Ser; Thr; alloThr; Hse; Val; Leu; Ile; Nle; Nva; Abu; Ala; Dab; Dap; Orn; Lys; or Arg;

T$^6$ is $^D$Pro; $^D$Azt; $^D$Tic; $^D$Ala; $^D$Abu; $^D$Leu; $^D$Val; $^D$Nva; $^D$Ile; $^D$Nle; $^D$Dab; $^D$Dap; $^D$Orn; $^D$Lys; or $^D$Arg;

T$^7$ is Pro; Pic; Oic; or Tic;

P$^8$ is Nle; Val; Leu; Ile; Nva; Abu; Ala; Cpg; Cpa; Trp; Tyr; or Phe;

P$^9$ is Gly; Sar; Ala; Abu; Leu; Nle; Ile; Val; Nva; Ser; Thr; alloThr; Hse; Dap; Dab; Orn; Lys; Arg; Asn; or Gln;

P$^{10}$ is Tyr; Phe; Trp; Phg; tBuGly; Ala; Val; Abu; Leu; Ile; Nle; or Nva;

P$^{11}$ is Dab; Dap; Orn; Lys; Arg; Asn; or Gln;

P$^{12}$ is Dab; Dap; Orn; Lys; Arg; Ser; Thr; alloThr; or Hse;

with the proviso that, if linker L is connected with module A by a carbonyl (C=O) point of attachment of P$^2$; P$^5$; or P$^{12}$; then P$^2$; P$^5$; or P$^{12}$; is Asp; Glu; $^D$Asp; or $^D$Glu;

or a pharmaceutically acceptable salt thereof.

In another particular embodiment (63) of the invention the elements of general formula (I) are defined as follows, for module A, if i=1, and P$^{13}$ and P$^{14}$, and P$^{14}$ and P$^1$are connected as aforementioned, and P$^2$ and P$^{11}$ taken together and/or P$^4$ and P$^9$ taken together may form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; Phe; NMeTrp; NMeTyr; NMePhe; Ala; Val; Nva; Abu; Leu; Ile; or Nle;

$P^2$ is Ser; Thr; alloThr; Hse; Dab; Dap; Orn; Lys; or Arg;

$P^3$ is tBuGly; Ala; Val; Abu; Leu; Ile; Nle; Nva; Tyr; Phe; Trp; or Phg;

$P^4$ is Ala; Val; Abu; Leu; Nle; Nva; Dap; Dab; Orn; Lys; Arg; Thr; Ser; alloThr; or Hse; Tyr; Phe; or Trp;

$P^5$ is Ser; Thr; alloThr; Hse; Val; Leu; Ile; Nle; Nva; Abu; Ala; Tyr; Phe; His; or Trp;

$T^6$ is $^D$Pro; $^D$Pro(4S)OH; $^D$Pic; $^D$Azt; $^D$Dab; $^D$Ala; $^D$Abu; $^D$Leu; $^D$Val; $^D$Nva; $^D$Ile; $^D$Nle; $^D$Dap; $^D$Orn; $^D$Lys; or $^D$Arg;

$T^7$ is Pro; Hyp; Pro(3S)OH; Pro(4R)F; Dab; Dap; Orn; Lys; or Arg;

$P^8$ is Nle; Val; Leu; Ile; Nva; Abu; Ala; Cpg; or Cpa;

$P^9$ is Gly; Ser; Thr; alloThr; Hse; Ala; Dap; Dab; Orn; Lys; Arg; or Dap(iPr)

$P^{10}$ is Tyr; Phe; Trp; or Phg;

$P^{11}$ is Gly; Ser; Thr; alloThr; Hse; Dab; Dap; Orn; Lys; or Arg;

$P^{12}$ is Gly; Dab; Dap; Orn; Lys; or Arg;

$P^{13}$ is Gly; $^D$Dab; $^D$Dap; $^D$Orn; $^D$Lys; or $^D$Arg; $^D$Ser; $^D$Thr; $^D$alloThr; or $^D$Hse;

$P^{14}$ is Dab; Dap; Orn; Lys; or Arg;

with the proviso that, if linker L is connected with module A by a carbonyl (C=O) point of attachment of $P^2$; $P^5$; $P^{12}$; $P^{13}$; or $P^{14}$; then $P^2$; $P^5$; $P^{12}$; $P^{13}$; or $P^{14}$; is Asp; Glu; $^D$Asp; or $^D$Glu;

or a pharmaceutically acceptable salt thereof.

In another particular embodiment (64) of the invention the elements of general formula (I) are defined as in particular embodiment (63), with the proviso that $P^4$ and $P^9$ taken together form an interstrand linking bis (amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage; and/or $P^1$ is Ala; Val; Nva; Abu; Leu; Ile; or Nle; and/or $P^2$ is Ser; Thr; alloThr; Hse; and/or $P^4$ is Tyr; Phe; or Trp; and/or $P^5$ is Tyr; Phe; His; or Trp; and/or $T^6$ is $^D$Pic; and/or $T^7$ is Dab; Dap; Orn; Lys; or Arg; and/or $P^{11}$ is Ser; Thr; alloThr; Hse;

or a pharmaceutically acceptable salt thereof.

In another particular embodiment (65) of the invention the elements of general formula (I) are defined as follows, for module A, if i=1, and $P^{13}$ and $P^{14}$, and $P^{14}$ and $P^1$ are connected as aforementioned, and $P^2$ and $P^{11}$ taken together may form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; or Phe;

$P^2$ is Dab; Dap; Orn; Lys; or Arg;

$P^3$ is tBuGly; Ala; Val; Abu; Leu; Ile; Nle; or Nva;

$P^4$ is Ala; Val; Abu; Leu; Nle; Nva; Dap; Dab; Thr; or Ser;

$P^5$ is Ser; Thr; alloThr; Hse; or Val;

$T^6$ is $^D$Pro; $^D$Dab; or $^D$Ala;

$T^7$ is Pro;

$P^8$ is Nle; Val; Leu; Ile; Nva; Abu; Ala; Cpg; or Cpa;

$P^9$ is Gly; Ser; Thr; alloThr; Hse; Ala; Dap; or Dab;

$P^{10}$ is Tyr; Phe; Trp; or Phg;

$P^{11}$ is Dab; Dap; Orn; Lys; or Arg;

$P^{12}$ is Dab; Dap; Orn; Lys; or Arg;

$P^{13}$ is $^D$Dab; $^D$Dap; $^D$Orn; $^D$Lys; or $^D$Arg;

$P^{14}$ is Dab; Dap; Orn; Lys; or Arg;

with the proviso that, if linker L is connected with module A by a carbonyl (C=O) point of attachment of $P^2$; $P^6$; $P^{12}$; $P^{13}$; or $P^{14}$; then $P^2$; $P^5$; $P^{12}$; $P^{13}$; or $P^{14}$; is Asp; Glu; $^D$Asp; or $^D$Glu;

or a pharmaceutically acceptable salt thereof.

In another particular embodiment (66) of the invention the elements of general formula (I) are defined as follows, for module A, if i=1, and $P^{14}$ and $P^1$, are not connected as aforementioned, and $P^2$ and $P^{11}$ taken together and/or $P^4$ and $P^9$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; Phe; NMeTrp; NMeTyr; NMePhe; Ac-Trp; Ac-Tyr; Ac-Phe; Gua-Trp; Gua-Tyr; Gua-Phe; TMG-Trp; TMG-Tyr; TMG-Phe; Ala; Abu; Leu; Val; Nva; Ile; Nle; Ac-Ala; Ac-Abu; Ac-Leu; Ac-Val; Ac-Nva; Ac-Ile; or Ac-Nle;

$P^2$ is Dab; Dap; Orn; Lys; Arg; Ser; Thr; alloThr; Hse; Ala; Val; Nva; Abu; Leu; Ile; or Nle;

$P^3$ is tBuGly; Ala; Val; Abu; Leu; Ile; Nle; Nva; Trp; Tyr; or Phe;

$P^4$ is Ala; Val; Abu; Leu; Ile; Nle; Nva; Dap; Dab; Orn; Lys; Arg; Ser; Thr; alloThr; or Hse; Tyr; Phe; or Trp;

$P^5$ is Ser; Thr; alloThr; Hse; Val; Leu; Ile; Nle; Nva; Abu; Ala; Dab; Dap; Orn; Lys; or Arg; Tyr; Phe; His; or Trp;

$T^6$ is Gly; $^D$Pro; $^D$Pic; $^D$Azt; $^D$Pro(4S)OH; $^D$Ala; $^D$Abu; $^D$Leu; $^D$Val; $^D$Nva; $^D$Ile; $^D$Nle; $^D$Dab $^D$Dap; $^D$Orn; $^D$Lys; $^D$Arg; $^D$Tyr; $^D$Phe; $^D$Trp; $^D$Ser; $^D$Thr; $^D$alloThr; or $^D$Hse;

$T^7$ is Pro; Hyp; Pro(4R)F; Ala; Val; Nva; Abu; Leu; Ile; or Nle; Tyr; Phe; Trp; Dab; Dap; Orn; Lys; Arg; Ser; Thr; alloThr; or Hse;

$P^8$ is Nle; Val; Leu; Ile; Nva; Abu; Ala; Cpg; or Cpa; Trp; Tyr; Phe; Ser; Thr; alloThr; or Hse;

P⁹ is Gly; Sar; Ala; Abu; Leu; Nle; Ile; Val; Nva; Ser; Thr; alloThr; or Hse; Dap; Dab; Orn; Lys; Arg; Dap(iPr); Tyr; Phe; His; Trp; Glu; or Asp;

P¹⁰ is Tyr; Phe; Trp; Phg; tBuGly; Ala; Val; Abu; Leu; Ile; Nle; Nva or Cha;

P¹¹ is Dab; Dap; Orn; Lys; Arg; Asn; or Gln; Ala; Val; Nva; Abu; Leu; Ile; or Nle;

P¹² is Gly; Sar; Aib; Ala; Val; Abu; Nva; Leu; Ile; Nle; Dab; Dap; Orn; Lys; Arg; Dap(Glu); Dab(Arg); ᴰAla; ᴰVal; ᴰAbu; ᴰNva; ᴰLeu; ᴰIle; ᴰNle; ᴰDab; ᴰOrn; or ᴰDap; ᴰLys; ᴰArg; Ser; Thr; alloThr; Hse; ᴰSer; ᴰThr; ᴰalloThr; ᴰHse; Tyr; Phe; Trp; ᴰTyr; ᴰPhe; ᴰTrp; Glu; Asp; ᴰGlu; or ᴰAsp;

P¹³ is Gly; Sar; Aib; Dab; Dap; Orn; Lys; Arg; Thr; alloThr; Ser; Hse; Ala; Val; Abu; Nva; Leu; Ile; Nle; ᴰAla; ᴰAbu; ᴰLeu; ᴰVal; ᴰNva; ᴰIle; ᴰNle; ᴰDab; ᴰOrn; ᴰDap; ᴰLys; ᴰArg; ᴰThr; ᴰalloThr; ᴰSer; ᴰHse; Tyr; Phe; Trp; ᴰTyr; ᴰPhe; or ᴰTrp;

P¹³ is Gly; Sar; Aib; Dab; Dap; Orn; Lys; Arg; Thr; alloThr; Ser Hse; ᴰAla; ᴰAbu; ᴰLeu; ᴰVal; ᴰNva; ᴰIle; ᴰNle; Ala; Abu; Leu; Ile; Nle; Val; Nva; ᴰDab; ᴰOrn; ᴰDap; ᴰLys; ᴰArg; ᴰSer; ᴰThr; ᴰalloThr; or ᴰHse;

with the proviso that,
if linker L is connected with module A by a carbonyl (C=O) point of attachment of P⁵; P¹²; or P¹³; then P⁵; P¹²; or P¹³; is
Asp; Glu; ᴰAsp; or ᴰGlu;

or a pharmaceutically acceptable salt thereof.

In another particular embodiment (67) of the invention the elements of general formula (I) are defined as in particular embodiment (66),
with the proviso that
P⁴ and P⁹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage; and/or P¹ is Ala; Val; Nva; Abu; Leu; Ile; or Nle; and/or
P² is Ser; Thr; alloThr; Hse; Ala; Val; Nva; Abu; Leu; Ile; or Nle; and/or
P⁴ is Gly; ᴰAla; ᴰVal; ᴰAbu; ᴰNva; ᴰLeu; ᴰIle; ᴰNle; Tyr; Phe; or Trp; and/or
P⁵ is Tyr; Phe; His; or Trp; and/or
T⁶ is Gly; ᴰPic; ᴰTyr; ᴰPhe; ᴰTrp; ᴰSer; ᴰThr; ᴰalloThr; or ᴰHse; and/or
T⁷ is Ala; Abu; Leu; Val; Nva; Ile; Nle; Tyr; Phe; Trp; Dab; Dap; Orn; Lys; Arg; Ser; Thr; alloThr; or Hse; and/or
P⁸ is Ser; Thr; alloThr; or Hse; and/or
P⁹ is Tyr; Phe; His; Trp; Glu; or Asp; and/or
P¹¹ is Ala; Val; Nva; Abu; Leu; Ile; or Nle; and/or
P¹² is Tyr; Phe; Trp; ᴰTyr; ᴰPhe; ᴰTrp; Glu; Asp; ᴰGlu; or ᴰAsp; and/or
P¹³ is ᴰTyr; ᴰPhe; ᴰTrp; Tyr; Phe; or Trp;

or a pharmaceutically acceptable salt thereof.

In another particular embodiment (68) of the invention the elements of general formula (I) are defined as follows,
for module A,
if i=1, and P¹⁴ and P¹, are not connected as aforementioned, and P² and P¹¹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;

P¹ is Trp; Tyr; Phe; Ac-Trp; Ac-Tyr; or Ac-Phe;
P³ is tBuGly; Ala; Val; Abu; Leu; Ile; Nle; or Nva;
P⁴ is Ala; Val; Abu; Leu; Ile; Nle; Nva; Dap; Dab; Orn; Lys; Arg; Ser; Thr; alloThr; or Hse;
P⁵ is Ser; Thr; alloThr; or Hse;
T⁶ is ᴰPro; or ᴰAla; ᴰAbu; ᴰLeu; ᴰVal; ᴰNva; ᴰIle; ᴰNle; ᴰDab; or ᴰDap;
T⁷ is Pro;
P⁸ is Nle; Val; Leu; Ile; Nva; Abu; Ala; Cpg; or Cpa;
P⁹ is Gly; Sar; Ala; Abu; Leu; Nle; Ile; Val; Nva; Ser; Thr; alloThr; or Hse;
P¹⁰ is Tyr; Phe; Trp; or Phg
P¹² is Gly; Sar; Aib; Ala; Val; Abu; Nva; Leu; Ile; Nle; Dab; Dap; Orn; Lys; Arg; Dap(Glu); Dab(Arg); ᴰAla; ᴰVal; ᴰAbu; ᴰNva; ᴰLeu; ᴰIle; ᴰNle; ᴰDab; ᴰOrn; or ᴰDap;
P¹³ is Gly; Sar; Aib; Dab; Dap; Orn; Lys; Arg; Thr; alloThr; Ser; Hse; Ala; Val; Abu; Nva; Leu; Ile; Nle; ᴰAla; ᴰAbu; ᴰLeu; ᴰVal; ᴰNva; ᴰIle; ᴰNle; ᴰDab; ᴰOrn; or ᴰDap;
P¹⁴ is Gly; Sar; Aib; Dab; Dap; Orn; Lys; Arg; Thr; alloThr; Ser Hse; ᴰAla; ᴰAbu; ᴰLeu; ᴰVal; ᴰNva; ᴰIle; ᴰNle; Ala; Abu; Leu; Ile; Nle; Val; Nva; ᴰDab; ᴰOrn; or ᴰDap;

with the proviso that,
if linker L is connected with module A by a carbonyl (C=O) point of attachment of P⁵; P¹²; or P¹³; then P⁵; P¹²; or P¹³; is
Asp; Glu; ᴰAsp; or ᴰGlu;

or a pharmaceutically acceptable salt thereof.

In another particular embodiment (69) of the invention the elements of general formula (I) are defined as follows,
for module A,
if i=1, and P¹³ and P¹⁴ are not connected as aforementioned, and P² and P¹¹ taken together and/or P⁴ and P⁹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;

P¹ is Trp; Tyr; Phe; NMeTrp; NMeTyr; NMePhe; Ala; Val; Nva; Abu; Leu; Ile; or Nle;
P² is Dab; Dap; Orn; Lys; Arg; Asn; Gln; Ser; Thr; alloThr; Hse; Ala; Val; Nva; Abu; Leu; Ile; or Nle;
P³ is tBuGly; Ala; Val; Abu; Leu; Ile; Nle; or Nva;
P⁴ is Ala; Val; Abu; Leu; Nle; Nva; Dap; Dab; Thr; or Ser;
P⁵ is Ser; Thr; alloThr; Hse; or Val; Leu; Ile; Nle; Nva; Abu; Ala; Dab; Dap; Orn; Lys; Arg; Tyr; Phe; His; or Trp;
T⁶ is ᴰPro; ᴰAzt; ᴰPic; ᴰPro(4S)OH; ᴰDab; or ᴰAla;
T⁷ is Pro; Hyp; or Pro(4R)F;
P⁸ is Nle; Val; Leu; Ile; Nva; Abu; Ala; Cpg; or Cpa;

P⁹ is Gly; Ser; Thr; alloThr; Hse; Ala; Dap; or Dab;
P¹⁰ is Tyr; Phe; Trp; Cha; or Phg;
P¹¹ is Gly; Sar; Dab; Dap; Orn; Lys; Arg; Asn; or Gln;
P¹² is Gly; Sar; Dab; Dap; Orn; Lys; Arg; Dap(Glu); Dab(Arg); $^D$Dab; $^D$Orn; $^D$Dap; $^D$Lys; or $^D$Arg;
P¹³ is Gly; Sar; Dab; Dap; Orn; Lys; Arg; Thr; alloThr; Ser; Hse; $^D$Dab; $^D$Orn; or $^D$Dap; $^D$Lys; $^D$Arg; $^D$Thr; $^D$alloThr; $^D$Ser; or $^D$Hse;
P¹⁴ is Gly; Sar; Aib; $^D$Dab; $^D$Dap; $^D$Orn; $^D$Lys; $^D$Arg; Dab; Dap; Orn; Lys; Arg; $^D$Thr; $^D$alloThr; $^D$Ser; $^D$Hse; Thr; alloThr; Ser; Hse; $^D$Ala; $^D$Abu; $^D$Leu; $^D$Val; $^D$Nva; $^D$Ile; $^D$Nle; Ala; Abu; Leu; Ile; Nle; Val; Nva; $^D$Glu; $^D$Asp; Glu; Asp; $^D$Gln; $^D$Asn; Gln; or Asn;
  Ac-Gly; Ac-Sar; Ac-Aib; Ac-$^D$Dab; Ac-$^D$Dap; Ac-$^D$Orn; Ac-$^D$Lys; Ac-$^D$Arg; Ac-Dab; Ac-Dap; Ac-Orn; Ac-Lys Ac-Arg; Ac-Thr; Ac-alloThr; Ac-Ser; Ac-Hse; Ac-$^D$Ala; Ac-$^D$Abu; Ac-$^D$Leu; Ac-$^D$Val; Ac-$^D$Nva; Ac-$^D$Ile; Ac-$^D$Nle; Ac-Ala; Ac-Abu; Ac-Leu; Ac-Ile; Ac-Nle; Ac-Val; Ac-Nva; Ac-$^D$Glu; Ac-$^D$Asp; Ac-Glu; Ac-Asp; Ac-$^D$Gln; Ac-$^D$Asn Ac-Gln; or Ac-Asn; Gua-Gly; Gua-Sar; Gua-Aib; Gua-$^D$Dab; Gua-$^D$Dap; Gua-$^D$Orn; Gua-$^D$Lys; Gua-$^D$Arg; Gua-Dab; Gua-Dap; Gua-Orn; Gua-Lys Gua-Arg; Gua-Thr; Gua-alloThr; Gua-Ser; Gua-Hse; Gua-$^D$Ala; Gua-$^D$Abu; Gua-$^D$Leu; Gua-$^D$Val; Gua-$^D$Nva; Gua-$^D$Ile; Gua-$^D$Nle; Gua-Ala; Gua-Abu; Gua-Leu; Gua-Ile; Gua-Nle; Gua-Val; Gua-Nva; Gua-$^D$Glu; Gua-$^D$Asp; Gua-Glu; Gua-Asp; Gua-$^D$Gln; Gua-$^D$Asn Gua-Gln; or Gua-Asn;
with the proviso that,
  if linker L is connected with module A by a carbonyl (C=O) point of attachment of P⁵; P¹²; or P¹⁴; then P⁵; P¹²; or P¹⁴; is
  Asp; Glu; $^D$Asp; or $^D$Glu;
or a pharmaceutically acceptable salt thereof.

In another particular embodiment (70) of the invention the elements of general formula (I) are defined as in particular embodiment (69),
with the proviso that
P⁴ and P⁹ taken together form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage; and/or
P¹ is Ala; Val; Nva; Abu; Leu; Ile; or Nle; and/or
P² is Ser; Thr; alloThr; Hse; Ala; Val; Nva; Abu; Leu; Ile; or Nle; and/or
P⁵ is Tyr; Phe; His; or Trp; and/or
T⁶ is $^D$Pic; and/or
P¹¹ is Gly; or Sar;
or a pharmaceutically acceptable salt thereof.

In another particular embodiment (71) of the invention the elements of general formula (I) are defined as follows,
for module A,
if i=1, and P¹³ and P¹⁴ are not connected as aforementioned, and
P² and P¹¹ taken together form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;
P¹ is Trp; Tyr; or Phe;
P³ is tBuGly; Ala; Val; Abu; Leu; Ile; Nle; or Nva;
P⁴ is Ala; Val; Abu; Leu; Nle; Nva; Dap; Dab; Thr; or Ser;
P⁵ is Ser; Thr; alloThr; Hse; or Val;
T⁶ is $^D$Pro; $^D$Dab; or $^D$Ala;
T⁷ is Pro;
P⁸ is Nle; Val; Leu; Ile; Nva; Abu; Ala; Cpg; or Cpa;
P⁹ is Gly; Ser; Thr; alloThr; Hse; Ala; Dap; or Dab;
P¹⁰ is Tyr; Phe; Trp; or Phg;
P¹² is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Orn; or $^D$Dap;
P¹³ is Gly; Sar; Aib; Dab; Dap; Orn; Lys; Arg; Thr; alloThr; Ser; Hse; Ala; Val; Abu; Nva; Leu; Ile; Nle; $^D$Ala; $^D$Abu; $^D$Leu; $^D$Val; $^D$Nva; $^D$Ile; $^D$Nle; $^D$Dab; $^D$Orn; or $^D$Dap;
P¹⁴ is Gly; Sar; Aib; Dab; Dap; Orn; Lys; Arg; Thr; alloThr; Ser; Hse; $^D$Ala; $^D$Abu; $^D$Leu; $^D$Val; $^D$Nva; $^D$Ile; $^D$Nle; Ala; Abu; Leu; Ile; Nle; Val; Nva; Glu; Asp; Gln; or Asn;
  Ac-Gly; Ac-Sar; Ac-Aib; Ac-Dab; Ac-Dap; Ac-Orn; Ac-Lys Ac-Arg; Ac-Thr; Ac-alloThr; Ac-Ser; Ac-Hse; Ac-$^D$Ala; Ac-$^D$Abu; Ac-$^D$Leu; Ac-$^D$Val; Ac-$^D$Nva; Ac-$^D$Ile; Ac-$^D$Nle; Ac-Ala; Ac-Abu; Ac-Leu; Ac-Ile; Ac-Nle; Ac-Val; Ac-Nva; Ac-Glu; Ac-Asp; Ac-Gln; or Ac-Asn;
with the proviso that,
  if linker L is connected with module A by a carbonyl (C=O) point of attachment of P⁵; P¹²; or P¹⁴; then P⁵; P¹²; or P¹⁴; is
  Asp; Glu; $^D$Asp; or $^D$Glu;
or a pharmaceutically acceptable salt thereof.

In another particular embodiment (72) of the invention the elements of general formula (I) are defined as follows,
for module A,
if i=0, and
P² and P¹¹ taken together and/or P⁴ and P⁹ taken together form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;
P¹ is Trp; Tyr; Phe; NMeTrp; NMeTyr; NMePhe; Ac-Trp; Ac-Tyr; Ac-Phe; Gua-Trp; Gua-Tyr; Gua-Phe; TMG-Trp; TMG-Tyr; TMG-Phe; Ala; Abu; Leu; Val; Nva; Ile; Nle; Ac-Ala; Ac-Abu; Ac-Leu; Ac-Val; Ac-Nva; Ac-Ile; or Ac-Nle;
P² is Dab; Dap; Orn; Lys; Arg; Asn; Gln; Ser; Thr; alloThr; Hse; Ala; Val; Nva; Abu; Leu; Ile; or Nle;
P³ is tBuGly; Ala; Val; Abu; Leu; Ile; Nle; Nva; Tyr; Phe; Trp; or Phg;
P⁴ is Ala; Val; Abu; Leu; Ile; Nle; Nva; Ser; Thr; alloThr; Hse; Dap; or Dab;
P⁵ is Ser; Thr; alloThr; Hse; Val; Leu; Ile; Nle; Nva; Abu; or Ala;

T⁶ is $^D$Pro; $^D$Pic; $^D$Azt; $^D$Pro(4S)OH; $^D$Dab; $^D$Dap; $^D$Orn; $^D$Lys; $^D$Arg; or $^D$Ala;

T⁷ is Pro; Hyp; or Pro(4R)F;

P⁸ is Nle; Val; Leu; Ile; Nva; Abu; Ala; Cpg; or Cpa;

P⁹ is Gly; Ser; Thr; alloThr; Hse; Dap; Dab; Orn; Lys; Arg; Dap(iPr); or Ala;

P¹⁰ is Tyr; Phe; Trp; Cha; Phg; tBuGly; Ala; Val; Abu; Leu; Ile; Nle; or Nva;

P¹¹ is Gly; Sar; Dab; Dap; Orn; Lys; Arg; Asn; or Gln;

P¹² is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Orn; $^D$Dap; $^D$Lys; or $^D$Arg;

P¹³ is Gly; Sar; Aib; $^D$Dab; $^D$Dap; $^D$Orn; $^D$Lys; $^D$Arg; Dab; Dap; Orn; Lys; Arg; Thr; alloThr; Ser; Hse; $^D$Thr; $^D$alloThr; $^D$Ser; $^D$Hse; Gln; Asn; $^D$Gln; or $^D$Asn;

with the proviso that,
if linker L is connected with module A by a carbonyl (C=O) point of attachment of P⁵; or P¹²; then
P⁵; or P¹²; is
Asp; Glu; $^D$Asp; or $^D$Glu;

or a pharmaceutically acceptable salt thereof.

In another particular embodiment (73) of the invention the elements of general formula (I) are defined as in particular embodiment (72), with the proviso that
P⁴ and P⁹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage; and/or P² is Ser; Thr; alloThr; Hse; Ala; Val; Nva; Abu; Leu; Ile; or Nle; and/or T⁶ is $^D$Pic; and/or P¹¹ is Gly; or Sar; and/or P¹³ is Gln; Asn; $^D$Gln; or $^D$Asn;

or a pharmaceutically acceptable salt thereof.

In another particular embodiment (74) of the invention the elements of general formula (I) are defined as follows,
for module A,
if i=0, and
P² and P¹¹ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;

P¹ is Trp; Tyr; Phe; Ac-Trp; Ac-Tyr; or Ac-Phe;

P³ is tBuGly; Ala; Val; Abu; Leu; Ile; Nle; Nva; Tyr; Phe; Trp; or Phg;

P⁴ is Ala; Val; Abu; Leu; Ile; Nle; Nva; Ser; Thr; alloThr; Hse; Dap; or Dab;

P⁵ is Ser; Thr; alloThr; Hse; Val; Leu; Ile; Nle; Nva; Abu; or Ala;

T⁶ is $^D$Pro; $^D$Dab; $^D$Dap; $^D$Orn; $^D$Lys; $^D$Arg; or $^D$Ala;

T⁷ is Pro;

P⁸ is Nle; Val; Leu; Ile; Nva; Abu; Ala; Cpg; or Cpa;

P⁹ is Gly; Ser; Thr; alloThr; Hse; Dap; Dab; Orn; Lys; Arg; or Ala;

P¹⁰ is Tyr; Phe; Trp; or Phg;

P¹² is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle; $^D$Dab; $^D$Orn; or $^D$Dap;

P¹³ is Gly; Sar; Aib; $^D$Dab; $^D$Dap; $^D$Orn; $^D$Lys; $^D$Arg; Dab; Dap; Orn; Lys; Arg; Ala; Val; Abu; Nva; Leu; Ile; Nle; $^D$Ala; $^D$Abu; $^D$Leu; $^D$Val; $^D$Nva; $^D$Ile; $^D$Nle; Thr; alloThr; Ser; or Hse;

with the proviso that,
if linker L is connected with module A by a carbonyl (C=O) point of attachment of P⁵; or P¹²; then
P⁵; or P¹²; is
Asp; Glu; $^D$Asp; or $^D$Glu;

or a pharmaceutically acceptable salt thereof.

In another particular embodiment (75) of the invention the elements of general formula (I) are defined as follows,
for module A,
if i=1, and P¹³ and P¹⁴ are not connected as aforementioned, and
P¹³ and P¹⁴ taken together form an interstrand linking bis(amino acid)-structure based on the linkage of two L amino acid residues; or two D amino acid residues; or an L amino acid residue with an D amino acid residue; following
connection of the side chain of Cys; Hcy; or Pen; Cys-NH₂; Hcy-NH₂; or Pen-NH₂; of P¹³ with the side chain of Cys; Hcy; or Pen; NMeCys; NMeHcy; or NMePen; Ac-Cys; Ac-Hcy; or Ac-Pen; Gua-Cys; Gua-Hcy; or Gua-Pen; of P¹⁴ by a disulfide linkage; or
connection of the side chain of Dap; Dab; Orn; or Lys; Dap-NH₂; Dab-NH₂; Orn-NH₂; or Lys-NH₂; of P¹³ with the side chain of Asp; Glu; or hGlu; NMeAsp; NMeGlu; or NMehGlu; Ac-Asp; Ac-Glu; or Ac-hGlu; Gua-Asp; Gua-Glu; or Gua-hGlu; of P¹⁴ by a lactam linkage; or
connection of the side chain of Asp; Glu; or hGlu; Asp-NH₂; Glu-NH₂; or hGlu-NH₂; of P¹³ with the side chain of Dap; Dab; Orn; or Lys; NMeDap; NMeDab; NMeOrn; or NMeLys; Ac-Dap; Ac-Dab; Ac-Orn; or Ac-Lys; Gua-Dap; Gua-Dab; Gua-Orn; or Gua-Lys; of P¹⁴ by a lactam linkage; and P² and P¹¹ taken together and/or P⁴ and P⁹ taken together may form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;

P¹ is Trp; Tyr; Phe; NMeTrp; NMeTyr; or NMePhe;

P² is Dab; Dap; Orn; Lys; Arg; Ser; Thr; alloThr; or Hse;

P³ is tBuGly; Ala; Val; Abu; Leu; Ile; Nle; Nva; Tyr; Phe; Trp; or Phg;

P⁴ is Ala; Val; Abu; Leu; Nle; Nva; Dap; Dab; Ser; Thr; alloThr; Hse; Asn; Gln; Tyr; Phe; or Trp;

P⁵ is Ser; Thr; alloThr; Hse; Val; Leu; Ile; Nle; Nva; Abu; Ala; Tyr; Phe; His; or Trp;
T⁶ is ᴰPro; ᴰPic; ᴰAzt; ᴰPro(4S)OH; ᴰDab; ᴰAla; ᴰDap; ᴰOrn; ᴰLys; or ᴰArg;
T⁷ is Pro; Hyp; Pro(4R)F; Dab; Dap; Orn; Lys; or Arg;
P⁸ is Nle; Val; Leu; Ile; Nva; Abu; Ala; Cpg; or Cpa;
P⁹ is Gly; Ser; Thr; alloThr; Hse; Ala; Dap; Dap(iPr); Dab; Orn; Lys; or Arg;
P¹⁰ is Tyr; Phe; Trp; Cha; or Phg;
P¹¹ is Dab; Dap; Orn; Lys; Arg; Asn; or Gln;
P¹² is Sar; Dab; Dap; Orn; Lys; or Arg;
with the proviso that,
    if linker L is connected with module A by a carbonyl (C=O) point of attachment of P²; P⁵; or P¹²; then
    P²; P⁵; or P¹²; is
    Asp; Glu; ᴰAsp; or ᴰGlu;
or a pharmaceutically acceptable salt thereof.

In another particular embodiment (76) of the invention the elements of general formula (I) are defined as in particular embodiment (75),
with the proviso that
P⁴ and P⁹ taken together form an interstrand linking bis (amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage; and/or
P² is Ser; Thr; alloThr; or Hse; and/or
P⁴ is Tyr; Phe; or Trp; and/or
P⁵ is Tyr; Phe; His; or Trp; and/or
T⁶ is ᴰPic; and/or
T⁷ is Dab; Dap; Orn; Lys; or Arg;
or a pharmaceutically acceptable salt thereof.

In another particular embodiment (77) of the invention the elements of general formula (I) are defined as follows,
for module A,
if i=1, and P¹³ and P¹⁴ are not connected as aforementioned, and
P¹³ and P¹⁴ taken together form an interstrand linking bis(amino acid)-structure based on the linkage of two L amino acid residues; or two D amino acid residues; or an L amino acid residue with an D amino acid residue; following
    connection of the side chain of Cys; Hcy; or Pen; at P¹³ with the side chain of Cys; Hcy; or Pen; Ac-Cys; Ac-Hcy; or Ac-Pen; at P¹⁴ by a disulfide linkage; or
    connection of the side chain of Dap; Dab; Orn; or Lys; at P¹³ with the side chain of Asp; Glu; hGlu; Ac-Asp; Ac-Glu; or Ac-hGlu; at P¹⁴ by a lactam linkage; or
    connection of the side chain of Asp; Glu; or hGlu; at P¹³ with the side chain of Dap; Dab; Orn; Lys; or Ac-Dap; Ac-Dab; Ac-Orn; or Ac-Lys; at P¹⁴ by a lactam linkage; and
P² and P¹¹ taken together may form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage;
P¹ is Trp; Tyr; or Phe;
P² is Dab; Dap; Orn; Lys; or Arg;
P³ is tBuGly; Ala; Val; Abu; Leu; Ile; Nle; Nva; or Tyr;
P⁴ is Ala; Val; Abu; Leu; Nle; Nva; Dap; Dab; Thr; or Ser;
P⁵ is Ser; Thr; alloThr; Hse; or Val;
T⁶ is ᴰPro; ᴰDab; or ᴰAla;
T⁷ is Pro;
P⁸ is Nle; Val; Leu; Ile; Nva; Abu; Ala; Cpg; or Cpa;
P⁹ is Gly; Ser; Thr; alloThr; Hse; Ala; Dap; or Dab;
P¹⁰ is Tyr; Phe; Trp; or Phg;
P¹¹ is Dab; Dap; Orn; Lys; or Arg;
P¹² is Dab; Dap; Orn; Lys; or Arg;
with the proviso that,
    if linker L is connected with module A by a carbonyl (C=O) point of attachment of P²; P⁵; or P¹²; then
    P²; P⁵; or P¹²; is
    Asp; Glu; ᴰAsp; or ᴰGlu;
or a pharmaceutically acceptable salt thereof.

In another particular embodiment (78) of the invention the elements of general formula (I) are defined as follows,
for module A,
if i=1, and P¹³ and P¹⁴, and P¹⁴ and P¹ are connected as aforementioned, and
P² and P¹¹ taken together and/or P⁴ and P⁹ taken together may form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage;
P¹ is Trp; or Leu;
P² is Dab; Hse; Ser; or Thr;
P³ is tBuGly; Val; or Tyr;
P⁴ is Ala; Dap; Thr; Ser; Hse; or Tyr;
P⁵ is Ser; Thr; Val; or Tyr;
T⁶ is ᴰPro; ᴰAzt; ᴰAla; or ᴰDab;
T⁷ is Pro; or Hyp;
P⁸ is Nle; Val; or Leu;
P⁹ is Ser; Hse; Thr; Dab; or Dap;
P¹⁰ is Tyr;
P¹¹ is Dab; Hse; Ser; Thr; or Gly;
P¹² is Orn; or Dab;
P¹³ is Gly; ᴰThr; or ᴰDab;
P¹⁴ is Dab; Hse; or Thr;
with the proviso that,
    if linker L is connected with module A by a carbonyl (C=O) point of attachment of P²; P⁵; P¹²; P¹³; or P¹⁴; then
    P²; P⁵; P¹²; P¹³; or P¹⁴; is
    Asp; Glu; ᴰAsp; or ᴰGlu;
or a pharmaceutically acceptable salt thereof.

In another particular embodiment (79) of the invention the elements of general formula (I) are defined as in particular embodiment (78), with the proviso that $P^4$ and $P^9$ taken together form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage; and/or
$P^1$ is Leu; and/or
$P^2$ is Hse; Ser; or Thr; and/or
$P^4$ is Tyr; and/or
$P^5$ is Tyr; and/or
$P^{11}$ is Gly; Hse; Ser; or Thr;
or a pharmaceutically acceptable salt thereof.

In another particular embodiment (80) of the invention the elements of general formula (I) are defined as follows, for module A,
if i=1, and $P^{13}$ and $P^{14}$, and $P^{14}$ and $P^1$ are connected as aforementioned, and
$P^2$ and $P^{11}$ taken together and/or $P^4$ and $P^9$ taken together may form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage;
$P^1$ is Trp; or Leu;
$P^2$ is Dab; Hse; or Thr;
$P^3$ is tBuGly; Val; or Tyr;
$P^4$ is Ala; Dap; Thr; Ser; or Tyr;
$P^5$ is Ser; Thr; Val; or Tyr;
$T^6$ is $^D$Pro; $^D$Azt; $^D$Ala; or $^D$Dab;
$T^7$ is Pro; or Hyp;
$P^8$ is Nle; Val; or Leu;
$P^9$ is Ser; Thr; Dab; or Dap;
$P^{10}$ is Tyr;
$P^{11}$ is Dab; Hse; Thr; or Gly;
$P^{12}$ is Orn;
$P^{13}$ is Gly; $^D$Thr; or $^D$Dab;
$P^{14}$ is Dab; Hse; or Thr;
with the proviso that,
    if linker L is connected with module A by a carbonyl (C=O) point of attachment of $P^2$; $P^5$; $P^{12}$; $P^{13}$; or $P^{14}$; then
    $P^2$; $P^5$; $P^{12}$; $P^{13}$; or $P^{14}$; is Asp; Glu; $^D$Asp; or $^D$Glu;
or a pharmaceutically acceptable salt thereof.

In another particular embodiment (81) of the invention the elements of general formula (I) are defined as in particular embodiment (80),
with the proviso that
$P^4$ and $P^9$ taken together form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; and/or
$P^1$ is Leu; and/or
$P^2$ is Hse; or Thr; and/or
$P^4$ is Tyr; and/or
$P^5$ is Tyr; and/or
$P^{11}$ is Gly; Hse; or Thr;
or a pharmaceutically acceptable salt thereof.

In another particular embodiment (82) of the invention the elements of general formula (I) are defined as follows, for module A,
if i=1, and $P^{13}$ and $P^{14}$, and $P^{14}$ and $P^1$ are connected as aforementioned, and
$P^2$ and $P^{11}$ taken together may form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage;
$P^1$ is Trp;
$P^2$ is Dab;
$P^3$ is tBuGly; Val; or Tyr;
$P^4$ is Ala; Dap; Thr; or Ser;
$P^5$ is Ser; Thr; or Val;
$T^6$ is $^D$Pro; $^D$Azt; $^D$Ala; or $^D$Dab;
$T^7$ is Pro; or Hyp;
$P^8$ is Nle; Val; or Leu;
$P^9$ is Ser; Thr; Dab; or Dap;
$P^{10}$ is Tyr;
$P^{11}$ is Dab;
$P^{12}$ is Orn;
$P^{13}$ is Gly; or $^D$Dab;
$P^{14}$ is Dab;
with the proviso that,
    if linker L is connected with module A by a carbonyl (C=O) point of attachment of $P^2$; $P^5$; $P^{12}$; $P^{13}$; or $P^{14}$; then
    $P^2$; $P^5$; $P^{12}$; $P^{13}$; or $P^{14}$; is Asp; Glu; $^D$Asp; or $^D$Glu;
or a pharmaceutically acceptable salt thereof.

In another particular embodiment (83) of the invention the elements of general formula (I) are defined as follows, for module A,
if i=1, and $P^{13}$ and $P^{14}$, and $P^{14}$ and $P^1$ are connected as aforementioned, and
$P^2$ and $P^{11}$ taken together may form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage;
$P^1$ is Trp; Tyr; or Phe;
$P^2$ is Dab; Dap; Orn; Lys; or Arg;
$P^3$ is tBuGly; Ala; Val; Abu; Leu; Ile; Nle; or Nva;

P⁴ is Ala; Val; Abu; Leu; Ile; Nle; or Nva;
P⁵ is Ser; Thr; alloThr; or Hse;
T⁶ is ᴰPro;
T⁷ is Pro;
P⁸ is Nle; Val; Leu; Ile; Nva; Abu; or Ala
P⁹ is Ser; Thr; alloThr; or Hse;
P¹⁰ is Tyr; Phe; Trp; or Phg;
P¹¹ is Dab; Dap; Orn; Lys; or Arg;
P¹² is ᴰDab; ᴰDap; ᴰOrn; ᴰLys; or ᴰArg;
P¹³ is ᴰDab; ᴰDap; ᴰOrn; ᴰLys; or ᴰArg;
P¹⁴ is Dab; Dap; Orn; Lys; or Arg;
with the proviso that,
    if linker L is connected with module A by a carbonyl (C=O) point of attachment of P²; P⁵; P¹²; P¹³; or P¹⁴; then
    P²; P⁵; P¹²; P¹³; or P¹⁴; is
    Asp; Glu; ᴰAsp; or ᴰGlu;
or a pharmaceutically acceptable salt thereof.

In another particular embodiment (84) of the invention the elements of general formula (I) are defined as follows,
for module A,
if i=1, and P¹⁴ and P¹, are not connected as aforementioned, and
P² and P¹¹ taken together and/or P⁴ and P⁹ taken together form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage;
P¹ is Trp; NMeTrp; Ac-Trp; Gua-Trp; TMG-Trp; Leu; Val; NMe-Leu; or Ac-Leu;
P² is Ala; Dab; Thr; Hse; or Ser;
P³ is tBuGly; Val; Leu; Trp; or Tyr;
P⁴ is Gly; Ala; ᴰAla; Dap; Dab; Arg; Ser; Thr; Hse; or Tyr;
P⁵ is Ser; Thr; alloThr; Val; Leu; Ala; Dap; Arg; Tyr; or His;
T⁶ is Gly; ᴰPro; ᴰPro((4S)OH); ᴰPic; ᴰAzt; ᴰAla; ᴰTyr; ᴰSer; or ᴰDab;
T⁷ is Pro; Hyp; Pro((4R)F; Ala; Leu; Tyr; Phe; Dab; Arg; or Thr;
P⁸ is Nle; Val; Ile; Leu; Cpa; Trp; Tyr; Phe; or Thr;
P⁹ is Gly; Sar; Ala; Ser; Thr; Hse; Asp; Dap; Dap(iPr); or His;
P¹⁰ is Tyr; Ala; Leu; or Cha;
P¹¹ is Dab; Asn; Thr; Ser; Hse; or Ala;
P¹² is Gly; Sar; Aib; Ala; Dab; Dap; Orn; Dap(Glu); Dab(Arg); ᴰAla; ᴰDab; Thr; ᴰThr; ᴰTyr; or Glu;
P¹³ is Gly; Sar; Aib; Dab; Thr; alloThr; ᴰDab; ᴰAla; Tyr; or ᴰPhe;
P¹⁴ is Dab; Dap; Thr; ᴰAla; ᴰDab; or ᴰThr;
with the proviso that,
    if linker L is connected with module A by a carbonyl (C=O) point of attachment of P⁶; P¹²; or P¹³; then
    P⁵; P¹²; or P¹³; is
    Asp; Glu; ᴰAsp; or ᴰGlu;
or a pharmaceutically acceptable salt thereof.

In another particular embodiment (85) of the invention the elements of general formula (I) are defined as in particular embodiment (84), with the proviso that P⁴ and P⁹ taken together form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage; or
    connection of the side chain of Dap; Dab; or Orn; with the side chain of Dap; Dab; or Orn; by an urea linkage; and/or
P¹ is Val; Leu; or Ac-Leu; and/or
P⁴ is Gly; ᴰAla; or Tyr; and/or
P⁵ is Tyr; or His; and/or
T⁶ is Gly; ᴰPic; ᴰTyr; or ᴰSer; and/or
T⁷ is Ala; Leu; Tyr; Phe; Dab; Arg; or Thr; and/or
P⁸ is Thr; and/or
P⁹ is Asp; or His; and/or
P¹¹ is Thr; Ser; Hse; or Ala; and/or
P¹² is ᴰTyr; or Glu; and/or
P¹³ is ᴰPhe; or Tyr;
or a pharmaceutically acceptable salt thereof.

In another particular embodiment (86) of the invention the elements of general formula (I) are defined as follows,
for module A,
if i=1, and P¹⁴ and P¹, are not connected as aforementioned, and
P² and P¹¹ taken together and/or P⁴ and P⁹ taken together form an interstrand linking bis(amino acid)-structure based on the linkage of two L amino acid residues; or two D amino acid residues; following
    connection of the side chain of Cys; Hcy; or Pen; with the side chain of Cys; Hcy; or Pen; by a disulfide linkage; or
    connection of the side chain of Dap; Dab; Orn; or Lys; with the side chain of Asp; Glu; or hGlu; by a lactam linkage;
P¹ is Trp; NMeTrp; Ac-Trp; Gua-Trp; TMG-Trp; Leu; Val; or Ac-Leu;
P² is Ala; Dab; or Ser;
P³ is tBuGly; Val; Leu; Trp; or Tyr;
P⁴ is Gly; Ala; ᴰAla; Dap; Dab; Arg; Ser; Thr; or Tyr;
P⁵ is Ser; Thr; alloThr; Val; Leu; Ala; Dap; Arg; Tyr; or His;
T⁶ is Gly; ᴰPro; ᴰPro((4S)OH); ᴰPic; ᴰAzt; ᴰAla; ᴰTyr; ᴰSer; or ᴰDab;
T⁷ is Pro; Hyp; Pro((4R)F; Ala; Leu; Tyr; Phe; Dab; Arg; or Thr;
P⁸ is Nle; Val; Ile; Leu; Cpa; Trp; Tyr; Phe; or Thr;
P⁹ is Gly; Sar; Ala; Ser; Thr; Asp; Dap; Dap(iPr); or His;
P¹⁰ is Tyr; Ala; Leu; or Cha;
P¹¹ is Dab; Asn; or Ala;
P¹² is Gly; Sar; Aib; Ala; Dab; Dap; Orn; Dap(Glu); Dab(Arg); ᴰAla; ᴰDab; Thr; ᴰThr; ᴰTyr; or Glu;
P¹³ is Gly; Sar; Aib; Dab; Thr; alloThr; ᴰDab; ᴰAla; Tyr; or ᴰPhe;
P¹⁴ is Dab; Dap; Thr; ᴰAla; ᴰDab; or ᴰThr;
with the proviso that,
    if linker L is connected with module A by a carbonyl (C=O) point of attachment of P⁵; P¹²; or P¹³; then
    P⁵; P¹²; or P¹³; is
    Asp; Glu; ᴰAsp; or ᴰGlu;
or a pharmaceutically acceptable salt thereof.

In another particular embodiment (87) of the invention the elements of general formula (I) are defined as in particular embodiment (86), with the proviso that
P⁴ and P⁹ taken together form an interstrand linking bis (amino acid)-structure based on the linkage of two L amino acid residues; or two D amino acid residues; following
   connection of the side chain of Cys; Hcy; or Pen; with the side chain of Cys; Hcy; or Pen; by a disulfide linkage; or
   connection of the side chain of Dap; Dab; Orn; or Lys; with the side chain of Asp; Glu; or hGlu; by a lactam linkage; and/or
P¹ is Val; Leu; or Ac-Leu; and/or
P⁴ is Gly; ᴰAla; or Tyr; and/or
P⁵ is Tyr; or His; and/or
T⁶ is Gly; ᴰPic; ᴰTyr; or ᴰSer; and/or
T⁷ is Ala; Leu; Tyr; Phe; Dab; Arg; or Thr; and/or
P⁸ is Thr; and/or
P⁹ is Asp; or His; and/or
P¹¹ is Ala; and/or
P¹² is ᴰTyr; or Glu; and/or
P¹³ is ᴰPhe; or Tyr;
or a pharmaceutically acceptable salt thereof.

In another particular embodiment (88) of the invention the elements of general formula (I) are defined as follows, for module A,
if i=1, and P¹⁴ and P¹, are not connected as aforementioned, and
P² and P¹¹ taken together form an interstrand linking bis (amino acid)-structure based on the linkage of two L amino acid residues; or two D amino acid residues; following
   connection of the side chain of Cys; Hcy; or Pen; with the side chain of Cys; Hcy; or Pen; by a disulfide linkage; or
   connection of the side chain of Dap; Dab; Orn; or Lys; with the side chain of Asp; Glu; or hGlu; by a lactam linkage; or
   connection of the side chain of Dap; Dab; or Orn; with the side chain of Dap; Dab; or Orn; by an urea linkage;
P¹ is Trp; NMeTrp; Ac-Trp; Gua-Trp; or TMG-Trp;
P³ is tBuGly; Val; Leu; Trp; or Tyr;
P⁴ is Ala; Dap; Dab; Arg; Ser; or Thr;
P⁵ is Ser; Thr; alloThr; Val; Leu; Ala; Dap; or Arg;
T⁶ is ᴰPro; ᴰPro((4S)OH); ᴰAla; or ᴰDab;
T⁷ is Pro; Hyp; or Pro((4R)F;
P⁸ is Nle; Val; Ile; Leu; Cpa; Trp; Tyr; or Phe;
P⁹ is Gly; Sar; Ala; Ser; Thr; Dap; or Dap(iPr);
P¹⁰ is Tyr; Ala; Leu; or Cha;
P¹² is Gly; Sar; Aib; Ala; Dab; Dap; Orn; Dap(Glu); Dab(Arg); ᴰAla; ᴰDab; Thr; or ᴰThr;
P¹³ is Gly; Aib; Dab; Thr; alloThr; ᴰDab; or ᴰAla;
P¹⁴ is Dab; Dap; Thr; ᴰAla; ᴰDab; or ᴰThr;
with the proviso that,
   if linker L is connected with module A by a carbonyl (C=O) point of attachment of P⁵; P¹²; or P¹³; then
   P⁵; P¹²; or P¹³; is
   Asp; Glu; ᴰAsp; or ᴰGlu;
or a pharmaceutically acceptable salt thereof.

In another particular embodiment (89) of the invention the elements of general formula (I) are defined as follows, for module A,
if i=1, and P¹⁴ and P¹, are not connected as aforementioned, and
P² and P¹¹ taken together form an interstrand linking bis (amino acid)-structure based on the linkage of two L amino acid residues; or two D amino acid residues; following
   connection of the side chain of Cys; Hcy; or Pen; with the side chain of Cys; Hcy; or Pen; by a disulfide linkage; or
   connection of the side chain of Dap; Dab; Orn; or Lys; with the side chain of Asp; Glu; or hGlu; by a lactam linkage; or
   connection of the side chain of Dap; Dab; or Orn; with the side chain of Dap; Dab; or Orn; by an urea linkage;
P¹ is Trp; Tyr; Phe; Ac-Trp; Ac-Tyr; or Ac-Phe;
P³ is tBuGly; Ala; Val; Abu; Leu; Ile; Nle; or Nva;
P⁴ is Ala; Val; Abu; Leu; Ile; Nle; Nva; Dap; Dab; Orn; Lys; Arg; Ser; Thr; alloThr; or Hse;
P⁵ is Ser; Thr; alloThr; or Hse;
T⁶ is ᴰPro; ᴰAla; ᴰAbu; ᴰLeu; ᴰVal; ᴰNva; ᴰIle; or ᴰNle;
T⁷ is Pro;
P⁸ is Nle; Val; Leu; Ile; Nva; Abu; or Ala
P⁹ is Gly; Sar; Ala; Abu; Leu; Nle; Ile; Val; Nva; Ser; Thr; alloThr; or Hse;
P¹⁰ is Tyr; Phe; Trp; or Phg
P¹² is Gly; Sar; Aib; Ala; Val; Abu; Nva; Leu; Ile; Nle; Dab; Dap; Orn; Lys; Arg; Dap(Glu); Dab(Arg); ᴰAla; ᴰVal; ᴰAbu; ᴰNva; ᴰLeu; ᴰIle; or ᴰNle;
P¹³ is Gly; Sar; Aib; Dab; Dap; Orn; Lys; Arg; Thr; alloThr; Ser; Hse; Ala; Val; Abu; Nva; Leu; Ile; Nle; ᴰAla; ᴰAbu; ᴰLeu; ᴰVal; ᴰNva; ᴰIle; or ᴰNle;
P¹⁴ is Gly; Sar; Aib; Dab; Dap; Orn; Lys; Arg; Thr; alloThr; Ser Hse; ᴰAla; ᴰAbu; ᴰLeu; ᴰVal; ᴰNva; ᴰIle; ᴰNle; Ala; Abu; Leu; Ile; Nle; Val; or Nva;
with the proviso that,
   if linker L is connected with module A by a carbonyl (C=O) point of attachment of P⁵; P¹²; or P¹³; then
   P⁵; P¹²; or P¹³; is
   Asp; Glu; ᴰAsp; or ᴰGlu;
or a pharmaceutically acceptable salt thereof.

In another particular embodiment (90) of the invention the elements of general formula (I) are defined as follows, for module A,
if i=1, and P¹³ and P¹⁴ are not connected as aforementioned, and
P² and P¹¹ taken together and/or P⁴ and P⁹ taken together form an interstrand linking bis(amino acid)-structure based on the linkage of two L amino acid residues; or two D amino acid residues; following
   connection of the side chain of Cys; Hcy; or Pen; with the side chain of Cys; Hcy; or Pen; by a disulfide linkage; or
   connection of the side chain of Dap; Dab; Orn; or Lys; with the side chain of Asp; Glu; or hGlu; by a lactam linkage; or
   connection of the side chain of Dap; Dab; or Orn; with the side chain of Dap; Dab; or Orn; by an urea linkage;
P¹ is Trp; or Leu;
P² is Dab; Dap; Orn; Lys; Arg; Asn; Gln; Ser; Thr; alloThr; or Hse;
P³ is tBuGly; or Val;
P⁴ is Ala; Ser; Thr; or Hse;
P⁵ is Ser; Dab; or Tyr;
T⁶ is ᴰPro; ᴰAzt; ᴰAla; or ᴰDab;
T⁷ is Pro; or Hyp;
P⁸ is Nle; Leu; or Cpa;
P⁹ is Ser; Thr; or Hse;
P¹⁰ is Tyr;
P¹¹ is Dab; Dap; Orn; Lys; Arg; Asn; Gln; Ser; Thr; or Hse;
P¹² is Sar; Dab; or Orn;
P¹³ is Dab; or Thr;
P¹⁴ is Gly; Sar; Aib; Dab; Dap; Orn; Arg; Thr; Ac-Dab; or Ac-Ala;

with the proviso that,
if linker L is connected with module A by a carbonyl (C=O) point of attachment of $P^5$; $P^{12}$; or $P^{14}$; then
$P^5$; $P^{12}$; or $P^{14}$; is
Asp; Glu; $^D$Asp; or $^D$Glu;
or a pharmaceutically acceptable salt thereof.

In another particular embodiment (91) of the invention the elements of general formula (I) are defined as in particular embodiment (90),
with the proviso that
$P^4$ and $P^9$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage; and/or
$P^1$ is Leu; and/or
$P^2$ is Ser; Thr; alloThr; or Hse; and/or
$P^5$ is Tyr; and/or
$P^{11}$ is Ser; Thr; or Hse;
or a pharmaceutically acceptable salt thereof.

In another particular embodiment (92) of the invention the elements of general formula (I) are defined as follows,
for module A,
if i=1, and $P^{13}$ and $P^{14}$ are not connected as aforementioned, and
$P^2$ and $P^{11}$ taken together and/or $P^4$ and $P^9$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage;
$P^1$ is Trp; or Leu;
$P^2$ is Dab; Dap; Orn; Lys; Arg; Asn; Gln; Ser; Thr; alloThr; or Hse;
$P^3$ is tBuGly; or Val;
$P^4$ is Ala;
$P^5$ is Ser; Dab; or Tyr;
$T^6$ is $^D$Pro;
$T^7$ is Pro;
$P^8$ is Nle; Leu; or Cpa;
$P^9$ is Ser;
$P^{10}$ is Tyr;
$P^{11}$ is Dab; Dap; Orn; Lys; Arg; Asn; or Gln;
$P^{12}$ is Sar; Dab; or Orn;
$P^{13}$ is Dab; or Thr;
$P^{14}$ is Gly; Sar; Aib; Dab; Dap; Orn; Arg; Thr; Ac-Dab; or Ac-Ala;
with the proviso that,
if linker L is connected with module A by a carbonyl (C=O) point of attachment of $P^5$; $P^{12}$; or $P^{14}$; then
$P^5$; $P^{12}$; or $P^{14}$; is
Asp; Glu; $^D$Asp; or $^D$Glu;
or a pharmaceutically acceptable salt thereof.

In another particular embodiment (93) of the invention the elements of general formula (I) are defined as in particular embodiment (92),
with the proviso that
$P^4$ and $P^9$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; and/or
$P^1$ is Leu; and/or
$P^2$ is Ser; Thr; alloThr; or Hse; and/or
$P^5$ is Tyr;
or a pharmaceutically acceptable salt thereof.

In another particular embodiment (94) of the invention the elements of general formula (I) are defined as follows,
for module A,
if i=1, and $P^{13}$ and $P^{14}$ are not connected as aforementioned, and
$P^2$ and $P^{11}$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;
$P^1$ is Trp;
$P^3$ is tBuGly; or Val;
$P^4$ is Ala;
$P^5$ is Ser; or Dab;
$T^6$ is $^D$Pro;
$T^7$ is Pro;
$P^8$ is Nle; Leu; or Cpa;
$P^9$ is Ser;
$P^{10}$ is Tyr;
$P^{12}$ is Sar; Dab; or Orn;
$P^{13}$ is Dab; or Thr;
$P^{14}$ is Gly; Sar; Aib; Dab; Dap; Orn; Arg; Thr; Ac-Dab; or Ac-Ala;
with the proviso that,
if linker L is connected with module A by a carbonyl (C=O) point of attachment of $P^5$; $P^{12}$; or $P^{14}$; then
$P^5$; $P^{12}$; or $P^{14}$; is
Asp; Glu; $^D$Asp; or $^D$Glu;
or a pharmaceutically acceptable salt thereof.

In another particular embodiment (95) of the invention the elements of general formula (I) are defined as follows,
for module A,
if i=1, and $P^{13}$ and $P^{14}$ are not connected as aforementioned, and
$P^2$ and $P^{11}$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; or Phe;
$P^3$ is tBuGly; Ala; Val; Abu; Leu; Ile; Nle; or Nva;
$P^4$ is Ala; Val; Abu; Leu; Ile; Nle; or Nva;
$P^5$ is Ser; Thr; alloThr; or Hse;
$T^6$ is $^D$Pro;
$T^7$ is Pro;
$P^8$ is Nle; Val; Leu; Ile; Nva; Abu; or Ala;
$P^9$ is Ser; Thr; alloThr; or Hse;
$P^{10}$ is Tyr; Phe; Trp; or Phg;
$P^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; or $^D$Nle;
$P^{13}$ is Gly; Sar; Aib; Dab; Dap; Orn; Lys; Arg; Thr; alloThr; Ser; Hse; Ala; Val; Abu; Nva; Leu; Ile; Nle; $^D$Ala; $^D$Abu; $^D$Leu; $^D$Val; $^D$Nva; $^D$Ile; or $^D$Nle;
$P^{14}$ is Gly; Sar; Aib; Dab; Dap; Orn; Lys; Arg; Thr; alloThr; Ser; Hse; $^D$Ala; $^D$Abu; $^D$Leu; $^D$Val; $^D$Nva; $^D$Ile; $^D$Nle; Ala; Abu; Leu; Ile; Nle; Val; Nva; Glu; Asp; Gln; or Asn; Ac-Gly; Ac-Sar; Ac-Aib; Ac-Dab; Ac-Dap; Ac-Orn; Ac-Lys Ac-Arg; Ac-Thr; Ac-alloThr; Ac-Ser; Ac-Hse; Ac-$^D$Ala; Ac-$^D$Abu; Ac-$^D$Leu; Ac-$^D$Val; Ac-$^D$Nva; Ac-$^D$Ile; Ac-$^D$Nle; Ac-Ala; Ac-Abu; Ac-Leu; Ac-Ile; Ac-Nle; Ac-Val; Ac-Nva; Ac-Glu; Ac-Asp; Ac-Gln; or Ac-Asn;
with the proviso that,
if linker L is connected with module A by a carbonyl (C=O) point of attachment of $P^5$; $P^{12}$; or $P^{14}$; then
$P^5$; $P^{12}$; or $P^{14}$; is
Asp; Glu; $^D$Asp; or $^D$Glu;
or a pharmaceutically acceptable salt thereof.

In another particular embodiment (96) of the invention the elements of general formula (I) are defined as follows, for module A,
if i=0, and
$P^2$ and $P^{11}$ taken together and/or $P^4$ and $P^9$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;
$P^1$ is Trp; Phe; Ac-Trp; Ac-Phe; NMeTrp; Leu; or NMe-Leu;
$P^2$ is Dab; Dap; Orn; Lys; Arg; Asn; Gln; Ser; Thr; alloThr; or Hse;
$P^3$ is tBuGly; Val; or Tyr;
$P^4$ is Ala; Ser; Hse; or Thr;
$P^5$ is Ser; Thr; Hse; or Val;
$L^6$ is $^D$Pro; $^D$Azt; $^D$Ala; or $^D$Dab;
$T^7$ is Pro; or Hyp;
$P^8$ is Nle; or Val;
$P^9$ is Ser; Thr; Hse; Dab; or Dap;
$P^{10}$ is Tyr; or Leu;
$P^{11}$ is Dab; Dap; Orn; Lys; Arg; Ser; Thr; Hse; Asn; or Gln;
$P^{12}$ is Dab; Dap; or Orn;
$P^{13}$ is $^D$Dab; or Dab;
with the proviso that,
if linker L is connected with module A by a carbonyl (C=O) point of attachment of $P^5$; or $P^{12}$; then
$P^5$; or $P^{12}$; is
Asp; Glu; $^D$Asp; or $^D$Glu;
or a pharmaceutically acceptable salt thereof.

In another particular embodiment (97) of the invention the elements of general formula (I) are defined as in particular embodiment (96), with the proviso that
$P^4$ and $P^9$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage; and/or
$P^1$ is Leu; or NMe-Leu; and/or
$P^2$ is Ser; Thr; alloThr; or Hse; and/or
$P^{11}$ is Ser; Thr; Hse;
or a pharmaceutically acceptable salt thereof.

In another particular embodiment (98) of the invention the elements of general formula (I) are defined as follows, for module A,
if i=0, and
$P^2$ and $P^{11}$ taken together and/or $P^4$ and $P^9$ taken together form an interstrand linking bis(amino acid)-structure based on the linkage of two L amino acid residues; or two D amino acid residues; following
connection of the side chain of Cys; Hcy; or Pen; with the side chain of Cys; Hcy; or Pen; by a disulfide linkage; or
connection of the side chain of Dap; Dab; Orn; or Lys; with the side chain of Asp; Glu; or hGlu; by a lactam linkage;
$P^1$ is Trp; Phe; Ac-Trp; or Ac-Phe;
$P^2$ is Dab; Dap; Orn; Lys; Arg; Asn; Gln; Ser; Thr; alloThr; or Hse;
$P^3$ is tBuGly; Val; or Tyr;
$P^4$ is Ala; Ser; or Thr;
$P^5$ is Ser; Thr; or Val;
$T^6$ is $^D$Pro; $^D$Azt; or $^D$Dab;
$T^7$ is Pro;
$P^8$ is Nle; or Val;
$P^9$ is Ser; or Dap;
$P^{10}$ is Tyr; or Leu;
$P^{11}$ is Dab; Dap; Orn; Lys; Arg; Asn; or Gln;
$P^{12}$ is Dab; Dap; or Orn;
$P^{13}$ is $^D$Dab; or Dab;
with the proviso that,
if linker L is connected with module A by a carbonyl (C=O) point of attachment of $P^5$; or $P^{12}$; then
$P^5$; or $P^{12}$; is
Asp; Glu; $^D$Asp; or $^D$Glu;
or a pharmaceutically acceptable salt thereof.

In another particular embodiment (99) of the invention the elements of general formula (I) are defined as in particular embodiment (98),
with the proviso that
$P^4$ and $P^9$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; and/or $P^2$ is Ser; Thr; alloThr; or Hse;

or a pharmaceutically acceptable salt thereof.

In another particular embodiment (100) of the invention the elements of general formula (I) are defined as follows, for module A, if i=0, and $P^2$ and $P^{11}$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Phe; Ac-Trp; or Ac-Phe;

$P^3$ is tBuGly; Val; or Tyr;

$P^4$ is Ala; Ser; or Thr;

$P^5$ is Ser; Thr; or Val;

$T^6$ is $^D$Pro; $^D$Azt; or $^D$Dab;

$T^7$ is Pro;

$P^8$ is Nle; or Val;

$P^9$ is Ser; or Dap;

$P^{10}$ is Tyr; or Leu;

$P^{12}$ is Dab; Dap; or Orn;

$P^{13}$ is $^D$Dab; or Dab;

with the proviso that, if linker L is connected with module A by a carbonyl (C=O) point of attachment of $P^5$; or $P^{12}$; then $P^5$; or $P^{12}$; is Asp; Glu; $^D$Asp; or $^D$Glu;

or a pharmaceutically acceptable salt thereof.

In another particular embodiment (101) of the invention the elements of general formula (I) are defined as follows, for module A, if i=0, and $P^2$ and $P^{11}$ taken together form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; Tyr; Phe; Ac-Trp; Ac-Tyr; or Ac-Phe;

$P^3$ is tBuGly; Ala; Val; Abu; Leu; Ile; Nle; Nva; Tyr; Phe; Trp; or Phg;

$P^4$ is Ala; Val; Abu; Leu; Ile; Nle; Nva; Ser; Thr; alloThr; or Hse;

$P^5$ is Ser; Thr; alloThr; Hse; Val; Leu; Ile; Nle; Nva; Abu; or Ala;

$T^6$ is $^D$Pro; $^D$Dab; $^D$Dap; $^D$Orn; $^D$Lys; or $^D$Arg;

$T^7$ is Pro;

$P^8$ is Nle; Val; Leu; Ile; Nva; Abu; or Ala;

$P^9$ is Ser; Thr; alloThr; Hse; Dap; Dab; Orn; Lys; or Arg;

$P^{10}$ is Tyr; Phe; Trp; or Phg;

$P^{12}$ is Gly; Sar; Aib; Ala; Val; Abu; Nva; Leu; Ile; Nle; Dab; Dap; Orn; Lys; Arg; Dap(Glu); Dab(Arg); $^D$Ala; $^D$Val; $^D$Abu; $^D$Nva; $^D$Leu; $^D$Ile; $^D$Nle;

$P^{13}$ is Gly; Sar; Aib; $^D$Dab; $^D$Dap; $^D$Orn; $^D$Lys; $^D$Arg; Dab; Dap; Orn; Lys; Arg; Ala; Val; Abu; Nva; Leu; Ile; Nle; $^D$Ala; $^D$Abu; $^D$Leu; $^D$Val; $^D$Nva; $^D$Ile; or $^D$Nle;

with the proviso that, if linker L is connected with module A by a carbonyl (C=O) point of attachment of $P^5$; or $P^{12}$; then $P^5$; or $P^{12}$; is Asp; Glu; $^D$Asp; or $^D$Glu;

or a pharmaceutically acceptable salt thereof.

In another particular embodiment (102) of the invention the elements of general formula (I) are defined as follows, for module A, if i=1, and $P^{13}$ and $P^{14}$ are not connected as aforementioned, and $P^{13}$ and $P^{14}$ taken together form an interstrand linking bis(amino acid)-structure based on the linkage of two L amino acid residues; or two D amino acid residues; or an L amino acid residue with an D amino acid residue; following connection of the side chain of Cys; Hcy; or Pen; Cys-NH$_2$; Hcy-NH$_2$; or Pen-NH$_2$; of $P^{13}$ with the side chain of Cys; Hcy; or Pen; NMeCys; NMeHcy; or NMePen; Ac-Cys; Ac-Hcy; or Ac-Pen; Gua-Cys; Gua-Hcy; or Gua-Pen; of $P^{14}$ by a disulfide linkage; or connection of the side chain of Dap; Dab; Orn; or Lys; Dap-NH$_2$; Dab-NH$_2$; Orn-NH$_2$; or Lys-NH$_2$; of $P^{13}$ with the side chain of Asp; Glu; or hGlu; NMeAsp; NMeGlu; or NMehGlu; Ac-Asp; Ac-Glu; or Ac-hGlu; Gua-Asp; Gua-Glu; or Gua-hGlu; of $P^{14}$ by a lactam linkage; or connection of the side chain of Asp; Glu; or hGlu; Asp-NH$_2$; Glu-NH$_2$; or hGlu-NH$_2$; of $P^{13}$ with the side chain of Dap; Dab; Orn; or Lys; NMeDap; NMeDab; NMeOrn; or NMeLys; Ac-Dap; Ac-Dab; Ac-Orn; or Ac-Lys; Gua-Dap; Gua-Dab; Gua-Orn; or Gua-Lys; of $P^{14}$ by a lactam linkage; and $P^2$ and $P^{11}$ taken together and/or $P^4$ and $P^9$ taken together may form an interstrand linking bis(amino acid)-structure based on the linkage of two L amino acid residues; or two D amino acid residues; following connection of the side chain of Cys; Hcy; or Pen; with the side chain of Cys; Hcy; or Pen; by a disulfide linkage; or connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

$P^1$ is Trp; or Leu;

$P^2$ is Dab; Ser; Hse; or Thr;

$P^3$ is tBuGly; Val; or Tyr;

$P^4$ is Ala; Ser; Thr, Hse; Asn; or Tyr;

$P^5$ is Ser; Val; or Tyr;

$T^6$ is $^D$Pro; $^D$Pro(4S)OH; $^D$Azt; $^D$Ala; or $^D$Dab;

$T^7$ is Pro; Hyp; or Arg;

$P^8$ is Nle; or Leu;

$P^9$ is Ser; Hse; Thr; Dab; or Dap;

$P^{10}$ is Tyr;

$P^{11}$ is Dab; Ser; Hse; Thr; or Asn;

$P^{12}$ is Sar; Dab; or Orn;

with the proviso that,
  if linker L is connected with module A by a carbonyl
    (C=O) point of attachment of $P^2$; $P^5$; or $P^{12}$; then
    $P^2$; $P^5$; or $P^{12}$; is
  Asp; Glu; $^D$Asp; or $^D$Glu;
or a pharmaceutically acceptable salt thereof.

In another particular embodiment (103) of the invention the elements of general formula (I) are defined as in particular embodiment (102),
with the proviso that
$P^4$ and $P^9$ taken together form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage; and/or
$P^1$ is Leu; and/or
$P^2$ is Ser; Hse; or Thr; and/or
$P^4$ is Tyr; and/or
$P^5$ is Tyr; and/or
$T^7$ is Arg; and/or
$P^{11}$ is Ser; Hse; Thr;
or a pharmaceutically acceptable salt thereof.

In another particular embodiment (104) of the invention the elements of general formula (I) are defined as follows, for module A,
if i=1, and $P^{13}$ and $P^{14}$ are not connected as aforementioned, and
$P^{13}$ and $P^{14}$ taken together form an interstrand linking bis(amino acid)-structure based on the linkage of two L amino acid residues; or two D amino acid residues; or an L amino acid residue with an D amino acid residue; following
  connection of the side chain of Cys; Hcy; or Pen; Cys-NH$_2$; Hcy-NH$_2$; or Pen-NH$_2$; of $P^{13}$ with the side chain of Cys; Hcy; or Pen; NMeCys; NMeHcy; or NMePen; Ac-Cys; Ac-Hcy; or Ac-Pen; Gua-Cys; Gua-Hcy; or Gua-Pen; of $P^{14}$ by a disulfide linkage; or
  connection of the side chain of Dap; Dab; Orn; or Lys; Dap-NH$_2$; Dab-NH$_2$;
Orn-NH$_2$; or Lys-NH$_2$; of $P^{13}$ with the side chain of Asp; Glu; or hGlu; NMeAsp; NMeGlu; or NMehGlu; Ac-Asp; Ac-Glu; or Ac-hGlu; Gua-Asp; Gua-Glu; or Gua-hGlu; of $P^{14}$ by a lactam linkage; or
  connection of the side chain of Asp; Glu; or hGlu; Asp-NH$_2$; Glu-NH$_2$; or hGlu-NH$_2$; of $P^{13}$ with the side chain of Dap; Dab; Orn; or Lys; NMeDap; NMeDab; NMeOrn; or NMeLys; Ac-Dap; Ac-Dab; Ac-Orn; or Ac-Lys; Gua-Dap; Gua-Dab; Gua-Orn; or Gua-Lys; of $P^{14}$ by a lactam linkage; and
$P^2$ and $P^{11}$ taken together and/or $P^4$ and $P^9$ taken together may form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage;

$P^1$ is Trp;
$P^2$ is Dab; or Ser;
$P^3$ is tBuGly; Val; or Tyr;
$P^4$ is Ala; Ser; Thr, Asn; or Tyr;
$P^5$ is Ser; Val; or Tyr;
$T^6$ is $^D$Pro; $^D$Pro(4S)OH; or $^D$Dab;
$T^7$ is Pro; or Arg;
$P^8$ is Nle; or Leu;
$P^9$ is Ser; or Dap;
$P^{10}$ is Tyr;
$P^{11}$ is Dab; or Asn;
$P^{12}$ is Sar; Dab; or Orn;
with the proviso that,
  if linker L is connected with module A by a carbonyl
    (C=O) point of attachment of $P^2$; $P^5$; or $P^{12}$; then
    $P^2$; $P^5$; or $P^{12}$; is
  Asp; Glu; $^D$Asp; or $^D$Glu;
or a pharmaceutically acceptable salt thereof.

In another particular embodiment (105) of the invention the elements of general formula (I) are defined as in particular embodiment (104),
with the proviso that
$P^4$ and $P^9$ taken together form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; and/or
$P^2$ is Ser; and/or
$P^4$ is Tyr; and/or
$P^5$ is Tyr; and/or
$T^7$ is Arg;
or a pharmaceutically acceptable salt thereof.

In another particular embodiment (106) of the invention the elements of general formula (I) are defined as follows, for module A,
if i=1, and $P^{13}$ and $P^{14}$ are not connected as aforementioned, and
$P^{13}$ and $P^{14}$ taken together form an interstrand linking bis(amino acid)-structure based on the linkage of two L amino acid residues; or two D amino acid residues; or an L amino acid residue with an D amino acid residue; following
  connection of the side chain of Cys; Hcy; or Pen; at $P^{13}$ with the side chain of Cys; Hcy; or Pen; Ac-Cys; Ac-Hcy; or Ac-Pen; at $P^{14}$ by a disulfide linkage; or
  connection of the side chain of Dap; Dab; Orn; or Lys; at $P^{13}$ with the side chain of Asp; Glu; hGlu; Ac-Asp; Ac-Glu; or Ac-hGlu; at $P^{14}$ by a lactam linkage; or
  connection of the side chain of Asp; Glu; or hGlu; at $P^{13}$ with the side chain of Dap; Dab; Orn; Lys; or Ac-Dap; Ac-Dab; Ac-Orn; or Ac-Lys; at $P^{14}$ by a lactam linkage; and
$P^2$ and $P^{11}$ taken together may form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or connection of the side chain of Dap; Dab; or Orn; with the side chain of Dap; Dab; or Orn; by an urea linkage;

P$^1$ is Trp;
P$^2$ is Dab;
P$^3$ is tBuGly; Val; or Tyr;
P$^4$ is Ala; Ser; Thr, or Asn;
P$^5$ is Ser; or Val;
T$^6$ is $^D$Pro; $^D$Pro(4S)OH; or $^D$Dab;
T$^7$ is Pro;
P$^8$ is Nle; or Leu;
P$^9$ is Ser; or Dap;
P$^{10}$ is Tyr;
P$^{11}$ is Dab; or Asn;
P$^{12}$ is Sar; Dab; or Orn;
with the proviso that,
  if linker L is connected with module A by a carbonyl (C=O) point of attachment of P$^2$; P$^5$; or P$^{12}$; then
  P$^2$; P$^5$; or P$^{12}$; is
  Asp; Glu; $^D$Asp; or $^D$Glu;
or a pharmaceutically acceptable salt thereof.

In another particular embodiment (107) of the invention the elements of general formula (I) are defined as follows,
for module A,
if i=1, and P$^{13}$ and P$^{14}$ are not connected as aforementioned, and
P$^{13}$ and P$^{14}$ taken together form an interstrand linking bis(amino acid)-structure based on the linkage of two L amino acid residues; or two D amino acid residues; or an L amino acid residue with an D amino acid residue; following
  connection of the side chain of Cys; Hcy; or Pen; at P$^{13}$ with the side chain of Cys; Hcy; or Pen; Ac-Cys; Ac-Hcy; or Ac-Pen; at P$^{14}$ by a disulfide linkage; or
  connection of the side chain of Dap; Dab; Orn; or Lys; at P$^{13}$ with the side chain of Asp; Glu; hGlu; Ac-Asp; Ac-Glu; or Ac-hGlu; at P$^{14}$ by a lactam linkage; or
  connection of the side chain of Asp; Glu; or hGlu; at P$^{13}$ with the side chain of Dap; Dab; Orn; Lys; or Ac-Dap; Ac-Dab; Ac-Orn; or Ac-Lys; at P$^{14}$ by a lactam linkage; and
P$^2$ and P$^{11}$ taken together may form an interstrand linking bis(amino acid)-structure based on the linkage of two L amino acid residues; or two D amino acid residues; following
  connection of the side chain of Cys; Hcy; or Pen; with the side chain of Cys; Hcy; or Pen; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;
P$^1$ is Trp; Tyr; or Phe;
P$^2$ is Dab; Dap; Orn; Lys; or Arg;
P$^3$ is tBuGly; Ala; Val; Abu; Leu; Ile; Nle; or Nva;
P$^4$ is Ala; Val; Abu; Leu; Ile; Nle; or Nva;
P$^5$ is Ser; Thr; alloThr; or Hse;
T$^6$ is $^D$Pro;
T$^7$ is Pro;
P$^8$ is Nle; Val; Leu; Ile; Nva; Abu; or Ala;
P$^9$ is Ser; Thr; alloThr; or Hse;
P$^{10}$ is Tyr; Phe; Trp; or Phg;
P$^{11}$ is Dab; Dap; Orn; Lys; or Arg;
P$^{12}$ is Dab; Dap; Orn; Lys; or Arg;
with the proviso that,
  if linker L is connected with module A by a carbonyl (C=O) point of attachment of P$^2$; P$^5$; or P$^{12}$; then
  P$^2$; P$^5$; or P$^{12}$; is
  Asp; Glu; $^D$Asp; or $^D$Glu;
or a pharmaceutically acceptable salt thereof.

Another alternative particular embodiment (108) of the invention relates to derivatives of general formula (I), wherein specifically
for linker L,
if k=1,
L$^1$ is Gly; Sar; Dab; NMeDab; Dab(Me); Dap; Orn; Lys; $^D$Dab; $^D$Dap; $^D$Orn; $^D$Lys; Thr; alloThr; Ser; Hse; $^D$Thr; $^D$alloThr; $^D$Ser; $^D$Hse; Ala; Abu; Leu; Ile; Nle; Val; Nva; $^D$Ala; $^D$Abu; $^D$Leu; $^D$Val; $^D$Nva; $^D$Ile; $^D$Nle; Gln; Asn; $^D$Gln; $^D$Asn; Tyr; Phe; Trp; $^D$Tyr; $^D$Phe; or $^D$Trp;
if k=2, the additional element
L$^2$ is Dab; Dab(Me); Dap; Orn; Lys; $^D$Dab; $^D$Dap; $^D$Orn; $^D$Lys; Thr; alloThr; Ser; Hse; $^D$Thr; $^D$alloThr; $^D$Ser; or $^D$Hse;
if k=3, the additional element
L$^3$ is Dab; Dab(Me); Dap; Orn; or Lys;
or a pharmaceutically acceptable salt thereof.

Another alternative particular embodiment (109) of the invention relates to derivatives of general formula (I) according to alternative particular embodiment (108) with the proviso that,
if k=1-3, then
L$^1$ is Gln; Asn; $^D$Gln; $^D$Asn; Tyr; Phe; Trp; $^D$Tyr; $^D$Phe; or $^D$Trp;
or a pharmaceutically acceptable salt thereof.

Another alternative particular embodiment (110) of the invention relates to derivatives of general formula (I), wherein specifically
for linker L,
if k=1,
L$^1$ is Gly; Dab; NMeDab; Dab(Me); Dap; Orn; Lys; $^D$Dab; $^D$Dap; $^D$Orn; $^D$Lys; Thr; alloThr; Ser; or Hse;
if k=2, the additional element
L$^2$ is Dab; Dab(Me); Dap; Orn; Lys; Thr; alloThr; Ser; or Hse;
if k=3, the additional element
L$^3$ is Dab; Dab(Me); Dap; Orn; or Lys;
or a pharmaceutically acceptable salt thereof.

Another alternative particular embodiment (111) of the invention relates to derivatives of general formula (I), wherein specifically
for linker L,
if k=1,
L$^1$ is Dab; NMeDab; Dab(Me); Dap; Orn; Lys; $^D$Dab; $^D$Dap; $^D$Orn; or $^D$Lys;
if k=2, the additional element
L$^2$ is Dab; Dab(Me); Dap; Orn; Lys; Thr; alloThr; Ser; or Hse;
if k=3, the additional element
L$^3$ is Dab; Dab(Me); Dap; Orn; or Lys;
or a pharmaceutically acceptable salt thereof.

Hereinafter follows a list of abbreviations, corresponding to generally adopted usual practice, of amino acids which, or the residues of which, are suitable for the purposes of the present invention and referred to in this document.

In spite of this specific determination of amino acids, it is noted that, for a person skilled in the art, it is obvious that derivatives of these amino acids, resembling alike structural and physico-chemical properties, lead to functional analogs with similar biological activity, and therefore still form part of the gist of this invention.

Ala L-Alanine
Arg L-Arginine
Asn L-Asparagine

Asp L-Aspartic acid
Cit L-Citrulline
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Orn L-Ornithine
Phe L-Phenylalanine
Pro L-Proline
Ser L-Serine
Thr L-Threonine
Trp L-Tryptophan
Tyr L-Tyrosine
Val L-Valine
Abu (S)-2-aminobutanoic acid
Abu(4N$_3$) (S)-2-amino-4-azidobutanoic acid
Agp (S)-2-amino-3-guanidinopropanoic acid
Ala(tBu) (S)-2-amino-4,4-dimethylpentanoic acid
Ala(4butoxyPhUr) (S)-2-amino-3-(3-(4-butoxyphenyl)ureido)propanoic acid
Ala(cHex) (S)-2-amino-3-cyclohexylpropanoic acid
Ala(cPr) (S)-2-amino-3-cyclopropylpropanoic acid
Ala(iPrUr) (S)-2-amino-3-(3-isopropylureido)propanoic acid
Ala(2ClPhUr) (S)-2-amino-3-(3-(2-chlorophenyl)ureido)propanoic acid
Ala(4ClPhUr) (S)-2-amino-3-(3-(4-chlorophenyl)ureido)propanoic acid
Ala(2Furyl) (S)-2-amino-3-(furan-2-yl)propanoic acid
Ala(3Furyl) (S)-2-amino-3-(furan-3-yl)propanoic acid
Ala(1Im) (S)-2-amino-3-(1H-imidazol-1-yl)propanoic acid
Ala(2Im) (S)-2-amino-3-(1H-imidazol-2-yl)propanoic acid
Ala(Ppz) (S)-2-amino-3-(piperazin-1-yl)propanoic acid
Ala(cPr) (S)-2-amino-3-cyclopropylpropanoic acid
Ala(Pyrazinyl) (S)-2-amino-3-(pyrazin-2-yl)propanoic acid
Ala(1Pyrazolyl) (S)-2-amino-3-(1H-pyrazol-1-yl)propanoic acid
Ala(3Pyrazolyl) (S)-2-amino-3-(1H-pyrazol-3-yl)propanoic acid
Ala(2Pyrimidin) (S)-2-amino-3-(pyrimidin-2-yl)propanoic acid
Ala(4Pyrimidin) (S)-2-amino-3-(pyrimidin-4-yl)propanoic acid
Ala(5Pyrimidin) (S)-2-amino-3-(pyrimidin-5-yl)propanoic acid
Ala(3PyrMeUr) (S)-2-amino-3-(3-(pyridin-3-ylmethyl)ureido)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Alb (S)-2-amino-3-ureidopropanoic acid
Azt (S)-azetidine-2-carboxylic acid
tBuGly (S)-2-amino-3,3-dimethylbutanoic acid
Bbta (S)-2-amino-3-(1-benzothiophen-3-yl)propanoic acid
Bip (S)-2-amino-3-(4-biphenylyl)propanoic acid
Cpa (S)-2-amino-3-cyclopentylpropanoic acid
Cha (S)-2-amino-3-cyclohexylpropanoic acid
Cpg (S)-2-amino-2-cyclopentylacetic acid
Chg (S)-2-amino-2-cyclohexylacetic acid
Dab (S)-2,4-diaminobutanoic acid
Dab(Ac) (S)-4-acetamido-2-aminobutanoic acid
Dab(cPr) (S)-2-amino-4-(cyclopropylamino)butanoic acid
Dab(iPr) (S)-2-amino-4-(isopropylamino)butanoic acid
Dab(Me) (S)-2-amino-4-(methylamino)butanoic acid
Dab(2PyrMe) (S)-2-amino-4-(pyridin-2-ylmethylamino)butanoic acid
Dab(Arg) (S)-2-amino-4-((S)-2-amino-5-guanidino-pentanamido)butanoic acid
Dap (S)-2,3-diaminopropanoic acid
Dap(Ac) (S)-3-acetamido-2-aminopropanoic acid
Dap(AcThr) (S)-3-((2S,3R)-2-acetamido-3-hydroxybutanamido)-2-aminopropanoic acid
Dap(cPr) (S)-2-amino-3-(cyclopropylamino)propanoic acid
Dap(iPr) (S)-2-amino-3-(isopropylamino)propanoic acid
Dap(MeSO$_2$) (S)-2-amino-3-(methylsulfonamido)propanoic acid
Dap(2,3-OHpropionyl) (2S)-2-amino-3-(2,3-dihydroxypropanamido)propanoic acid
Dap(Thr) (S)-2-amino-3-((2S,3R)-2-amino-3-hydroxybutanamido)-propanoic acid
Dap(Glu) (S)-4-amino-5-((S)-2-amino-2-carboxyethylamino)-5-oxo-pentanoic acid
Dab(Trp) (S)-2-amino-4-((2S)-2-amino-3-(1H-indol-3-yl)propanamido)-butanoic acid
Gly(cPr) (S)-2-amino-2-cyclopropylacetic acid
hAla(1Im) (S)-2-amino-3-(1H-imidazol-1-yl)-butanoic acid
hAla(2Im) (S)-2-amino-3-(1H-imidazol-2-yl)-butanoic acid
hArg (S)-2-amino-6-guanidinohexanoic acid
hCha (S)-2-amino-4-cyclohexylbutanoic acid
hCys, hCy, Hcy (S)-2-amino-4-mercaptobutanoic acid
hGlu (S)-2-amino-hexanedioic acid
hHis (S)-2-amino-4-(1H-imidazol-5-yl)butanoic acid
hLeu (S)-2-amino-5-methylhexanoic acid
hLys (S)-2,7-diaminoheptanoic acid
h2Pal (S)-2-amino-4-(pyridin-2-yl)-butanoic acid
h3Pal (S)-2-amino-4-(pyridine-3-yl)-butanoic acid
h4Pal (S)-2-amino-4-(pyridine-4-yl)-butanoic acid
hSer, Hse (S)-2-amino-4-hydroxybutanoic acid
hTrp (S)-2-amino-4-(1H-indol-3-yl)butanoic acid
hTyr (S)-2-amino-4-(4-hydroxyphenyl)butanoic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Lys(Bz) (S)-2-amino-6-benzamidohexanoic acid
Lys(Me) (S)-2-amino-6-(methylamino)hexanoic acid
Lys(Nic) (S)-2-amino-6-(nicotinamido)hexanoic acid
Met(O$_2$) (S)-2-amino-4-(methylsulfonyl)butanoic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
Nle(6OBn) (S)-2-amino-6-(benzyloxy)hexanoic acid
NMeGly N-Methylglycine
NMeAla L-N-Methylalanine
NMeAbu N-Methyl-(S)-2-aminobutanoic acid
NMeAsp L-N-Methylaspartic acid
NMeDap (S)-2-methylamino-3-aminopropanoic acid
NMeGlu L-N-Methylglutamic acid
NMehGlu (S)-2methylamino-hexanedioic acid
NMeVal L-N-Methylvaline
NMeNva L-N-Norvaline
NMeLeu L-N-Methylleucine
NMeIle L-N-Methylisoleucine
NMeNle L-N-Methylnorleucine
NMeAla L-N-Methylalanine
NMeAbu (S)-2-methylaminobutanoic acid
NMeTrp L-N-Methyltryptophan
NMeTyr L-N-Methyltyrosine
NMePhe L-N-Methylphenylalanine NMeCys L-N-Methylcysteine
NMehCy (S)-2-methylamino-4-mercaptobutanoic acid
NMePen (S)-2-methylamino-3-methyl-3-sulfanyl-butanoic acid
NMeDab (S)-2-methylamino-4-aminobutanoic acid
NMeOrn L-N-Methylornithine
NMeLys L-N-Methyllysine
Nva (S)-2-aminopentanoic acid
OctG (S)-2-aminodecanoic acid
Oic (2S,3aS,7aS)-octahydro-1H-indole-2-carboxylic acid
Orn(Ac) (S)-5-acetamido-2-aminopentanoic acid
Orn(cPr) (S)-2-amino-5-(cyclopropylamino)pentanoic acid
Orn(iPr) (S)-2-amino-5-(isopropylamino)pentanoic acid
2Pal (S)-2-amino-3-(pyridine-2-yl) propionic acid
3Pal (S)-2-amino-3-(pyridine-3-yl)propionic acid
4Pal (S)-2-amino-3-(pyridine-4-yl)propionic acid
Pen (S)-2-amino-3-methyl-3-sulfanyl-butanoic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl$_2$) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(3,4F$_2$) (S)-2-amino-3-(3,4-difluorophenyl)propanoic acid
Phe(3CN) (S)-2-amino-3-(3-cyanophenyl)propanoic acid
Phe(4CN) (S)-2-amino-3-(4-cyanophenyl)propanoic acid
Phe(2CF$_3$) (S)-2-amino-3-(2-(trifluoromethyl)phenyl)propanoic acid
Phe(3CF$_3$) (S)-2-amino-3-(3-(trifluoromethyl)phenyl)propanoic acid
Phe(4CF$_3$) (S)-2-amino-3-(4-(trifluoromethyl)phenyl)propanoic acid
Phe(3,4(CF$_3$)$_2$) (S)-2-amino-3-(3,4-bis(trifluoromethyl)phenyl)propanoic acid
Phe(4COOMe) (S)-2-amino-3-(4-(methoxycarbonyl)phenyl)propanoic acid
Phe(4NH$_2$) (S)-2-amino-3-(4-aminophenyl)propanoic acid
Phe(3OH) (S)-2-amino-3-(3-hydroxyphenyl)propanoic acid
Phg (S)-2-amino-2-phenylacetic acid
Pic (S)-piperidine-2-carboxylic acid
Pip 4-aminopiperidine-4-carboxylic acid
Pra L-propargylglycine
Pro((4R)NH$_2$) (2S,4R)-4-aminopyrrolidine-2-carboxylic acid
Pro((4S)NH$_2$) (2S,4S)-4-aminopyrrolidine-2-carboxylic acid
Pro((3R)OH) (2S,3R)-3-hydroxypyrrolidine-2-carboxylic acid
Pro((3S)OH), Pro(3S)OH (2S,3S)-3-hydroxypyrrolidine-2-carboxylic acid
Pro((4R)OH), Hyp (2S,4R)-4-hydroxypyrrolidine-2-carboxylic acid
Pro((4S)OH), Pro(4S)OH (2S,4S)-4-hydroxypyrrolidine-2-carboxylic acid
Pro((4R)F), Pro(4R)F (2S,4R)-4-fluoropyrrolidine-2-carboxylic acid
Pro((4R)OBn) (2S,4R)-4-(benzyloxy)pyrrolidine-2-carboxylic acid
Pro((4S)OBn) (2S,4S)-4-(benzyloxy)pyrrolidine-2-carboxylic acid
Sar; NMeGly N-Methylglycine
Ser(Bn) (S)-2-amino-3-(benzyloxy)propanoic acid
Ser(Me) (S)-2-amino-3-methoxy-propanoic acid
Thi (S)-2-amino-3-(thiophen-2-yl)propanoic acid
alloThr (2S,3S)-2-amino-3-hydroxybutanoic acid
Thr(Bn) (2S,3R)-2-amino-3-(benzyloxy)butanoic acid
Thr(Me) (2S,3R)-2-amino-3-(methyloxy)butanoic acid
Thz (R)-thiazolidine-4-carboxylic acid
Thz(5,5Me$_2$) (R)-2,2-dimethylthiazolidine-4-carboxylic acid
Tic (S)-1,2,3,4-Tetrahydroisoquinoline-3-carboxylic acid
Tic(7OH) (S)-7-hydroxy-1,2,3,4-tetrahydroisoquinoline-3-carboxylic acid
Trp(7Aza) (S)-2-amino-3-(1H-pyrrolo[2,3-b]pyridin-3-yl)propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF$_3$) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(Ph) (S)-2-amino-3-(4-phenoxyphenyl)propanoic acid
Tyr(4OHPh) (S)-2-amino-3-[4-(4-hydroxyphenoxy)phenyl]propanoic acid
Tyr(3F) (S)-2-amino-3-(3-fluoro-4-hydroxyphenyl)propanoic acid
Tza (S)-2-amino-3-(thiazol-4-yl)propanoic acid The abbreviation of D-isomers, e.g.; $^D$Lys corresponds to the epimer at the 2-position of the appropriate amino acid described above. Same applies for the generic descriptions of the amino acids, e.g. AA1 which has AA1$^D$ as the corresponding α-epimer. The abbreviation "Ac-" followed by an abbreviation of an amino acid, or amino acid residue, as listed above, corresponds to the N-acetylated amino acid, or amino acid residue, like, for example:
Ac-Trp N-acetyl-L-tryptophan
  ((S)-2-acetylamino-3-(1H-indol-3-yl)propanoic acid
The abbreviation "Gua-" followed by an abbreviation of an amino acid, or amino acid residue, as listed above, corresponds to the N-amidinylated amino acid, or amino acid residue, like, for example:
Gua-Glu N-amidino-L-glutamic acid
  (S)-2-guanidino-pentanedioic acid
The abbreviation "TMG-" followed by an abbreviation of an amino acid, or amino acid residue, as listed above, corresponds to the amino acid, or amino acid residue, like, for example:
TMG-Trp (S)-2-(N,N,N',N'-tetramethylguanidino)-3-(1H-indol-3-yl)propanoic acid
The abbreviation of an amino acid, or amino acid residue, as listed above, followed by "—NH$_2$" corresponds to the C-terminal amidated amino acid, or amino acid residue, like, for example:
Cys-N H2 (S)-2-amino-3-sulfhydrylpropanamide In a preferred embodiment (112) of the invention the β-hairpin peptidomimetics of general formula (I) are selected from the group consisting of
Ex. 1 to 216, the sequences of which are shown in Table 1; or a pharmaceutically acceptable salt thereof.

In a preferred embodiment (113) of the invention the β-hairpin peptidomimetics of general formula (I) are selected from the group consisting of
Ex. 1 to 63, 64 to 76, 78, 79, 80 to 85, 88, 89, 91 to 94, 98, 101, 104, 106, 107, 111, 114, 116, 117, 121 to 124, 131 to 135, 139, 141, 142, 145, 147, 148, 150, 152, 173 to 175, 183 to 185, 187, 188 to 190, 192, 193 to 200, 204 to 206, 208, 210, 214, 215, the sequences of which are shown in Table 1;
or a pharmaceutically acceptable salt thereof.

In a preferred embodiment (114) of the invention the β-hairpin peptidomimetics of general formula (I) are selected from the group consisting of
Ex. 77, 86, 87, 90, 95 to 97, 99, 100, 102, 103, 105, 108 to 110, 112, 113, 115, 118 to 120, 125 to 130, 136 to 138, 140, 143, 144, 146, 149, 151, 153 to 172, 176 to 182, 186, 191, 201 to 203, 207, 209, 211 to 213, 216, the sequences of which are shown in Table 1;
or a pharmaceutically acceptable salt thereof.

In a preferred embodiment (115) of the invention the β-hairpin peptidomimetics of general formula (I) are selected from the group consisting of Ex. 1 to 63, the sequences of which are shown in Table 1;
or a pharmaceutically acceptable salt thereof.

In another preferred embodiment (116) of the invention the β-hairpin peptidomimetics of general formula (I) are selected from the group consisting of
Ex. 1 to 11, 64 to 103, the sequences of which are shown in Table 1;
or a pharmaceutically acceptable salt thereof.

In another preferred embodiment (117) of the invention the β-hairpin peptidomimetics of general formula (I) are selected from the group consisting of
Ex. 1 to 11, 64 to 76, 78, 79, 80 to 85, 88, 89, 91 to 94, 98, 101, the sequences of which are shown in Table 1;
or a pharmaceutically acceptable salt thereof.

In another preferred embodiment (118) of the invention the β-hairpin peptidomimetics of general formula (I) are selected from the group consisting of
Ex. 77, 86, 87, 90, 95 to 97, 99, 100, 102, 103, the sequences of which are shown in Table 1;
or a pharmaceutically acceptable salt thereof.

In another preferred embodiment (119) of the invention the β-hairpin peptidomimetics of general formula (I) are selected from the group consisting of
Ex. 1 to 11, the sequences of which are shown in Table 1;
or a pharmaceutically acceptable salt thereof.

In another preferred embodiment (120) of the invention the β-hairpin peptidomimetics of general formula (I) are selected from the group consisting of
Ex. 12 to 34, 104 to 182, the sequences of which are shown in Table 1; or a pharmaceutically acceptable salt thereof.

In another preferred embodiment (121) of the invention the β-hairpin peptidomimetics of general formula (I) are selected from the group consisting of
Ex. 12 to 34, 104, 106, 107, 111, 114, 116, 117, 121 to 124, 131 to 135, 139, 141, 142, 145, 147, 148, 150, 152, 173 to 175, the sequences of which are shown in Table 1;
or a pharmaceutically acceptable salt thereof.

In another preferred embodiment (122) of the invention the β-hairpin peptidomimetics of general formula (I) are selected from the group consisting of
Ex. 105, 108 to 110, 112, 113, 115, 118 to 120, 125 to 130, 136 to 138, 140, 143, 144, 146, 149, 151, 153 to 172, 176 to 182, the sequences of which are shown in Table 1;
or a pharmaceutically acceptable salt thereof.

In another preferred embodiment (123) of the invention the β-hairpin peptidomimetics of general formula (I) are selected from the group consisting of
Ex. 12 to 34, the sequences of which are shown in Table 1;
or a pharmaceutically acceptable salt thereof.

In another preferred embodiment (124) of the invention the β-hairpin peptidomimetics of general formula (I) are selected from the group consisting of
Ex. 35 to 44, 183 to 187, the sequences of which are shown in Table 1;
or a pharmaceutically acceptable salt thereof.

In another preferred embodiment (125) of the invention the β-hairpin peptidomimetics of general formula (I) are selected from the group consisting of
Ex. 35 to 44, 183 to 185, 187, the sequences of which are shown in Table 1;
or a pharmaceutically acceptable salt thereof.

In another preferred embodiment (126) of the invention the β-hairpin peptidomimetics of general formula (I) is Ex. 186, the sequences of which is shown in Table 1;
or a pharmaceutically acceptable salt thereof.

In another preferred embodiment (127) of the invention the β-hairpin peptidomimetics of general formula (I) are selected from the group consisting of
Ex. 35 to 44, the sequences of which are shown in Table 1;
or a pharmaceutically acceptable salt thereof.

In another preferred embodiment (128) of the invention the β-hairpin peptidomimetics of general formula (I) are selected from the group consisting of
Ex. 45 to 56, 188 to 192, the sequences of which are shown in Table 1;
or a pharmaceutically acceptable salt thereof.

In another preferred embodiment (129) of the invention the β-hairpin peptidomimetics of general formula (I) are selected from the group consisting of
Ex. 45 to 56, 188 to 190, 192, the sequences of which are shown in Table 1;
or a pharmaceutically acceptable salt thereof.

In another preferred embodiment (130) of the invention the β-hairpin peptidomimetics of general formula (I) is Ex. 191, the sequences of which is shown in Table 1;
or a pharmaceutically acceptable salt thereof.

In another preferred embodiment (131) of the invention the β-hairpin peptidomimetics of general formula (I) are selected from the group consisting of
Ex. 45 to 56, the sequences of which are shown in Table 1;
or a pharmaceutically acceptable salt thereof.

In another preferred embodiment (132) of the invention the β-hairpin peptidomimetics of general formula (I) are selected from the group consisting of
Ex. 57 to 63, 193 to 216, the sequences of which are shown in Table 1;
or a pharmaceutically acceptable salt thereof.

In another preferred embodiment (133) of the invention the β-hairpin peptidomimetics of general formula (I) are selected from the group consisting of
Ex. 57 to 63, 193 to 200, 204 to 206, 208, 210, 214, 215, the sequences of which are shown in Table 1;
or a pharmaceutically acceptable salt thereof.

In another preferred embodiment (134) of the invention the β-hairpin peptidomimetics of general formula (I) are selected from the group consisting of
Ex. 201 to 203, 207, 209, 211 to 213, 216, the sequences of which are shown in Table 1;
or a pharmaceutically acceptable salt thereof.

In another preferred embodiment (135) of the invention the β-hairpin peptidomimetics of general formula (I) are selected from the group consisting of Ex. 57 to 63, the sequences of which are shown in Table 1; or a pharmaceutically acceptable salt thereof.

In accordance with the present invention these β-hairpin peptidomimetics can be prepared by a process A and/or process B, as further specified below.

Process A is based on continuous synthesis of the peptides and comprises:

(a) coupling an appropriately functionalized solid support with an appropriately N-protected derivative of that amino acid which in the desired end-product is at position $Q^7$ of module B, as defined above, any functional group which may be present in said N-protected amino acid derivative being likewise appropriately protected;

(b) removing the N-protecting group from the product obtained in step (a);

(c) coupling the product thus obtained with an appropriately N-protected derivative of that amino acid which in the desired end-product corresponds to $Q^6$, any functional group which may be present in said N-protected amino acid derivative being likewise appropriately protected;

(d) if desired, selectively deprotecting one or several protected functional group(s) present in the molecule and appropriately substituting the reactive group(s) thus liberated by attaching one or several moieties derived from acids, amino acids or amines;

(e) further effecting steps substantially corresponding to steps (b) to (d) using appropriately N-protected derivatives of amino acids which in the desired end-product are at positions $Q^5$ to $Q^1$, any functional group(s) which may be present in said N-protected amino acid derivatives being likewise appropriately protected;

(f) if coupling to the solid support in step (a) is via a hydroxyl group of the amino acid residue at position $Q^7$, performing the following chemical conversion, if desired, subsequent to step (e) or, if desired and required, subsequent to a later coupling with an appropriately N-protected derivative of an amino acid, as described below:
selectively removing an N-protecting group at position $Q^1$ and a carboxyl-protecting group at position $Q^7$; and generating a macrolactam cycle, as defined above, by formation of an amide bond between the thus liberated carboxyl group at position $Q^7$ and the amino group at $Q^1$ of module B;

(g) if L is present (k=1, 2, or 3), as defined above, effecting steps substantially corresponding to steps (b) to (d) using appropriately N-protected derivatives of amino acids which in the desired end-product are at positions $L^k$ to $L^1$, any functional group(s) which may be present in said N-protected amino acid derivatives being likewise appropriately protected;

(h) if $P^{14}$ is not present in module A (i=0), as defined above, effecting steps substantially corresponding to steps (b) to (d) using appropriately N-protected derivatives of amino acids which in the desired end-product are at positions $P^{13}$ to $P^8$, $T^7$, $T^6$, $P^5$ to $P^1$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as defined above; and, if desired, selectively removing the N-protecting group at position $P^1$ and chemically transforming the thus liberated amino group;

(l) if $P^{14}$ is present in module A (i=1), as defined above, effecting steps substantially corresponding to steps (b) to (d) using an appropriately N-protected derivative of an amino acid which in the desired end-product is at position $P^n$ (n=2, 5, 12, 13, or 14), any functional group(s) which may be present in said N-protected amino acid derivative being likewise appropriately protected; and if n=2, further performing steps comprising:

(j1) effecting steps substantially corresponding to steps (b) to (d) using appropriately N-protected derivatives of amino acids which in the desired end-product are at positions $P^1$, $P^{14}$ to $P^8$, $T^7$, $T^6$, and $P^5$ to $P^3$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as defined above; and (k1) selectively removing a carboxyl-protecting group at position $P^2$ and the N-protecting group at position $P^3$; and generating a macrolactam cycle, as defined above, by formation of an amide bond between the thus liberated carboxyl and amino functions;

if n=5, further performing steps which comprise:

(j2) further effecting steps substantially corresponding to steps (b) to (d) using appropriately N-protected derivatives of amino acids which in the desired end-product are at positions $P^4$ to $P^1$, $P^{14}$ to $P^8$, $T^7$, and $T^6$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as defined above; and (k2) selectively removing a carboxyl-protecting group at position $P^5$ and the N-protecting group at position $T^6$; and generating a macrolactam cycle, as defined above, by formation of an amide bond between the thus liberated carboxyl and amino functions;

if n=12, further performing steps comprising:

(j3) further effecting steps substantially corresponding to steps (b) to (d) using appropriately N-protected derivatives of amino acids which in the desired end-product are at positions $P^{11}$ to $P^8$, $T^7$, $T^6$, $P^5$ to $P^1$, $P^{14}$ and $P^{13}$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as to defined above; and (k3) selectively removing a carboxyl-protecting group at position $P^{12}$ and the N-protecting group at position $P^{13}$; and generating a macrolactam cycle, as defined above, by formation of an amide bond between the thus liberated carboxyl and amino functions;

if n=13, further performing steps comprising:

(j4) further effecting steps substantially corresponding to steps (b) to (d) using appropriately N-protected derivatives of amino acids which in the desired end-product are at positions $P^{12}$ to $P^8$, $T^7$, $T^6$, $P^5$ to $P^1$, and $P^{14}$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as defined above;

(k4) if desired, selectively removing the N-protecting group at position $P^{14}$, and chemically transforming the thus obtained amino function; and (l4) if desired, performing one of the following chemical conversions:

(1) selectively removing a carboxyl-protecting group at position $P^{13}$ and an N-protecting group at position $P^{14}$; and generating a macrolactam cycle, as defined above, by formation of an amide bond between the thus liberated carboxyl and amino functions;

or (2) selectively removing a protecting group at position $P^{13}$ and a protecting group at position $P^{14}$; and chemically transforming the reactive groups thus liberated to generate an interstrand linkage, as defined above;

or (3) implementing chemical transformations of a group present at position $P^{13}$ and a group present at position $P^{14}$ to generate an interstrand linkage, as defined above;

if n=14, performing steps comprising:

(j5) further effecting steps substantially corresponding to steps (b) to (d) using appropriately N-protected derivatives of amino acids which in the desired end-product are at positions $P^{13}$ to $P^8$, $T^7$, $T^6$, $P^5$ to $P^1$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as defined above;

(k5) if desired, selectively removing the N-protecting group at position $P^1$, and chemically transforming the thus obtained amino function; and (l5) if desired, selectively removing a carboxyl-protecting group at position $P^{14}$ and an N-protecting group at position $P^1$; and generating a macrolactam cycle, as defined above, by formation of an amide bond between the thus liberated carboxyl and amino functions;

(m) if desired, selectively deprotecting one or several protected functional group(s) present in the molecule and chemically transforming the reactive group(s) thus liberated to form an interstrand linkage(s), as defined above;

(n) if desired, implementing additional chemical transformations of one or more group(s) present in the molecule;

(o) if desired, selectively deprotecting one or several protected functional group(s) present in the molecule and appropriately substituting the reactive group(s) thus liberated by attaching one or several moieties derived from acids, amino acids or amines;

(p) if coupling to the solid support in step (a) is via a carboxyl group of the amino acid residue at position $Q^7$ of module B, as described above, selectively removing an N-protecting group at position $Q^1$ of module B;

(q) detaching the product thus obtained from the solid support;

(r) if coupling to the solid support in step (a) is via a carboxyl group of the amino acid residue at position $Q^7$ of module B, as described above, generating a macrolactam cycle by formation of an amide bond between the thus liberated carboxyl group at position $Q^7$ and the amino group at position $Q^1$ of module B, as defined above;

(s) if desired or required, implementing additional chemical transformations of one or more group(s) present in the molecule;

(t) if desired or required, selectively deprotecting one or several protected functional group(s) present in the molecule and chemically transforming the reactive group(s) thus liberated;

(u) removing any protecting groups present on functional groups of any members of the chain of amino acid residues and, if desired, any protecting group(s) which may in addition be present in the molecule;

(v) if desired, implementing additional chemical transformations of one or more reactive group(s) present in the molecule; and (w) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

Process B is based on a peptide fragment coupling strategy and comprises:

(I) generating a fully protected peptide fragment comprising amino acid residues of module B and of L, as defined above, by performing steps comprising:

(a) to (f), corresponding to steps (a) to (f) as described in process A above;

(g) if coupling to the solid support in step (a) is via a carboxyl group of the amino acid residue at position $Q^7$ of module B, as described above, performing the following chemical conversion:

selectively removing an N-protecting group at position $Q^1$; detaching the product thus obtained from the solid support; and generating a macrolactam cycle, as defined above, by formation of an amide bond between the thus liberated carboxyl group at position $Q^7$ and the amino group at position $Q^1$;

(h) if coupling to the solid support in step (a) is via a hydroxyl group of the amino acid residue at position $Q^7$ of module B, as described above, detaching the product thus obtained from the solid support;

(i) if L is present, removing an N-protecting group at position $L^1$; and (j) if L is not present, removing an N-protecting group at position $Q^1$;

(IIa) either, generating a fully protected peptide fragment comprising amino acid residues of module A, as defined above, if i=0, by performing steps comprising:

(a) coupling an appropriately functionalized solid support with an appropriately N-protected derivative of that amino acid which in the desired end-product is at position $P^{13}$, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is at position $P^{12}$, any functional group which may be present in said N-protected amino acid derivative being likewise appropriately protected;

(d) if desired, selectively deprotecting one or several protected functional group(s) present in the molecule and appropriately substituting the reactive group(s) thus liberated by attaching one or several moieties derived from acids, amino acids or amines;

(e) further effecting steps substantially corresponding to steps (b) to (d) using appropriately N-protected derivatives of amino acids which in the desired end-product are at positions $P^{11}$ to $P^8$; $T^7$; $T^6$, $P^5$ to $P^1$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage (s), as defined above;

(f) if desired, selectively deprotecting one or several protected functional group(s) present in the molecule and appropriately substituting the reactive group(s) thus liberated by attaching one or several moieties derived from acids, amino acids or amines;

(g) if desired, selectively removing the N-protecting group at position $P^1$; and chemically transforming the amino group thus liberated;

(h) if desired, selectively deprotecting one or several protected functional group(s) present in the molecule and chemically transforming the reactive group(s) thus liberated to form an interstrand linkage, as defined above;

(i) if desired, implementing additional chemical transformations of one or more group(s) present in the molecule;

(j) if desired, selectively removing a carboxyl protecting group at position $P^5$, $P^{12}$ or $P^{13}$;

(k) detaching the product thus obtained from the solid support and, if desired, removing in the same step a carboxyl protecting group at position $P^5$, $P^{12}$ or $P^{13}$;

(l) if desired or required, selectively protecting any carboxyl group(s) present in the molecule;

(m) if desired or required, implementing additional chemical transformations of one or more group(s) present in the molecule;

(n) if desired or required, selectively deprotecting one or several protected functional group(s) present in the molecule and chemically transforming the reactive group(s) thus liberated; and (o) if desired or required, selectively removing a carboxyl protecting group at position $P^5$, $P^{12}$ or $P^{13}$;

(IIb) or, generating a fully protected peptide fragment comprising amino acid residues of module A, as defined above,
if =1, and $P^{14}$ and $P^1$ are not connected as aforementioned;
by performing steps comprising:

(a) coupling an appropriately functionalized solid support with an appropriately N-protected derivative of that amino acid which in the desired end-product is at position $P^{14}$, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is at position $P^{13}$, any functional group which may be present in said N-protected amino acid derivative being likewise appropriately protected;

(d) if desired, selectively deprotecting one or several protected functional group(s) present in the molecule and appropriately substituting the reactive group(s) thus liberated by attaching one or several moieties derived from acids, amino acids or amines;

(e) further effecting steps substantially corresponding to steps (b) to (d) using appropriately N-protected derivatives of amino acids which in the desired end-product are at positions $P^{12}$ to $P^8$, and $P^5$ to $P^1$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage (s), as defined above;

(f) if desired, selectively deprotecting one or several protected functional group(s) present in the molecule and appropriately substituting the reactive group(s) thus liberated by attaching one or several moieties derived from acids, amino acids or amines;

(g) if desired, selectively removing the N-protecting group at position $P^1$; and chemically transforming the amino group thus liberated;

(h) if desired, selectively deprotecting one or several protected functional group(s) present in the molecule and chemically transforming the reactive group(s) thus liberated to form an interstrand linkage, as defined above;

(i) if desired, implementing additional chemical transformations of one or more group(s) present in the molecule;

(j) if desired, selectively removing a carboxyl protecting group at $P^2$, $P^5$, $P^{12}$, $P^{13}$, or $P^{14}$;

(k) detaching the product thus obtained from the solid support and, if desired, removing in the same step a carboxyl protecting group at position $P^2$, $P^5$, $P^{12}$, $P^{13}$, or $P^{14}$;

(l) if desired or required, selectively protecting any carboxyl group(s) present in the molecule;

(m) if desired or required, selectively deprotecting one or several protected functional group(s) present in the molecule and chemically transforming the reactive group(s) thus liberated;

(n) if desired or required, implementing additional chemical transformations of one or more group(s) present in the molecule;

(o) if an interstrand linkage is present between positions $P^2$ and $P^{11}$, and additionally an interstrand linkage is present between positions $P^4$ and $P^9$, and if desired or required, selectively removing a carboxyl protecting group at position $P^5$, $P^{12}$, $P^{13}$, or $P^{14}$;

(p) if an interstrand linkage is present between positions $P^2$ and $P^{11}$, and if desired or required, selectively removing a carboxyl protecting group at position $P^5$, $P^{12}$, $P^{13}$, or $P^{14}$; and (q) if an interstrand linkage is present between positions $P^4$ and $P^9$, and if desired or required, selectively removing a carboxyl protecting group at position $P^2$, $P^5$, $P^{12}$, $P^{13}$, or $P^{14}$;

(IIc) or, generating a fully protected peptide fragment comprising amino acid residues of module A, as defined above,
if i=1, and $P^{13}$ and $P^{14}$, and $P^{14}$ and $P^1$ are connected as aforementioned;

or $P^{13}$ and $P^{14}$ are not connected as aforementioned;
by performing steps comprising:
(a) coupling an appropriately functionalized solid support with an appropriately N-protected derivative of that amino acid which in the desired end-product is at position $P^{13}$ of module A, as defined above, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product is at position $P^{12}$, any functional group which may be present in said N-protected amino acid derivative being likewise appropriately protected;
(d) if desired, selectively deprotecting one or several protected functional group(s) present in the molecule and appropriately substituting the reactive group(s) thus liberated by attaching one or several moieties derived from acids, amino acids or amines;
(e) further effecting steps substantially corresponding to steps (b) to (d) using appropriately N-protected derivatives of amino acids which in the desired end-product are at positions $P^{11}$ to $P^8$, $T^7$, $T^6$, $P^5$ to $P^1$, and $P^{14}$, any functional group(s) which may be present in said N-protected amino acid derivatives being likewise appropriately protected and, if desired, following each coupling, selectively deprotecting one or several protected functional group(s) present in the molecule and chemically transforming the reactive group(s) thus liberated to form an interstrand linkage(s), as defined above;
(f) if desired, selectively deprotecting one or several protected functional group(s) present in the molecule and appropriately substituting the reactive group(s) thus liberated by attaching one or several moieties derived from acids, amino acids or amines;
(g) if desired, selectively removing the N-protecting group at position $P^{14}$; and chemically transforming the amino group thus liberated;
(h) if desired, selectively deprotecting one or several protected functional group(s) present in the molecule and chemically transforming the reactive group(s) thus liberated;
(i) if desired, implementing additional chemical transformations of one or more group(s) present in the molecule;
(j) if an interstrand linkage, as defined above, is not present between positions $P^{13}$ and $P^{14}$, and if desired, performing steps comprising:
(j1) selectively removing an N-protecting group at position $P^{14}$;
(j2) detaching the product thus obtained from the solid support;
(j3) generating a macrolactam cycle, as defined above, by formation of an amide bond between the thus liberated carboxyl function at position $P^{13}$ and the amino function at position $P^{14}$;
(j4) if desired, selectively deprotecting one or several protected functional group(s) present in the molecule and chemically transforming the reactive group(s) thus liberated; and
(j5) if desired, implementing additional chemical transformations of one or more group(s) present in the molecule;

(k) if step (j) is not performed, performing steps comprising:
(k1) detaching the product thus obtained from the solid support and, if desired, removing in the same step a carboxyl protecting group at $P^2$, $P^5$, $P^{12}$, $P^{13}$, or $P^{14}$;
(k2) if desired or required, selectively protecting any carboxyl group(s) present in the molecule;
(k3) if desired or required, selectively deprotecting one or several protected functional group(s) present in the molecule and chemically transforming the reactive group(s) thus liberated; and
(k4) if desired or required, implementing additional chemical transformations of one or more group(s) present in the molecule;
(l) if $P^{13}$ and $P^{14}$, and $P^{14}$ and $P^1$ are connected as aforementioned, and if desired or required, selectively removing a carboxyl protecting group at position $P^2$, $P^5$, $P^{12}$, $P^{13}$, or $P^{14}$;
(m) if $P^{13}$ and $P^{14}$, and $P^{14}$ and $P^1$ are connected as aforementioned, and an interstrand linkage is present between positions $P^4$ and $P^9$, and if desired or required, selectively removing a carboxyl protecting group at position $P^2$, $P^5$, $P^{12}$, $P^{13}$, or $P^{14}$;
(n) if $P^{13}$ and $P^{14}$, and $P^{14}$ and $P^1$ are connected as aforementioned, and an interstrand linkage is present between positions $P^2$ and $P^{11}$, and if desired or required, selectively removing a carboxyl protecting group at position $P^5$; $P^{12}$; $P^{13}$; or $P^{14}$;
(o) if $P^{13}$ and $P^{14}$, and $P^{14}$ and $P^1$ are connected as aforementioned, and an interstrand linkage is present between positions $P^2$ and $P^{11}$, and additionally an interstrand linkage is present between positions $P^4$ and $P^9$, and if desired or required, selectively removing a carboxyl protecting group at position $P^5$, $P^{12}$, $P^{13}$, or $P^{14}$;
(p) if $P^{13}$ and $P^{14}$ are not connected as aforementioned, and an interstrand linkage is present between positions $P^{13}$ and $P^{14}$ and/or an interstrand linkage is present between positions $P^4$ and $P^9$, and if desired or required, selectively removing a carboxyl protecting group at position $P^2$, $P^5$, $P^{12}$, or $P^{13}$;
(q) if $P^{13}$ and $P^{14}$ are not connected as aforementioned, and an interstrand linkage is present between positions $P^2$ and $P^{11}$, and additionally an interstrand linkage is present between positions $P^4$ and $P^9$ and/or an interstrand linkage is present between positions $P^{13}$ and $P^{14}$, and if desired or required, selectively removing a carboxyl protecting group at position $P^5$, $P^{12}$, $P^{13}$, or $P^{14}$; and
(r) if $P^{13}$ and $P^{14}$ are not connected as aforementioned, and an interstrand linkage is present between positions $P^2$ and $P^{11}$, and if desired or required, selectively removing a carboxyl protecting group at position $P^5$, $P^{12}$, $P^{13}$, or $P^{14}$;
(III) coupling of two fully protected peptide fragments by formation of an amide bond between the free amino function in the peptide fragment obtained from procedure (I) and the free carboxyl function in the peptide fragment obtained from procedure (IIa), (IIb), or (IIc);
(IV) performing further steps, comprising,
(a) removing any protecting groups present on functional groups of any members of the chain of amino acid residues and, if desired, any protecting group(s) which may in addition be present in the molecule;

(b) if desired, implementing additional chemical transformations of one or more reactive group(s) present in the molecule; and (c) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

Enantiomers of the compounds defined herein before form also part of the present invention. These enantiomers can be prepared by a modification of the above process wherein enantiomers of all chiral starting materials are utilized.

The β hairpin peptidomimetics of the invention can be obtained by applying process A and/or process B, the main process steps of which are described in more detail in the following sections.

The β hairpin peptidomimetics of the invention can be obtained by applying process A and/or process B, the main process steps of which are described in more detail in the following sections.

The process of the invention can advantageously be carried out as parallel array synthesis to yield libraries of β-hairpin peptidomimetics of the invention. Such parallel syntheses allow one to obtain arrays of numerous (normally 12 to 576, typically 96) compounds as described above in moderate to high yields and defined purities, minimizing the formation of dimeric and polymeric by-products. The proper choice of the functionalized solid-support (i.e. solid support plus linker molecule) and site of macrolactam formation (cyclization) play thereby key roles.

The functionalized solid support is conveniently derived from polystyrene crosslinked with, preferably 1-5%, divinylbenzene; polystyrene coated with polyethyleneglycol spacers (Tentagel™); and polyacrylamide resins (see also D. Obrecht, J.-M. Villalgordo, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, Tetrahedron Lett. 1987, 28, 3783-3790). Linkers of this kind form amides of the carboxyl group of the amino acids; examples of resins functionalized by such linker structures include 4-[(((2,4-dimethoxyphenyl)Fmoc-aminomethyl) phenoxyacetamido) aminomethyl] PS resin, 4-[(((2,4-dimethoxyphenyl) Fmoc-aminomethyl)phenoxyacetamido) aminomethyl]-4-methyl-benzydrylamine PS resin (Rink amide MBHA PS Resin), and 4-[(((2,4-dimethoxy-phenyl) Fmoc-aminomethyl)phenoxyacetamido) aminomethyl] benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin™ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array synthesis the process of the invention can be advantageously carried out as described herein below but it will be immediately apparent to those skilled in the art how these procedures will have to be modified in case it is desired to synthesize one single compound of the invention.

A number of reaction vessels (normally 12 to 576, typically 96) equal to the total number of compounds to be synthesized by the parallel method are loaded with 25 to 1000 mg, preferably 60 mg, of the appropriate functionalized solid support, preferably 1 to 5% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, J. Am. Chem. Soc. 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin™ linker, Mergler et al., Tetrahedron Lett. 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, Tetrahedron Lett. 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheinner & Riniker, 1991, Peptides 1990: Proceedings of the Twenty-First European Peptide Symposium, 131) which is also cleaved with 1% TFA/DCM in order to yield a peptide fragment containing all acid labile side-chain protective groups; and, in addition, the 2-chlorotritylchloride linker (Barlos et al., Tetrahedron Lett. 1989, 30, 3943-3946), which allows the peptide detachment using a mixture of glacial acetic acid/trifluoroethanol/DCM (1:2:7) for 30 min. Attachment to the linker via an alcohol group provides alternative strategies for the synthesis of peptides using, for example, the 2-chlorotritylchloride linker (L. Rizzi et al., Tetrahedron Lett. 2011, 52, 2808-2811).

Suitable protecting groups for amino acids and, respectively, for their residues are, for example, for the amino group (as is present e.g. also in the side-chain of lysine)
Cbz benzyloxycarbonyl
Boc tert.-butyloxycarbonyl Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenylmethyl or trityl
ivDde 1-(4,4-dimethyl-2,6-dioxocyclohex-1-ylidene)-3-methylbutyl;
for the carboxyl group (as is present e.g. also in the side-chain of aspartic and glutamic acid) by conversion into esters with the alcohol components
tBu tert.-butyl
Bn benzyl
Me methyl
Ph phenyl
Pac phenacyl
allyl
Tse trimethylsilylethyl
Tce trichloroethyl
Dmab 4-N-(1-[dimethyl-2,6-dioxocyclohexylidene]-3-methylbutyl)-amino benzyl
2-PhiPr 2-phenyl-isopropyl;
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl;
and for the hydroxy group (as is present e.g. in the side-chain of threonine and serine)
tBu tert.-butyl
Bn benzyl
Trt trityl
Alloc allyloxycarbonyl.

The 9-fluorenylmethoxycarbonyl-(Fmoc)-protected amino acid derivatives are preferably used as the building blocks for the construction of the β-hairpin peptidomimetics of the invention. For the deprotection, i.e. cleaving off of the Fmoc group, 20% piperidine in DMF or 2% DBU/2% piperidine in DMF can be used as well as 25% hexafluoroisopropanol in CH$_2$Cl$_2$.

The quantity of the reactant, i.e. of the amino acid derivative, is usually 1 to 20 equivalents (eq) based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of a carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxy benzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Ethyl(hydroxyimino)cyanoacetate (Oxyma Pure) is an alternative to HOBt in carbodiimide-mediated coupling reactions (M. Itoh, *Bull. Chem. Soc. Jpn* 1973, 46, 2219-2221; J. Izdebski, *Pol. J. Chem.* 1979, 53, 1049-1057).

Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; Synthesis 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoro borate (TATU) or O-(7-aza-benzotriazol-1-yl)-N,N,N',N'-tetramethyluronium hexa fluorophosphate (HATU)/7-aza-1-hydroxybenzotriazole (HOAt, Carpino et al., *Tetrahedron Lett.* 1994, 35, 2279-2281) or O-(6-Chloro-1H-benzotriazol-1-yl-)-N,N,N',N'-1,1,3,3-tetramethyl uronium tetrafluoroborate (TCTU), or hexafluoro phosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-bis(tetramethylene)chlorouronium hexafluorophosphate (PyClU) especially for coupling of N-methylated amino acids (J. Coste, E. Frérot, P. Jouin, B. Castro, *Tetrahedron Lett.* 1991, 32, 1967) or pentafluorophenyl diphenylphosphinate (FDPP, S. Chen, J. Xu, *Tetrahedron Lett.* 1991, 32, 6711).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide or peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, either to chemically transform one or more groups present in the molecule, e.g. by formation of a disulfide bridge starting from still trityl-protected Cys residues, as described below, or to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced. Other well known orthogonal protecting groups which can be selectively removed are allyl, dmab or 2-PhiPr, examples for carboxyl protecting groups, or ivdDe, a further amino protecting group. The selective removal of the allyl protecting group by e.g. means of Pd° and phenylsilane in $CH_2Cl_2$ can be used, for example, in the course of the macrolactam formation of module A (backbone cyclization) following process A, as described above, on solid support, whereas an ivdDe deprotection step of an amino group being conducted by e.g. means of 5% of hydrazine in DMF (v/v) while the fully protected peptide is still attached on solid support can, for example, play a key role in the course of the macrolactam formation of module B (backbone cyclization) following process A, or process B, as described above.

After detachment of the fully protected linear peptide from the solid support (cleavage) the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Backbone cyclization, e.g. macrolactam formation of module B following process A, as described above, or, if desired, macrolactam formation of module A following process B, as described above, is then effected in solution using solvents such as DCM, DMF, dioxane, THF and the like. Various coupling reagents which were mentioned earlier as activators for the amide bond formation can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS, or 87.5% TFA, 2.5% DODT, 5% thioanisol, 5% $H_2O$ or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefore. The aqueous layer is collected and evaporated to dryness, and the fully deprotected cyclic peptide is obtained. Alternatively the deprotected cyclic peptide can be precipitated and washed using cold $Et_2O$.

For some compounds of the present invention according general formula (I) additional synthetic steps are required. These transformations can be applied either on a fully protected or partially deprotected linear or cyclic peptide, attached to or already released from the solid support or on the final deprotected molecule.

Various methods are known to form interstrand linkages including those described by: J. P. Tam et al., *Synthesis* 1979, 955-957; J. M. Stewart et al., *Solid Phase Peptide Synthesis*, 2d Ed., Pierce Chemical Company, Rockford, Ill., 1984; A. K. Ahmed et al., *J. Biol. Chem.* 1975, 250, 8477-8482; and M. W. Pennington et al., *Peptides*, pages 164-166, Giralt and Andreu, Eds., ESCOM Leiden, The Netherlands, 1990; C. E. Schafmeister et al., *J. Am. Chem. Soc.* 2000, 122, 5891. The most widely known linkage is the disulfide bridge formed by e.g. cysteines and homo-cysteines positioned at opposite positions of the β-strand.

For instance, the formation of a disulfide bridge can be carried out after assembly of the linear peptide on resin by employing, for example, on trityl protected cysteine amino acid residues, 10 eq of iodine solution in DMF for 1.5 h and repetition of the oxidation step with a fresh iodine solution for additional 3 h. Alternatively, disulfide bridge formation can be performed in solution, e.g. after backbone cyclization of module B and/or, if desired, module A, but before deprotection of the peptide by employing, for example, on trityl protected cysteine amino acid residues, 2 eq of an iodine solution in a hexafluoroisopropanol/$CH_2Cl_2$-mixture for 1 h followed by addition of 1M aqueous solution of ascorbic acid to quench the oxidation reaction. Another possibility to form disulfide bridges remains after deprotection of either the backbone-cyclized peptide of process A, or of the optionally backbone-cyclized peptide fragment of module A derived from process B by, for example, the application of a mixture of DMSO and acetic acid solution, buffered with 5% $NaHCO_3$ to pH 5-6 for 4 h, or in water after adjusting to pH 8 with ammonium hydroxide solution by stirring for 24 h.

Another well established interstrand linkage is the lactam bridge formed by linking e.g. the amino group-bearing side chains of ornithine and lysine, respectively, with the carboxyl group-bearing side chains of glutamic and aspartic acid residues located at opposite β-strand positions by means of an amide bond formation. Preferred protective groups for the side chain amino-groups of ornithine and lysine are allyloxycarbonyl (alloc) and for the side chain carboxyl-groups of aspartic and glutamic acid allylesters (allyl).

For instance, the formation of a lactam bridge can be carried out after assembly of the linear peptide on resin by applying 0.2 eq tetrakis(triphenyl-phosphine)palladium(0) (10 mM) in dry $CH_2Cl_2$ and 10 eq phenylsilane to selectively remove alloc- and allyl-protecting groups from amino and carboxyl functional groups of the side chains of amino acid residues to be linked. After repetition of the above procedure, the lactam bridge is formed by adding 4 eq of DIPEA in DMF and subsequent addition of 2 eq HATU in DMF.

By applying an appropriate orthogonal protecting group strategy lactam bridges may also be formed in a later stage of the synthesis, e.g. after deprotection of an backbone cyclized peptide, or of an optionally backbone-cyclized peptide fragment of module A.

Interstrand linkages can also be established by linking side chain amino groups of amino acid residues like e.g.

L-1,3-diamino propionic acid and ornithine located at opposite β-strand positions with reagents such as N,N-carbonylimidazole or di(N-succinimidyl)carbonate to form cyclic ureas. Allyloxycarbonyl (alloc) as orthogonal protecting group for amino functions may be preferably used.

For instance, the formation of an urea bridge can be carried out in solution after e.g. backbone cyclization of module B, or of an optionally backbone-cyclized peptide fragment of module A, but before full deprotection of the peptide, by applying 30 eq phenylsilane as well as a solution of 0.2 eq tetrakis(triphenylphosphine)-palladium(0) in $CH_2Cl_2$. After removal of the alloc protecting groups and precipitation of the selectively deprotected peptide the urea bridge is formed by adding 6 eq DIPEA dissolved in $CH_2Cl_2$ and subsequent dropwise addition of 1.2 eq of di(N-succinimidyl)carbonate in $CH_2Cl_2$.

Recently, a further type of interstrand linkages based on 1,4-disubstituted 1,2,3-triazole-containing alkanediyl groups have been introduced. The linkage is obtained through a 1,3-dipolar cycloaddition between the ω-yne group of the side chain of an amino acid residue like e.g. L-propargylglycine and the ω-azido group of the side chain of an amino acid residue like e.g. (S)-2-amino-4-azidobutanoic acid, both residues located at opposite β-strand positions.

For instance, the formation of such a triazole-containing bridge is performed by stirring the purified fully deprotected backbone-cyclized peptide, or an optionally backbone-cyclized peptide fragment of module A in a mixture of $H_2O$/tBuOH, 4.4 eq of $CuSO_4 \times 5H_2O$ and 6.6 eq of ascorbic acid for 12 h.

Depending on its purity, the final product as obtained following the procedures above can be used directly for biological assays, or has to be further purified, for example by preparative HPLC.

As mentioned earlier, it is thereafter possible, if desired, to convert the fully deprotected product thus obtained into a pharmaceutically acceptable salt or to convert a pharmaceutically acceptable, or unacceptable, salt thus obtained into the corresponding free or into a different, pharmaceutically acceptable, salt. Any of these operations can be carried out by methods well known in the art.

In general the building blocks for the peptidomimetics of the present invention can be synthesized according to the literature methods, which are known to a person skilled in the art or are commercially available. All other corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron (Report)* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257-279). Kinetic resolution using hydrolytic enzymes involves hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

Process B embraces a peptide fragment coupling step which can be performed in solution according to methods known in the art (see e.g. W. C. Chan, P. D. White "Fmoc solid phase peptide synthesis: A practical approach", Oxford University Press Inc., New York, 2000, reprinted 2003, chapter 9, section 4.1, page 223f).

Finally, it will be apparent to those skilled in the art how to modify or adapt the above described processes A or B, or the process steps of which, to obtain the β hairpin peptidomimetics of the invention.

The β-hairpin peptidomimetics of the invention can be used in a wide range of applications in order to inhibit the growth of or to kill microorganisms leading to the desired therapeutic effect in man or, due to their similar etiology, in other mammals. In particular they can be used to inhibit the growth of or to kill Gram-negative bacteria such as *Klebsiella pneumoniae* and/or *Acinetobacter baumannii* and/or *Escherichia coli* and/or *Pseudomonas aeruginosa*.

They can be used for example as disinfectants or as preservatives for materials such as foodstuffs, cosmetics, medicaments and other nutrient-containing materials.

The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other antimicrobial agents.

The β-hairpin peptidomimetics of the invention can be used to treat or prevent infections or diseases related to such infections, particularly nosocomial infections caused by Gram-negative bacteria related to diseases such as ventilator-associated pneumonia (VAP), hospital-acquired pneumonia (HAP), healthcare-associated pneumonia (HCAP); catheter-related and non-catheter-related infections such as urinary tract infections (UTIs) or bloodstream infections (BSIs); infections related to respiratory diseases such as cystic fibrosis, emphysema, asthma or pneumonia; infections related to skin or soft tissue diseases such as surgical wounds, traumatic wounds or burn; infections related to gastrointestinal diseases such as epidemic diarrhea, necrotizing enterocolitis, typhlitis, gastroenteritis or pancreatitis; infections related to eye diseases such as keratitis and endophthalmitis; infections related to ear diseases such as otitis; infections related to CNS diseases such as brain abscess and meningitis or encephalitis; infections related to bone diseases such as osteochondritis and osteomyelitis; infections related to cardiovascular diseases such as endocartitis and pericarditis; infections related to genitourinary diseases such as epididymitis, prostatitis and urethritis; or infection-induced sepsis. They can be administered singly, as mixtures of several β-hairpin peptidomimetics, in combination with other antimicrobial or antibiotic agents, or anti cancer agents, or antiviral (e.g. anti-HIV) agents, or in combination with other pharmaceutically active agents. The β-hairpin peptidomimetics can be administered per se or as pharmaceutical compositions.

The β-hairpin peptidomimetics of the invention may be administered per se or may be applied as an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use. For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For example, for use as a disinfectant or preservative, an antimicrobially effective amount of a β-hairpin peptidomimetic of the invention, or a composition thereof, is applied or added to the material to be desinfected or preserved. By antimicrobially effective amount is meant an amount of a β-hairpin peptidomimetic of the invention, or a composition thereof, that inhibits the growth of, or is lethal to, a target microbe population. While the antimicrobially effective amount will depend on a particular application, for use as disinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a disinfectant solution or material to be preserved, preferably less than 1% by weight and more preferably less than 0.1% by weight. An ordinary skilled expert will be able to determine antimicrobially effective amounts of particular β-hairpin peptidomimetics of the invention for particular applications without undue experimentation using, for example, the results of the in vitro assays provided in the examples.

For use to treat or prevent microbial infections or diseases related to such infections, the β-hairpin peptidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art, especially in view of the detailed disclosure provided herein. As in the case of disinfectants and preservatives, for topical administration to treat or prevent bacterial infections and/or viral infections a therapeutically effective dose can be determined using, for example, the results of the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-infective agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example anti-HIV agents or anti-cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the present invention but are not to be construed as limiting its scope in any way.

Abbreviations:
Ac Acetyl;
BSA Bovine serum albumin;
Boc tert-Butyloxycarbonyl;
DCHA Dicyclohexylamine;
DEAD Diethyl azodicarboxylate;
DIC N,N'-Diisopropylcarbodiimide;
DIPEA Diisopropylethylamine;
DMEM Dulbecco's Modified Eagle's Medium;
DMF Dimethylformamide;
DODT 3,6-dioxa-1,8-octanedithiol;
FCS Fetal Calf Serum;
FDPP Pentafluorophenyl diphenyl-phosphinate;
Fmoc Fluorenylmethyloxycarbonyl;
HATU O-(7-Aza-benzotriazole-1-yl)-N,N,N',N'-tetramethyluronoium hexafluorophosphate;
HBSS Hank's Buffered Salt Solution;
HBTU O-(Benzotriazol-1-yl)-N,N,N',N'-tetramethyluronium hexafluorophosphate;
HCTU 0-(6-Chlorobenzotriazol-1-yl)-N,N,N',N'-tetramethyluronium hexafluorophosphate;
Hepes 4-(2-hydroxyethyl)-1-piperazineethanesulfonic acid;
HFIP Hexafluoroisopropanol;
HOAt 1-Hydroxy-7-azabenzotriazole;
IMDM Iscove's Modified Dulbecco's Media;
NMM N-Methylmorpholine;
NMP N-Methyl-2-pyrrolidone;
Oxyma Pure Ethyl(hydroxyimino)cyanoacetate;
PyBop® (Benzotriazol-1-yloxy)tripyrrolidinophosphonium hexafluorophosphate;
TIS Triisopropylsilane;
TPP Triphenylphosphine;
RPMI Roswell Park Memorial Institute medium;
rt Room temperature.

EXAMPLES

1. Peptide Synthesis
1.1 General Synthetic Procedures

A general method for the synthesis of the peptidomimetics of the present invention is exemplified in the following. This is to demonstrate the principal concept and does not limit or restrict the present invention in any way. A person skilled in the art is easily able to modify these procedures, especially, but not limited to, choosing a different strategy for formation of a disulfide interstrand linkage and/or a different fragment coupling strategy, to still achieve the preparation of the claimed cyclic peptidomimetic compounds of the present invention.

1.1.1 Coupling of the First Protected Amino Acid Residue to the Resin
1.1.1.1 Coupling to the Resin Via a Carboxyl Group In a dried flask, 2-chlorotritylchloride resin (polystyrene, 1% crosslinked; loading: 1.4 mMol/g) was swollen in dry $CH_2Cl_2$ for 30 min (7 mL $CH_2Cl_2$ per g resin). A solution of 0.8 eq of the Fmoc-protected amino acid and 6 eq of DIPEA in dry $CH_2Cl_2$/DMF (4/1, v/v) (10 mL per g resin) was added. After shaking for 2-4 h at rt the resin was filtered off and washed successively with $CH_2Cl_2$, DMF, $CH_2Cl_2$, DMF and $CH_2Cl_2$. Then a solution of dry $CH_2Cl_2$/MeOH/DIPEA (17:2:1, v/v/v) was added (10 mL per g resin). After shaking for 3×30 min the resin was filtered off in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

Loading was typically 0.6-0.7 mMol/g.

The following preloaded resins were prepared: Fmoc-Thr(tBu)-2-chlorotrityl resin, Fmoc-$^D$Thr(tBu)-2-chlorotrityl resin, Fmoc-Val-2-chlorotrityl resin, Fmoc-$^D$Val-2-chlorotrityl resin, Fmoc-Arg(Pbf)-2-chlorotrityl resin and Fmoc-$^D$Arg(Pbf)-2-chlorotrityl resin.

1.1.1.2 Coupling to the Resin Via a Side Chain Hydroxyl Group

In a dried flask, 2-chlorotritylchloride resin (polystyrene, 1% crosslinked; loading: 1.4 mMol/g) was swollen in dry 1,2 dichloroethane for 30 min (4.5 mL 1,2 dichloroethane per g resin). A suspension of 3.2 eq of the Fmoc-protected amino acid ester and 2 eq of NMM in dry 1,2-dichloroethane (10 mL per g resin) was added. After stirring under reflux for 1-2 h the resin was filtered off and washed with 1,2 dichloroethane (3×) and with $CH_2Cl_2$. Then a solution of dry $CH_2Cl_2$/MeOH/DIPEA (17:2:1, v/v/v) was added (10 mL per g resin). After shaking for 3×30 min the resin was filtered off in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

Loading was typically 0.2-0.3 mMol/g.

The following preloaded resin was prepared: Fmoc-Thr(-2-chlorotrityl resin)-allyl.

1.1.2 Methods for Synthesis on Solid Support of the Fully Protected Peptide Fragment and of Fully Protected Peptide Fragments for Fragment Coupling The synthesis was carried out on a Syro-peptide synthesizer (MultiSynTech GmbH) using 24 to 96 reaction vessels. Unless otherwise indicated, in each vessel were placed 0.05 mMol of the resin, obtained from procedure 1.1.1.1 as described above, and the resin was swelled in $CH_2Cl_2$ and DMF for 15 min, respectively.

The following reaction cycles were programmed and carried out as described in the methods A-L, as described herein below:

| Step | Reagent | Time |
|---|---|---|
| 1 | $CH_2Cl_2$, wash and swell (manual) | 1 × 3 min |
| 2 | DMF, wash and swell | 2 × 30 min |
| 3 | 20% piperidine/DMF | 1 × 5 min and 1 × 15 min |
| 4 | DMF, wash | 5 × 1 min |
| 5 [a] | 3.6 eq appropriately protected amino acid and 3.6 eq HOAt in DMF or NMP + 3.6 eq DIC in DMF | 1 × 40 min |
| 6 | 3.6 eq appropriately protected amino acid and 3.6 eq HOAt in DMF or NMP + 3.6 eq HATU + 7.2 eq DIPEA in NMP | 1 × 40 min |
| 7 | DMF, wash | 5 × 1 min |
| 8 | 20% piperidine/DMF | 1 × 5 min and 1 × 15 min or 2 × 2 min [b] |
| 9 | DMF, wash | 5 × 1 min |
| 10 | $CH_2Cl_2$, wash (at the end of the synthesis) | 3 × 1 min |

[a] In the coupling cycle following coupling of an N-alkyl amino acid residue and for coupling of the first protected amino acid residue to Sieber amide resin, step 5 was omitted and step 6 was performed twice instead.
[b] Reduced times were used for Fmoc deprotection of an amino acid residue having a carboxyl group protected as allyl ester, and for the Fmoc deprotection step of the following coupling cycle.

The term "macrolactam cycle", as used herein below, refers to a cyclic peptide moiety that is generated through formation of an amide bond between two amino acid residues, involving—for module A an α-carboxyl group and an α-amino group; or an α-carboxyl group and a side-chain amino group; or a side-chain carboxyl group and an α-amino group; or involving for module B an α-carboxyl group and a side-chain amino group.

The term "lactam interstrand linkage", as used herein, refers to a linkage of two amino acid residues by an amide bond, involving a side-chain carboxyl group and a side-chain amino group.

1.1.2.1 Method A

The reaction cycles, as described herein above, were applied for the assembly of the fully protected peptide fragment, using appropriately protected Fmoc amino acid building blocks. Steps 5 to 9 are repeated to add each amino acid residue.

1.1.2.2 Method B

The reaction cycles, as described herein above, were applied for the assembly of the fully protected peptide fragment, using appropriately protected Fmoc amino acid building blocks, except for the last coupling. For the latter an appropriately protected Boc amino acid building block was used. Steps 5 to 9 are repeated to add each amino acid residue, except for the last amino acid residue, which was added by steps 5 to 7, followed by step 10.

1.1.2.3 Method C

The reaction cycles, as described herein above, were applied for the assembly of the fully protected peptide fragment, using appropriately protected Fmoc amino acid building blocks. Steps 5 to 9 are repeated to add each amino acid residue, except for the case, where the amino group-bearing side chain of the added amino acid residue is connected with a further amino acid to form a dipeptidic amino acid residue. In this case, coupling of the alloc protected Fmoc amino acid by steps 5 to 7 was followed by coupling of an appropriately protected Boc amino acid according to procedure A, as described herein below. Subsequently, steps 8 to 9 for Fmoc deprotection and washing were performed.

1.1.2.4 Method D

The reaction cycles, as described herein above, were applied for the assembly of the fully protected peptide fragment, using appropriately protected Fmoc amino acid building blocks. In a first part, Steps 5 to 9 are repeated to add each amino acid residue, except for the case, where the carboxyl group-bearing side chain of the added amino acid residue is involved in the formation of a lactam interstrand linkage. In this case, coupling of the allyl protected Fmoc amino acid by step 5 to 7 was followed by formation of a lactam interstrand linkage (module A) as described in the corresponding section of procedure E2 herein below. Subsequently, steps 8 to 9 for Fmoc deprotection and washing were performed.

Assembly of the fully protected peptide fragment was then completed. Steps 5 to 9 were repeated to add each remaining amino acid residue.

1.1.2.5 Method E

The reaction cycles, as described herein above, were applied for the assembly of the fully protected peptide fragment for fragment coupling, using 0.05 mMol of the resin obtained from procedure 1.1.1.2 and appropriately protected Fmoc amino acid building blocks.

In a first part, a fully protected peptide fragment encompassing amino acid residues of module B was prepared. Steps 5 to 9 are repeated to add each amino acid residue, except for the last amino acid residue of this peptide fragment, which was added by steps 5 to 7. Subsequently, macrolactam cycle formation (module B) was performed as described in the corresponding section of procedure G herein below, followed by steps 8 to 9 for Fmoc deprotection and washing.

Assembly of the fully protected peptide fragment was then continued. Steps 5 to 9 were repeated to add each amino acid residue.

1.1.2.6 Method F

The reaction cycles, as described herein above, were applied for the assembly of the fully protected peptide fragment for fragment coupling, using 0.05 mMol of Sieber amide resin (polystyrene, 1% crosslinked; loading: 0.65 mMol/g) and appropriately protected Fmoc amino acid building blocks. Steps 5 to 9 are repeated to add each amino acid residue.

1.1.2.7 Method G

The reaction cycles, as described herein above, were applied for the assembly of the fully protected peptide fragment for fragment coupling, using 0.05 mMol of Sieber amide resin (polystyrene, 1% crosslinked; loading: 0.65 mMol/g) and appropriately protected Fmoc amino acid building blocks, except for the last coupling. For the latter an appropriately protected Boc amino acid building block was used. Steps 5 to 9 are repeated to add each amino acid residue, except for the last amino acid residue, which was added by steps 5 to 7, followed by step 10.

1.1.2.8 Method H

The reaction cycles, as described herein above, were applied for the assembly of the fully protected peptide fragment, using 0.05 mMol of the resin obtained from procedure 1.1.1.2 and appropriately protected Fmoc amino acid building blocks. In a first part, a fully protected peptide fragment encompassing amino acid residues of module B was prepared. Steps 5 to 9 are repeated to add each amino acid residue, except for the last amino acid residue, which was added by steps 5 to 7. Subsequently, macrolactam cycle formation (module B) was performed as described in the corresponding section of procedure G herein below, followed by steps 8 to 9 for Fmoc deprotection and washing.

Assembly of the fully protected peptide fragment was then continued. Steps 5 to 9 were repeated to add each amino acid residue, except for the case, where the carboxyl group-bearing side chain of the added amino acid residue is involved in the formation of a lactam interstrand linkage. In this case, coupling of the allyl protected Fmoc amino acid by step 5 to 7 was followed by formation of a lactam interstrand linkage (module A) as described in the corresponding section of procedure E2 herein below. Subsequently, steps 8 to 9 for Fmoc deprotection and washing were performed. Assembly of the fully protected peptide fragment was then completed. Steps 5 to 9 were repeated to add each remaining amino acid residue.

1.1.2.9 Method I

The reaction cycles, as described herein above, were applied for the assembly of the fully protected peptide fragment, using 0.05 mMol of the resin obtained from procedure 1.1.1.2 and appropriately protected Fmoc amino acid building blocks. In a first part, a fully protected peptide fragment encompassing amino acid residues of module B was prepared. Steps 5 to 9 are repeated to add each amino acid residue, except for the last amino acid residue of this peptide fragment, which was added by steps 5 to 7. Subsequently, macrolactam cycle formation (module B) was performed as described in the corresponding section of procedure G herein below, followed by steps 8 to 9 for Fmoc deprotection and washing.

Assembly of the fully protected peptide fragment was then completed. Steps 5 to 9 were repeated to add each amino acid residue.

1.1.2.10 Method J

The reaction cycles, as described herein above, were applied for the assembly of the fully protected peptide fragment, using appropriately protected Fmoc amino acid building blocks, except for the last coupling. For the latter an appropriately protected Boc amino acid building block was used.

In a first part, steps 5 to 9 are repeated to add each amino acid residue, except for the case, where the carboxyl group-bearing side chain of the added amino acid residue is involved in the formation of a lactam interstrand linkage. In this case, coupling of the allyl protected Fmoc amino acid by step 5 to 7 was followed by formation of a lactam interstrand linkage (module A) as described in the corresponding section of procedure E2 herein below. Subsequently, steps 8 to 9 for Fmoc deprotection and washing were performed.

Assembly of the fully protected peptide fragment was then completed. Steps 5 to 9 are repeated to add each remaining amino acid residue, except for the last amino acid residue, which was added by steps 5 to 7, followed by step 10.

1.1.2.11 Method K

The reaction cycles, as described herein above, were applied for the assembly of the fully protected peptide fragment, using 0.05 mMol of the resin obtained from procedure 1.1.1.2 and appropriately protected Fmoc amino acid building blocks, except for the last coupling. For the latter an appropriately protected Boc amino acid building block was used.

In a first part, a fully protected peptide fragment encompassing amino acid residues of module B was prepared. Steps 5 to 9 are repeated to add each amino acid residue, except for the last amino acid residue of this peptide fragment, which was added by steps 5 to 7. Subsequently, macrolactam cycle formation (module B) was performed as described in the corresponding section of procedure G herein below, followed by steps 8 to 9 for Fmoc deprotection and washing.

Assembly of the fully protected peptide fragment was then completed. Steps 5 to 9 were repeated to add each remaining amino acid residue, except for the last amino acid residue, which was added by steps 5 to 7, followed by step 10.

1.1.2.12 Method L

The reaction cycles, as described herein above, were applied for the assembly of the fully protected peptide fragment, using appropriately protected Fmoc amino acid building blocks, except for the last coupling. For the latter an appropriately protected Boc amino acid building block was used, which was added by steps 5 to 7, followed by step 10.

Steps 5 to 9 are repeated to add each amino acid residue, except for the case, where the amino group-bearing side chain of the added amino acid residue is connected with a further amino acid to form a dipeptidic amino acid residue. In this case, coupling of the alloc protected Fmoc amino acid by steps 5 to 7 was followed by coupling of an appropriately protected Boc amino acid according to procedure A, as described herein below. Subsequently, steps 8 to 9 for Fmoc deprotection and washing were performed.

1.1.2.13 Procedure A:

Attachment of Amino Acids to Amino Group-Bearing Side Chains

To remove the alloc protecting group from amino functions present in the resin bound peptide, the latter (0.05 mMol) was swollen in 1 mL dry $CH_2Cl_2$ for at least 10 min, washed twice with iPrOH and twice with $iPr_2O$, followed by addition of 40 eq triphenylsilane in 0.5 mL NMP, shaking of the mixture for 1 minute, and addition of 0.2 eq tetrakis(triphenylphosphine)palladium(0) in 0.5 mL dry $CH_2Cl_2$. After shaking the reaction mixture for 5 min at rt, the resin was filtered off and washed with three times with 1 mL dry $CH_2Cl_2$. The deprotection procedure was repeated with fresh solutions of reagents, applying a shaking time of 15 min after addition of the palladium catalyst. LC-MS was used to monitor the deprotection reaction and, if required, the deprotection procedure was repeated. Subsequently the resin was thoroughly washed with $CH_2Cl_2$, DMF, iPrOH, and finally again with $CH_2Cl_2$.

The attachment of an appropriately protected amino acid was accomplished by adding to the resin a mixture of 3.6 eq of the desired amino acid and 3.6 eq HOAt in 0.4 mL DMF or NMP, and 3.6 eq DIC in 0.3 mL DMF. The reaction mixture was then allowed to stand for 1 h with occasional shaking, and subsequently the resin was filtered and washed twice with 1 mL DMF. The coupling was completed by repeating the procedure with a solution of a mixture of 3.6 eq of the desired amino acid and 3.6 eq HOAt in 0.4 mL DMF or NMP, 3.6 eq HATU in 0.3 mL DMF and 7.2 eq DIPEA in 0.2 mL NMP.

In the examples of the present invention, the protected amino acid used to be coupled by the above described protocol was e.g. N-Boc protected glutamic acid, the side-chain carboxyl group being protected by tBu.

1.1.3 Further Procedures for the Preparation of the Peptides

One of the procedures B Q, as described herein below, was adopted for preparation of the peptides.

1.1.3.1 Procedure B:

Preparation of a Peptide Having Macrolactam Cycles in Module A and Module B

The linear peptide was assembled on solid support according to Method A, as described above, and subsequently the following steps were performed:

Allyl Deprotection (Module A)

Selective removal of the allyl protecting group from a carboxyl function was performed as described in the corresponding section in procedure A for removal of the alloc protecting group.

Macrolactam Cycle Formation (Module A)

To the resin in $CH_2Cl_2$, 2 eq FDPP in 0.5 mL DMF and 2 eq DIPEA in 0.5 mL $CH_2Cl_2$ were added. After stirring the reaction mixture for approximately 16 h, the resin was filtered off, and fresh solutions of reagents were added to repeat the procedure. Subsequently, the resin was washed three times with DMF.

IvDde Deprotection (Module B)

The resin was swollen in 1 mL DMF for 10 min and subsequently filtered off. For deprotection, 1 mL of a 5% solution of hydrazine monohydrate in DMF (v/v) was added and the reaction mixture was shaken for 30 min. The reaction mixture was then filtered off and washed with 1 mL DMF. The deprotection step was repeated by employing the same amount of reagents. LC-MS was used to monitor the deprotection reaction and, if required, the deprotection procedure was repeated again. Finally, the resin was thoroughly washed with DMF, $CH_2Cl_2$, DMF, and iPrOH, and finally washed again with $CH_2Cl_2$.

Cleavage of Peptide from Resin

After two washings with $CH_2Cl_2$, the resin was suspended in 1 mL of 20% HFIP in $CH_2Cl_2$ (v/v) for 30 min. After filtration the procedure was repeated, and the resin was washed three times with 1 mL of $CH_2Cl_2$. The combined filtrates and washings were evaporated to dryness.

Macrolactam Cycle Formation (Module B)

The protected peptide was first solubilized in 0.5 mL $CH_2Cl_2$, followed by the addition of 8 mL DMF. Then 4 eq DIPEA in 2 mL DMF, and 2 eq HATU and 2 eq HOAt in 2 mL DMF were added, and the reaction mixture was stirred for approximately 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full Deprotection

To fully deprotect the peptide, 7 mL of cleavage cocktail $TFA/TIS/H_2O$ (95:2.5:2.5, v/v/v) were added, and the mixture was kept for 2.5-4 h at room temperature. The reaction mixture was evaporated close to dryness, the peptide precipitated with 7 mL of cold $Et_2O$/pentane (1:1, v/v) and finally washed three times with 3 mL of cold $Et_2O$/pentane (1:1, v/v).

Finally, the peptide was purified by preparative reverse phase LC-MS, as described herein below.

1.1.3.2 Procedure C:

Preparation of a Peptide Having a Disulfide Interstrand Linkage(s) in Module A and being Acetylated at the N-Terminal Amino Group The linear peptide was assembled on solid support according to Method A, as described above. Appropriately protected Fmoc amino acid building blocks with a thiol group protected as trityl thioether were used for addition of amino acid residues that are involved in the formation of a disulfide interstrand linkage(s).

Subsequently, the following steps were performed:

Acetylation

After assembly of the peptide on the resin, steps 5 to 7 of the programmed reaction cycles were performed using 3.6 eq AcOH instead of 3.6 eq protected amino acid, followed by step 10.

IvDde Deprotection (Module B), Cleavage and Macrolactam Cycle Formation (Module B)

Subsequent ivDde deprotection (module B), cleavage of the peptide from the resin, and macrolactam cycle formation (module B) were performed as described in the corresponding sections of procedure B.

Formation of Disulfide Interstrand Linkage(s) (Module A)

The protected peptide was dissolved in 8 mL of HFIP/$CH_2Cl_2$ (1:4, v/v) and 2 eq iodine in 2 mL of HFIP/$CH_2Cl_2$ (1:4, v/v) were added. After shaking for 20-45 minutes, 3 mL of a 1 M aqueous solution of ascorbic acid were added to quench excess reagent, and the mixture was further shaken for 10 min. The aqueous phase was then discarded, optionally applying a centrifugation step for phase separation. The organic phase was washed with 4 mL of $H_2O$, and concentrated to dryness.

Full Deprotection

The modified peptide was deprotected as described in the corresponding section of procedure B.

Finally, the peptide was purified by preparative reverse phase LC-MS, as described herein below.

1.1.3.3 Procedure D:

Preparation of a Peptide Having a Disulfide Interstrand Linkage(s) in Module A and Having a Free N-Terminal Amino Group The linear peptide was assembled on solid support according to Method B, as described above. Appropriately protected amino acid building blocks with a thiol group protected as trityl thioether were used for addition of amino acid residues that are involved in the formation of a disulfide interstrand linkage. For addition of the last amino acid residue of the peptide chain an appropriately protected Boc amino acid building block was used.

Subsequent ivDde deprotection (module B), cleavage, macrolactam cycle formation (module B), formation of a disulfide interstrand linkage(s) (module A), and full deprotection were performed as described in the corresponding sections of procedure C, following the same order.

Finally, the peptide was purified by preparative reverse phase LC-MS, as described herein below.

1.1.3.4 Procedure E1:

Preparation of a Peptide Having a Lactam Interstrand Linkage in Module A and being Acetylated at the N-Terminal Amino Group The linear peptide was assembled according to Method A, as described above. After acetylation, performed as described in the corresponding section of procedure C, the lactam interstrand linkage in module A was formed as follows:

Formation of Lactam Interstrand Linkage (Module A)

Selective removal of the allyl and alloc protecting groups from carboxyl and amino functions was performed as described in the corresponding section in procedure A for removal of the alloc protecting group. Subsequently, 2 eq FDPP in 0.5 mL DMF and 2 eq DIPEA in 0.5 mL $CH_2Cl_2$ were added to the resin in $CH_2Cl_2$. After stirring the reaction mixture for approximately 16 h, the resin was filtered, and fresh solutions of reagents were added to repeat the procedure. Afterwards, the resin was washed three times with DMF.

Subsequent ivDde deprotection (module B), cleavage of the peptide from the resin, macrolactam cycle formation (module B), and full deprotection were performed as described in the corresponding sections of procedure B, following the same order.

Finally, the peptide was purified by preparative reverse phase LC-MS, as described herein below.

1.1.3.5 Procedure E2:

Preparation of a Peptide Having a Lactam Interstrand Linkage in Module A and being Acetylated at the N-Terminal Amino Group The peptide was assembled according to Method D, as described above, including the formation of a lactam interstrand linkage (module A) which was performed as follows:

Formation of Lactam Interstrand Linkage (Module A)

Selective removal of the allyl and alloc protecting groups from carboxyl and amino functions was performed as described in the corresponding section in procedure A for removal of the alloc protecting group. Subsequently, 1 eq OxymaPure in 0.4 mL $CH_2Cl_2$ and 2 eq DIC in 0.6 mL $CH_2Cl_2$ were added to the resin in $CH_2Cl_2$. After stirring the reaction mixture for approximately 2-3 h, the resin was filtered, and fresh solutions of reagents were added to repeat the procedure. The resin was subsequently filtered and was washed with $CH_2Cl_2$, DMF, iPrOH, and finally again with $CH_2Cl_2$.

Acetylation was then performed as described in procedure C. Subsequently, ivDde deprotection (module B), cleavage of the peptide from the resin, macrolactam cycle formation (module B), and full deprotection were performed as described in the corresponding sections of procedure B, following the same order.

Finally, the peptide was purified by preparative reverse phase LC-MS, as described herein below.

1.1.3.6 Procedure F:

Preparation of an N-Terminally Acetylated Peptide Having a Disulfide Interstrand Linkage in Module A and Having an Amino Acid Attached to an Amino Group-Bearing Side Chain The linear peptide was assembled on solid support according to Method C, as described above, using Fmoc-Cys(Trt)-OH for addition of Cys residues and performing the attachment of a further amino acid to an amino group-bearing side chain as indicated in procedure A.

Subsequent acetylation, ivDde deprotection (module B), cleavage, macrolactam cycle formation (module B), formation of disulfide interstrand linkage (module A), and full deprotection were performed as described in the corresponding sections of procedure C, following the same order.

Finally, the peptide was purified by preparative reverse phase LC-MS, as described herein below.

1.1.3.7 Procedure G:

Preparation of a Peptide Having a Lactam Interstrand Linkage in Module A Having a Carboxylamide Group at the C-Terminus of Module A and Having a Free N-Terminal Amino Group The peptide was prepared based on a fragment coupling strategy.

(I) Preparation of a Protected Peptide Fragment (Module B and Linker L)

The protected peptide fragment encompassing amino acid residues of module B and linker L was assembled on solid support according to Method E as described above, including macrolactam cycle formation (module B) which was performed as follows:

Macrolactam Cycle Formation (Module B)

Selective removal of the allyl and alloc protecting groups from carboxyl and amino functions was performed as described in the corresponding section in procedure A for removal of the alloc protecting group. Subsequently, 1 eq OxymaPure in 0.4 mL $CH_2Cl_2$ and 2 eq DIC in 0.6 mL $CH_2Cl_2$ were added to the resin in $CH_2Cl_2$. After stirring the reaction mixture for approximately 2-3 h, the resin was filtered, and fresh solutions of reagents were added to repeat the procedure. The resin was subsequently filtered and washed with $CH_2Cl_2$, DMF, iPrOH, and finally again with $CH_2Cl_2$.

Cleavage of the peptide from the resin was performed as described in the corresponding section of procedure B. The obtained protected peptide fragment was then dissolved in 4 mL of MeOH/$CH_2Cl_2$ (1:4, v/v) and washed twice with 2 mL of aq. $Na_2CO_3$ (0.1 M). The organic layer was dried ($Na_2SO_4$), filtered, and evaporated to dryness.

(II) Preparation of a Protected Peptide Fragment (Module A)

The linear peptide fragment encompassing amino acid residues of module A was assembled on solid support according to Method G, as described above.

Subsequently, the formation of an interstrand lactam linkage was performed as described in the corresponding section of procedure E1.

Cleavage of the peptide from the resin and removal of the 2-phenyl-isopropyl protecting group from the side chain carboxyl function was performed as described in the corresponding section of procedure I.

(III) Coupling of Two Protected Peptide Fragments

The protected peptide fragment (module A) was solubilized in 0.5 mL DMF, followed by addition of 2 eq HATU and 2 eq HOAt in 0.5 mL DMF, 4 eq DIPEA in 0.5 mL DMF and protected peptide fragment (module B and linker L) in 0.5 ml DMF. The reaction mixture was stirred for approximately 16 h, and subsequently the volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full deprotection was performed as described in the corresponding section of procedure B.

Finally, the peptide was purified by preparative reverse phase LC-MS, as described herein below.

1.1.3.8 Procedure H:

Preparation of a Peptide Having a Disulfide Interstrand Linkage in Module A Having a Carboxylamide Group at the C-Terminus of Module A and being Acetylated at the N-Terminal Amino Group The peptide was prepared based on a fragment coupling strategy.

(I) Preparation of a Fully Protected Peptide Fragment (Module B and Linker L)

The fully protected peptide fragment (module B and linker L) was prepared as described in the corresponding section of procedure G.

(II) Preparation of a Fully Protected Peptide Fragment (Module A)

The linear peptide encompassing amino acid residues of module A was assembled on solid support according to Method F, as described above. In cases where an amino acid residue is involved in the formation of a disulfide interstrand linkage, appropriately protected Fmoc amino acid building blocks with a thiol group protected as trityl thioether were used in the corresponding coupling cycles.

Subsequent acetylation was performed as described in the corresponding section of procedure C. Following cleavage of the peptide fragment from resin as indicated in the corresponding section of procedure G, the formation of a disulfide interstrand linkage was performed as described in the corresponding section of procedure C.

To remove the allyl protecting group from the carboxyl function, the protected peptide fragment was first solubilized in 1.8 mL of $CH_2Cl_2$, followed by addition of 15 eq triphenylsilane, stirring of the mixture for 1 minute, and addition of 0.15 eq tetrakis(triphenylphosphine)palladium (0) in 0.3 mL dry $CH_2Cl_2$. The reaction mixture was stirred for 1 h at rt and subsequently cooled to 0° C. The reaction mixture was then filtered and the peptide was precipitated with 5 mL of cold $Et_2O$/pentane (1:1, v/v). Thereafter, the precipitated peptide was washed with 5 mL of cold $Et_2O$/pentane (1:1, v/v) and dried.

(III) Coupling of Two Fully Protected Peptide Fragments

The protected peptide fragment (module A) was solubilized in 0.5 mL DMF, followed by addition of 2 eq HATU and 2 eq HOAt in 0.5 mL DMF, 4 eq DIPEA in 0.5 mL DMF and protected peptide fragment (module B and linker L) in 0.5 ml DMF. The reaction mixture was stirred for approximately 16 h, and subsequently the volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full deprotection was performed as described in the corresponding section of procedure B.

Finally, the peptide was purified by preparative reverse phase LC-MS, as described herein below.

1.1.3.9 Procedure I:

Preparation of a Peptide Having Macrolactam Cycles in Module A and Module B and Having a Lactam Interstrand Linkage in Module A The fully protected peptide fragment was assembled on solid support according to Method H as described above. Subsequently, the following steps were performed:

Cleavage of Peptide from Resin and Removal of the 2-Phenyl-Isopropyl Protecting Group from the Carboxyl Function The resin was swollen in 1 mL $CH_2Cl_2$ (2×10 min). After filtration, the resin was suspended in 1 mL of 1% TFA in $CH_2Cl_2$ (v/v) for 10-30 min. The resin was then filtered and washed three times with 1 mL of $CH_2Cl_2$, and a solution of 1 mL of 40% DIPEA in $CH_2Cl_2$ (v/v) was added to the combined filtrate and washings. LC-MS was used to monitor the cleavage and, if required, the cleavage procedure was repeated 3-5 times. The combined filtrate and washings were evaporated to dryness.

Macrolactam Cycle Formation (Module A)

The protected peptide was first solubilized in 0.5 mL $CH_2Cl_2$, followed by the addition of 8 mL DMF. Then 6 eq NMM in 2 mL DMF, and 2 eq HATU and 1 eq HOAt in 2 mL DMF were added, and the reaction mixture was stirred for approximately 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

Full deprotection was performed as described in the corresponding section of procedure B.

Finally, the peptide was purified by preparative reverse phase LC-MS, as described herein below.

1.1.3.10 Procedure J:

Preparation of a Peptide Having Macrolactam Cycles in Module a and Module B and Having a Disulfide Interstrand Linkage in Module a The fully protected peptide fragment was assembled on solid support according to Method I, as described above. In cases where an amino acid residue is involved in the formation of disulfide interstrand linkage, Fmoc amino acid building blocks with a thiol group protected as trityl thioether were used in the corresponding coupling cycles.

Subsequently, removal of the allyl protecting group from the carboxyl function was performed as described in the corresponding section in procedure A for removal of the alloc protecting group. Cleavage of the peptide from the resin was then performed as described in procedure B, and subsequent macrolactam cycle formation (module A) was performed as described in the corresponding section of procedure I.

Formation of a disulfide interstrand linkage (module A), and full deprotection were then performed as described in the corresponding sections of procedure C, following the same order.

Finally, the peptide was purified by preparative reverse phase LC-MS, as described herein below.

1.1.3.11 Procedure K1:

Preparation of a Peptide Having a Disulfide Interstrand Linkage and a Lactam Interstrand Linkage in Module A and Having a Free N-Terminal Amino Group The linear peptide was assembled on solid support according to Method B, as described above. In cases where an amino acid residue is involved in the formation of a disulfide interstrand linkage, appropriately protected amino acid building blocks with a thiol group protected as trityl thioether were used in the corresponding coupling cycles.

Subsequent formation of a lactam interstrand linkage (module A) was performed as described in the corresponding section of procedure E1.

Thereafter, ivDde deprotection (module B), cleavage of the peptide from the resin, macrolactam cycle formation (module B), formation of a disulfide interstrand linkage (module A), and full deprotection were performed as indicated in the corresponding sections of procedure C, following the same order.

Finally, the peptide was purified by preparative reverse phase LC-MS, as described herein below.

1.1.3.12 Procedure K2:

Preparation of a Peptide Having a Disulfide Interstrand Linkage and a Lactam Interstrand Linkage in Module A and Having a Free N-Terminal Amino Group The fully protected peptide fragment was assembled on solid support according to Method J, as described above. In cases where an amino acid residue is involved in the formation of a disulfide interstrand linkage, appropriately protected amino acid building blocks with a thiol group protected as trityl thioether were used in the corresponding coupling cycles.

Thereafter, ivDde deprotection (module B), cleavage of the peptide from the resin, macrolactam cycle formation (module B), formation of a disulfide interstrand linkage (module A), and full deprotection were performed as described in the corresponding sections of procedure C, following the same order.

Finally, the peptide was purified by preparative reverse phase LC-MS, as described herein below.

1.1.3.13 Procedure L:

Preparation of a Peptide Having a Disulfide Interstrand Linkage and a Lactam Interstrand Linkage in Module A and Having an N-Terminal Guanidine Group The linear peptide was assembled on solid support according to Method A, as described above. In cases where an amino acid residue is involved in the formation of a disulfide interstrand linkage, appropriately protected Fmoc amino acid building blocks with a thiol group protected as trityl thioether were used in the corresponding coupling cycles. Subsequently, the guanidine group was formed as follows:

Guanidinylation

To the resin in $CH_2Cl_2$, 10 eq N,N'-bis-Boc-1-guanylpyrazole in 5 mL $CH_2Cl_2$/DMF (1:1, v/v) were added. After stirring the mixture for approximately 24 h, the resin was filtered, and a fresh solution of the reagent was added to repeat the procedure. Afterwards, the resin was washed three times with $CH_2Cl_2$.

Subsequent formation of a lactam interstrand linkage (module A) was performed as described in the corresponding section of procedure E1.

Thereafter, ivDde deprotection (module B), cleavage of the peptide from the resin, macrolactam cycle formation (module B), formation of a disulfide interstrand linkage (module A), and full deprotection were performed as described in the corresponding sections of procedure C, following the same order.

Finally, the peptide was purified by preparative reverse phase LC-MS, as described herein below.

1.1.3.14 Procedure M:

Preparation of a Peptide Having a Disulfide Interstrand Linkage in Module A and Having an N-Terminal Guanidine Group The linear peptide was assembled on solid support according to Method A, as described above. In cases where an amino acid residue is involved in the formation of a disulfide interstrand linkage, appropriately protected Fmoc amino acid building blocks with a thiol group protected as trityl thioether were used in the corresponding coupling cycles.

Subsequent guanidinylation was performed as described in the corresponding section of procedure L. Thereafter, ivDde deprotection (module B), cleavage of the peptide from the resin, macrolactam cycle formation (module B), formation of a disulfide interstrand linkage (module A), and full deprotection were performed as indicated in the corresponding sections of procedure C, following the same order.

Finally, the peptide was purified by preparative reverse phase LC-MS, as described herein below.

1.1.3.15 Procedure N:

Preparation of a Peptide Having a Lactam Interstrand Linkage in Module A and Having an N-Terminal Guanidine Group The fully protected peptide fragment was assembled on solid support according to Method D, as described above.

Subsequent guanidinylation was performed as described in the corresponding section of procedure L. Thereafter, ivDde deprotection (module B), cleavage of the peptide from the resin, macrolactam cycle formation (module B) and full deprotection were performed as described in the corresponding sections of procedure B, following the same order.

Finally, the peptide was purified by preparative reverse phase LC-MS, as described herein below.

1.1.3.16 Procedure 0:

Preparation of a Peptide Having a Disulfide Interstrand Linkage in Module A and Having an N-Terminal Tetramethylguanidine Group The linear peptide was assembled on solid support according to Method A, as described above. In cases where an amino acid residue is involved in the formation of a disulfide interstrand linkage, appropriately protected Fmoc amino acid building blocks with a thiol group protected as trityl thioether were used in the corresponding coupling cycles. Subsequently, the tetramethylguanidine group was formed as follows:

Tetramethylguanidinylation

To the resin in NMP, 6 eq HATU and 12 eq NMM in 1 mL NMP were added. After stirring the mixture for approximately 12 h, the resin was filtered, and washed twice with NMP. The procedure was then repeated twice, each with a fresh solution of the reagents. Afterwards, the resin was washed twice with DMF and three times with $CH_2Cl_2$.

Thereafter, ivDde deprotection (module B), cleavage of the peptide from the resin, macrolactam cycle formation (module B), formation of a disulfide interstrand linkage (module A), and full deprotection were performed as indicated in the corresponding sections of procedure C, following the same order.

Finally, the peptide was purified by preparative reverse phase LC-MS, as described herein below.

1.1.3.17 Procedure P:

Preparation of a Peptide Having a Lactam Interstrand Linkage in Module A and Having a Free N-Terminal Amino Group The fully protected peptide fragment was assembled on solid support according to Method K, as described above.

Subsequently, removal of the alloc protecting group from the amino function was performed as described in the corresponding section in procedure A. Cleavage and removal of the 2-phenyl-isopropyl protecting group from the carboxyl function was then performed as described in the corresponding section of procedure I. Subsequent formation of a lactam interstrand linkage was performed as described for macrolactam cycle formation (module B) in the corresponding section of procedure B. Thereafter, full deprotection was performed as described in the corresponding section of procedure B.

Finally, the peptide was purified by preparative reverse phase LC-MS, as described herein below.

1.1.3.18 Procedure Q:

Preparation of a Peptide Having a Disulfide Interstrand Linkage in Module A and Having an Amino Acid Attached to an Amino Group-Bearing Side Chain and Having a Free N-Terminal Amino Group The linear peptide was assembled on solid support according to Method L, as described above, using Fmoc-Cys(Trt)-OH for addition of Cys residues and performing the attachment of a further amino acid to an amino group-bearing side chain as indicated in procedure A.

Subsequent ivDde deprotection (module B), cleavage, macrolactam cycle formation (module B), formation of disulfide interstrand linkage (module A), and full deprotection were performed as indicated in the corresponding sections of procedure C, following the same order.

Finally, the peptide was purified by preparative reverse phase LC-MS, as described herein below.

1.1.4 Purification Procedure (Preparative Reverse Phase LC-MS)

Compounds were purified by reverse phase chromatography using a Waters XBridge C8 OBD column, 30×150 mm, 5 μm (Cat No. 186003083), or a Waters XSelect C18 OBD column, 30×150 mm, 5 μm (Cat. 186005426).

Mobile phases used were:

A: 0.1% TFA in Water/Acetonitrile 98/2 v/v

B: 0.1% TFA in Acetonitrile

Gradient slopes in the preparative runs were adapted each time based on analytical LC-MS analysis of the crude product. As an example, a typical run (purification of Ex. 15) was executed using two Waters XBridge C8 OBD columns in series with a flow rate of 35 mL/min running a gradient from 0-1 min 0% B, at 1.1 min 28% B to 13 min 38% B, and finally 13.1-19.9 min 100% B (retention time: 12.12 min in this case).

Detection: MS and UV @ 220 nm

Fractions collected were evaporated using a Genevac HT4/HT12 evaporator or a Büchi system.

Alternatively for larger amounts the following LC-purification system was used:

Column: Waters XBridge C18 OBD column, 50×250 mm, 10 μm (Cat No. 186003900)

Mobile phase A: 0.1% TFA in Water/Acetonitrile 98/2 v/v

Mobile phase B: 0.1% TFA in Acetonitrile

Flow rate: 150 mL/min

Detection: UV @ 220 nm

After lyophilisation the products were obtained typically as white to off-white powders and analysed by HPLC-ESI-MS methods as described below.

1.2 Analytical Methods 1.2.1 Analytical Method A

Analytical HPLC retention times (rt, in minutes) were determined using an Ascentis Express C8 column, 100×3 mm, 2.7 μm (Supelco, 53852-U) with the following solvents A ($H_2O$+0.1% TFA) and B ($CH_3CN$+0.085% TFA) and the gradient: 0-0.1 min: 95% A, 5% B; 7 min: 15% A, 85% B; 7.02-7.5 min: 3% A, 97% B; 7.52-7.8 min: 95% A, 5% B. Flow rate=1.4 mL/min at 55° C.

1.2.2 Analytical Method B

Analytical HPLC retention times (rt, in minutes) were determined using an Ascentis Express C8 column, 100×3 mm, 2.7 μm (Supelco, 53852-U) with the following solvents A ($H_2O$+0.1% TFA) and B ($CH_3CN$+0.085% TFA) and the gradient: 0-0.1 min: 95% A, 5% B; 11 min: 15% A, 85% B; 11.02-12.5 min: 3% A, 97% B; 12.55-13.5 min: 95% A, 5% B. Flow rate=0.750 mL/min at 55° C.

1.2.3 Analytical Method C

Analytical HPLC retention times (rt, in minutes) were determined using an Ascentis Express C8 column 100×3 mm, 2.7 μm (Supelco, 53852-U) with the following solvents A ($H_2O$+0.1% TFA) and B ($CH_3CN$+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 55° C.

1.2.4 Analytical Method D

Analytical HPLC retention times (rt, in minutes) were determined using an Ascentis Express C8 column 100×3 mm, 2.7 μm (Supelco, 53852-U) with the following solvents A ($H_2O$+0.1% TFA) and B ($CH_3CN$+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 70° C.

1.2.5 Analytical method E

Analytical HPLC retention times (rt, in minutes) were determined using a Poroshell Bonus RP 100×3 mm, 2.7 μm (Agilent technologies, 695968-301) with the following solvents A ($H_2O$+0.1% TFA) and B ($CH_3CN$+0.085% TFA) and the gradient: 0-0.1 min: 95% A, 5% B; 7 min: 45% A, 55% B; 7.02-7.5 min: 3% A, 97% B; 7.52-7.8 min: 95% A, 5% B. Flow rate=1.4 mL/min at 70° C.

1.2.6 Analytical Method F

Analytical HPLC retention times (rt, in minutes) were determined using an Ascentis Express C8 column, 100×3 mm, 2.7 μm (Supelco, 53852-U) with the following solvents A ($H_2O$+0.1% TFA) and B ($CH_3CN$+0.085% TFA) and the gradient: 0-0.1 min: 95% A, 5% B; 7 min: 15% A, 85% B; 7.02-7.5 min: 3% A, 97% B; 7.52-7.8 min: 95% A, 5% B. Flow rate=1.4 mL/min at 70° C.

1.2.7 Analytical Method G

Analytical HPLC retention times (rt, in minutes) were determined using a Poroshell Bonus RP 100×3 mm, 2.7 μm (Agilent technologies, 695968-301) with the following solvents A ($H_2O$+0.1% TFA) and B ($CH_3CN$+0.085% TFA) and the gradient: 0-0.1 min: 95% A, 5% B; 7 min: 15% A, 85% B; 7.02-7.5 min: 3% A, 97% B; 7.52-7.8 min: 95% A, 5% B. Flow rate=1.4 mL/min at 55° C.

1.3 Synthesis of Peptide Sequences

Example 1 is shown in Table 1.

Procedure B, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-$^D$Glu-allyl ester for addition of the amino acid residue at $P^{13}$. Assembly of the peptide was in the following sequence:

Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, allyl deprotection at $P^{13}$, macrolactam cycle formation (module A) by an amide bond between the liberated α-carboxyl group of; $^D$Glu at $P^{13}$ and the α-amino group of Dab at $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 1 in Table 2.

Examples 2 and 3 are shown in Table 1.

Procedure B, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, using Fmoc protection for the α-amino group and allyl protection for the α-carboxyl group for the addition of the amino acid residue at $P^{13}$. Assembly of the peptides was in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, allyl deprotection at $P^{13}$, macrolactam cycle formation (module A) by an amide bond between the liberated α-carboxyl group of the amino acid residue at $P^{13}$ and the α-amino group of the amino acid residue at $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptides were purified, as described above, and characterized by HPLC-MS. For analytical data, see Ex. 2 and 3 in Table 2.

Examples 4, 5, 6, 74, 77 and 78 are shown in Table 1.

Procedure B, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, using Fmoc protection for the α-amino group and allyl protection for the α-carboxyl group for the addition of the amino acid residue at $P^{13}$. Assembly of the peptides was in the following sequence:

Resin-Thr-$Q^6$-$Q^5$-$Q^4$-$Q^3$-$Q^2$-$Q^1$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, allyl deprotection at $P^{13}$, macrolactam cycle formation (module A) by an amide bond between the liberated α-carboxyl group of the amino acid residue at $P^{13}$ and the α-amino group of the amino acid residue at $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptides were purified, as described above, and characterized by HPLC-MS. For analytical data, see Ex. 4, 5, 6, 74, 77 and 78 in Table 2.

Example 7, 80 to 85, 88 to 93, 95 to 97 and 99 to 103 are shown in Table 1. Procedure B, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, using Fmoc-Glu-allyl ester for addition of the amino acid residue at $P^{12}$. Assembly of the peptides was in the following sequence: Resin-Thr-$Q^6$-$Q^5$-$Q^4$-$Q^3$-$Q^2$-$Q^1$-$L^3$-$L^2$-$L^1$-$P^{12}$-$P^{11}$-$P^{10}$-$P^9$-$P^8$-$T^7$-$T^6$-$P^5$-$P^4$-$P^3$-$P^2$-$P^1$-$P^{14}$-$P^{13}$.

Subsequently, allyl deprotection at $P^{12}$, macrolactam cycle formation (module A) by an amide bond between the liberated α-carboxyl group of Glu at $P^{12}$ and the α-amino group of the amino acid residue at $P^{13}$, ivDde deprotection at $Q^1$, cleavage of the peptide from the resin, macrolactam cycle formation (module B) by an amide bond between the α-carboxyl group of Thr at $W$ and the γ-amino group of Dab at $Q^1$, and full deprotection were performed as indicated in procedure B above. Finally, the peptides were purified, as described above, and characterized by HPLC-MS. For analytical data, see Ex. 7, 80 to 85, 88 to 93, 95 to 97 and 99 to 103 in Table 2.

Example 8 is shown in Table 1.

Procedure B, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-Asp(Allyl)-OH for addition of the amino acid residue at $P^{13}$. Assembly of the peptide was in the following sequence:

Resin-Thr-$Q^6$-$Q^5$-$Q^4$-$Q^3$-$Q^2$-$Q^1$-$L^3$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, allyl deprotection at $P^{13}$, macrolactam cycle formation (module A) by an amide bond between the liberated β-carboxyl group of Asp at $P^{13}$ and the α-amino group of Dab at $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 8 in Table 2.

Example 9 is shown in Table 1.

Procedure B, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-$^D$Glu-allyl ester for addition of the amino acid residue at $P^{13}$. Assembly of the peptide was in the following sequence:

Resin-Thr-$Q^6$-$Q^5$-$Q^4$-$Q^3$-$Q^2$-$Q^1$-$L^3$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, allyl deprotection at $P^{13}$, macrolactam cycle formation (module A) by an amide bond between the liberated α-carboxyl group of $^D$Glu at $P^{13}$ and the α-amino group of Dab at $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 9 in Table 2.

Example 10 and 94 is shown in Table 1.

Procedure B, as described above, was used for the preparation of the peptides.

The peptide were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, using Fmoc-Glu-allyl ester for addition of the amino acid residue at $P^{14}$. Assembly of the peptides was in the following sequence:

Resin-Thr-$Q^6$-$Q^5$-$Q^4$-$Q^3$-$Q^2$-$Q^1$-$L^3$-$L^2$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, allyl deprotection at $P^{14}$, macrolactam cycle formation (module A) by an amide bond between the liberated α-carboxyl group of Glu at $P^{14}$ and the α-amino group of Trp at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptides were purified, as described above, and characterized by HPLC-MS. For analytical data, see Ex. 10 and 94 in Table 2.

Example 11 is shown in Table 1.

Procedure B, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-Glu-allyl ester for addition of the amino acid residue at $P^2$. Assembly of the peptide was in the following sequence:

Resin-Thr-$Q^6$-$Q^5$-$Q^4$-$Q^3$-$Q^2$-$Q^1$-$L^3$-$L^2$-$L^1$-$P^2$-$P^1$-$P^{14}$-$P^{13}$-$P^{12}$-$P^{11}$-$P^{10}$-$P^9$-$P^8$-$T^7$-$T^6$-$P^5$-$P^4$-$P^3$.

Subsequently, allyl deprotection at $P^2$, macrolactam cycle formation (module A) by an amide bond between the liberated α-carboxyl group of Glu at $P^2$ and the α-amino group of tBuGly at $P^3$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 11 in Table 2.

Examples 12, 13, 17 to 23, 110 to 113 and 115 to 118 are shown in Table 1.

Procedure C, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$P^{14}$-$P^{13}$-$P^{12}$-$P^{11}$-$P^{10}$-$P^9$-$P^8$-$P^7$-$P^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure C above. Finally, the peptides were purified, as described above, and characterized by HPLC-MS. For analytical data, see Ex. 12, 13, 17 to 23, 110 to 113 and 115 to 118 in Table 2.

Example 14 is shown in Table 1.

Procedure E1, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, in the following sequence:

Resin-Thr-$Q^6$-$Q^5$-$Q^4$-$Q^3$-$Q^2$-$Q^1$-$P^{14}$-$P^{13}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, formation of the lactam interstrand linkage by an amide bond between the side-chain functional groups of Glu at $P^2$ and Dab at $P^{11}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure E1 above. Finally, the peptide was purified, as described above, and characterized by HPLC-MS. For analytical data, see Ex. 14 in Table 2.

Examples 15, 16, 104 to 109 and 114 are shown in Table 1.

Procedure D, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according method B, as described above, in the following sequence:

Resin-Thr-$Q^6$-$Q^5$-$Q^4$-$Q^3$-$Q^2$-$Q^1$-$P^{14}$-$P^{13}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 15, 16, 104 to 109 and 114 in Table 2.

Example 24 is shown in Table 1.

Procedure F, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method C, as described above, including procedure A for formation of the dipeptidic amino acid residue at $P^{12}$. Following coupling of Fmoc-Dap(Alloc)-OH at $P^{12}$, procedure A was applied to attach Boc-Glu(tBu)-OH to the β-amino group of Dap. Assembly of the peptide was in the following sequence:

Resin-Thr-$Q^6$-$Q^5$-$Q^4$-$Q^3$-$Q^2$-$Q^1$-$P^{14}$-$P^{13}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed in the order as indicated in procedure F above. Finally, the peptide was purified, as described above, and characterized by HPLC-MS. For analytical data, see Ex. 24 in Table 2.

Example 25 is shown in Table 1.

Procedure F, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method C, as described above, including procedure A for formation of the dipeptidic amino acid residue at $Q^6$. Following coupling of Fmoc-Dap(Alloc)-OH at $Q^6$, procedure A was applied to attach Boc-Glu(tBu)-OH to the (3-amino group of Dap. Assembly of the peptide was in the following sequence:

Resin-Thr-$Q^6$-$Q^5$-$Q^4$-$Q^3$-$Q^2$-$Q^1$-$P^{14}$-$P^{13}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed in the order as indicated in procedure F above. Finally, the peptide was purified, as described above, and characterized by HPLC-MS. For analytical data, see Ex. 25 in Table 2.

Examples 26 to 34, 137 to 139, 142, 144 and 146 are shown in Table 1. Procedure C, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above in the following sequence:

Resin-Thr-$Q^6$-$Q^5$-$Q^4$-$Q^3$-$Q^2$-$Q^1$-$P^{14}$-$P^{13}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure C above. Finally, the peptides were purified, as described above, and characterized by HPLC-MS. For analytical data, see Ex. 26 to 34, 137 to 139, 142, 144 and 146 in Table 2.

Example 35 is shown in Table 1.

Procedure C, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, in the following sequence:

Resin-Thr-$Q^6$-$Q^5$-$Q^4$-$Q^3$-$Q^2$-$Q^1$-$P^{13}$-$P^{11}$-$P^{10}$-$P^9$-$P^8$-$T^7$-$T^6$-$P^5$-$P^4$-$P^3$-$P^2$-$P^1$.

Subsequently, acetylation at $P^{14}$, ivDde deprotection at $Q^1$, cleavage of the peptide from the resin, macrolactam cycle formation (module B) by an amide bond between the α-carboxyl group of Thr at W and the γ-amino group of Dab at $Q^1$, formation of the disulfide interstrand linkage between $P^2$ and $P^{11}$, and full deprotection were performed as indicated in procedure C above. Finally, the peptide was purified, as described above, and characterized by HPLC-MS. For analytical data, see Ex. 35 in Table 2.

Examples 36 and 41 are shown in Table 1.

Procedure C, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, acetylation at $P^{14}$, ivDde deprotection at $Q^1$, cleavage of the peptide from the resin, macrolactam cycle formation (module B) by an amide bond between the α-carboxyl group of Thr at W and the γ-amino group of Dab at $Q^1$, formation of the disulfide interstrand linkage between $P^2$ and $P^{11}$, and full deprotection were performed as indicated in procedure C above. Finally, the peptides were purified, as described above, and characterized by HPLC-MS. For analytical data, see Ex. 36 and 41 in Table 2.

Examples 37 to 40 and 42 to 44 are shown in Table 1.

Procedure D, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 37 to 40 and 42 to 44 in Table 2.

Examples 45, 188, 189 and 192 are shown in Table 1.

Procedure D as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:

Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 45, 188, 189 and 192 in Table 2.

Examples 46 to 55 are shown in Table 1.

Procedure C, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure C above. Finally, the peptides were purified, as described above, and characterized by HPLC-MS. For analytical data, see Ex. 46 to 55 in Table 2.

Example 56 is shown in Table 1.

Procedure E1, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, in the following sequence:

Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, formation of the lactam interstrand linkage by an amide bond between the side-chain functional groups of Asp at $P^2$ and Dab at $P^{11}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure E1 above. Finally, the peptide was purified, as described above, and characterized by HPLC-MS. For analytical data, see Ex. 56 in Table 2.

Examples 57 and 60 are shown in Table 1.

Procedure C, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, acetylation at $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^{13}$ and $P^{14}$, and full deprotection were performed as indicated in procedure C above. Finally, the peptides were purified, as described above, and characterized by HPLC-MS. For analytical data, see Ex. 57 and 60 in Table 2.

Examples 58, 59, 196 and 197 are shown in Table 1.

Procedure E1, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, acetylation at $P^{14}$, formation of the lactam interstrand linkage by an amide bond between the side-chain functional groups of amino acid residues at $P^{13}$ and $P^{14}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure E1 above. Finally, the peptides were purified, as described above, and characterized by HPLC-MS. For analytical data, see Ex. 58, 59, 196 and 197 in Table 2.

Example 61 is shown in Table 1.

Procedure C, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, in the following sequence:

Resin-Thr-$Q^6$-$Q^5$-$Q^4$-$Q^3$-$Q^2$-$Q^1$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, acetylation at $P^{14}$, ivDde deprotection at $Q^1$, cleavage of the peptide from the resin, macrolactam cycle formation (module B) by an amide bond between the α-carboxyl group of Thr at W and the γ-amino group of Dab at $Q^1$, formation of the disulfide interstrand linkage between $P^{13}$ and $P^{14}$, and full deprotection were performed as indicated in procedure C above. Finally, the peptide was purified, as described above, and characterized by HPLC-MS. For analytical data, see 61 in Table 2.

Examples 62 and 63 are shown in Table 1.

Procedure C, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$L^3$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, acetylation at $P^{14}$, ivDde deprotection at $Q^1$, cleavage of the peptide from the resin, macrolactam cycle formation (module B) by an amide bond between the α-carboxyl group of Thr at W and the γ-amino group of Dab at $Q^1$, formation of the disulfide interstrand linkage between $P^{13}$ and $P^{14}$, and full deprotection were performed as indicated in procedure C above. Finally, the peptides were purified, as described above, and characterized by HPLC-MS. For analytical data, see Ex. 62 and 63 in Table 2.

Example 64 is shown in Table 1.

Procedure B, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-Asp-allyl ester for addition of the amino acid residue at $P^{12}$. Assembly of the peptide was in the following sequence:

Resin-Thr-$Q^6$-$Q^5$-$Q^4$-$Q^3$-$Q^2$-$Q^1$-$P^{12}$-$P^{11}$-$P^{10}$-$P^9$-$P^8$-$T^7$-$T^6$-$P^5$-$P^4$-$P^3$-$P^2$-$P^1$-$P^{14}$-$P^{13}$.

Subsequently, allyl deprotection at $P^{12}$, macrolactam cycle formation (module A) by an amide bond between the liberated α-carboxyl group of Asp at $P^{12}$ and the α-amino group of; $^D$Dab at $P^{13}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 64 in Table 2.

Examples 65 to 69 and 71 to 73 are shown in Table 1.

Procedure B, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, using Fmoc protection for the α-amino group and allyl protection for the α-carboxyl group for the addition of the amino acid residue at $P^{12}$. Assembly of the peptides was in the following sequence:

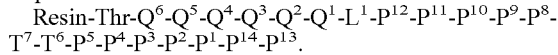
Resin-Thr-$Q^6$-$Q^5$-$Q^4$-$Q^3$-$Q^2$-$Q^1$-$L^1$-$P^{12}$-$P^{11}$-$P^{10}$-$P^9$-$P^8$-$T^7$-$T^6$-$P^5$-$P^4$-$P^3$-$P^2$-$P^1$-$P^{14}$-$P^{13}$.

Subsequently, allyl deprotection at $P^{12}$, macrolactam cycle formation (module A) by an amide bond between the liberated α-carboxyl group of the amino acid residue at $P^{12}$ and the α-amino group of the amino acid residue at $P^{13}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptides were purified, as described above, and characterized by HPLC-MS. For analytical data, see 65 to 69 and 71 to 73 in Table 2.

Example 70 is shown in Table 1.

Procedure B, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-Glu-allyl ester for addition of the amino acid residue at $P^{14}$. Assembly of the peptide was in the following sequence:

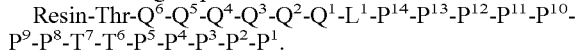
Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, allyl deprotection at $P^{14}$, macrolactam cycle formation (module A) by an amide bond between the liberated α-carboxyl group of Glu at $P^{14}$ and the α-amino group of Trp at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see 70 in Table 2.

Example 75 is shown in Table 1.

Procedure B, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-Glu-allyl ester for addition of the amino acid residue at $P^{14}$. Assembly of the peptide was in the following sequence:

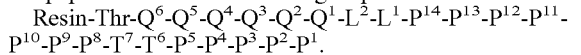
Resin-Thr-$Q^6$-$Q^5$-$Q^4$-$Q^3$-$Q^2$-$Q^1$-$L^2$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, allyl deprotection at $P^{14}$, macrolactam cycle formation (module A) by an amide bond between the liberated α-carboxyl group of Glu at $P^{14}$ and the α-amino group of Trp at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 75 in Table 2.

Example 76 is shown in Table 1.

Procedure B, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, using Fmoc-Asp-allyl ester for addition of the amino acid residue at $P^{12}$. Assembly of the peptide was in the following sequence:

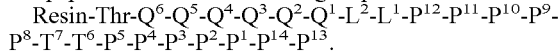
Resin-Thr-$Q^6$-$Q^5$-$Q^4$-$Q^3$-$Q^2$-$Q^1$-$L^2$-$L^1$-$P^{12}$-$P^{11}$-$P^{10}$-$P^9$-$P^8$-$T^7$-$T^6$-$P^5$-$P^4$-$P^3$-$P^2$-$P^1$-$P^{14}$-$P^{13}$.

Subsequently, allyl deprotection at $P^{12}$, macrolactam cycle formation (module A) by an amide bond between the liberated α-carboxyl group of Asp at $P^{12}$ and the α-amino group of; $^D$Dab at $P^{13}$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure B above. Finally, the peptide was purified, as described above, and characterized by HPLC-MS. For analytical data, see Ex. 76 in Table 2.

Example 79 is shown in Table 1.

Procedure J, as described above, was used for the preparation of the peptide.

The peptide was synthesized starting with the amino acid Fmoc-Thr-allyl ester, which was grafted to the resin (Fmoc-Thr(-2-chlorotrityl resin)-allyl). The peptide was synthesized on the solid support according to method I, as described above, including macrolactam cycle formation (module B) and using Fmoc-Glu(Allyl)-OH for addition of the amino acid residue at $P^{13}$. Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G.

Assembly of the peptide was in the following sequence:

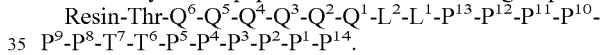
Resin-Thr-$Q^6$-$Q^5$-$Q^4$-$Q^3$-$Q^2$-$Q^1$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, removal of the allyl protection group at $P^{13}$, cleavage of the peptide from the resin, macrolactam cycle formation (module A) by an amide bond between the liberated γ-carboxyl group of Glu at $P^{13}$ and the α-amino group of Dab at $P^{14}$, formation of a disulfide interstrand linkage between $P^2$ and $P^{11}$, and full deprotection were performed as indicated in procedure 0.1 above. Finally, the peptide was purified, as described above, and characterized by HPLC-MS. For analytical data, see Ex. 79 in Table 2.

Examples 86 and 87 is shown in Table 1.

Procedure I, as described above, was used for the preparation of the peptides.

The peptides were synthesized starting with the amino acid Fmoc-Thr-allyl ester, which was grafted to the resin (Fmoc-Thr(-2-chlorotrityl resin)-allyl). The peptides were synthesized on the solid support according to method H, as described above, including macrolactam cycle formation (module B) and formation of a lactam interstrand linkage, and using Fmoc-Glu-2-PhiPr ester for addition of the amino acid residue at $P^{12}$. Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G; and subsequent to the coupling of Fmoc-Asp(Allyl)-OH at $P^4$, the lactam interstrand linkage by an amide bond between the side-chain functional groups of Asp at $P^4$ and Dab at $P^9$ was formed as described in the corresponding section of procedure E2.

Assembly of the peptides was in the following sequence:

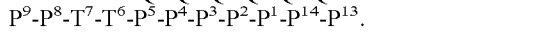
Resin-Thr-$Q^6$-$Q^5$-$Q^4$-$Q^3$-$Q^2$-$Q^1$-$L^3$-$L^2$-$L^1$-$P^{12}$-$P^{11}$-$P^{10}$-$P^9$-$P^8$-$T^7$-$T^6$-$P^5$-$P^4$-$P^3$-$P^2$-$P^1$-$P^{14}$-$P^{13}$.

Subsequently, cleavage of the peptide from the resin and removal of the 2-phenyl-isopropyl protecting group at $P^{12}$, macrolactam cycle formation (module A) by an amide bond between the liberated α-carboxyl group of Glu at $P^{12}$ and the α-amino group of; $^D$Dab at $P^{13}$, and full deprotection were performed as indicated in procedure I above. Finally, the peptides were purified, as described above, and characterized by HPLC-MS. For analytical data, see 86 and 87 in Table 2.

Example 98 is shown in Table 1.

Procedure J, as described above, was used for the preparation of the peptide.

The peptide was synthesized starting with the amino acid Fmoc-Thr-allyl ester, which was grafted to the resin (Fmoc-Thr(-2-chlorotrityl resin)-allyl). The peptide was synthesized on the solid support according to method I, as described above, including macrolactam cycle formation (module B) and using Fmoc-Glu-allyl ester for addition of the amino acid residue at $P^{12}$. Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G.

Assembly of the peptide was in the following sequence:
Resin-Thr-$Q^6$-$Q^5$-$Q^4$-$Q^3$-$Q^2$-$Q^1$-$L^3$-$L^2$-$L^1$-$P^{12}$-$P^{11}$-$P^{10}$-$P^9$-$P^8$-$T^7$-$T^6$-$P^5$-$P^4$-$P^3$-$P^2$-$P^1$-$P^{14}$-$P^{13}$.

Subsequently, removal of the allyl protecting group at $P^{12}$, cleavage of the peptide from the resin, macrolactam cycle formation (module A) by an amide bond between the liberated α-carboxyl group of Glu at $P^{12}$ and the α-amino group of; $^D$Dab at $P^{13}$, formation of a disulfide interstrand linkage between $P^2$ and $P^{11}$, and full deprotection were performed as indicated in procedure 0.1 above. Finally, the peptide was purified, as described above, and characterized by HPLC-MS. For analytical data, see Ex. 98 in Table 2.

Examples 119 and 120 are shown in Table 1.

Procedure C, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:
Resin-Thr-$Q^6$-$Q^5$-$Q^4$-$Q^3$-$Q^2$-$Q^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^4$ and $P^9$, and full deprotection were performed as indicated in procedure C above. Finally, the peptides were purified, as described above, and characterized by HPLC-MS. For analytical data, see Ex. 119 and 120 in Table 2.

Examples 121 to 132, 134, 136, 140, 141, 143, 145, 147 to 159, 175 and 178 are shown in Table 1.

Procedure D, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:
Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 121 to 132, 134, 136, 140, 141, 143, 145, 147 to 159, 175 and 178 in Table 2.

Example 133 is shown in Table 1.

Procedure 0, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above in the following sequence:
Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, tetramethylguanidinylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure 0 above. Finally, the peptide was purified, as described above, and characterized by HPLC-MS. For analytical data, see Ex. 133 in Table 2.

Example 135 is shown in Table 1.

Procedure M, as described above, was used for the preparation of the peptide. The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above in the following sequence:
Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, guanidinylation at $P^1$, ivDde deprotection at $Q^1$, cleavage of the peptide from the resin, macrolactam cycle formation (module B) by an amide bond between the α-carboxyl group of Thr at Wand the γ-amino group of Dab at $Q^1$, formation of the disulfide interstrand linkage between $P^2$ and $P^{11}$, and full deprotection were performed as indicated in procedure M above. Finally, the peptide was purified, as described above, and characterized by HPLC-MS. For analytical data, see Ex. 135 in Table 2.

Examples 160 and 171 are shown in Table 1.

Procedure C, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:
Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^4$ and $P^9$, and full deprotection were performed as indicated in procedure C above. Finally, the peptides were purified, as described above, and characterized by HPLC-MS. For analytical data, see Ex. 160 and 171 in Table 2.

Examples 161 to 166, 169 and 170 are shown in Table 1.

Procedure D, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according method B, as described above, in the following sequence:

Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^4$ and $P^9$, and full deprotection were performed as indicated in procedure D above. Finally, the peptides were purified, as described above, and characterized by HPLC-MS. For analytical data, see 161 to 166, 169 and 170 in Table 2.

Examples 167 and 168 are shown in Table 1.

Procedure E2, as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method D, including formation of a lactam interstrand linkage. Following coupling of Fmoc-Asp(Allyl)-OH at $P^4$, the lactam interstrand linkage by an amide bond between the side-chain functional groups of Asp at $P^4$ and Dab at $P^9$ was formed as described in the corresponding section of procedure E2 above. Assembly of the peptides was in the following sequence:

Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, acetylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure E2 above. Finally, the peptides were purified, as described above, and characterized by HPLC-MS. For analytical data, see 167 and 168 in Table 2.

Example 172 is shown in Table 1.

Procedure N, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The peptide was synthesized on the solid support according to method D as described above, including formation of a lactam interstrand linkage. Following coupling of Fmoc-Asp(Allyl)-OH at $P^4$, the lactam interstrand linkage by an amide bond between the side-chain functional groups of Asp at $P^4$ and Dab at $P^9$ was formed as described in the corresponding section of procedure E2. Assembly of the peptide was in the following sequence:

Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, guanidinylation at $P^1$, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, and full deprotection were performed as indicated in procedure N above. Finally, the peptide was purified, as described above, and characterized by HPLC-MS. For analytical data, see Ex. 172 in Table 2.

Examples 173 and 174 are shown in Table 1.

Procedure M as described above, was used for the preparation of the peptides. The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method A, as described above, in the following sequence:

Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, guanidinylation at $P^1$, ivDde deprotection at $Q^1$, cleavage of the peptide from the resin, macrolactam cycle formation (module B) by an amide bond between the α-carboxyl group of Thr at Wand the γ-amino group of Dab at $Q^1$, formation of the disulfide interstrand linkage between $P^2$ and $P^{11}$, and full deprotection were performed as indicated in procedure M above. Finally, the peptides were purified, as described above, and characterized by HPLC-MS. For analytical data, see Ex. 173 and 174 in Table 2.

Examples 176 is shown in Table 1.

Procedure P, as described above, was used for the preparation of the peptide.

The peptide was synthesized starting with the amino acid Fmoc-Thr-allyl ester, which was grafted to the resin (Fmoc-Thr(-2-chlorotrityl resin)-allyl). The peptide was synthesized on the solid support according to method K, as described above, including macrolactam cycle formation (module B) and using Fmoc-Asp(2-PhiPr)—OH for addition of the amino acid residue at $P^4$. Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G. Assembly of the peptide was in the following sequence:

Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, removal of the alloc protecting group at $P^9$, cleavage of the peptide from the resin and removal of the 2-phenyl-isopropyl protecting group at $P^4$, formation of a lactam interstrand linkage by an amide bond between the liberated β-carboxyl group of Asp at $P^4$ and the γ-amino group of Dab at $P^9$, and full deprotection were performed as indicated in procedure P above. Finally, the peptide was purified, as described above, and characterized by HPLC-MS. For analytical data, see Ex. 176 in Table 2.

Example 177 is shown in Table 1.

Procedure Q, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method L, as described above, including procedure A for formation of the dipeptidic amino acid residue at $Q^6$. Following coupling of Fmoc-Dab(Alloc)-OH at $Q^6$, procedure A was applied to attach Boc-Arg(Pbf)-OH to the γ-amino group of Dab. Assembly of the peptide was in the following sequence:

Resin-Thr-$Q^6$-$Q^5$-$Q^4$-$Q^3$-$Q^2$-$Q^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed in the order as indicated in procedure F above. Finally, the peptide was purified, as described above, and characterized by HPLC-MS. For analytical data, see Ex. 177 in Table 2.

Example 179 is shown in Table 1.

Procedure D, as described above, was used for the preparation of the peptide.

The peptide was synthesized starting with the amino acid Fmoc-Val-OH, which was grafted to the resin (Fmoc-Val-2-chlorotrityl resin). The linear peptide was synthesized on the solid support according to method B, as described above, in the following sequence:

Resin-Thr-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Val at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 179 in Table 2.

Example 180 is shown in Table 1.

Procedure D, as described above, was used for the preparation of the peptide. The peptide was synthesized starting with the amino acid Fmoc-$^D$Val-OH, which was grafted to the resin (Fmoc-$^D$Val-2-chlorotrityl resin). The linear peptide was synthesized on the solid support according to method B, as described above, in the following sequence:

Resin-$^D$Val-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of; $^D$Val at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 180 in Table 2.

Example 181 is shown in Table 1.

Procedure D, as described above, was used for the preparation of the peptide.

The peptide was synthesized starting with the amino acid Fmoc-Arg(Pbf)-OH, which was grafted to the resin (Fmoc-Arg(Pbf)-2-chlorotrityl resin). The linear peptide was synthesized on the solid support according to method B, as described above, in the following sequence:

Resin-Arg(Pbf)-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Arg at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 181 in Table 2.

Example 182 is shown in Table 1.

Procedure D, as described above, was used for the preparation of the peptide.

The peptide was synthesized starting with the amino acid Fmoc-$^D$Arg(Pbf)-OH, which was grafted to the resin (Fmoc-$^D$Arg(Pbf)-2-chlorotrityl resin). The linear peptide was synthesized on the solid support according to method B, as described above, in the following sequence:

Resin-$^D$Arg(Pbf)-$Q^6$-$Q^5$-$Q^4$-$Q^3$-$Q^2$-$Q^1$-$L^1$-$P^{14}$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of; $^D$Arg at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 182 in Table 2.

Example 183 is shown in Table 1.

Procedure D, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method B, as described above, in the following sequence:

Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure D above. Finally, the peptide was purified, as described above, and characterized by HPLC-MS. For analytical data, see Ex. 183 in Table 2.

Examples 184, 185 and 186 are shown in Table 1.

Procedure D, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:

Resin-Thr-$Q^6$-$Q^5$-$Q^4$-$Q^3$-$Q^2$-$Q^1$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure D above. Finally, the peptides were purified, as described above, and characterized by HPLC-MS. For analytical data, see Ex. 184, 185 and 186 in Table 2.

Example 187 is shown in Table 1.

Procedure Q, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method L, as described above, including procedure A for formation of the dipeptidic amino acid residue at $Q^6$. Following coupling of Fmoc-Dab(Alloc)-OH at $Q^6$, procedure A was applied to attach Boc-Arg(Pbf)-OH to the γ-amino group of Dab. Assembly of the peptide was in the following sequence:

Resin-Thr-$Q^6$-$Q^5$-$Q^4$-$Q^3$-$Q^2$-$Q^1$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, ivDde deprotection at $Q^1$, cleavage of peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed in the order as indicated in procedure F above. Finally, the peptide was purified, as described above, and characterized by HPLC-MS. For analytical data, see Ex. 187 in Table 2.

Example 190 is shown in Table 1.

Procedure P, as described above, was used for the preparation of the peptide.

The peptide was synthesized starting with the amino acid Fmoc-Thr-allyl ester, which was grafted to the resin (Fmoc-Thr(-2-chlorotrityl resin)-allyl). The peptide was synthesized on the solid support according to method K, as described above, including macrolactam cycle formation (module B) and using Fmoc-Asp(2-PhiPr)—OH for addition of the amino acid residue at $P^{11}$. Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G.

Assembly of the peptide was in the following sequence:
Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, removal of the alloc protecting group at $P^2$, cleavage of the peptide from the resin and removal of the 2-phenyl-isopropyl protecting group at $P^{11}$, formation of a lactam interstrand linkage by an amide bond between the liberated β-carboxyl group of Asp at $P^{11}$ and the γ-amino group of Dab at $P^2$, and full deprotection were performed as indicated in procedure P above. Finally, the peptide was purified, as described above, and characterized by HPLC-MS. For analytical data, see Ex. 190 in Table 2.

Example 191 is shown in Table 1.

Procedure K2, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The peptide was synthesized on the solid support according to method J, as described above, including formation of a lactam interstrand linkage. Following coupling of Fmoc-Asp(Allyl)-OH at $P^4$, the lactam interstrand linkage by an amide bond between the side-chain functional groups of Asp at $P^4$ and Dab at $P^9$ was formed as described in the corresponding section of procedure E2.

Assembly of the peptide was in the following sequence:
Resin-Thr-$Q^6$-$Q^5$-$Q^4$-$Q^3$-$Q^2$-$Q^1$-$P^{13}$-$P^{12}$-$P^{11}$-$P^{10}$-$P^9$-$P^8$-$T^7$-$T^6$-$P^5$-$P^4$-$P^3$-$P^2$-$P^1$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^2$ and $P^{11}$, and full deprotection were performed as indicated in procedure K2 above. Finally, the peptide was purified, as described above, and characterized by HPLC-MS. For analytical data, see Ex. 191 in Table 2.

Example 193 is shown in Table 1.

Procedure G, as described above, was used for the preparation of the peptide, applying a fragment coupling strategy.

(I) The protected peptide fragment (module B and linker L) was synthesized starting with the amino acid Fmoc-Thr-allyl ester, which was grafted to the resin (Fmoc-Thr(-2-chlorotrityl resin)-allyl). The peptide was synthesized on the solid support according to method E, as described above, including macrolactam cycle formation (module B). Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G.

Assembly of the peptide was in the following sequence:
Resin-Thr-$Q^6$-$Q^5$-$Q^4$-$Q^3$-$Q^2$-$Q^1$-$L^1$.

Subsequently, cleavage of the peptide from the resin and preparation of the free base peptide were performed as indicated in procedure G above.

(II) The protected peptide fragment (module A) was synthesized starting with the amino acid Fmoc-Dab(Alloc)-OH. The linear peptide was synthesized on the solid support according to method G, as described above, using Fmoc-Dab(Alloc)-OH in the first coupling cycle and using Fmoc-Glu(2-PhiPr)—OH for addition of the amino acid residue at $P^{12}$.

Assembly of the peptide was in the following sequence:
Resin-Dab-$P^{12}$-$P^{11}$-$P^{10}$-$P^9$-$P^8$-$T^7$-$T^6$-$P^6$-$P^4$-$P^3$-$P^2$-$P^1$-$P^{14}$.

Subsequently, formation of the lactam interstrand linkage by an amide bond between the side-chain functional groups of Glu at $P^{14}$ and Dab at $P^{13}$, cleavage of the peptide from the resin and removal of the 2-phenyl-isopropyl protecting group were performed as indicated in procedure G above.

(III) Coupling of the two fully protected peptide fragments by an amide bond between the γ-carboxyl group of Glu at $P^{12}$ in the protected peptide fragment (module A) and the α-amino group of; $^D$Dab at $L^1$ in the protected peptide fragment (module B and linker L) was performed as described in the corresponding section of procedure G. Subsequently, full deprotection was performed as indicated in procedure G above. Finally, the peptide was purified, as described above, and characterized by HPLC-MS. For analytical data, see Ex. 193 in Table 2.

Example 194 is shown in Table 1.

Procedure H, as described above, was used for the preparation of the peptide, applying a fragment coupling strategy.

(I) The protected peptide fragment (module B and linker L) was synthesized as described above in the corresponding section in the synthesis of Ex. 193.

(II) The protected peptide fragment (module A) was synthesized starting with the amino acid Fmoc-Cys(Trt)-OH. The linear peptide was synthesized on the solid support according to method F, as described above, using Fmoc-Cys(Trt)-OH in the first coupling cycle and using Fmoc-Glu(Allyl)-OH for addition of the amino acid residue at $P^{12}$.

Assembly of the peptide was in the following sequence:
Resin-Cys-$P^{12}$-$P^{11}$-$P^{10}$-$P^9$-$P^8$-$T^7$-$T^6$-$P^6$-$P^4$-$P^3$-$P^2$-$P^1$-$P^{14}$.

Subsequently, acetylation, cleavage of the peptide from the resin, formation of the disulfide interstrand linkage between $P^{13}$ and $P^{14}$, and allyl deprotection at $P^{12}$ were performed as indicated in procedure H above.

(III) Coupling of the two fully protected peptide fragments by an amide bond between the γ-carboxyl group of Glu at $P^{12}$ in the protected peptide fragment (module A) and the α-amino group of; $^D$Dab at $L^1$ in the protected peptide fragment (module B and linker L), and full deprotection were performed as indicated in procedure H above. Finally, the peptide was purified, as described above, and characterized by HPLC-MS. For analytical data, see Ex. 194 in Table 2.

Examples 195, 206 to 209 and 215 are shown in Table 1.

Procedure D, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^{13}$ and $P^{14}$, and full deprotection were performed as indicated in procedure D above. Finally, the peptides were purified, as described above, and characterized by HPLC-MS. For analytical data, see Ex. 195, 206 to 209 and 215 in Table 2.

Example 198 is shown in Table 1.

Procedure P, as described above, was used for the preparation of the peptide.

The peptide was synthesized starting with the amino acid Fmoc-Thr-allyl ester, which was grafted to the resin (Fmoc-Thr(-2-chlorotrityl resin)-allyl). The peptide was synthesized on the solid support according to method K, as described above, including macrolactam cycle formation (module B) and using Boc-Glu(2-PhiPr)—OH for addition of the amino acid residue at $P^{14}$. Following coupling of the Fmoc amino acid building block at position $Q^1$, macrolactam cycle formation (module B) by an amide bond between the α-carboxyl group of Thr at $Q^7$ and the γ-amino group of Dab at $Q^1$ was performed as described in the corresponding section of procedure G.

Assembly of the peptide was in the following sequence:
Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, cleavage of the peptide from the resin and removal of the 2-phenyl-isopropyl protecting group at $P^{14}$, formation of a lactam interstrand linkage by an amide bond between the liberated γ-carboxyl group of Glu at $P^{14}$ and the γ-amino group of Dab at $P^{13}$, and full deprotection were performed as indicated in procedure P above. Finally, the peptide was purified, as described above, and characterized by HPLC-MS. For analytical data, see Ex. 198 in Table 2.

Examples 199 to 205 are shown in Table 1.

Procedure D, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, deprotection at $Q^1$, cleavage of the peptide from the resin, macrolactam cycle formation (module B) by an amide bond between the α-carboxyl group of Thr at Wand the γ-amino group of Dab at $Q^1$, formation of the disulfide interstrand linkage between $P^{13}$ and $P^{14}$, and full deprotection were performed as indicated in procedure D above. Finally, the peptides were purified, as described above, and characterized by HPLC-MS. For analytical data, see Ex. 199 to 205 in Table 2.

Example 210 is shown in Table 1.

Procedure K1, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method B, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, formation of the lactam interstrand linkage by an amide bond between the side-chain functional groups of Glu at $P^2$ and Dab at $P^{11}$, ivDde deprotection at $Q^1$, cleavage of the peptide from the resin, macrolactam cycle formation (module B) by an amide bond between the α-carboxyl group of Thr at Wand the γ-amino group of Dab at $Q^1$, formation of the disulfide interstrand linkage between $P^{13}$ and $P^{14}$, and full deprotection were performed as indicated in procedure K1 above. Finally, the peptide was purified, as described above, and characterized by HPLC-MS. For analytical data, see Ex. 210 in Table 2.

Example 211 is shown in Table 1.

Procedure C, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method A, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, acetylation at $P^{14}$, ivDde deprotection at $Q^1$, cleavage of the peptide from the resin, macrolactam cycle formation (module B) by an amide bond between the α-carboxyl group of Thr at Wand the γ-amino group of Dab at $Q^1$, formation of the disulfide interstrand linkages between $P^{13}$ and $P^{14}$ and between $P^4$ and $P^9$, and full deprotection were performed as indicated in procedure C above. Finally, the peptide was purified, as described above, and characterized by HPLC-MS. For analytical data, see Ex. 211 in Table 2.

Examples 212 and 213 are shown in Table 1.

Procedure D, as described above, was used for the preparation of the peptides.

The peptides were synthesized starting with the amino acid Fmoc-Thr(tBu)-OH, which was grafted to the resin (Fmoc-Thr(tBu)-2-chlorotrityl resin). The linear peptides were synthesized on the solid support according to method B, as described above, in the following sequence:

Resin-Thr-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkages between $P^{13}$ and $P^{14}$ and between $P^4$ and $P^9$, and full deprotection were performed as indicated in procedure D above. Finally, the peptides were purified, as described above, and characterized by HPLC-MS. For analytical data, see Ex. 212 and 213 in Table 2.

Example 214 is shown in Table 1.

Procedure D, as described above, was used for the preparation of the peptide.

The peptide was synthesized starting with the amino acid Fmoc-Thr(tBu)-OH, which was grafted to the resin (Fmoc-Thr(tBu)-2-chlorotrityl resin). The linear peptide was synthesized on the solid support according to method B, as described above, in the following sequence:

Resin-Thr-$Q^6$-$Q^5$-$Q^4$-$Q^3$-$Q^2$-$Q^1$-$L^3$-$L^2$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, ivDde deprotection at $Q^1$, cleavage of the peptide from the resin, macrolactam cycle formation (module B) by an amide bond between the α-carboxyl group of Thr at $Q^7$ and the γ-amino group of Dab at $Q^1$, formation of the disulfide interstrand linkage between $P^{13}$ and $P^{14}$, and full deprotection were performed as indicated in procedure D above. Finally, the peptide was purified, as described above, and characterized by HPLC-MS. For analytical data, see Ex. 214 in Table 2.

Example 216 is shown in Table 1.

Procedure D, as described above, was used for the preparation of the peptide.

The peptide was synthesized starting with the amino acid Fmoc-Val-OH, which was grafted to the resin (Fmoc-Val-2-chlorotrityl resin). The linear peptide was synthesized on the solid support according to method B, as described above, in the following sequence:

Resin-Val-$Q^6$-$Q^5$-$Q^4$-$Q^3$-$Q^2$-$Q^1$-$L^1$-$P^{13}$-$P^{12}$-$P^{11}$-$P^{10}$-$P^9$-$P^8$-$T^7$-$T^6$-$P^5$-$P^4$-$P^3$-$P^2$-$P^1$-$P^{14}$.

Subsequently, deprotection at $Q^1$, cleavage of the peptide from the resin, macrolactam cycle formation (module B) by an amide bond between the α-carboxyl group of Val at $Q^7$ and the γ-amino group of Dab at $Q^1$, formation of the disulfide interstrand linkage between $P^{13}$ and $P^{14}$, and full deprotection were performed as indicated in procedure D above. Finally, the peptide was purified, as described above, and characterized by HPLC-MS. For analytical data, see Ex. 216 in Table 2.

TABLE 1

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
| --- | --- |
| Ex. 1 | cyclo(-Trp-Dab-tBuGly-Ala-Ser-$^D$Pro-Pro-Nle-Ser-Tyr-Dab-Orn... Dab-) ... cyclo(... Dab-$^D$Phe-Leu-Dab-Dab-Thr-) |
| Ex. 2 | cyclo(-Trp-Dab-tBuGly-Ala-Ser-$^D$Pro-Pro-Nle-Ser-Tyr-Dab-Orn... Dab-) ... Dab ... cyclo(... Dab-$^D$Phe-Leu-Dab-Dab-Thr-) |
| Ex. 3 | cyclo(-Trp-Dab-tBuGly-Ala-Ser-$^D$Pro-Pro-Nle-Ser-Tyr-Dab-Orn... Dab-) ... Dab ... cyclo(... Dab-$^D$Phe-Leu-Dab-Dab-Thr-) |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 4 | 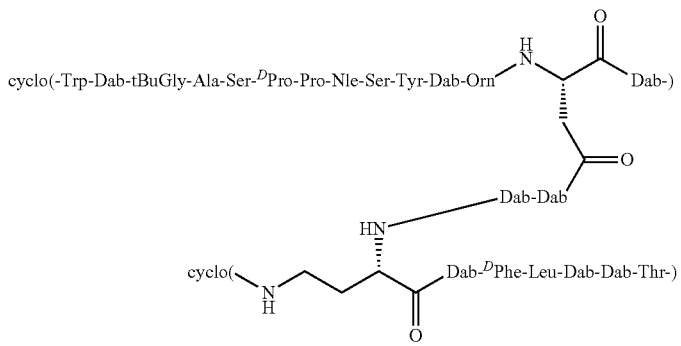 |
| Ex. 5 | 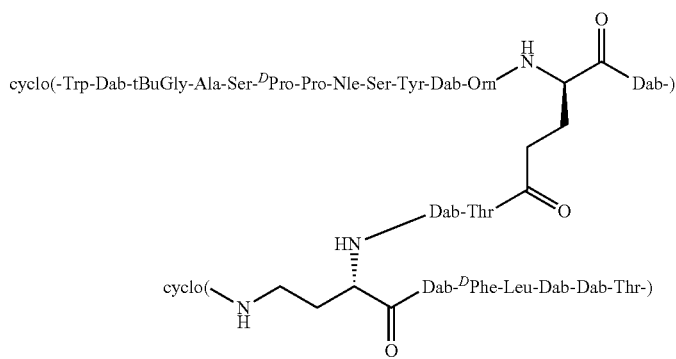 |
| Ex. 6 | 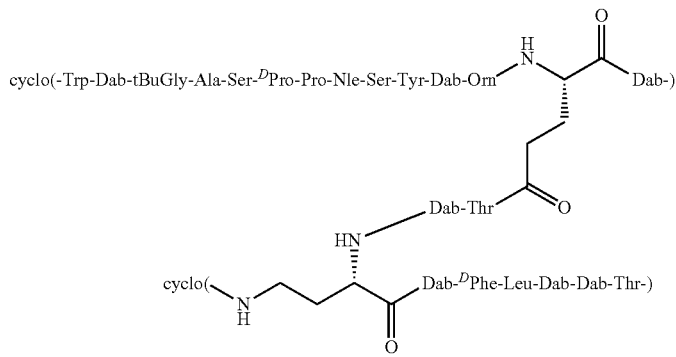 |
| Ex. 7 | 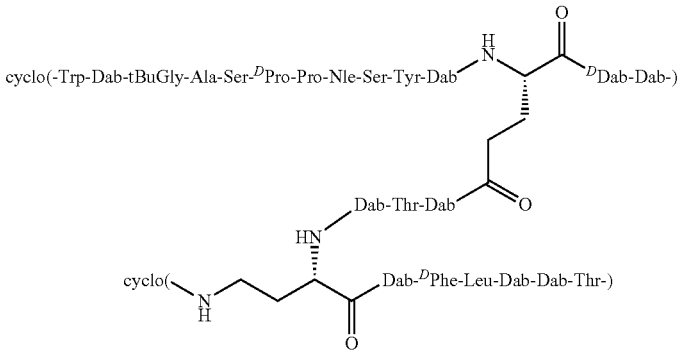 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 8 | 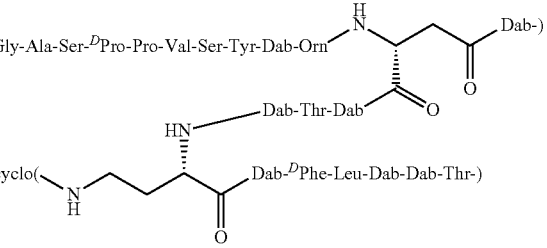 |
| Ex. 9 | 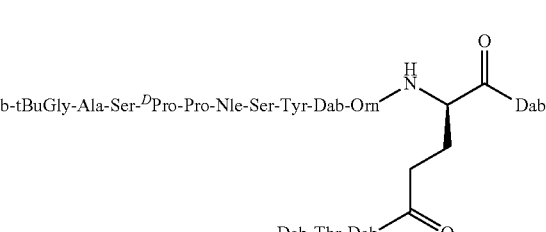 |
| Ex. 10 | 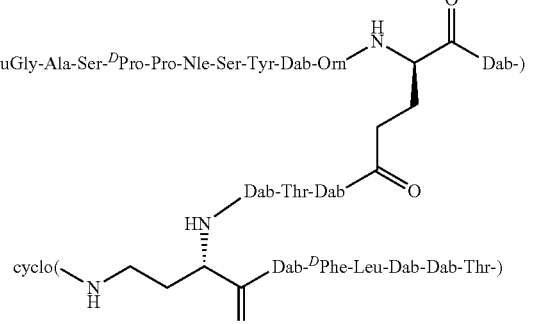 |
| Ex. 11 |  |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified
| Ex. No. | Sequence |
|---|---|
| Ex. 12[a] | 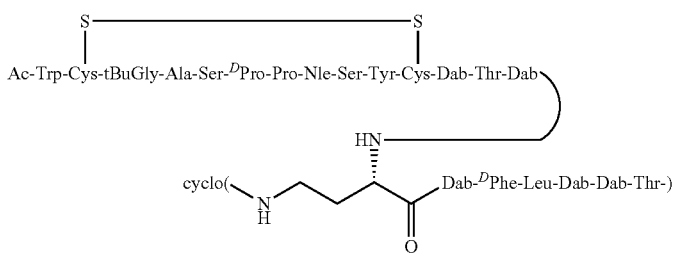 |
| Ex. 13[a] | 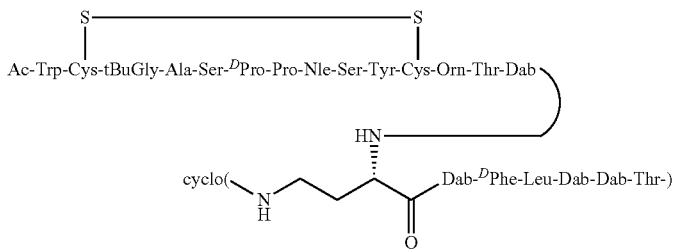 |
| Ex. 14[b] | 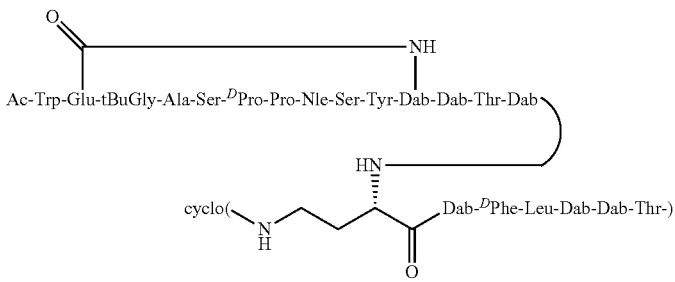 |
| Ex. 15[a] | 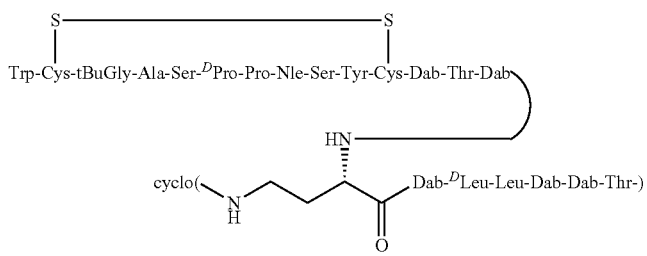 |
| Ex. 16[a] | 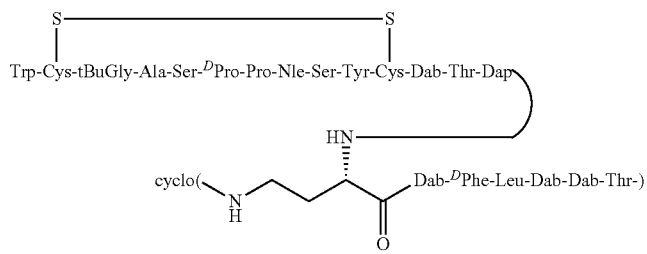 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 17[a)] | 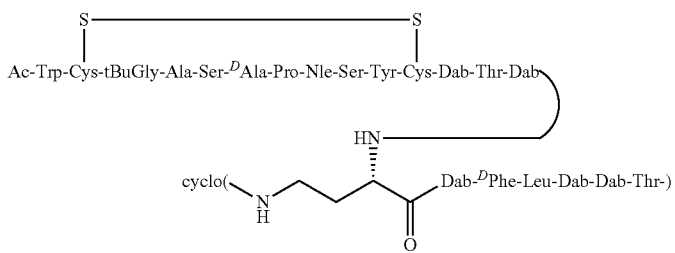 Ac-Trp-Cys-tBuGly-Ala-Ser-[D]Ala-Pro-Nle-Ser-Tyr-Cys-Dab-Thr-Dab cyclo(Dab-[D]Phe-Leu-Dab-Dab-Thr-) |
| Ex. 18[a)] | 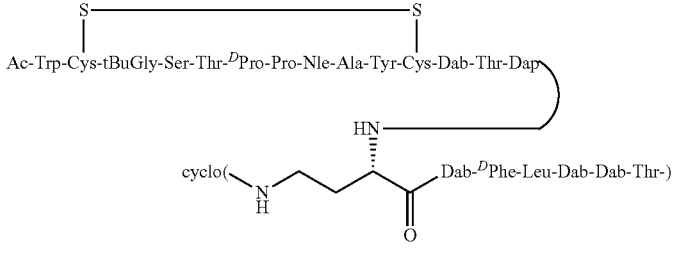 Ac-Trp-Cys-tBuGly-Ser-Thr-[D]Pro-Pro-Nle-Ala-Tyr-Cys-Dab-Thr-Dap cyclo(Dab-[D]Phe-Leu-Dab-Dab-Thr-) |
| Ex. 19[a)] | 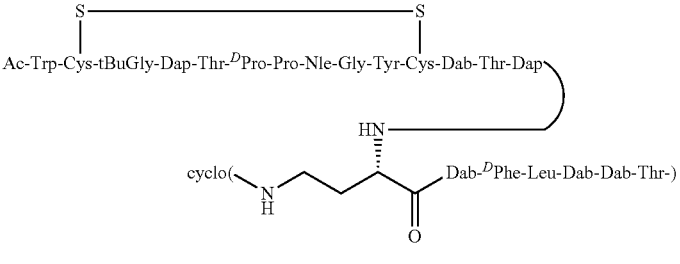 Ac-Trp-Cys-tBuGly-Dap-Thr-[D]Pro-Pro-Nle-Gly-Tyr-Cys-Dab-Thr-Dap cyclo(Dab-[D]Phe-Leu-Dab-Dab-Thr-) |
| Ex. 20 | 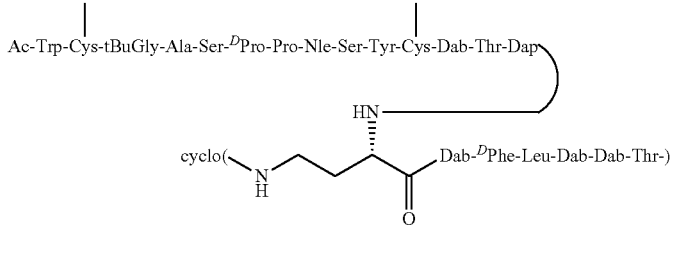 Ac-Trp-Cys-tBuGly-Ala-Ser-[D]Pro-Pro-Nle-Ser-Tyr-Cys-Dab-Thr-Dap cyclo(Dab-[D]Phe-Leu-Dab-Dab-Thr-) |
| Ex. 21[a)] | 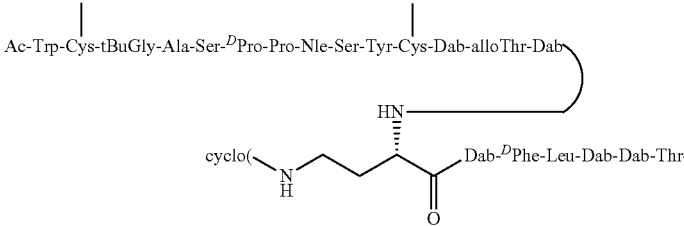 Ac-Trp-Cys-tBuGly-Ala-Ser-[D]Pro-Pro-Nle-Ser-Tyr-Cys-Dab-alloThr-Dab cyclo(Dab-[D]Phe-Leu-Dab-Dab-Thr-) |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 22[a)] | 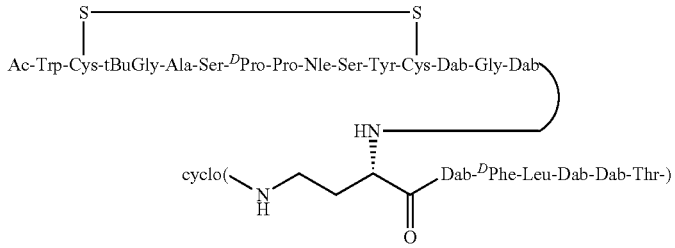 |
| Ex. 23[a)] | 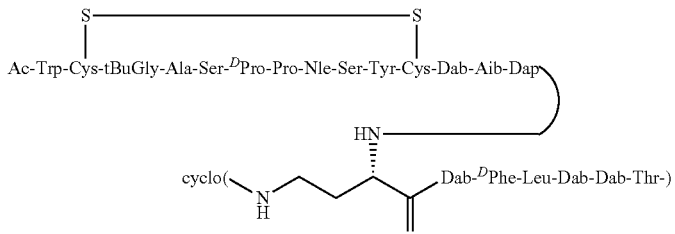 |
| Ex. 24[a) c)] | 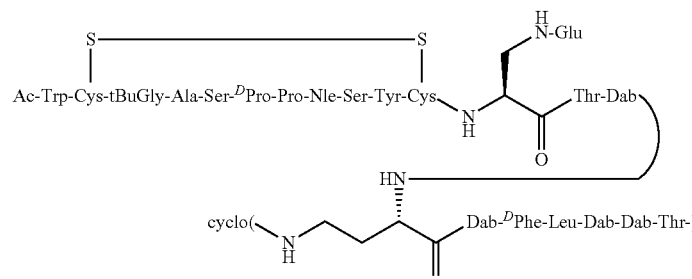 |
| Ex. 25[a) c)] | 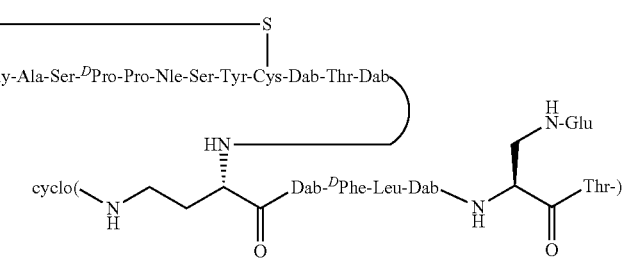 |
| Ex. 26[a)] | 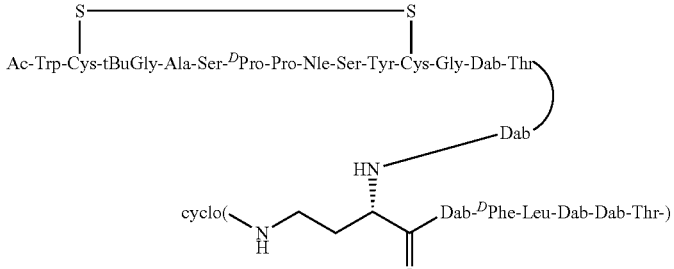 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 27[a)] | S————————S<br>\|                                  \|<br>Ac-Trp-Cys-tBuGly-Ala-Ser-$^D$Pro-Pro-Nle-Ser-Tyr-Cys-Dab-Dab-Thr⟶Dab⟶HN⟶cyclo(-NH-CH₂CH₂-CH(-)-C(=O)-Dab-$^D$Phe-Leu-Dab-Dab-Thr-) |
| Ex. 28[a)] | S————————S<br>\|                                  \|<br>Ac-Trp-Cys-tBuGly-Ala-Ser-$^D$Pro-Pro-Nle-Ser-Tyr-Cys-Ala-Dab-Thr⟶Dab⟶HN⟶cyclo(-NH-CH₂CH₂-CH(-)-C(=O)-Dab-$^D$Phe-Leu-Dab-Dab-Thr-) |
| Ex. 29[a)] | S————————S<br>\|                                  \|<br>Ac-Trp-Cys-tBuGly-Ala-Ser-$^D$Pro-Pro-Nle-Ser-Tyr-Cys-$^D$Ala-Dab-Thr⟶Dab⟶HN⟶cyclo(-NH-CH₂CH₂-CH(-)-C(=O)-Dab-$^D$Phe-Leu-Dab-Dab-Thr-) |
| Ex. 30[a)] | S————————S<br>\|                                  \|<br>Ac-Trp-Cys-tBuGly-Ala-Ser-$^D$Pro-Pro-Nle-Ser-Tyr-Cys-Aib-Dab-Thr⟶Dab⟶HN⟶cyclo(-NH-CH₂CH₂-CH(-)-C(=O)-Dab-$^D$Phe-Leu-Dab-Dab-Thr-) |
| Ex. 31[a)] | S————————S<br>\|                                  \|<br>Ac-Trp-Cys-tBuGly-Ala-Ser-$^D$Pro-Pro-Nle-Ser-Tyr-Cys-Dab-Gly-Thr⟶Dab⟶HN⟶cyclo(-NH-CH₂CH₂-CH(-)-C(=O)-Dab-$^D$Phe-Leu-Dab-Dab-Thr-) |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 32[a)] | 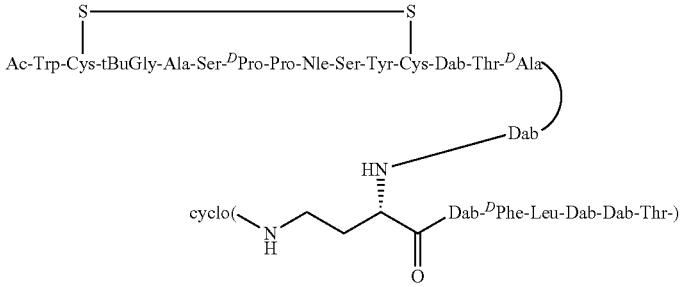 |
| Ex. 33[a)] | 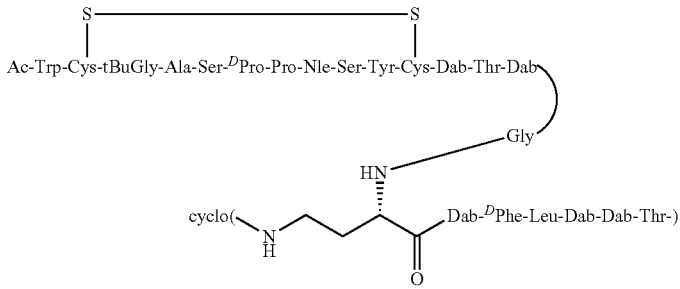 |
| Ex. 34[a)] | 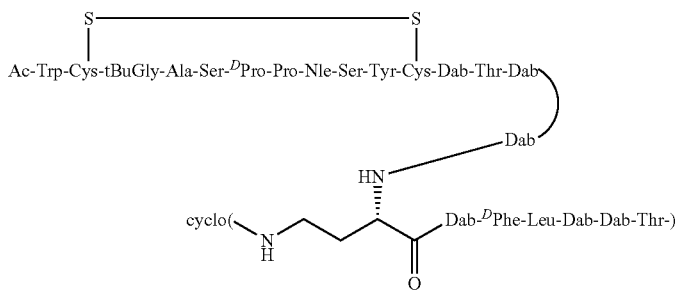 |
| Ex. 35[a)] | 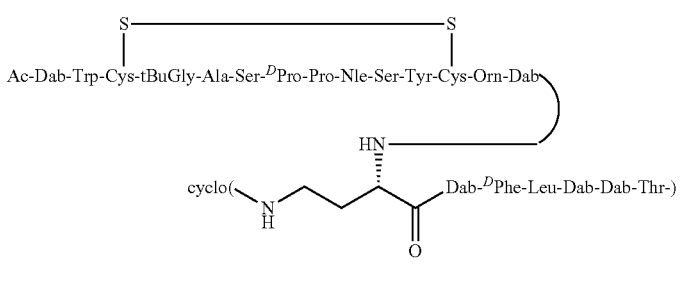 |
| Ex. 36[a)] | 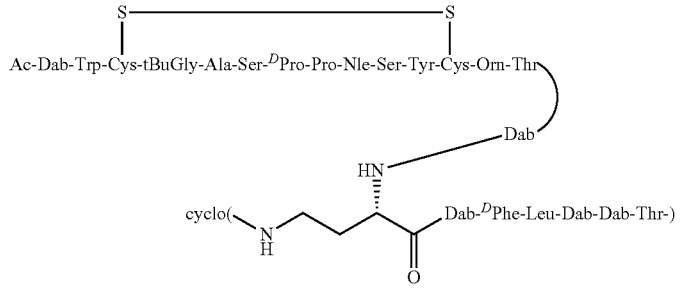 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 37[a)] | S—————S<br>\|   \|<br>Dap-Trp-Cys-tBuGly-Ala-Ser-[D]Pro-Pro-Nle-Ser-Tyr-Cys-Dab-Thr⟩<br>                                                              ⟩-Dab<br>                                            HN—⟨<br>        cyclo(—NH—⟨—⟩—Dab-[D]Phe-Leu-Dab-Dab-Thr-)<br>                          ‖<br>                          O |
| Ex. 38[a)] | S—————S<br>\|   \|<br>Orn-Trp-Cys-tBuGly-Ala-Ser-[D]Pro-Pro-Nle-Ser-Tyr-Cys-Dab-Thr⟩<br>                                                              ⟩-Dab<br>                                            HN—⟨<br>        cyclo(—NH—⟨—⟩—Dab-[D]Phe-Leu-Dab-Dab-Thr-)<br>                          ‖<br>                          O |
| Ex. 39[a)] | S—————S<br>\|   \|<br>Arg-Trp-Cys-tBuGly-Ala-Ser-[D]Pro-Pro-Nle-Ser-Tyr-Cys-Dab-Thr⟩<br>                                                              ⟩-Dab<br>                                            HN—⟨<br>        cyclo(—NH—⟨—⟩—Dab-[D]Phe-Leu-Dab-Dab-Thr-)<br>                          ‖<br>                          O |
| Ex. 40[a)] | S—————S<br>\|   \|<br>Glu-Trp-Cys-tBuGly-Ala-Ser-[D]Pro-Pro-Nle-Ser-Tyr-Cys-Dab-Thr⟩<br>                                                              ⟩-Dab<br>                                            HN—⟨<br>        cyclo(—NH—⟨—⟩—Dab-[D]Phe-Leu-Dab-Dab-Thr-)<br>                          ‖<br>                          O |
| Ex. 41[a)] | S—————S<br>\|   \|<br>Ac-Ala-Trp-Cys-tBuGly-Ala-Ser-[D]Pro-Pro-Nle-Ser-Tyr-Cys-Dab-Thr⟩<br>                                                              ⟩-Dab<br>                                            HN—⟨<br>        cyclo(—NH—⟨—⟩—Dab-[D]Phe-Leu-Dab-Dab-Thr-)<br>                          ‖<br>                          O |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 42[a)] | S————————S<br>\|　　　　　　　　　　　　　　\|<br>Dab-Trp-Cys-tBuGly-Ala-Ser-$^D$Pro-Pro-Nle-Ser-Tyr-Cys-Dab-Thr⟩<br>　　　　　　　　　　　　　　　　　　　　⎬—Dab<br>　　　　　　　　　　HN—<br>cyclo(＼N／＼＊／＼Dab-$^D$Phe-Leu-Dab-Dab-Thr-)<br>　　　　H　　　　O |
| Ex. 43[a)] | S————————S<br>\|　　　　　　　　　　　　　　\|<br>Thr-Trp-Cys-tBuGly-Ala-Ser-$^D$Pro-Pro-Nle-Ser-Tyr-Cys-Dab-Thr⟩<br>　　　　　　　　　　　　　　　　　　　　⎬—Dab<br>　　　　　　　　　　HN—<br>cyclo(＼N／＼＊／＼Dab-$^D$Phe-Leu-Dab-Dab-Thr-)<br>　　　　H　　　　O |
| Ex. 44[a)] | S————————S<br>\|　　　　　　　　　　　　　　\|<br>Aib-Trp-Cys-tBuGly-Ala-Ser-$^D$Pro-Pro-Nle-Ser-Tyr-Cys-Dab-Thr⟩<br>　　　　　　　　　　　　　　　　　　　　⎬—Dab<br>　　　　　　　　　　HN—<br>cyclo(＼N／＼＊／＼Dab-$^D$Phe-Leu-Dab-Dab-Thr-)<br>　　　　H　　　　O |
| Ex. 45[a)] | S————————————S<br>\|　　　　　　　　　　　　　　　　\|<br>Trp-Cys-tBuGly-Ala-Ser-$^D$Pro-Pro-Nle-Ser-Tyr-Cys-Orn-Dab⟩<br>　　　　　　　　HN—<br>cyclo(＼N／＼＊／＼Dab-$^D$Phe-Leu-Dab-Dab-Thr-)<br>　　　　H　　　　O |
| Ex. 46[a)] | S————————————S<br>\|　　　　　　　　　　　　　　　　\|<br>Ac-Trp-Cys-tBuGly-Ala-Ser-$^D$Pro-Pro-Nle-Dap-Tyr-Cys-Orn-Dab⟩<br>　　　　　　　　　HN—<br>cyclo(＼N／＼＊／＼Dab-$^D$Phe-Leu-Dab-Dab-Thr-)<br>　　　　H　　　　O |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 47[a)] | 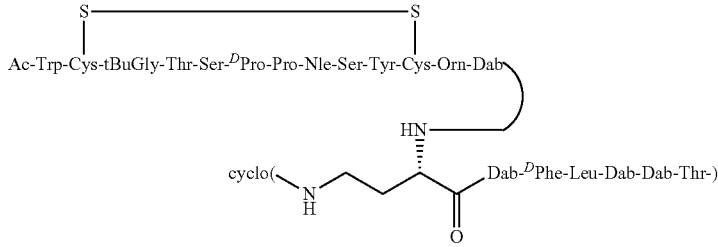 Ac-Trp-Cys-tBuGly-Thr-Ser-$^D$Pro-Pro-Nle-Ser-Tyr-Cys-Orn-Dab, cyclo(-Dab-$^D$Phe-Leu-Dab-Dab-Thr-) |
| Ex. 48[a)] | 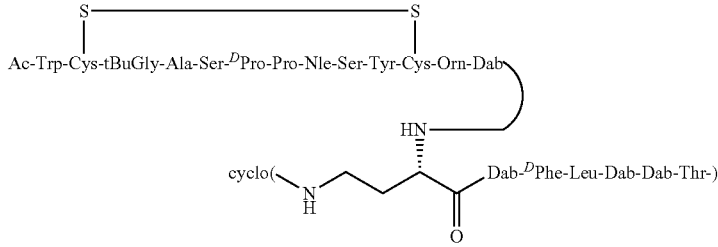 Ac-Trp-Cys-tBuGly-Ala-Ser-$^D$Pro-Pro-Nle-Ser-Tyr-Cys-Orn-Dab, cyclo(-Dab-$^D$Phe-Leu-Dab-Dab-Thr-) |
| Ex. 49[a)] | 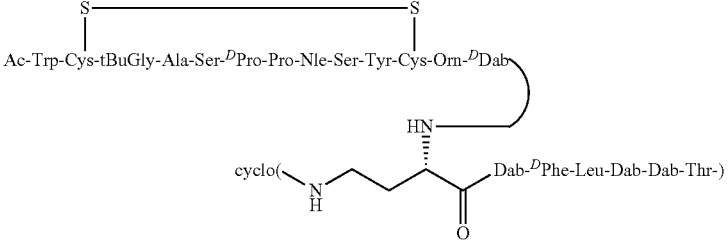 Ac-Trp-Cys-tBuGly-Ala-Ser-$^D$Pro-Pro-Nle-Ser-Tyr-Cys-Orn-$^D$Dab, cyclo(-Dab-$^D$Phe-Leu-Dab-Dab-Thr-) |
| Ex. 50[a)] | 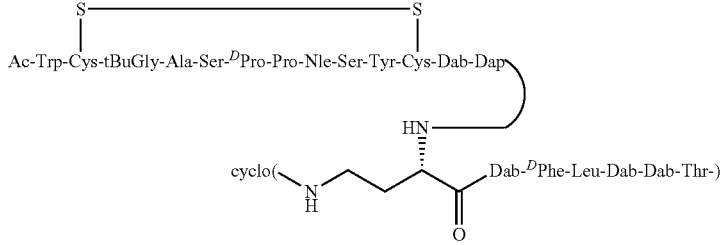 Ac-Trp-Cys-tBuGly-Ala-Ser-$^D$Pro-Pro-Nle-Ser-Tyr-Cys-Dab-Dap, cyclo(-Dab-$^D$Phe-Leu-Dab-Dab-Thr-) |
| Ex. 51[a)] | 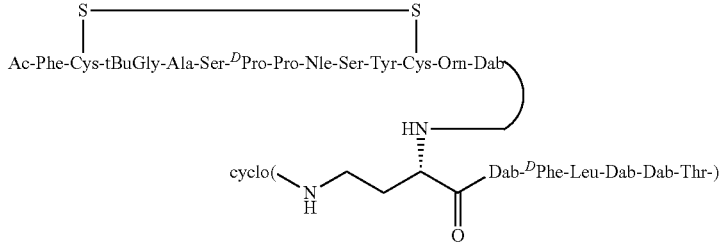 Ac-Phe-Cys-tBuGly-Ala-Ser-$^D$Pro-Pro-Nle-Ser-Tyr-Cys-Orn-Dab, cyclo(-Dab-$^D$Phe-Leu-Dab-Dab-Thr-) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified
| Ex. No. | Sequence |
|---|---|
| Ex. 52[a)] | 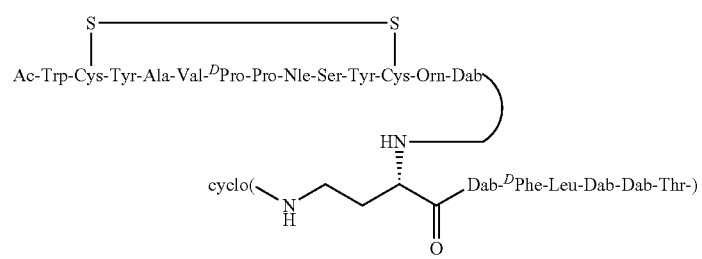 |
| Ex. 53[a)] | 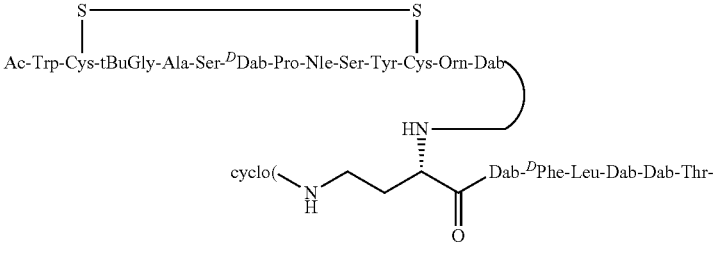 |
| Ex. 54[a)] | 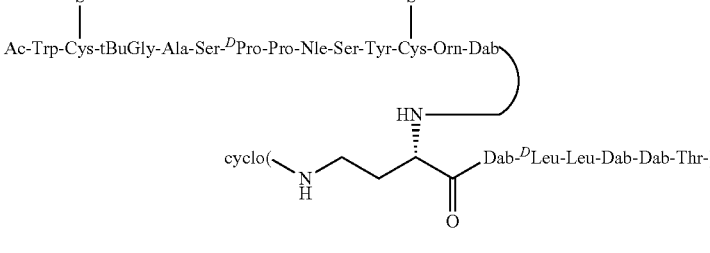 |
| Ex. 55[a)] | 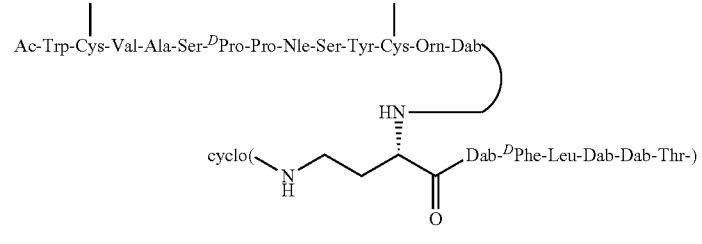 |
| Ex. 56[b)] | 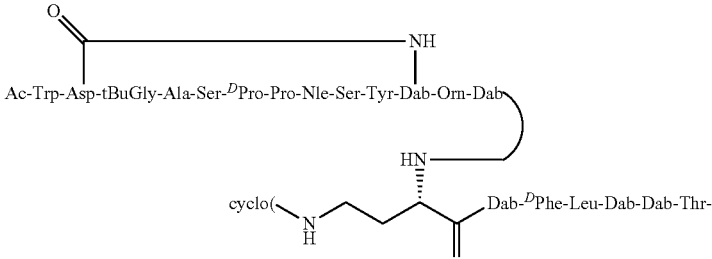 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 57[a)] | S—————S<br>\|　　　　　　\|<br>Ac-Cys-Trp-Dab-tBuGly-Ala-Ser-$^D$Pro-Pro-Nle-Ser-Tyr-Dab-Orn-Cys⟩<br>　　　　　　　　　　　　　　　　　　　　—Dab<br>　　　　　　　HN———<br>cyclo(—N—⎡⎤—Dab-$^D$Phe-Leu-Dab-Dab-Thr-)<br>　　　H　　O |
| Ex. 58[b)] | O　　　　　　　　　　　　　　　　　　　　NH<br>\|\|　　　　　　　　　　　　　　　　　　　　\|<br>Ac-Glu-Trp-Dab-tBuGly-Ala-Ser-$^D$Pro-Pro-Nle-Ser-Tyr-Dab-Orn-Dab⟩<br>　　　　　　　　　　　　　　　　　　　　—Dab<br>　　　　　　　HN———<br>cyclo(—N—⎡⎤—Dab-$^D$Phe-Leu-Dab-Dab-Thr-)<br>　　　H　　O |
| Ex. 59[b)] | 　　　　　　　　　　　　　　　　　　　　　　O<br>HN———————————————————\|\|<br>\|<br>Ac-Dab-Trp-Dab-tBuGly-Ala-Ser-$^D$Pro-Pro-Nle-Ser-Tyr-Dab-Orn-Glu⟩<br>　　　　　　　　　　　　　　　　　　　　—Dab<br>　　　　　　　HN———<br>cyclo(—N—⎡⎤—Dab-$^D$Phe-Leu-Dab-Dab-Thr-)<br>　　　H　　O |
| Ex. 60[a)] | S—————S<br>\|　　　　　　\|<br>Ac-Cys-Trp-Dab-tBuGly-Ala-Ser-$^D$Pro-Pro-Nle-Ser-Tyr-Dab-Orn-Cys⟩<br>　　　　　　　　　　　　　　　　　　　　—$^D$Dab<br>　　　　　　　HN———<br>cyclo(—N—⎡⎤—Dab-$^D$Phe-Leu-Dab-Dab-Thr-)<br>　　　H　　O |
| Ex. 61[a)] | S—————S<br>\|　　　　　　\|<br>Ac-Cys-Trp-Dab-tBuGly-Ala-Ser-$^D$Pro-Pro-Nle-Ser-Tyr-Dab-Orn-Cys⟩<br>　　　　　　　　　　　　　　　　　　—Dab-Dab<br>　　　　　　　HN———<br>cyclo(—N—⎡⎤—Dab-$^D$Phe-Leu-Dab-Dab-Thr-)<br>　　　H　　O |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 62[a)] | 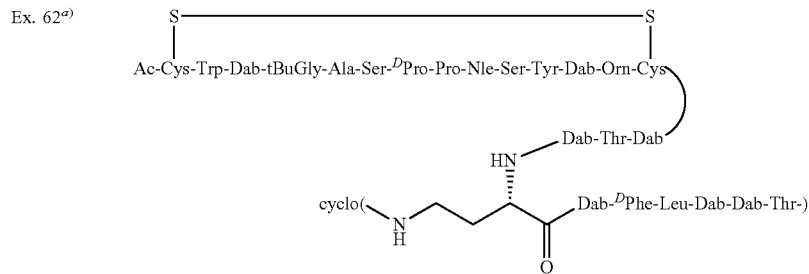 |
| Ex. 63[a)] | 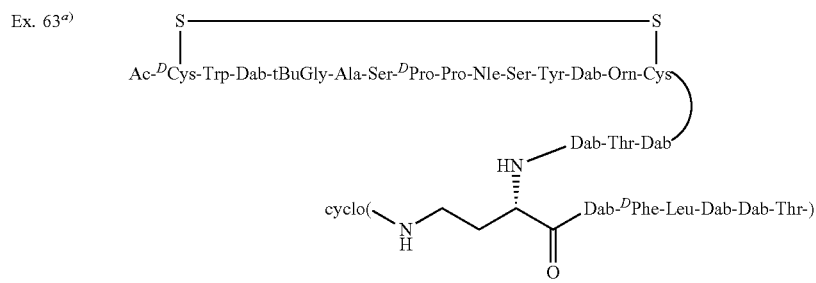 |
| Ex. 64 | 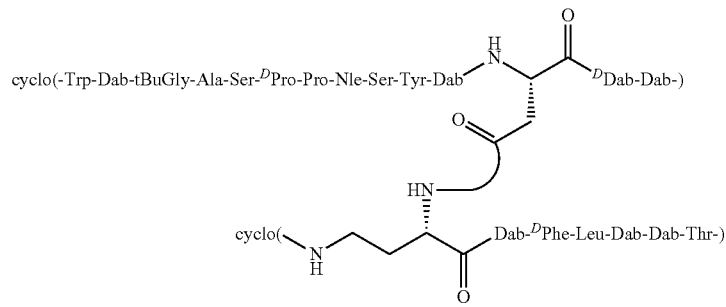 |
| Ex. 65 | 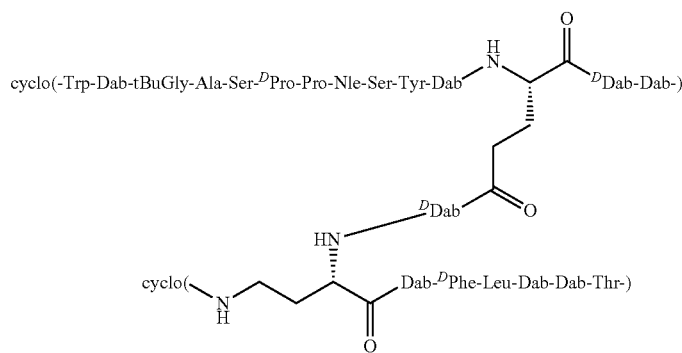 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 66 | 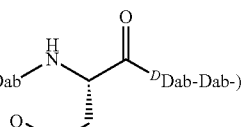 |
| Ex. 67 | 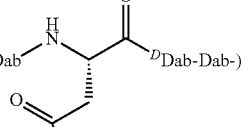 |
| Ex. 68 | 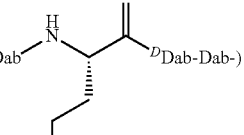 |
| Ex. 69 | 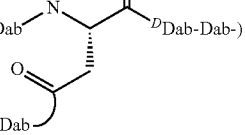 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 70 | 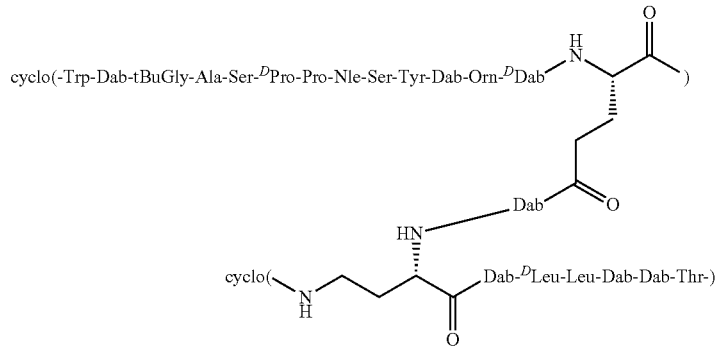 |
| Ex. 71 | 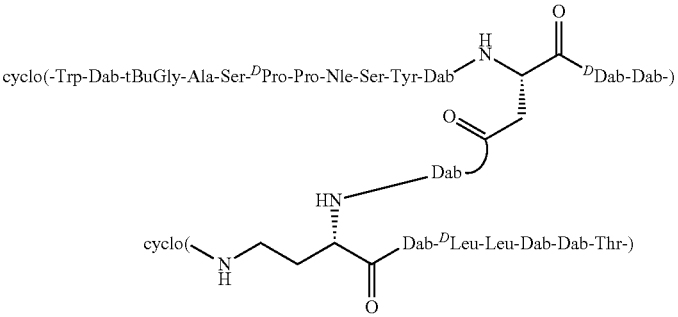 |
| Ex. 72 | 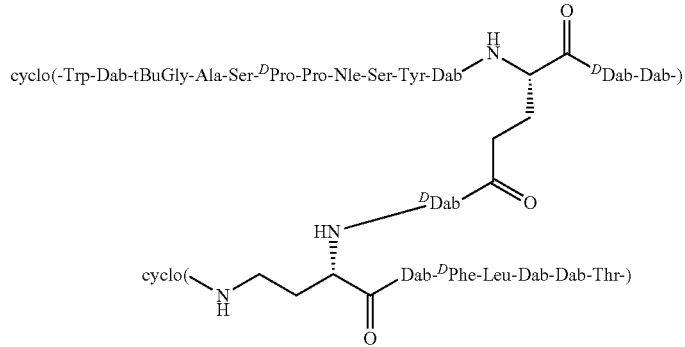 |
| Ex. 73 | 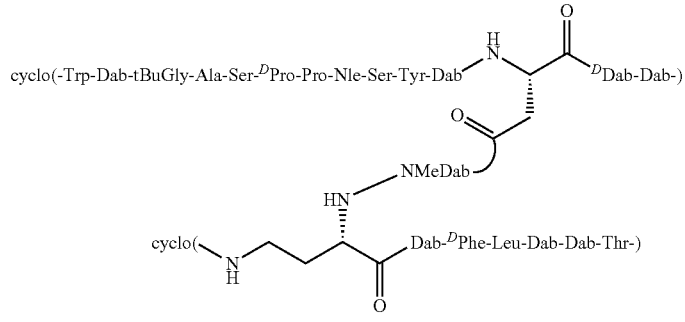 |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified
| Ex. No. | Sequence |
|---|---|
| Ex. 74 | 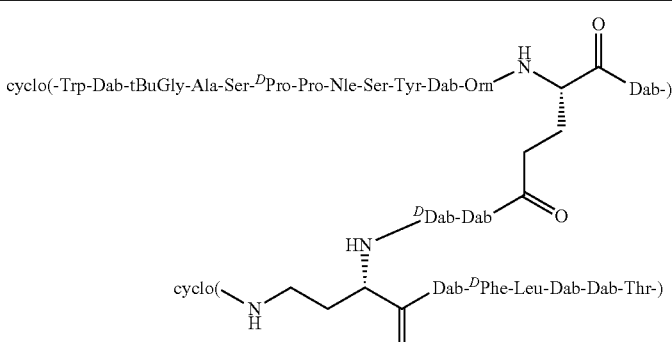 |
| Ex. 75 | 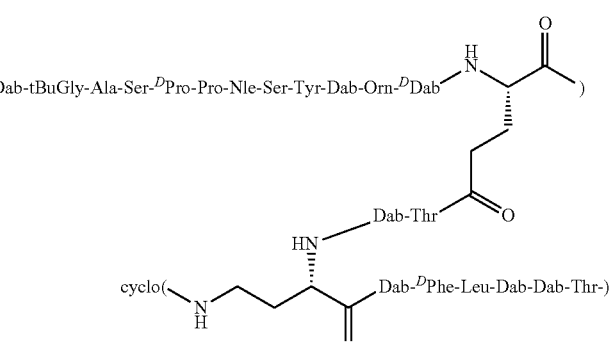 |
| Ex. 76 | 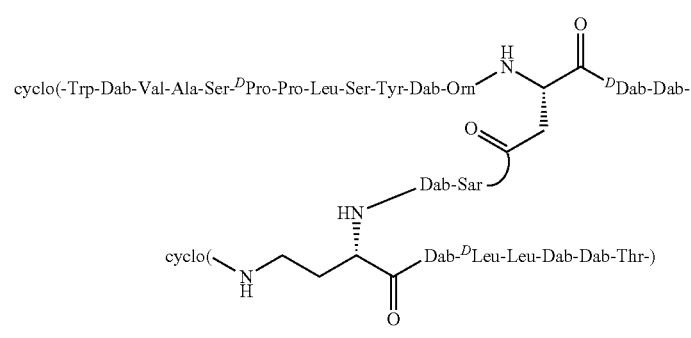 |
| Ex. 77 | 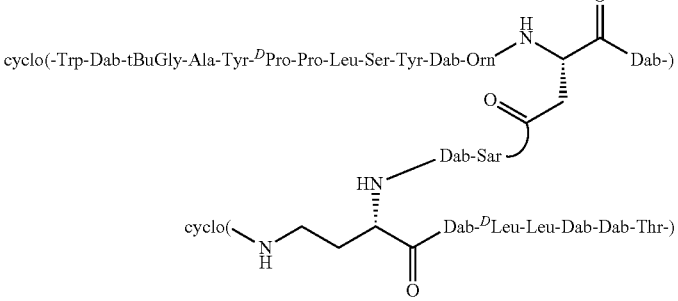 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 78 | 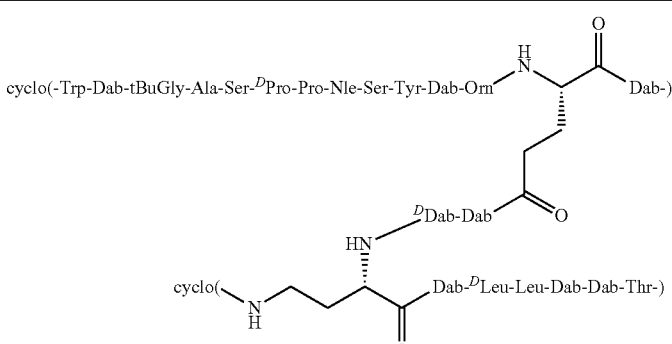 |
| Ex. 79[a)] | 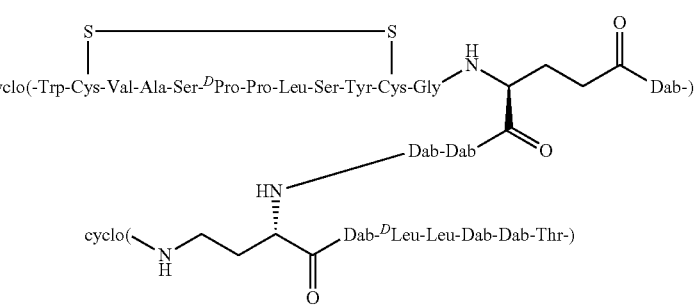 |
| Ex. 80 | 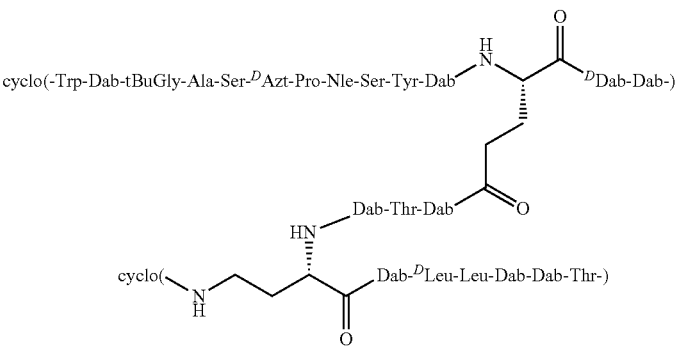 |
| Ex. 81 | 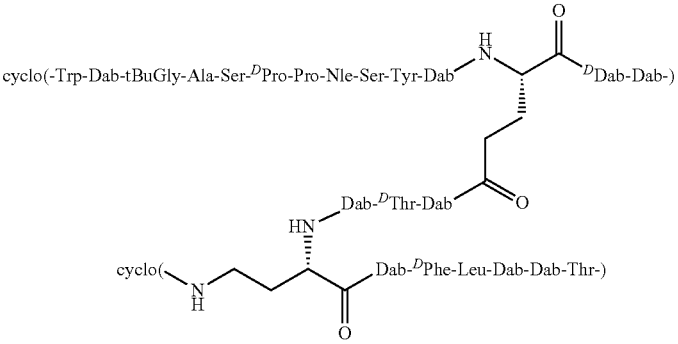 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 82 | cyclo(-Trp-Dab-tBuGly-Ala-Ser-$^D$Azt-Pro-Val-Thr-Tyr-Dab-[Glu side chain branch]-$^D$Dab-Dab-) with branch: Dab-Thr-Dab-HN- linked via Glu side chain; cyclo(-NH-CH(...)-C(=O)-Dab-$^D$Leu-Leu-Dab-Dab-Thr-) |
| Ex. 83 | cyclo(-Trp-Dab-tBuGly-Ser-Ser-$^D$Pro-Pro-Nle-Dap-Tyr-Dab-[Glu side chain branch]-$^D$Dab-Dab-) with branch: Dab-Thr-Dab-HN-; cyclo(-NH-CH(...)-C(=O)-Dab-$^D$Leu-Leu-Dab-Dab-Thr-) |
| Ex. 84 | cyclo(-Trp-Dab-tBuGly-Dap-Ser-$^D$Pro-Pro-Nle-Ser-Tyr-Dab-[Glu side chain branch]-$^D$Dab-Dab-) with branch: Dab-Thr-Dab-HN-; cyclo(-NH-CH(...)-C(=O)-Dab-$^D$Leu-Leu-Dab-Dab-Thr-) |
| Ex. 85 | cyclo(-Trp-Dab-Val-Ala-Ser-$^D$Pro-Pro-Val-Dap-Tyr-Dab-[Glu side chain branch]-$^D$Dab-Dab-) with branch: Dab-Thr-Dab-HN-; cyclo(-NH-CH(...)-C(=O)-Dab-$^D$Leu-Leu-Dab-Dab-Thr-) |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 86[b)] | 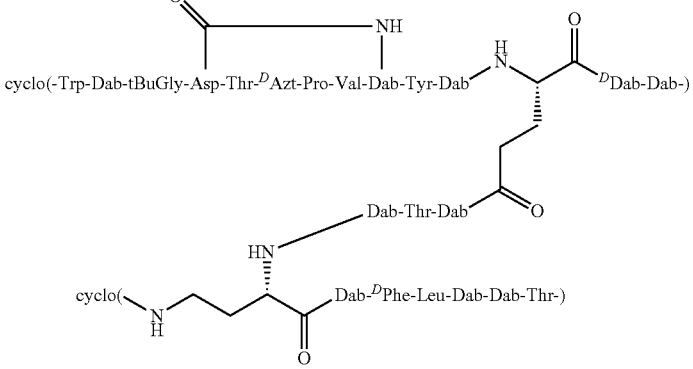 |
| Ex. 87[b)] | 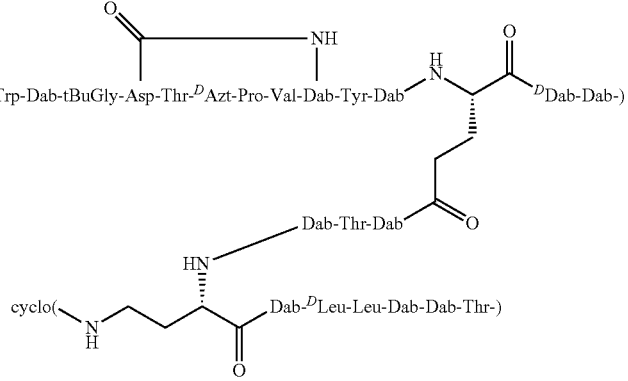 |
| Ex. 88 | 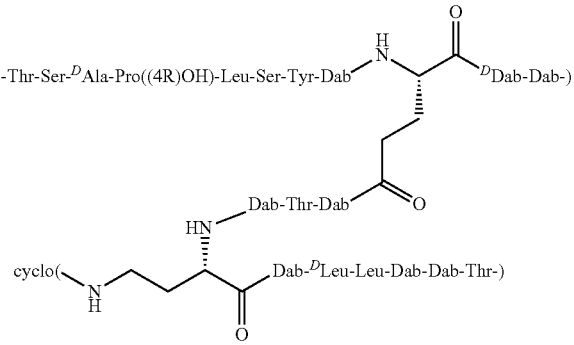 |
| Ex. 89 | 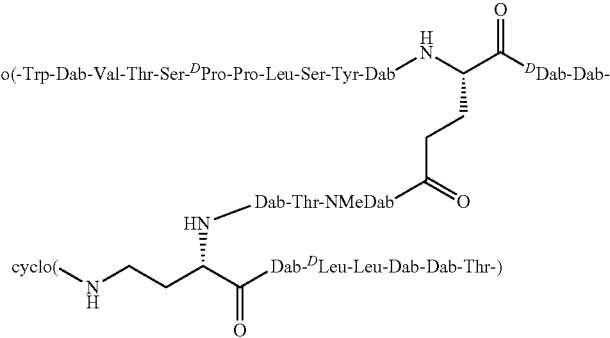 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 90 | 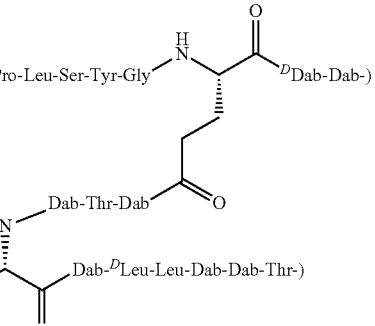 |
| Ex. 91 | 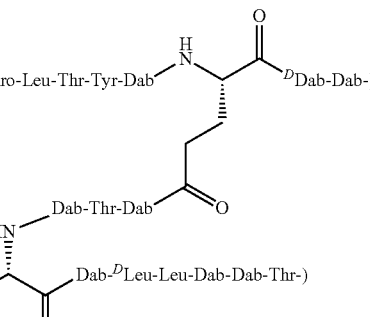 |
| Ex. 92 | 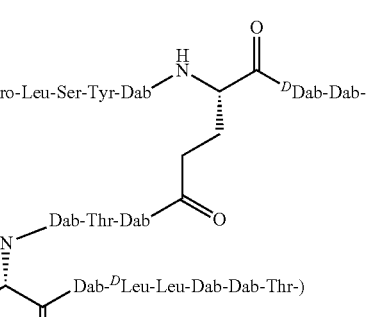 |
| Ex. 93 | 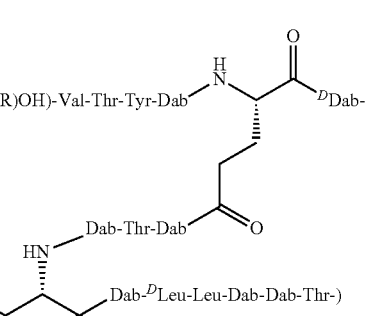 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 94 | 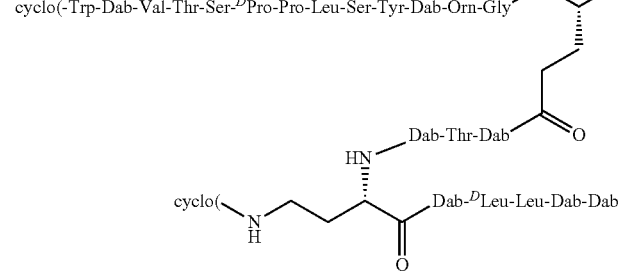 |
| Ex. 95 | 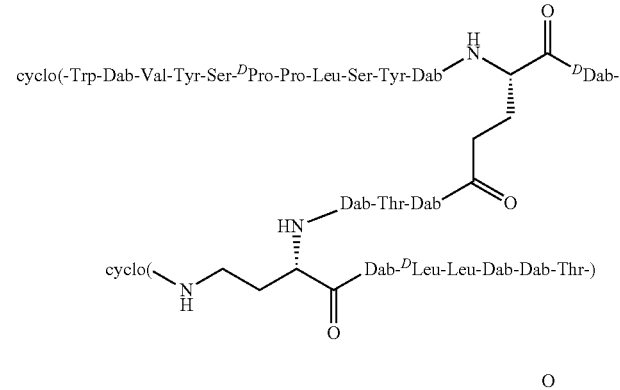 |
| Ex. 96 | 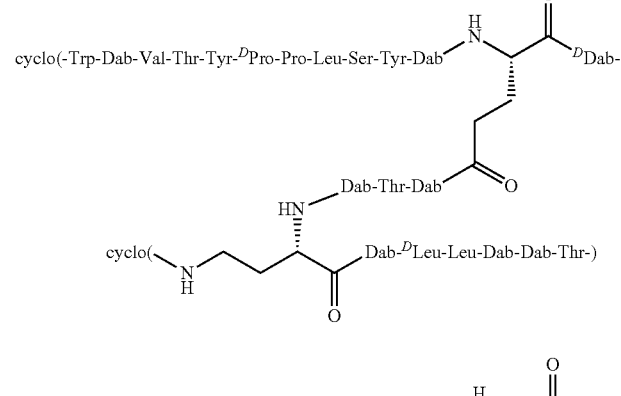 |
| Ex. 97 | 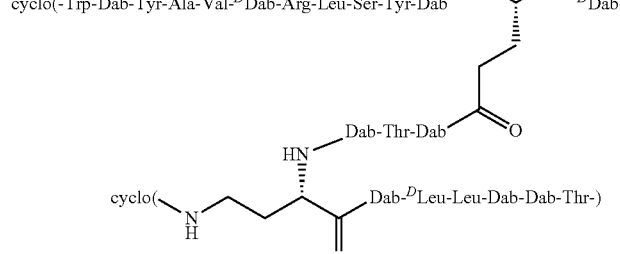 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 98[a)] | cyclo(-Trp-Cys-tBuGly-Thr-Ser-$^D$Pro-Pro-Leu-Ser-Tyr-Cys- ... -$^D$Dab-Dab-) with S—S bridge; branch: Dab-Thr-Dab, Dab-$^D$Leu-Leu-Dab-Dab-Thr- |
| Ex. 99 | cyclo(-Leu-Dab-Val-Thr-Tyr-$^D$Pro-Pro-Leu-Ser-Tyr-Dab- ... -$^D$Dab-Dab-); branch: Dab-Thr-Dab, Dab-$^D$Leu-Leu-Dab-Dab-Thr- |
| Ex. 100 | cyclo(-Trp-Thr-tBuGly-Ala-Thr-$^D$Azt-Pro-Val-Thr-Tyr-Thr- ... -$^D$Thr-Thr-); branch: Dab-Thr-Dab, Dab-$^D$Leu-Leu-Dab-Dab-Thr- |
| Ex. 101 | cyclo(-Trp-Dab-tBuGly-Ala-Ser-$^D$Azt-Pro-Val-Thr-Tyr-Dab- ... -$^D$Dab-Dab-); branch: Dab-Thr-Dab, Dab-$^D$Leu-Leu-Dab-Dab-Thr- |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 102 | cyclo(-Trp-Hse-tBuGly-Ala-Ser-$^D$Ala-Pro-Val-Thr-Tyr-Hse—NH—CH(—$^D$Dab-Hse-)—CH$_2$CH$_2$—C(=O)—Dab-Thr-Dab—NH—cyclo(—NH—CH(—Dab-$^D$Leu-Leu-Dab-Dab-Thr-)—C(=O)—) |
| Ex. 103 | cyclo(-Trp-Hse-tBuGly-Ala-Ser-$^D$Ala-Pro-Val-Thr-Tyr-Dab—NH—CH(—$^D$Dab-Hse-)—CH$_2$CH$_2$—C(=O)—Dab-Thr-Dab—NH—cyclo(—NH—CH(—Dab-$^D$Leu-Leu-Dab-Dab-Thr-)—C(=O)—) |
| Ex. 104[a)] | S—S bridge: Trp-Cys-tBuGly-Ser-Ser-$^D$Pro-Pro-Nle-Ser-Tyr-Cys-Orn-$^D$Ala-$^D$Dab—HN—CH(—Dab-$^D$Phe-Leu-Dab-Dab-Thr-)—cyclo(—NH—...—C(=O)—) |
| Ex. 105[a)] | S—S bridge: Trp-Cys-tBuGly-Ser-Ser-$^D$Pro-Pro-Nle-Ser-Tyr-Cys-Orn-$^D$Phe-$^D$Dab—HN—CH(—Dab-$^D$Phe-Leu-Dab-Dab-Thr-)—cyclo(—NH—...—C(=O)—) |
| Ex. 106[a)] | S—S bridge: Trp-Cys-tBuGly-Ser-Ser-$^D$Pro-Pro-Nle-Ser-Tyr-Cys-$^D$Dab-Dab-$^D$Dab—HN—CH(—Dab-$^D$Phe-Leu-Dab-Dab-Thr-)—cyclo(—NH—...—C(=O)—) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified
| Ex. No. | Sequence |
|---|---|
| Ex. 107[a)] | 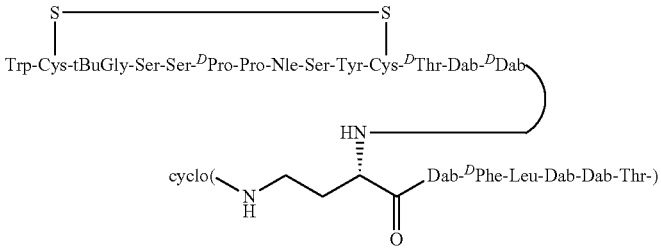 |
| Ex. 108[a)] | 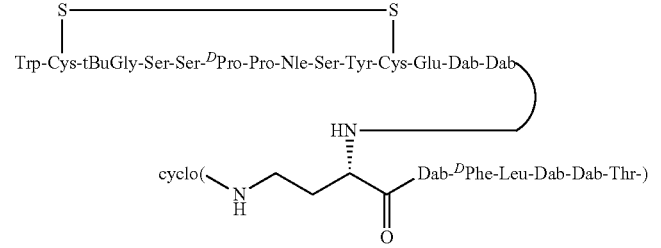 |
| Ex. 109[a)] | 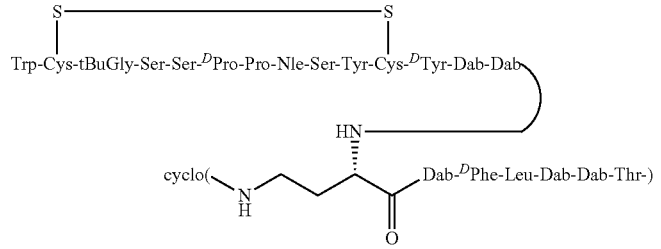 |
| Ex. 110[a)] | 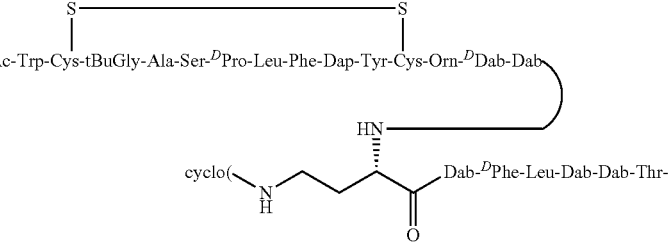 |
| Ex. 111[a)] | 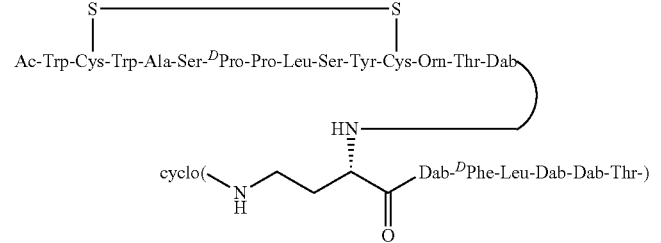 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 112[a)] | Ac-Trp-Cys-tBuGly-$^D$Ala-Ser-$^D$Pro-Pro-Leu-Ser-Tyr-Cys-Orn-Dab-Dab- (S–S bridge between the two Cys); cyclo(-NH-CH2-CH2-CH(HN-)-C(=O)-Dab-$^D$Phe-Leu-Dab-Dab-Thr-) |
| Ex. 113[a)] | Ac-Trp-Cys-tBuGly-Ala-alloThr-$^D$Pro-Pro-Leu-His-Cha-Cys-Orn-Thr-Dab- (S–S bridge between the two Cys); cyclo(-NH-CH2-CH2-CH(HN-)-C(=O)-Dab-$^D$Phe-Leu-Dab-Dab-Thr-) |
| Ex. 114[a)] | Trp-Cys-tBuGly-Ala-Ser-$^D$Pic-Pro-Leu-Ser-Tyr-Cys-Dab-Thr-Dab- (S–S bridge between the two Cys); cyclo(-NH-CH2-CH2-CH(HN-)-C(=O)-Dab-$^D$Phe-Leu-Dab-Dab-Thr-) |
| Ex. 115[a)] | Ac-Trp-Cys-Val-Thr-Val-$^D$Pro-Arg-Leu-Thr-Tyr-Cys-Dab-Dab-Dab- (S–S bridge between the two Cys); cyclo(-NH-CH2-CH2-CH(HN-)-C(=O)-Dab-$^D$Phe-Leu-Dab-Dab-Thr-) |
| Ex. 116[a)] | Ac-Trp-Cys-tBuGly-Dap-Thr-$^D$Pro-Pro-Nle-Gly-Tyr-Cys-Dab-Thr-Dab- (S–S bridge between the two Cys); cyclo(-NH-CH2-CH2-CH(HN-)-C(=O)-Dab-$^D$Phe-Leu-Dab-Dab-Thr-) |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified

| Ex. No. | Sequence |
|---|---|
| Ex. 117[a)] | Ac-Trp-Cys-tBuGly-Dap-Ser-$^D$Pro-Pro-Leu-Gly-Tyr-Cys-Orn-Thr-Dab-(S-S bridge between Cys residues)-cyclo(-NH-Dab-$^D$Phe-Leu-Dab-Dab-Thr-) |
| Ex. 118[a)] | Ac-Trp-Cys-tBuGly-Ala-Leu-$^D$Pro-Pro-Thr-Ser-Tyr-Cys-Orn-Thr-Dab-(S-S bridge between Cys residues)-cyclo(-NH-Dab-$^D$Phe-Leu-Dab-Dab-Thr-) |
| Ex. 119[a)] | Ac-Leu-Dab-Val-Cys-Tyr-$^D$Pro-Pro-Ile-Cys-Tyr-Dab-Orn-$^D$Dab-Dab-(S-S bridge between Cys residues)-cyclo(-NH-Dab-$^D$Phe-Leu-Dab-Dab-Thr-) |
| Ex. 120[a)] | Ac-Trp-Ala-Val-Cys-Val-$^D$Pro-Dab-Leu-Cys-Tyr-Ala-Orn-$^D$Dab-Dab-(S-S bridge between Cys residues)-cyclo(-NH-Dab-$^D$Phe-Leu-Dab-Dab-Thr-) |
| Ex. 121[a)] | Trp-Cys-Val-Ala-Ser-$^D$Pro-Pro-Leu-Ser-Tyr-Cys-Orn-Dab-$^D$Thr-Dab-(S-S bridge between Cys residues)-cyclo(-NH-Dab-$^D$Leu-Leu-Dab-Dab-Thr-) |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 122[a)] | S————————S<br>\|                      \|<br>Trp-Pen-Val-Ala-Ser-$^D$Pro-Pro-Leu-Ser-Tyr-Pen-Dab-Dab-Thr⏋<br>                                              —Dab<br>                       HN<br>cyclo(−N(H)−CH₂−CH₂−CH(−)−C(=O)−Dab-$^D$Leu-Leu-Dab-Dab-Thr-) |
| Ex. 123[a)] | S————————S<br>\|                      \|<br>Trp-Cys-Val-Ala-Ser-$^D$Pro-Pro((4R)OH)-Leu-Ser-Tyr-Cys-Dab-Dab-Thr⏋<br>                                              —Dab<br>                     HN<br>cyclo(−N(H)−CH₂−CH₂−CH(−)−C(=O)−Dab-$^D$Leu-Leu-Dab-Dab-Thr-) |
| Ex. 124[a)] | S————————S<br>\|                      \|<br>Trp-Cys-Val-Ala-Ser-$^D$Pro-Pro((4R)F)-Leu-Ser-Tyr-Cys-Dab-Dab-Thr⏋<br>                                              —Dab<br>                     HN<br>cyclo(−N(H)−CH₂−CH₂−CH(−)−C(=O)−Dab-$^D$Leu-Leu-Dab-Dab-Thr-) |
| Ex. 125[a)] | S————————S<br>\|                      \|<br>Trp-Cys-Val-Ala-Ser-$^D$Pro-Ala-Leu-Ser-Tyr-Cys-Dab-Dab-Thr⏋<br>                                              —Dab<br>                     HN<br>cyclo(−N(H)−CH₂−CH₂−CH(−)−C(=O)−Dab-$^D$Leu-Leu-Dab-Dab-Thr-) |
| Ex. 126[a)] | S————————S<br>\|                      \|<br>Trp-Cys-Val-Ala-Ser-$^D$Pro-Thr-Leu-Ser-Tyr-Cys-Gly-Dab-Thr⏋<br>                                              —Dab<br>                     HN<br>cyclo(−N(H)−CH₂−CH₂−CH(−)−C(=O)−Dab-$^D$Leu-Leu-Dab-Dab-Thr-) |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified

| Ex. No. | Sequence |
|---|---|
| Ex. 127[a] | S—————S<br>\|　　　　　　\|<br>Trp-Cys-Val-Ala-Ser-$^D$Pro-Dab-Leu-Ser-Tyr-Cys-Dab-Dab-Thr⎞<br>　　　　　　　　　　　　　　　　　　　　　　　　⎟<br>　　　　　　　　　　　　　　　HN—Dab⎠<br>cyclo(–NH–CH₂–CH₂–C*H(HN–)–C(=O)–Dab-$^D$Leu-Leu-Dab-Dab-Thr-) |
| Ex. 128[a] | S—————S<br>\|　　　　　　\|<br>Trp-Cys-Val-Ala-Ser-Gly-Pro-Leu-Ser-Tyr-Cys-Dab-Dab-Thr⎞<br>　　　　　　　　　　　　　　　　　　　　　　　　⎟<br>　　　　　　　　　　　　　　　HN—Dab⎠<br>cyclo(–NH–CH₂–CH₂–C*H(HN–)–C(=O)–Dab-$^D$Leu-Leu-Dab-Dab-Thr-) |
| Ex. 129[a] | S—————S<br>\|　　　　　　\|<br>Trp-Cys-Val-Ala-Ser-$^D$Pro((4S)OH)-Ala-Leu-Ser-Tyr-Cys-Dab-Dab-Thr⎞<br>　　　　　　　　　　　　　　　　　　　　　　　　⎟<br>　　　　　　　　　　　　　　　HN—Dab⎠<br>cyclo(–NH–CH₂–CH₂–C*H(HN–)–C(=O)–Dab-$^D$Leu-Leu-Dab-Dab-Thr-) |
| Ex. 130[a] | S—————S<br>\|　　　　　　\|<br>Trp-Cys-Val-Ala-Ser-$^D$Ser-Pro-Leu-Ser-Tyr-Cys-Gly-Dab-Thr⎞<br>　　　　　　　　　　　　　　　　　　　　　　　　⎟<br>　　　　　　　　　　　　　　　HN—Dab⎠<br>cyclo(–NH–CH₂–CH₂–C*H(HN–)–C(=O)–Dab-$^D$Leu-Leu-Dab-Dab-Thr-) |
| Ex. 131[a] | S—————S<br>\|　　　　　　\|<br>Trp-Cys-Val-Ala-Ser-$^D$Pro-Pro-Leu-Ser-Tyr-Cys-Gly-Dab-Thr⎞<br>　　　　　　　　　　　　　　　　　　　　　　　　⎟<br>　　　　　　　　　　　　　　　HN—Dab⎠<br>cyclo(–NH–CH₂–CH₂–C*H(HN–)–C(=O)–Dab-$^D$Leu-Leu-Dab-Dab-Thr-) |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 132[a)] | Trp-Cys-Val-Ala-Ser-[D]Pro-Pro-Cpa-Ser-Tyr-Cys-Gly-Dab-Thr-Dab-cyclo(-Dab-[D]Phe-Leu-Dab-Dab-Thr-) (disulfide Cys-Cys) |
| Ex. 133[a) e)] | (dimethylguanidino)-Trp-Cys-Val-Ala-Ser-[D]Pro-Pro-Leu-Ser-Tyr-Cys-Gly-Dab-Thr-Dab-cyclo(-Dab-[D]Leu-Leu-Dab-Dab-Thr-) (disulfide Cys-Cys) |
| Ex. 134[a)] | Trp-Cys-Val-Ala-Ser-[D]Pro-Pro-Leu-Ser-Tyr-Hcy-Gly-Dab-Thr-Dab-cyclo(-Dab-[D]Leu-Leu-Dab-Dab-Thr-) (disulfide Cys-Hcy) |
| Ex. 135[a) d)] | guanidino-Trp-Cys-Val-Ala-Ser-[D]Pro-Pro-Leu-Ser-Tyr-Cys-[D]Ala-Dab-Thr-Dab-cyclo(-Dab-[D]Leu-Leu-Dab-Dab-Thr-) (disulfide Cys-Cys) |
| Ex. 136[a)] | Trp-Cys-Val-Gly-Ser-[D]Pro-Pro-Val-Dap-Tyr-Cys-Orn-Thr-[D]Dab-Dab-cyclo(-Dab-[D]Leu-Leu-Dab-Dab-Thr-) (disulfide Cys-Cys) |

TABLE 1-continued
Examples (Ex.)
In the below-mentioned examples, amino acid residues are connected in either direction from the α carbonyl (C═O) point of attachment to the α nitrogen (N) of the next element, unless otherwise indicated. Other linkages and modifications are as specified
| Ex. No. | Sequence |
|---|---|
| Ex. 137[a)] | 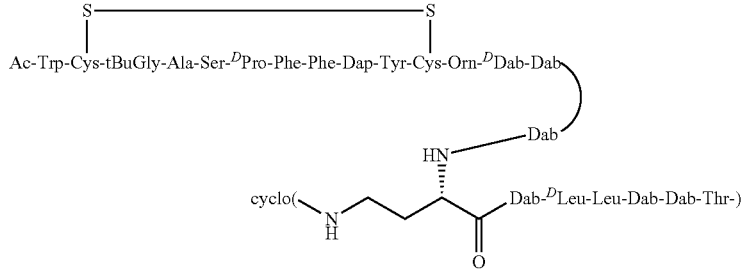 |
| Ex. 138[a)] | 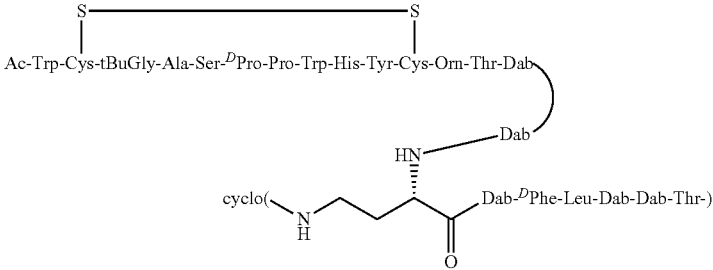 |
| Ex. 139[a)] | 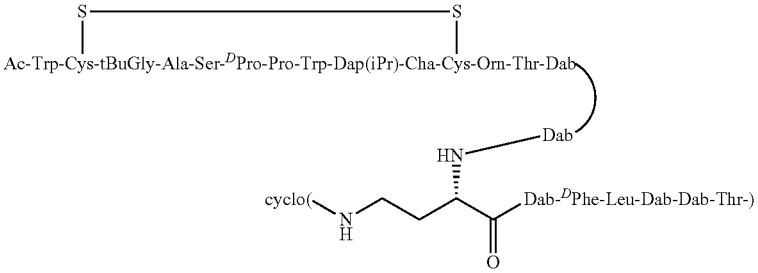 |
| Ex. 140[a)] | 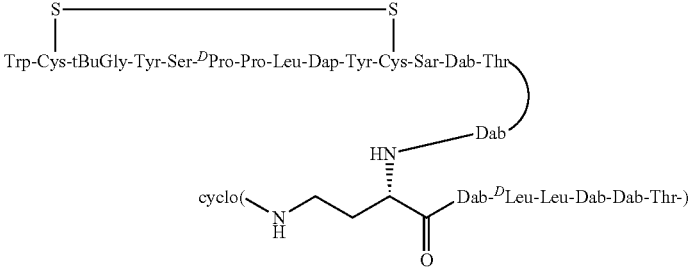 |
| Ex. 141[a)] | 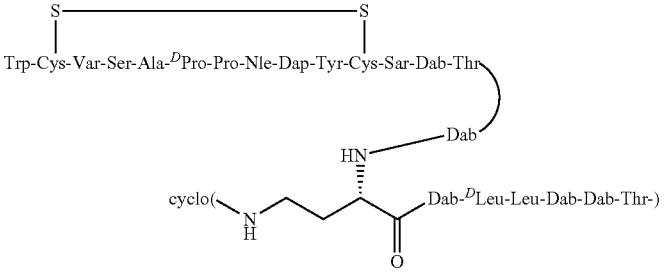 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 142[a)] | 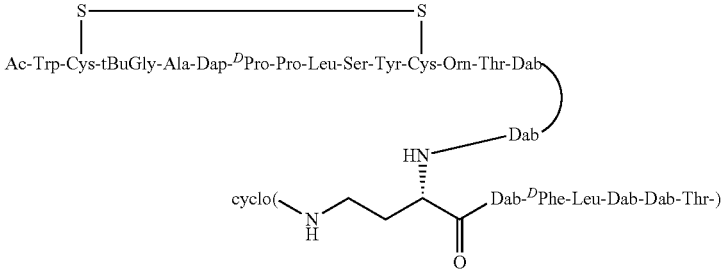 |
| Ex. 143[a)] | 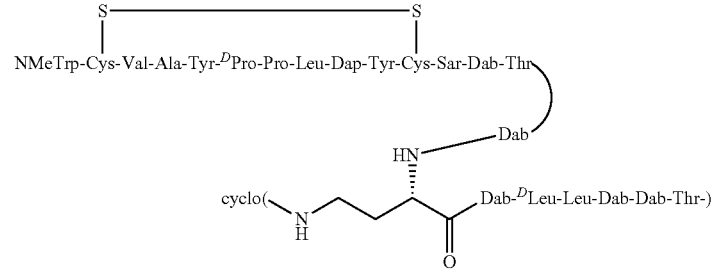 |
| Ex. 144[a)] | 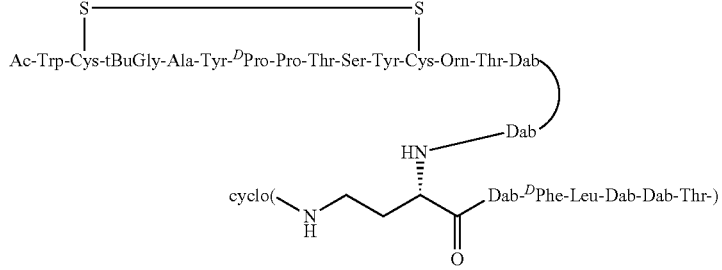 |
| Ex. 145[a)] | 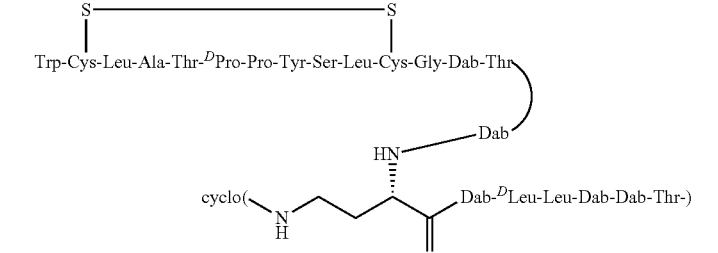 |
| Ex. 146[a)] | 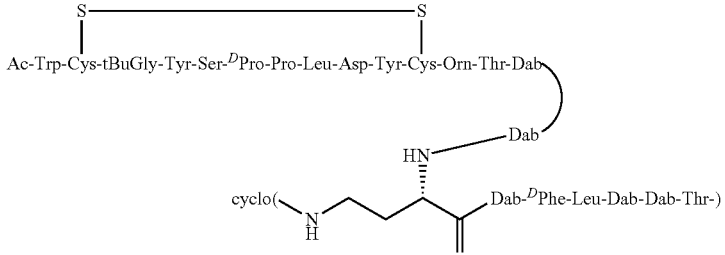 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified

| Ex. No. | Sequence |
|---|---|
| Ex. 147[a)] | S————————S<br>\|　　　　　　　\|<br>Trp-Cys-tBuGly-Tyr-Ser-Ser-$^D$Pro-Pro-Nle-Dap-Tyr-Cys-Sar-Dab-Thr⎞<br>　　　　　　　　　　　　　　　　　　　　　　　　⎟<br>　　　　　　　　　　　　　　　　　　　　　—Dab⎟<br>　　　　　　　　　　　HN⎯⎯⎯⎯⎯⎯⎠<br>cyclo(⎯⎯N⎯⎯⎯⎯⎯⎯⎯⎯Dab-$^D$Leu-Leu-Dab-Dab-Thr-)<br>　　　　　　H　　　　　‖<br>　　　　　　　　　　　O |
| Ex. 148[a)] | S————————S<br>\|　　　　　　　\|<br>Trp-Cys-Val-Ser-Ser-$^D$Pro-Pro-Val-Dap-Tyr-Cys-Orn-$^D$Dab-Dab⎞<br>　　　　　　　　　　　　　　　　　　　　　—Dab⎟<br>　　　　　　　　　　HN⎯⎯⎯⎯⎯⎯⎠<br>cyclo(⎯⎯N⎯⎯⎯⎯⎯⎯⎯⎯Dab-$^D$Leu-Leu-Dab-Dab-Thr-)<br>　　　　　　H　　　　　‖<br>　　　　　　　　　　　O |
| Ex. 149[a)] | S————————S<br>\|　　　　　　　\|<br>Trp-Cys-Val-Ser-Ser-$^D$Pro-Tyr-Val-Dap-Tyr-Cys-Orn-Thr-$^D$Dab⎞<br>　　　　　　　　　　　　　　　　　　　　　—Dab⎟<br>　　　　　　　　　　HN⎯⎯⎯⎯⎯⎯⎠<br>cyclo(⎯⎯N⎯⎯⎯⎯⎯⎯⎯⎯Dab-$^D$Leu-Leu-Dab-Dab-Thr-)<br>　　　　　　H　　　　　‖<br>　　　　　　　　　　　O |
| Ex. 150[a)] | S————————S<br>\|　　　　　　　\|<br>Trp-Cys-Val-Ser-Ser-$^D$Pro-Pro-Nle-Dap-Ala-Cys-Sar-Dab-Thr⎞<br>　　　　　　　　　　　　　　　　　　　　　—Dab⎟<br>　　　　　　　　　　HN⎯⎯⎯⎯⎯⎯⎠<br>cyclo(⎯⎯N⎯⎯⎯⎯⎯⎯⎯⎯Dab-$^D$Leu-Leu-Dab-Dab-Thr-)<br>　　　　　　H　　　　　‖<br>　　　　　　　　　　　O |
| Ex. 151[a)] | S————————S<br>\|　　　　　　　\|<br>Trp-Cys-Val-Ser-Ser-$^D$Pro-Pro-Leu-Asp-Tyr-Cys-Orn-Thr-Dab⎞<br>　　　　　　　　　　　　　　　　　　　　—Dab⎟<br>　　　　　　　　　　HN⎯⎯⎯⎯⎯⎯⎠<br>cyclo(⎯⎯N⎯⎯⎯⎯⎯⎯⎯⎯Dab-$^D$Leu-Leu-Dab-Dab-Thr-)<br>　　　　　　H　　　　　‖<br>　　　　　　　　　　　O |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
| --- | --- |
| Ex. 152[a)] | S———————S<br>\|　　　　　　　　　　\|<br>Trp-Cys-Val-Arg-Arg-*D*Pro-Pro-Leu-Ser-Tyr-Cys-Sar-Dab-Thr⎤<br>　　　　　　　　　　　　　　　　　　　　　　—Dab⎦<br>　　　　　　　　　　　　　　HN—<br>cyclo(＼N／￣＼／Dab-*D*Leu-Leu-Dab-Dab-Thr-)<br>　　　　　　H　　　　‖<br>　　　　　　　　　　O |
| Ex. 153[a)] | S———————S<br>\|　　　　　　　　　　\|<br>Trp-Cys-Val-Ala-Tyr-*D*Pro-Pro-Tyr-Ser-Leu-Cys-Gly-Dab-Thr⎤<br>　　　　　　　　　　　　　　　　　　　　　　—Dab⎦<br>　　　　　　　　　　　　　　HN—<br>cyclo(＼N／￣＼／Dab-*D*Leu-Leu-Dab-Dab-Thr-)<br>　　　　　　H　　　　‖<br>　　　　　　　　　　O |
| Ex. 154[a)] | S———————S<br>\|　　　　　　　　　　\|<br>Leu-Cys-Val-Ala-Thr-*D*Pro-Pro-Leu-Ser-Leu-Cys-Gly-Dab-Thr⎤<br>　　　　　　　　　　　　　　　　　　　　　　—Dab⎦<br>　　　　　　　　　　　　　　HN—<br>cyclo(＼N／￣＼／Dab-*D*Leu-Leu-Dab-Dab-Thr-)<br>　　　　　　H　　　　‖<br>　　　　　　　　　　O |
| Ex. 155[a)] | S———————S<br>\|　　　　　　　　　　\|<br>Val-Cys-Val-Ala-Val-*D*Pro-Pro-Tyr-Ser-Leu-Cys-Gly-Dab-Thr⎤<br>　　　　　　　　　　　　　　　　　　　　　　—Dab⎦<br>　　　　　　　　　　　　　　HN—<br>cyclo(＼N／￣＼／Dab-*D*Leu-Leu-Dab-Dab-Thr-)<br>　　　　　　H　　　　‖<br>　　　　　　　　　　O |
| Ex. 156[a)] | S———————S<br>\|　　　　　　　　　　\|<br>Leu-Cys-Val-Ala-His-*D*Pro-Pro-Tyr-Ser-Leu-Cys-Gly-Dab-Thr⎤<br>　　　　　　　　　　　　　　　　　　　　　　—Dab⎦<br>　　　　　　　　　　　　　　HN—<br>cyclo(＼N／￣＼／Dab-*D*Leu-Leu-Dab-Dab-Thr-)<br>　　　　　　H　　　　‖<br>　　　　　　　　　　O |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified
| Ex. No. | Sequence |
|---|---|
| Ex. 157[a] | 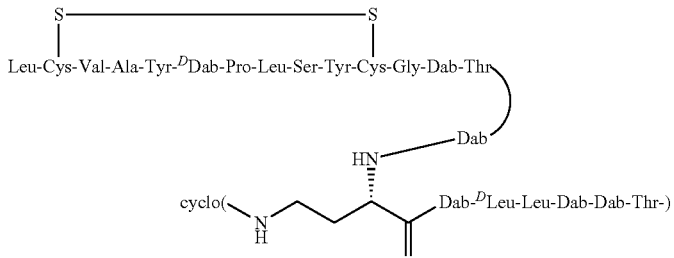 |
| Ex. 158[a] | 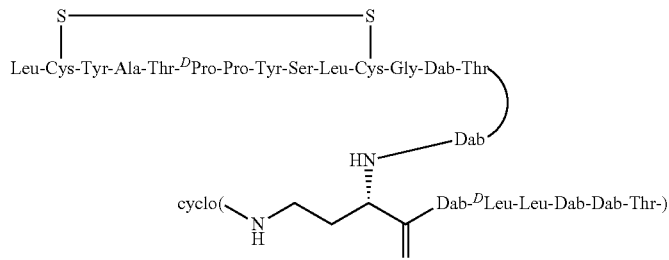 |
| Ex. 159[a] | 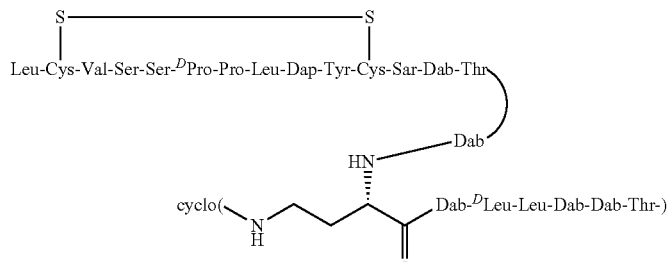 |
| Ex. 160[a] | 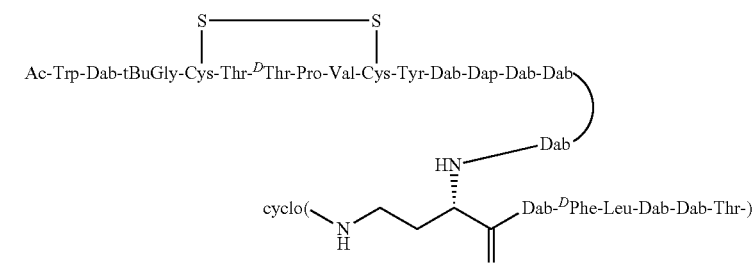 |
| Ex. 161[a] | 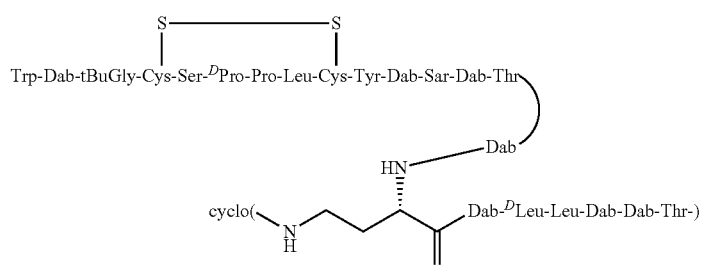 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified

| Ex. No. | Sequence |
|---|---|
| Ex. 162<sup>a)</sup> | S————S<br>\|  \|<br>Trp-Dab-Val-Cys-Ser-<sup>D</sup>Pro-Pro-Leu-Pen-Tyr-Dab-Gly-Dab-Thr⎞<br>⎟<br>Dab<br>HN<br>cyclo(–N(H)–CH₂CH₂–C*H–C(=O)–Dab-<sup>D</sup>Leu-Leu-Dab-Dab-Thr-) |
| Ex. 163<sup>a)</sup> | S————S<br>\|  \|<br>Trp-Dab-Val-Cys-Ser-<sup>D</sup>Dab-Dab-Leu-Cys-Tyr-Dab-Gly-Dab-Thr⎞<br>⎟<br>Dab<br>HN<br>cyclo(–N(H)–CH₂CH₂–C*H–C(=O)–Dab-<sup>D</sup>Leu-Leu-Dab-Dab-Thr-) |
| Ex. 164<sup>a)</sup> | S————S<br>\|  \|<br>Trp-Dab-Val-Cys-Ser-<sup>D</sup>Ala-Pro((4R)OH)-Leu-Cys-Tyr-Dab-Gly-Dab-Thr⎞<br>⎟<br>Dab<br>HN<br>cyclo(–N(H)–CH₂CH₂–C*H–C(=O)–Dab-<sup>D</sup>Leu-Leu-Dab-Dab-Thr-) |
| Ex. 165<sup>a)</sup> | S————S<br>\|  \|<br>Trp-Dab-Tyr-Cys-Ser-<sup>D</sup>Pro-Pro-Leu-Cys-Tyr-Dab-Gly-Dab-Thr⎞<br>⎟<br>Dab<br>HN<br>cyclo(–N(H)–CH₂CH₂–C*H–C(=O)–Dab-<sup>D</sup>Leu-Leu-Dab-Dab-Thr-) |
| Ex. 166<sup>a)</sup> | S————S<br>\|  \|<br>Trp-Dab-Tyr-Cys-Val-<sup>D</sup>Dab-Arg-Leu-Cys-Tyr-Dab-Gly-Dab-Thr⎞<br>⎟<br>Dab<br>HN<br>cyclo(–N(H)–CH₂CH₂–C*H–C(=O)–Dab-<sup>D</sup>Leu-Leu-Dab-Dab-Thr-) |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 167[b)] | 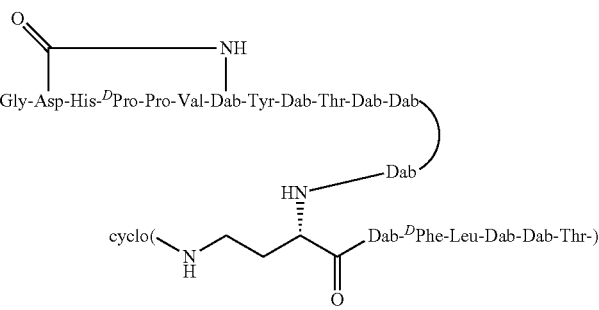 |
| Ex. 168[b)] | 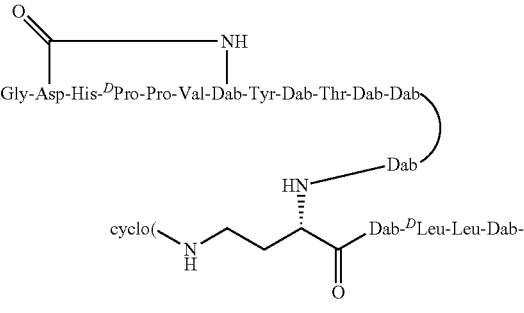 |
| Ex. 169[a)] | 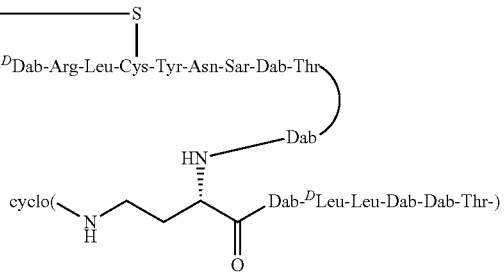 |
| Ex. 170[a)] | 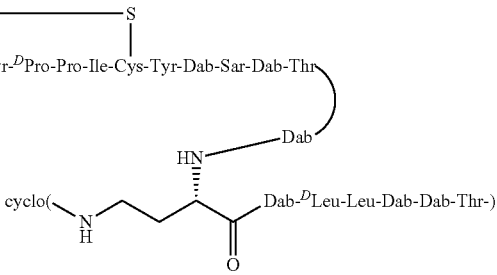 |
| Ex. 171[a)] | 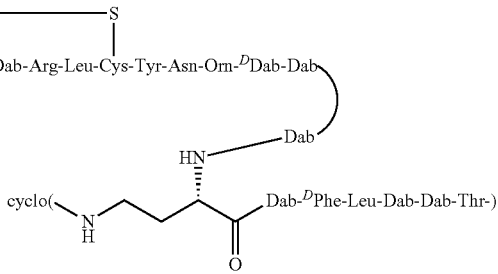 |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
Ex. 172[b) d)]
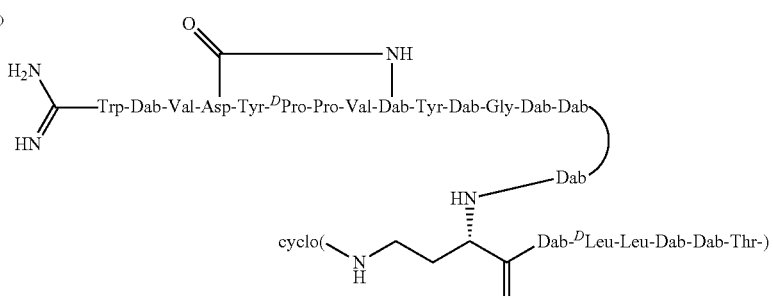
Ex. 173[a) d)]
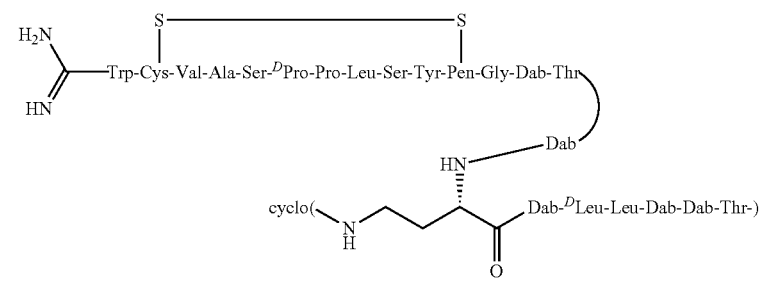
Ex. 174[a) d)]
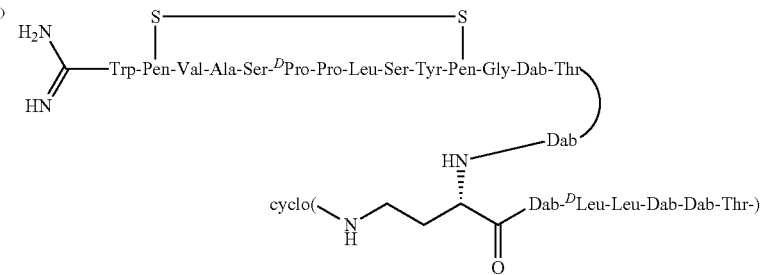
Ex. 175[a)]
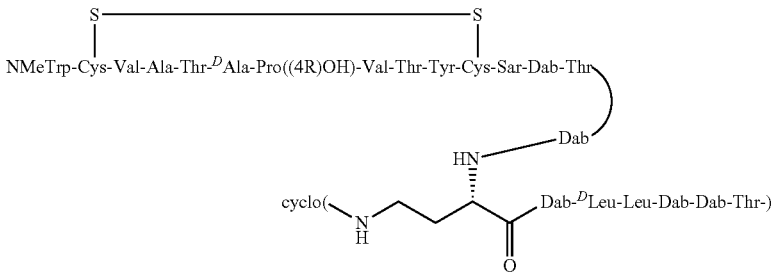

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 176[b] | 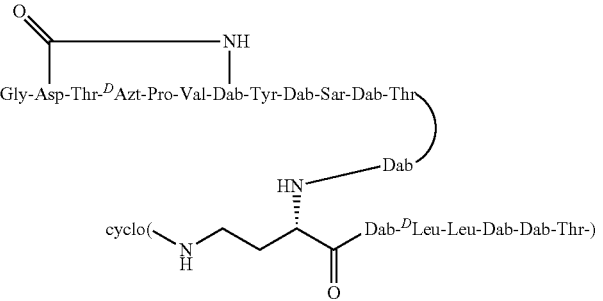 |
| Ex. 177[a) c)] | 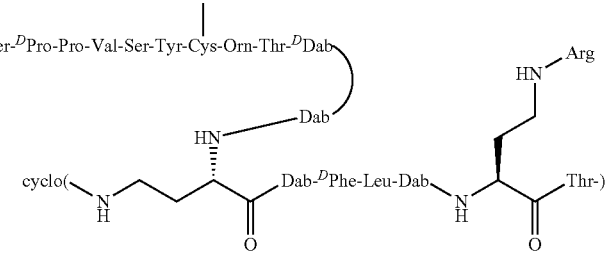 |
| Ex. 178[a)] | 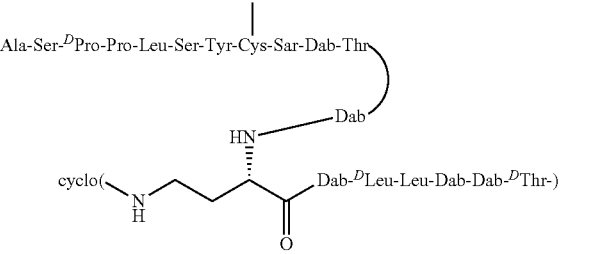 |
| Ex. 179[a)] | 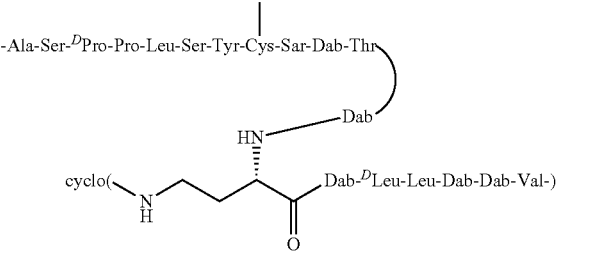 |
| Ex. 180[a)] | 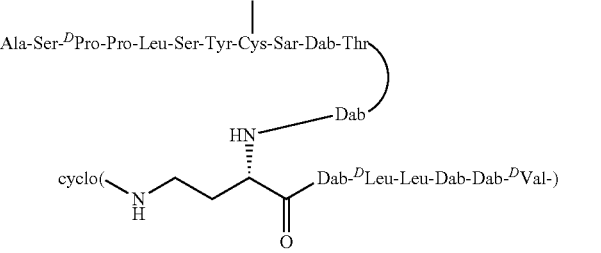 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 181[a] | Trp-Cys-Val-Ala-Ser-$^D$Pro-Pro-Leu-Ser-Tyr-Cys-Sar-Dab-Thr, Dab, cyclo(-NH-CH(-)-C(=O)-Dab-$^D$Leu-Leu-Dab-Dab-Arg-), with S—S bridge between the two Cys |
| Ex. 182[a] | Trp-Cys-Val-Ala-Ser-$^D$Pro-Pro-Leu-Ser-Tyr-Cys-Sar-Dab-Thr, Dab, cyclo(-NH-CH(-)-C(=O)-Dab-$^D$Leu-Leu-Dab-Dab-$^D$Arg-), with S—S bridge between the two Cys |
| Ex. 183[a] | Gly-Trp-Cys-tBuGly-Ala-Ser-$^D$Pro-Pro-Cpa-Ser-Tyr-Cys-Orn-Dab, cyclo(-NH-CH(-)-C(=O)-Dab-$^D$Phe-Leu-Dab-Dab-Thr-), with S—S bridge between the two Cys |
| Ex. 184[a] | Sar-Trp-Cys-Val-Ala-Ser-$^D$Pro-Pro-Leu-Ser-Tyr-Cys-Sar-Thr, Dab-Dab, cyclo(-NH-CH(-)-C(=O)-Dab-$^D$Leu-Leu-Dab-Dab-Thr-), with S—S bridge between the two Cys |
| Ex. 185[a] | Sar-Trp-Cys-Val-Ala-Dab-$^D$Pro-Pro-Leu-Ser-Tyr-Cys-Sar-Dab, Dab-Thr, cyclo(-NH-CH(-)-C(=O)-Dab-$^D$Leu-Leu-Dab-Dab-Thr-), with S—S bridge between the two Cys |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 186[a)] | S—S bridge across Sar-Leu-Cys-Val-Ala-Tyr-$^D$Pro-Pro-Leu-Ser-Tyr-Cys-Sar-Dab–Dab-Thr–HN–cyclo(NH–CH(C=O)–Dab-$^D$Leu-Leu-Dab-Dab-Thr-) |
| Ex. 187[a) c)] | S—S bridge across Sar-Trp-Cys-Val-Ala-Ser-$^D$Pro-Pro-Leu-Ser-Tyr-Cys-Sar-Dab–Dab-Thr–HN–cyclo(NH–CH(C=O)–Dab-$^D$Leu-Leu-Dab–NH–CH(C=O)(HN-Arg)–Thr-) |
| Ex. 188[a)] | S—S bridge across Trp-Cys-tBuGly-Ala-Ser-$^D$Pro-Pro-Val-Ser-Leu-Cys-Orn-Dab–HN–cyclo(NH–CH(C=O)–Dab-$^D$Phe-Leu-Dab-Dab-Thr-) |
| Ex. 189[a)] | S—S bridge across Trp-Cys-tBuGly-Ala-Thr-$^D$Azt-Pro-Val-Ser-Tyr-Cys-Dap-Dab–HN–cyclo(NH–CH(C=O)–Dab-$^D$Leu-Leu-Dab-Dab-Thr-) |
| Ex. 190[b)] | HN–C(=O) bridge across Trp-Dab-tBuGly-Ala-Ser-$^D$Pro-Pro-Nle-Ser-Tyr-Asp-Orn-Dab–HN–cyclo(NH–CH(C=O)–Dab-$^D$Phe-Leu-Dab-Dab-Thr-) |

TABLE 1-continued
Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified
| Ex. No. | Sequence |
|---|---|
| Ex. 191[a) b)] | 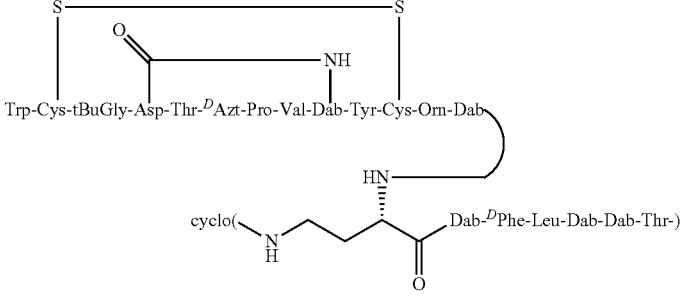 |
| Ex. 192[a)] | 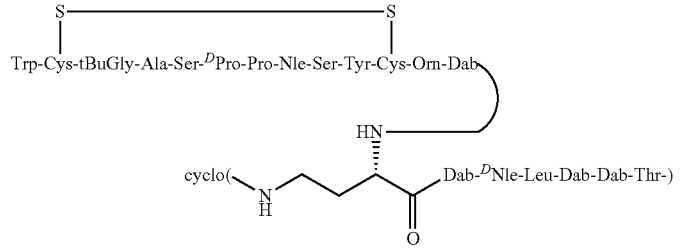 |
| Ex. 193[b)] | 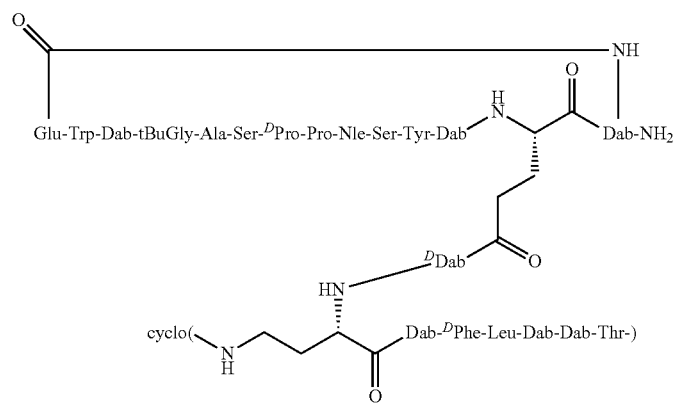 |
| Ex. 194[a)] | 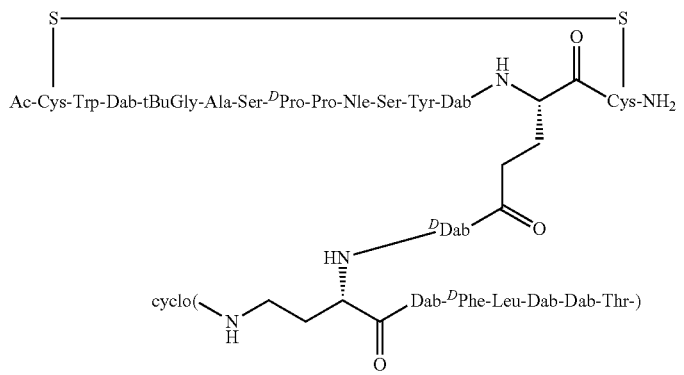 |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 195[a)] | S—————————S<br>\|　　　　　　　\|<br>Cys-Trp-Dab-tBuGly-Ala-Ser-$^D$Pro-Pro-Nle-Ser-Tyr-Dab-Orn-Cys<br>　　　　　　　　　　　　　　　$^D$Dab<br>　　　　　　　HN<br>cyclo(—N—　　　Dab-$^D$Leu-Leu-Dab-Dab-Thr-)<br>　　　　H<br>　　　　　O |
| Ex. 196[b)] | HN————————————O<br>\|　　　　　　　　　　\|<br>Ac-Dab-Trp-Dab-tBuGly-Ala-Ser-$^D$Pro-Pro-Nle-Ser-Tyr-Dab-Orn-Glu<br>　　　　　　　　　　　　　　　$^D$Dab<br>　　　　　　　HN<br>cyclo(—N—　　　Dab-$^D$Leu-Leu-Dab-Dab-Thr-)<br>　　　　H<br>　　　　　O |
| Ex. 197[b)] | HN————————————O<br>\|　　　　　　　　　　\|<br>Ac-Dab-Trp-Dab-tBuGly-Ala-Ser-$^D$Pro-Pro-Nle-Ser-Tyr-Dab-Orn-Glu<br>　　　　　　　　　　　　　　　$^D$Dab<br>　　　　　　　HN<br>cyclo(—N—　　　Dab-$^D$Phe-Leu-Dab-Dab-Thr-)<br>　　　　H<br>　　　　　O |
| Ex. 198[b)] | O————————————NH<br>\|\|　　　　　　　　　　\|<br>Glu-Trp-Dab-tBuGly-Ala-Ser-$^D$Pro-Pro-Nle-Ser-Tyr-Dab-Orn-Dab<br>　　　　　　　　　　　　　　　$^D$Dab<br>　　　　　　　HN<br>cyclo(—N—　　　Dab-$^D$Phe-Leu-Dab-Dab-Thr-)<br>　　　　H<br>　　　　　O |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 199[a] | S—————————————S<br>\|  \|<br>Cys-Trp-Dab-tBuGly-Ser-Ser-$^D$Pro-Pro-Nle-Ser-Tyr-Dab-Orn-Cys⟩<br>            $^D$Dab-Ala⟋<br>         HN—<br>   cyclo(—NH—⋮—Dab-$^D$Phe-Leu-Dab-Dab-Thr-)<br>              ‖<br>              O |
| Ex. 200[a] | S—————————————S<br>\|  \|<br>Cys-Trp-Dab-tBuGly-Ser-Ser-$^D$Pro-Pro-Nle-Ser-Tyr-Dab-Orn-Cys⟩<br>            $^D$Dab-$^D$Nle⟋<br>         HN—<br>   cyclo(—NH—⋮—Dab-$^D$Phe-Leu-Dab-Dab-Thr-)<br>              ‖<br>              O |
| Ex. 201[a] | S—————————————S<br>\|  \|<br>Cys-Trp-Dab-tBuGly-Ser-Ser-$^D$Pro-Pro-Nle-Ser-Tyr-Dab-Orn-Cys⟩<br>            $^D$Dab-Tyr⟋<br>         HN—<br>   cyclo(—NH—⋮—Dab-$^D$Phe-Leu-Dab-Dab-Thr-)<br>              ‖<br>              O |
| Ex. 202[a] | S—————————————S<br>\|  \|<br>Cys-Trp-Dab-tBuGly-Ser-Ser-$^D$Pro-Pro-Nle-Ser-Tyr-Dab-Orn-Cys⟩<br>            Dab-$^D$Trp⟋<br>         HN—<br>   cyclo(—NH—⋮—Dab-$^D$Phe-Leu-Dab-Dab-Thr-)<br>              ‖<br>              O |

TABLE 1-continued

Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified

| Ex. No. | Sequence |
|---|---|
| Ex. 203[a] | S—————S<br>\|              \|<br>Cys-Trp-Dab-tBuGly-Ser-Ser-$^D$Pro-Pro-Nle-Ser-Tyr-Dab-Orn-Cys<br>$^D$Dab-Gln<br>HN<br>cyclo(−NH−...−Dab-$^D$Phe-Leu-Dab-Dab-Thr-) |
| Ex. 204[a] | S—————S<br>\|              \|<br>Cys-Trp-Dab-tBuGly-Ser-Ser-$^D$Pro-Pro-Nle-Ser-Tyr-Dab-Orn-Cys<br>$^D$Dab-$^D$Thr<br>HN<br>cyclo(−NH−...−Dab-$^D$Phe-Leu-Dab-Dab-Thr-) |
| Ex. 205[a] | S—————S<br>\|              \|<br>Cys-Trp-Dab-tBuGly-Ser-Ser-$^D$Pro-Pro-Nle-Ser-Tyr-Dab-Orn-Cys<br>$^D$Dab-Dab<br>HN<br>cyclo(−NH−...−Dab-$^D$Phe-Leu-Dab-Dab-Thr-) |
| Ex. 206[a] | S—————S<br>\|              \|<br>Cys-Trp-Dab-tBuGly-Ala-Ser-$^D$Pro-Pro-Leu-Ser-Tyr-Dab-Sar-Cys<br>$^D$Dab<br>HN<br>cyclo(−NH−...−Dab-$^D$Leu-Leu-Dab-Dab-Thr-) |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified

| Ex. No. | Sequence |
|---|---|
| Ex. 207[a)] | S—————————————S<br>│                                            │<br>NMeCys-Trp-Dab-tBuGly-Tyr-Ser-$^D$Pro-Pro-Nle-Ser-Tyr-Dab-Orn-Cys⟩<br>                                               $^D$Dab<br>                                HN<br>cyclo(—NH—…—Dab-$^D$Leu-Leu-Dab-Dab-Thr-) |
| Ex. 208[a)] | S——————————————S<br>Pen-Trp-Dab-Val-Ser-Ser-$^D$Pro((4S)OH)-Pro-Leu-Ser-Tyr-Dab-Orn-Cys⟩<br>                                        $^D$Dab<br>cyclo(—NH—…—Dab-$^D$Leu-Leu-Dab-Dab-Thr-) |
| Ex. 209[a)] | S——————————S<br>Cys-Trp-Dab-Val-Thr-Tyr-$^D$Pro-Pro-Leu-Ser-Tyr-Dab-Dab-Cys⟩<br>                                $^D$Dab<br>cyclo(—NH—…—Dab-$^D$Leu-Leu-Dab-Dab-Thr-) |
| Ex. 210[a) b)] | S———————————————S<br>│  O                             NH<br>Cys-Trp-Glu-tBuGly-Ala-Ser-$^D$Pro-Pro-Nle-Dab-Tyr-Dab-Orn-Cys⟩<br>                                        $^D$Dab<br>cyclo(—NH—…—Dab-$^D$Phe-Leu-Dab-Dab-Thr-) |

TABLE 1-continued
Examples (Ex.)
In the below-mentioned examples, amino acid residues are connected in either direction from the α carbonyl (C=O) point of attachment to the α nitrogen (N) of the next element, unless otherwise indicated. Other linkages and modifications are as specified
| Ex. No. | Sequence |
|---|---|
| Ex. 211[a)] | 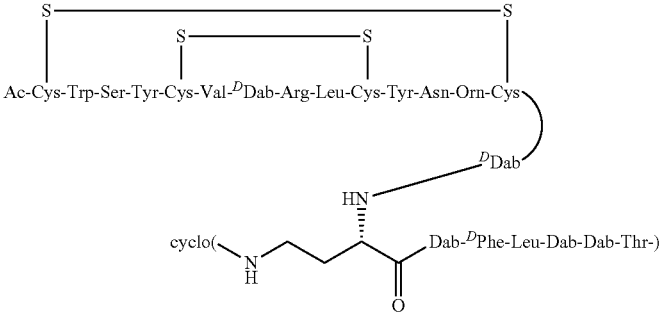 |
| Ex. 212[a)] | 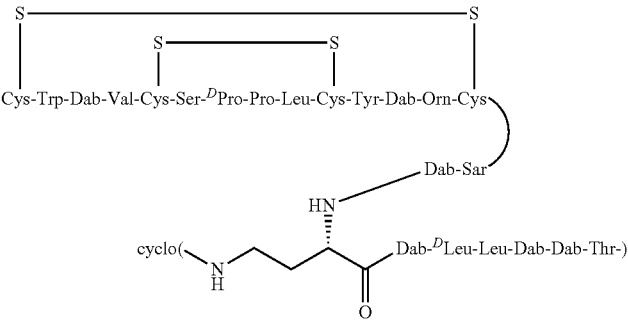 |
| Ex. 213[a)] | 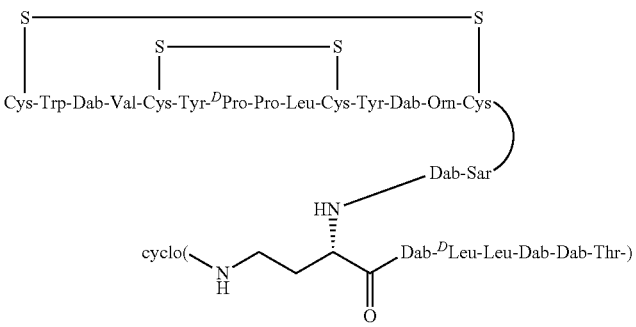 |
| Ex. 214[a)] | 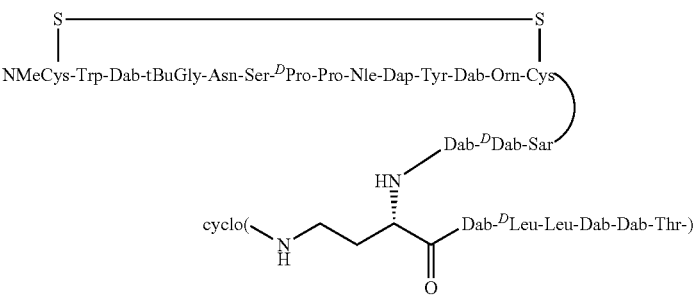 |

TABLE 1-continued

Examples (Ex.)
In the below-mentioned examples, amino acid residues are connected in either
direction from the α carbonyl (C=O) point of attachment to the α nitrogen (N) of the
next element, unless otherwise indicated. Other linkages and modifications are as
specified

| Ex. No. | Sequence |
|---|---|
| Ex. 215[a] | S——————S<br>Cys-Trp-Dab-tBuGly-Ala-Ser-$^D$Pro-Pro-Nle-Ser-Tyr-Dab-Orn-Cys<br>$^D$Dab<br>HN<br>cyclo(N — Dab-$^D$Phe-Leu-Dab-Dab-Thr-) |
| Ex. 216[a] | S——————S<br>Cys-Trp-Dab-tBuGly-Ala-Ser-$^D$Pro-Pro-Nle-Ser-Tyr-Dab-Orn-Cys<br>$^D$Dab<br>HN<br>cyclo(N — Dab-$^D$Phe-Leu-Dab-Dab-Val-) |

[a] Disulfide interstrand linkage(s) between indicated amino acid residues, involving a disulfide bond(s) between a pair(s) of side-chain thiol groups as specified.
[b] Lactam interstrand linkage between the two indicated amino acid residues, involving an amide bond between a side-chain amino group and a side-chain carboxyl group.
[c] Dipeptidic amino acid residue at the indicated position, comprising an amide bond between the α-carboxyl group of the terminal amino acid residue and the side-chain amino group of the other amino acid residue as specified.
[d] Guanidine group comprising the amino group of the N-terminal amino acid residue.
[e] Tetramethylguanidine group comprising the amino group of the N-terminal amino acid residue.

TABLE 2

Analytical data

| Ex. | Analyt. Meth. | MS [a] | RT [min] | Purity [%] |
|---|---|---|---|---|
| 1 | A | 768.0 | 2.77 | 90 |
| 2 | A | 801.4 | 2.73 | 94 |
| 3 | B | 802.0 | 4.46 | 89 |
| 4 | A | 830.0 | 2.73 | 86 |
| 5 | A | 835.3 | 2.74 | 90 |
| 6 | C | 835.3 | 3.79 | 84 |
| 7 | A | 863.9 | 2.57 | 95 |
| 8 | A | 859.6 | 2.59 | 84 |
| 9 | A | 868.6 | 2.70 | 91 |
| 10 | A | 868.7 | 2.67 | 91 |
| 11 | A | 868.6 | 2.63 | 95 |
| 12 | A | 775.4 | 2.97 | 92 |
| 13 | A | 780.0 | 2.95 | 85 |
| 14 | A | 777.8 | 2.82 | 91 |
| 15 | A | 750.2 | 2.92 | 92 |
| 16 | A | 756.8 | 2.93 | 95 |
| 17 | A | 766.8 | 2.96 | 84 |
| 18 | A | 780.2 | 3.13 | 91 |
| 19 | A | 775.0 | 3.05 | 93 |
| 20 | A | 771.0 | 2.99 | 77 |
| 21 | A | 775.5 | 2.99 | 89 |
| 22 | A | 760.8 | 2.97 | 81 |
| 23 | A | 770.0 | 3.02 | 88 |
| 24 | A | 813.8 | 2.99 | 91 |
| 25 | A | 813.7 | 3.07 | 92 |
| 26 | C | 794.4 | 4.27 | 70 |
| 27 | A | 809.0 | 2.92 | 71 |
| 28 | A | 799.0 | 3.08 | 70 |
| 29 | A | 799.0 | 2.98 | 76 |
| 30 | A | 803.5 | 3.11 | 80 |
| 31 | A | 794.4 | 2.98 | 81 |
| 32 | A | 799.0 | 3.02 | 87 |
| 33 | A | 794.4 | 2.99 | 80 |
| 34 | A | 808.7 | 2.93 | 77 |
| 35 | A | 779.8 | 2.77 | 78 |
| 36 | A | 813.7 | 2.78 | 83 |
| 37 | A | 790.3 | 2.79 | 88 |
| 38 | A | 799.8 | 2.71 | 81 |
| 39 | A | 813.5 | 2.74 | 89 |
| 40 | A | 804.4 | 2.83 | 90 |
| 41 | A | 799.0 | 2.97 | 85 |
| 42 | A | 794.8 | 2.72 | 95 |
| 43 | A | 795.0 | 2.84 | 76 |
| 44 | A | 789.4 | 2.84 | 82 |
| 45 | A | 732.4 | 2.89 | 92 |
| 46 | A | 746.4 | 2.82 | 73 |
| 47 | A | 756.5 | 2.94 | 94 |
| 48 | B | 747.0 | 4.95 | 91 |
| 49 | A | 746.4 | 3.00 | 84 |
| 50 | A | 737.3 | 2.99 | 89 |
| 51 | A | 733.8 | 2.96 | 96 |
| 52 | A | 767.3 | 3.23 | 77 |

TABLE 2-continued

Analytical data

| Ex. | Analyt. Meth. | MS a) | RT [min] | Purity [%] |
|---|---|---|---|---|
| 53 | A | 747.5 | 2.65 | 71 |
| 54 | A | 735.2 | 2.92 | 91 |
| 55 | A | 741.8 | 2.88 | 93 |
| 56 | A | 744.4 | 2.99 | 92 |
| 57 | A | 813.3 | 2.64 | 79 |
| 58 | A | 815.8 | 2.65 | 85 |
| 59 | A | 815.7 | 2.63 | 74 |
| 60 | A | 813.2 | 2.72 | 85 |
| 61 | A | 846.9 | 2.62 | 84 |
| 62 | A | 880.4 | 2.62 | 90 |
| 63 | A | 880.3 | 2.53 | 88 |
| 64 | A | 758.9 | 2.79 | 95 |
| 65 | A | 797.0 | 2.64 | 86 |
| 66 | A | 792.3 | 2.71 | 94 |
| 67 | A | 792.3 | 2.65 | 87 |
| 68 | A | 801.7 | 2.63 | 90 |
| 69 | F | 797.2 | 2.58 | 85 |
| 70 | A | 790.4 | 2.66 | 95 |
| 71 | A | 781.2 | 2.69 | 95 |
| 72 | A | 785.8 | 2.62 | 95 |
| 73 | D | 785.8 | 3.52 | 95 |
| 74 | D | 835.2 | 3.60 | 90 |
| 75 | A | 835.3 | 2.68 | 93 |
| 76 | A | 800.2 | 2.49 | 90 |
| 77 | A | 834.5 | 2.83 | 86 |
| 78 | F | 823.7 | 2.50 | 94 |
| 79 | A | 801.4 | 2.79 | 95 |
| 80 | A | 859.6 | 2.34 | 90 |
| 81 | A | 864.2 | 2.57 | 79 |
| 82 | A | 848.2 | 2.32 | 92 |
| 83 | D | 857.8 | 3.38 | 81 |
| 84 | A | 857.9 | 2.45 | 89 |
| 85 | A | 843.2 | 2.29 | 85 |
| 86 | A | 872.6 | 2.52 | 89 |
| 87 | G | 861.1 | 2.23 | 93 |
| 88 | A | 854.5 | 2.21 | 84 |
| 89 | D | 862.9 | 3.29 | 84 |
| 90 | A | 843.8 | 2.56 | 85 |
| 91 | A | 862.8 | 2.38 | 78 |
| 92 | A | 858.1 | 2.40 | 90 |
| 93 | A | 854.0 | 2.08 | 89 |
| 94 | A | 848.5 | 2.50 | 83 |
| 95 | A | 878.7 | 2.47 | 83 |
| 96 | A | 883.6 | 2.63 | 90 |
| 97 | A | 894.2 | 2.15 | 90 |
| 98 | A | 864.2 | 2.61 | 93 |
| 99 | A | 859.2 | 2.58 | 86 |
| 100 | C | 853.9 | 3.83 | 82 |
| 101 | E | 848.3 | 2.67 | 95 |
| 102 | E | 845.2 | 3.00 | 92 |
| 103 | E | 844.9 | 2.84 | 95 |
| 104 | A | 761.5 | 2.86 | 83 |
| 105 | A | 787.2 | 2.93 | 93 |
| 106 | A | 766.7 | 2.86 | 84 |
| 107 | A | 766.9 | 2.78 | 94 |
| 108 | A | 776.4 | 2.90 | 71 |
| 109 | A | 787.8 | 2.86 | 91 |
| 110 | A | 796.5 | 2.97 | 77 |
| 111 | A | 804.5 | 3.02 | 85 |
| 112 | D | 780.3 | 4.51 | 95 |
| 113 | A | 798.4 | 3.12 | 87 |
| 114 | A | 766.4 | 2.97 | 89 |
| 115 | A | 808.9 | 2.76 | 95 |
| 116 | A | 775.3 | 2.99 | 84 |
| 117 | A | 775.3 | 2.77 | 87 |
| 118 | A | 785.3 | 3.13 | 76 |
| 119 | A | 790.5 | 2.82 | 71 |
| 120 | A | 775.4 | 2.86 | 95 |
| 121 | A | 783.8 | 2.71 | 72 |
| 122 | A | 797.8 | 2.74 | 85 |
| 123 | A | 784.8 | 2.47 | 86 |
| 124 | A | 785.3 | 2.60 | 77 |
| 125 | A | 770.5 | 2.51 | 81 |
| 126 | A | 766.0 | 2.52 | 87 |
| 127 | A | 779.8 | 2.34 | 78 |
| 128 | A | 765.9 | 2.51 | 95 |
| 129 | A | 775.7 | 2.39 | 84 |
| 130 | A | 761.3 | 2.56 | 86 |
| 131 | A | 764.8 | 2.70 | 88 |
| 132 | A | 784.7 | 2.88 | 92 |
| 133 | A | 797.5 | 2.82 | 95 |
| 134 | A | 769.5 | 2.68 | 84 |
| 135 | A | 783.4 | 2.70 | 87 |
| 136 | A | 774.2 | 2.55 | 86 |
| 137 | A | 836.5 | 2.95 | 81 |
| 138 | A | 854.9 | 2.77 | 81 |
| 139 | A | 848.5 | 3.06 | 83 |
| 140 | A | 804.5 | 2.82 | 76 |
| 141 | A | 769.0 | 2.95 | 85 |
| 142 | D | 813.3 | 3.52 | 81 |
| 143 | A | 799.3 | 2.88 | 79 |
| 144 | A | 835.3 | 2.71 | 87 |
| 145 | A | 774.0 | 2.96 | 82 |
| 146 | A | 854.0 | 2.93 | 84 |
| 147 | A | 779.0 | 2.74 | 95 |
| 148 | A | 783.7 | 2.44 | 86 |
| 149 | A | 806.0 | 2.45 | 80 |
| 150 | A | 743.7 | 2.55 | 78 |
| 151 | D | 823.7 | 3.77 | 71 |
| 152 | A | 820.9 | 2.43 | 78 |
| 153 | A | 782.5 | 2.72 | 78 |
| 154 | A | 728.3 | 3.02 | 72 |
| 155 | A | 739.8 | 3.06 | 81 |
| 156 | A | 756.9 | 2.31 | 90 |
| 157 | A | 766.7 | 2.54 | 92 |
| 158 | A | 766.5 | 2.61 | 86 |
| 159 | A | 750.0 | 2.59 | 71 |
| 160 | D | 840.2 | 3.60 | 85 |
| 161 | D | 787.8 | 3.42 | 76 |
| 162 | A | 787.9 | 2.42 | 85 |
| 163 | A | 780.7 | 2.08 | 70 |
| 164 | A | 775.7 | 2.22 | 82 |
| 165 | A | 800.2 | 2.37 | 77 |
| 166 | A | 824.4 | 3.16 | 79 |
| 167 | A | 832.8 | 2.36 | 91 |
| 168 | F | 821.4 | 2.26 | 95 |
| 169 | A | 829.8 | 2.40 | 80 |
| 170 | F | 784.4 | 2.57 | 72 |
| 171 | A | 828.2 | 2.59 | 77 |
| 172 | A | 810.5 | 2.66 | 88 |
| 173 | E | 788.2 | 3.41 | 72 |
| 174 | A | 797.3 | 2.90 | 82 |
| 175 | E | 775.4 | 2.99 | 95 |
| 176 | D | 785.8 | 3.21 | 95 |
| 177 | A | 842.4 | 2.56 | 92 |
| 178 | A | 769.4 | 2.78 | 86 |
| 179 | A | 768.4 | 2.78 | 77 |
| 180 | A | 768.7 | 2.86 | 84 |
| 181 | A | 787.8 | 2.71 | 74 |
| 182 | A | 787.8 | 2.74 | 88 |
| 183 | A | 760.3 | 2.91 | 94 |
| 184 | A | 793.2 | 2.72 | 90 |
| 185 | A | 797.4 | 2.44 | 76 |
| 186 | A | 793.9 | 2.97 | 91 |
| 187 | A | 845.4 | 2.66 | 95 |
| 188 | A | 711.4 | 2.90 | 81 |
| 189 | A | 707.3 | 2.80 | 83 |
| 190 | A | 730.2 | 2.77 | 93 |
| 191 | A | 741.0 | 2.90 | 90 |
| 192 | A | 721.4 | 2.88 | 75 |
| 193 | A | 806.4 | 2.64 | 92 |
| 194 | C | 818.0 | 3.83 | 84 |
| 195 | A | 788.3 | 2.65 | 73 |
| 196 | A | 804.4 | 2.63 | 95 |
| 197 | D | 815.7 | 3.71 | 84 |
| 198 | A | 801.8 | 2.69 | 77 |
| 199 | A | 828.5 | 2.62 | 94 |
| 200 | A | 842.5 | 2.67 | 95 |
| 201 | A | 859.2 | 2.64 | 95 |
| 202 | A | 866.9 | 2.68 | 80 |

TABLE 2-continued

Analytical data

| Ex. | Analyt. Meth. | MS [a] | RT [min] | Purity [%] |
|---|---|---|---|---|
| 203 | A | 847.5 | 2.62 | 95 |
| 204 | A | 838.2 | 2.61 | 95 |
| 205 | A | 838.2 | 2.63 | 95 |
| 206 | A | 774.0 | 2.70 | 85 |
| 207 | D | 823.4 | 3.82 | 77 |
| 208 | D | 803.3 | 3.30 | 76 |
| 209 | A | 814.4 | 2.82 | 76 |
| 210 | A | 802.8 | 2.60 | 91 |
| 211 | A | 870.7 | 2.53 | 95 |
| 212 | A | 822.5 | 2.56 | 85 |
| 213 | A | 847.9 | 2.87 | 95 |
| 214 | A | 863.9 | 2.52 | 82 |
| 215 | A | 804.2 | 2.65 | 87 |
| 216 | A | 803.5 | 2.69 | 88 |

[a] MS: m/z for $[M + 3H]^{3+}$.

2. Biological Methods

2.1 Preparation of the Peptides

Lyophilized peptides were weighed on a Microbalance (Mettler MT5) and dissolved in sterile water to a final concentration of 1 mg/mL. Stock solutions were kept at +4° C., light protected.

2.2 Antimicrobial Activity of the Peptides

The in vitro antimicrobial activities of the peptides were determined in 96-well plates (Greiner, polystyrene) by the standard CLSI broth microdilution method (Clinical and Laboratory Standards Institute 2014. Performance standards for antimicrobial susceptibility testing, 24th informational supplement. Approved standard CLSI M100-S24; Clinical and Laboratory Standards Institute, Wayne, Pa.). Inocula of the microorganisms were diluted into Mueller-Hinton II (MH-cation adjusted) broth and compared with a 0.5 McFarland standard to give appr. $10^6$ colony forming units (CFU)/mL. Aliquots (90 μL) of inoculate were added to 10 μL of MH-II broth+P-80 (Polysorbate 80, 0.002% final concentration, v/v) containing the peptide in serial two-fold dilutions. The following microorganisms were used to determine antibiotic activity of the peptides: *Escherichia coli* ATCC 25922, *Klebsiella pneumoniae* SSI #3010[a], *Acinetobacter baumannii* DSM 30008, *Pseudomonas aeruginosa* ATCC 27853 and the clinical isolates *Escherichia coli* 926415[b], *Klebsiella pneumoniae* 968733[b] and *Acinetobacter baumannii* 872842[b]. Antimicrobial activities of the peptides were expressed as the minimal inhibitory concentration (MIC) in μg/mL at which no visible growth was observed after 18-20 hours of incubation at 35° C.

[a] Obtained from Statens Serum Institut (SSI), Copenhagen, Denmark
[b] Obtained from International Health Management Associates, Inc. (IHMA Europe Sàrl), Epalinges, Switzerland

2.3 Hemolysis

The peptides were tested for their hemolytic activity against human red blood cells (hRBC). Fresh hRBC were washed three times with phosphate buffered saline (PBS) and centrifuged for 10 min at 2000×g. Compounds (100 μg/mL) were incubated with 20% hRBC (v/v) for 1 h at 37° C. and shaking at 300 rpm. The final erythrocyte concentration was approximately $0.9 \times 10^9$ cells/mL. A value of 0% and 100% cell lyses, respectively, was determined by incubation of hRBC in the presence of PBS containing 0.001% acetic acid and 2.5% Triton X-100 in $H_2O$, respectively. The samples were centrifuged, the supernatants were 8-fold diluted in PBS buffer and the optical densities (OD) were measured at 540 nm. The 100% lyses value ($OD_{540}H_2O$) gave an $OD_{540}$ of approximately 0.5-1.0.

Percent hemolysis was calculated as follows: ($OD_{540}$peptide/$OD_{540}H_2O$)×100%.

The results of the experiments described in 2.2-2.3 are indicated in Tables 3 and 4 herein below.

TABLE 3

Minimal inhibitory concentrations (MIC) in Mueller-Hinton II broth and Hemolysis

| Ex. | *Escherichia coli* ATCC 25922 MIC [μg/mL] | *Klebsiella pneumoniae* SSI #3010 MIC [μg/mL] | *Acinetobacter baumannii* DSM 30008 MIC [μg/mL] | *Pseudomonas aeruginosa* ATCC 27853 MIC [μg/mL] | Hemolysis at 100 μg/mL [%] |
|---|---|---|---|---|---|
| 1 | 0.25 | 0.5 | 0.125 | 0.5 | 1 |
| 2 | 0.5 | 1 | 1 | 0.25 | 1 |
| 3 | 0.5 | 0.5 | 1 | 0.25 | <1 |
| 4 | 1 | 1 | 1 | 0.25 | 1 |
| 5 | 2 | 0.5 | 0.5 | 0.5 | 1 |
| 6 | 0.25 | 0.5 | 2 | 0.5 | <1 |
| 7 | 0.125 | 0.25 | 1 | 0.25 | 1 |
| 8 | 0.25 | 0.25 | 0.5 | 0.25 | 1 |
| 9 | 0.25 | 0.5 | 0.25 | 0.5 | 1 |
| 10 | 0.125 | 0.25 | 1 | 0.5 | 1 |
| 11 | 2 | 1 | 1 | 0.5 | 1 |
| 12 | 0.125 | 0.125 | 0.0625 | 0.5 | <1 |
| 13 | 0.5 | 0.5 | 0.125 | 0.5 | 1 |
| 14 | 0.5 | 1 | 0.5 | 1 | <1 |
| 15 | 0.125 | 0.25 | 0.5 | 1 | 1 |
| 16 | 0.5 | 0.25 | 0.25 | 0.25 | 3 |
| 17 | 0.25 | 0.5 | 0.5 | 0.5 | 3 |
| 18 | 0.125 | 2 | 0.25 | 0.5 | 6 |
| 19 | 1 | 1 | 0.25 | 1 | <1 |
| 20 | 0.125 | 0.25 | 0.5 | 0.25 | 1 |
| 21 | 0.25 | 0.25 | 0.25 | 0.5 | <1 |
| 22 | 0.125 | 0.25 | 0.5 | 0.25 | <1 |
| 23 | 0.25 | 0.25 | 0.5 | 0.5 | 1 |
| 24 | 2 | 4 | 2 | 4 | 1 |
| 25 | 2 | 4 | 1 | 4 | 3 |
| 26 | 0.0625 | 0.25 | 0.5 | 0.25 | <1 |
| 27 | 0.0625 | 0.125 | 0.125 | 0.25 | <1 |
| 28 | 0.25 | 0.25 | 0.5 | 0.5 | 1 |
| 29 | 0.125 | 0.25 | 0.25 | 0.5 | <1 |
| 30 | 0.25 | 0.25 | 0.25 | 0.5 | <1 |
| 31 | 0.5 | 0.25 | 0.125 | 1 | 2 |
| 32 | 0.125 | 0.25 | 0.125 | 0.25 | 2 |
| 33 | 0.25 | 0.5 | 0.125 | 0.5 | 1 |
| 34 | 0.0625 | 0.125 | 0.25 | 0.125 | 1 |
| 35 | 0.25 | 0.25 | 0.5 | 1 | 1 |
| 36 | 0.25 | 0.25 | 0.25 | 0.5 | <1 |
| 37 | 0.125 | 0.125 | 0.125 | 0.5 | 2 |
| 38 | 0.25 | 0.25 | 0.5 | 0.25 | 1 |
| 39 | 0.25 | 0.125 | 0.25 | 0.25 | 4 |
| 40 | 0.125 | 0.25 | 0.25 | 0.5 | 2 |
| 41 | 2 | 0.25 | 0.5 | 0.5 | <1 |
| 42 | 0.125 | 0.25 | 0.25 | 0.25 | <1 |
| 43 | 0.125 | 0.25 | 0.5 | 0.5 | 1 |
| 44 | 0.125 | 0.25 | 0.125 | 0.25 | <1 |
| 45 | 0.125 | 0.125 | 0.125 | 0.5 | 1 |
| 46 | 0.125 | 0.25 | 0.25 | 2 | <1 |
| 47 | 0.25 | 0.5 | 0.25 | 0.5 | 1 |
| 48 | 0.125 | 0.25 | 0.5 | 1 | 2 |
| 49 | 0.25 | 0.5 | 0.25 | 1 | <1 |
| 50 | 0.25 | 0.25 | 0.25 | 1 | 1 |
| 51 | 0.25 | 0.5 | 0.5 | 1 | <1 |
| 52 | 0.5 | 0.5 | 0.5 | 4 | 2 |
| 53 | 0.25 | 0.5 | 0.25 | 2 | 1 |
| 54 | 0.25 | 0.5 | 0.5 | 2 | 1 |
| 55 | 0.5 | 1 | 1 | 2 | 1 |
| 56 | 0.5 | 4 | 2 | 4 | <1 |
| 57 | 0.25 | 0.25 | 1 | 0.5 | <1 |
| 58 | 0.125 | 0.125 | 0.25 | 0.5 | <1 |
| 59 | 0.25 | 0.5 | 0.5 | 1 | <1 |
| 60 | 0.0625 | 0.25 | 1 | 0.5 | <1 |
| 61 | 0.5 | 1 | 1 | 0.25 | <1 |
| 62 | 0.25 | 0.5 | 0.5 | 0.5 | 1 |
| 63 | 0.5 | 2 | 2 | 0.5 | <1 |
| 64 | 2 | 2 | 1 | 4 | <1 |

TABLE 3-continued

Minimal inhibitory concentrations (MIC) in Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 100 µg/mL [%] |
|---|---|---|---|---|---|
| 65 | 1 | 1 | 2 | 1 | <1 |
| 66 | 0.25 | 1 | 1 | 1 | 1 |
| 67 | 1 | 2 | 1 | 1 | <1 |
| 68 | 2 | 2 | 2 | 0.5 | <1 |
| 69 | 0.5 | 1 | 1 | 1 | 2 |
| 70 | 1 | 2 | 1 | 0.5 | <1 |
| 71 | 0.125 | 2 | 0.5 | 0.5 | <1 |
| 72 | 1 | 1 | 1 | 1 | <1 |
| 73 | 0.25 | 0.5 | 0.25 | 0.25 | 1 |
| 74 | 2 | 1 | 1 | 1 | 2 |
| 75 | 0.5 | 0.5 | 0.5 | 0.25 | <1 |
| 76 | 2 | 2 | 1 | 0.5 | 1 |
| 77 | 1 | 1 | 1 | 1 | <1 |
| 78 | 0.5 | 0.5 | 0.5 | 0.25 | 1 |
| 79 | 0.5 | 1 | 0.5 | 0.5 | <1 |
| 80 | 0.25 | 0.25 | 0.5 | 0.25 | <1 |
| 81 | 0.5 | 1 | 1 | 0.5 | 1 |
| 82 | 0.5 | 0.5 | 1 | 0.5 | <1 |
| 83 | 2 | 2 | 1 | 1 | 1 |
| 84 | 1 | 2 | 1 | 2 | 1 |
| 85 | 1 | 2 | 1 | 1 | <1 |
| 86 | 0.25 | 0.25 | 1 | 0.5 | 1 |
| 87 | 0.125 | 0.25 | 0.25 | 0.25 | <1 |
| 88 | 0.125 | 0.25 | 0.5 | 0.5 | 1 |
| 89 | 0.125 | 0.25 | 0.125 | 0.25 | 1 |
| 90 | 0.125 | 0.125 | 0.125 | 0.25 | 1 |
| 91 | 0.125 | 0.125 | 0.25 | 0.5 | 1 |
| 92 | 0.125 | 0.25 | 0.25 | 0.25 | 1 |
| 93 | 0.5 | 0.25 | 2 | 0.25 | 1 |
| 94 | 0.0625 | 0.125 | 0.0625 | 0.25 | 1 |
| 95 | 0.25 | 0.5 | 0.5 | 0.5 | 1 |
| 96 | 0.125 | 0.25 | 0.25 | 0.5 | 4 |
| 97 | 0.5 | 0.5 | 2 | 0.5 | 1 |
| 98 | 0.125 | 0.125 | 0.0625 | 0.25 | 2 |
| 99 | 0.125 | 0.25 | 0.25 | 0.5 | 4 |
| 100 | 0.0625 | 0.125 | 0.0625 | 0.125 | 2 |
| 101 | 1 | 1 | 2 | 0.25 | 4 |
| 102 | 0.0625 | 0.125 | 0.0625 | 0.125 | <1 |
| 103 | 0.625 | 0.0625 | 0.0625 | 0.125 | 1 |
| 104 | 0.25 | 0.5 | 0.5 | 1 | 3 |
| 105 | 0.25 | 0.5 | 0.5 | 1 | 1.7 |
| 106 | 0.125 | 0.125 | 0.25 | 0.25 | 1 |
| 107 | 0.125 | 0.5 | 0.0625 | 0.25 | 0.3 |
| 108 | 1 | 2 | 1 | 1 | 2 |
| 109 | 0.25 | 1 | 0.5 | 1 | <1 |
| 110 | 0.5 | 0.5 | 0.25 | 1 | 2 |
| 111 | 0.25 | 1 | 0.25 | 1 | 2 |
| 112 | 1 | 0.5 | 1 | 4 | 1 |
| 113 | 1 | 2 | 1 | 1 | 5 |
| 114 | 0.125 | 0.25 | 0.5 | 0.5 | 6 |
| 115 | 0.5 | 0.5 | 0.5 | 0.5 | 1 |
| 116 | 0.125 | 0.25 | 0.25 | 1 | <1 |
| 117 | 0.5 | 1 | 0.25 | 2 | <1 |
| 118 | 0.5 | 0.5 | 0.25 | 2 | 2 |
| 119 | 0.25 | 1 | 0.5 | 0.25 | 0.5 |
| 120 | 1 | 1 | 0.25 | 1 | <1 |
| 121 | 0.125 | 0.25 | 0.125 | 0.5 | <1 |
| 122 | 0.0625 | 0.5 | 0.125 | 0.5 | 2 |
| 123 | 0.125 | 0.125 | 0.25 | 1 | <1 |
| 124 | 0.0625 | 0.125 | 0.125 | 0.5 | 1 |
| 125 | 0.0625 | 0.125 | 0.125 | 0.5 | 1 |
| 126 | 0.0625 | 0.0625 | 0.0625 | 0.5 | 1 |
| 127 | 1 | 0.25 | 0.25 | 0.5 | 1 |
| 128 | 0.125 | 0.125 | 0.125 | 0.5 | 1 |
| 129 | 0.0625 | 0.125 | 0.125 | 0.125 | 1 |
| 130 | 0.0625 | 0.0625 | 0.0625 | 0.25 | <1 |
| 131 | 0.0625 | 0.125 | 0.125 | 0.5 | <1 |
| 132 | 0.0625 | 0.125 | 0.0625 | 0.25 | <1 |
| 133 | 0.25 | 1 | 1 | 1 | <1 |
| 134 | 0.125 | 0.25 | 0.125 | 1 | <1 |
| 135 | 0.125 | 0.5 | 0.25 | 0.5 | 1 |
| 136 | 0.5 | 1 | 1 | 0.25 | <1 |
| 137 | 0.25 | 0.5 | 0.5 | 1 | 4 |
| 138 | 0.25 | 0.5 | 0.5 | 4 | 3 |
| 139 | 2 | 2 | 1 | 2 | 4 |
| 140 | 0.0625 | 0.0625 | 0.125 | 0.5 | <1 |
| 141 | 0.0625 | 0.125 | 0.125 | 2 | <1 |
| 142 | 0.5 | 0.5 | 0.25 | 0.25 | <1 |
| 143 | 0.03125 | 0.125 | 0.0625 | 0.25 | <1 |
| 144 | 0.25 | 0.25 | 0.125 | 0.25 | 4 |
| 145 | 0.0625 | 0.0625 | 0.03125 | 0.5 | 3 |
| 146 | 0.25 | 0.25 | 0.125 | 0.5 | 3 |
| 147 | 0.0625 | 0.0625 | 0.03125 | 1 | <1 |
| 148 | 0.25 | 1 | 0.5 | 0.125 | <1 |
| 149 | 0.5 | 0.25 | 0.5 | 0.5 | <1 |
| 150 | 0.125 | 0.25 | 0.25 | 1 | <1 |
| 151 | 0.25 | 1 | 1 | 0.5 | <1 |
| 152 | 0.25 | 0.25 | 0.25 | 2 | 1 |
| 153 | 0.0625 | 0.0625 | 0.125 | 0.5 | <1 |
| 154 | 0.0625 | 0.0625 | 0.0625 | 1 | <1 |
| 155 | 0.0625 | 0.0625 | 0.03125 | 1 | <1 |
| 156 | 0.125 | 0.125 | 0.125 | 0.25 | <1 |
| 157 | 0.0625 | 0.125 | 0.0625 | 0.5 | <1 |
| 158 | 0.125 | 0.125 | 0.25 | 0.5 | <1 |
| 159 | 0.5 | 1 | 0.5 | 2 | <1 |
| 160 | 0.5 | 1 | 0.5 | 0.25 | <1 |
| 161 | 0.0625 | 0.125 | 0.25 | 0.5 | <1 |
| 162 | 0.0625 | 0.25 | 0.5 | 1 | <1 |
| 163 | 2 | 2 | 1 | 2 | <1 |
| 164 | 0.0625 | 0.5 | 0.25 | 0.5 | <1 |
| 165 | 0.5 | 1 | 2 | 1 | 1 |
| 166 | 2 | 2 | 2 | 2 | 3 |
| 167 | 0.25 | 0.25 | 0.5 | 0.125 | <1 |
| 168 | 0.5 | 1 | 2 | 0.25 | 3 |
| 169 | 0.5 | 0.25 | 1 | 1 | 1 |
| 170 | 0.5 | 1 | 1 | 0.5 | 1 |
| 171 | 1 | 1 | 2 | 0.5 | 2 |
| 172 | 0.0625 | 0.125 | 0.0625 | 0.125 | 1 |
| 173 | 0.125 | 0.125 | 0.125 | 0.5 | 1 |
| 174 | 0.25 | 0.5 | 0.5 | 2 | 1 |
| 175 | 0.0625 | 0.0625 | 0.0625 | 0.25 | <1 |
| 176 | 0.03125 | 0.0625 | 0.03125 | 0.25 | <1 |
| 177 | 1 | 1 | 1 | 0.5 | 1.4 |
| 178 | 0.5 | 0.5 | 1 | 4 | <1 |
| 179 | 0.0625 | 0.125 | 0.0625 | 1 | <1 |
| 180 | 0.125 | 0.125 | 0.25 | 1 | <1 |
| 181 | 0.0625 | 0.125 | 0.125 | 0.5 | <1 |
| 182 | 0.5 | 0.5 | 0.75 | 4 | 1 |
| 183 | 0.125 | 0.125 | 0.25 | 0.5 | 2 |
| 184 | 0.5 | 0.5 | 0.5 | 0.75 | <1 |
| 185 | 0.25 | 1 | 0.25 | 1 | 1 |
| 186 | 0.125 | 0.125 | 0.1251 | 0.25 | <1 |
| 187 | 0.125 | 0.125 | 0.125 | 1 | <1 |
| 188 | 0.25 | 0.25 | 0.25 | 1 | <1 |
| 189 | 0.25 | 0.5 | 0.5 | 2 | 1 |
| 190 | 0.5 | 0.5 | 0.5 | 1 | <1 |
| 191 | 0.5 | 0.25 | 0.5 | 1 | 6 |
| 192 | 0.25 | 0.25 | 0.25 | 2 | 5 |
| 193 | 0.5 | 0.5 | 1 | 2 | <1 |
| 194 | 0.25 | 0.5 | 0.5 | 2 | <1 |
| 195 | 0.125 | 0.125 | 0.5 | 1 | <1 |
| 196 | 0.125 | 0.25 | 0.25 | 1 | <1 |
| 197 | 0.0625 | 0.25 | 0.5 | 2 | 2 |
| 198 | 0.0625 | 0.125 | 0.25 | 0.5 | 1 |
| 199 | 0.25 | 0.5 | 2 | 2 | <1 |
| 200 | 0.125 | 0.25 | 0.5 | 2 | <1 |
| 201 | 0.25 | 1 | 1 | 1 | <1 |
| 202 | 0.25 | 1 | 1 | 1 | 2 |
| 203 | 0.5 | 1 | 2 | 1 | <1 |
| 204 | 0.25 | 0.25 | 0.5 | 0.5 | 3 |

TABLE 3-continued

Minimal inhibitory concentrations (MIC) in Mueller-Hinton II broth and Hemolysis

| Ex. | Escherichia coli ATCC 25922 MIC [µg/mL] | Klebsiella pneumoniae SSI #3010 MIC [µg/mL] | Acinetobacter baumannii DSM 30008 MIC [µg/mL] | Pseudomonas aeruginosa ATCC 27853 MIC [µg/mL] | Hemolysis at 100 µg/mL [%] |
|---|---|---|---|---|---|
| 205 | 0.25 | 2 | 2 | 0.25 | <1 |
| 206 | 0.5 | 1 | 4 | 4 | 1 |
| 207 | 0.125 | 0.125 | 2 | 2 | 1 |
| 208 | 0.25 | 1 | 1 | 2 | <1 |
| 209 | 0.125 | 0.25 | 0.5 | 1 | 3 |
| 210 | 0.25 | 0.5 | 1 | 1 | 1 |
| 211 | 0.5 | 1 | 1 | 2 | 2 |
| 212 | 0.5 | 2 | 1 | 0.5 | 1 |
| 213 | 0.125 | 0.5 | 0.5 | 0.5 | 3 |
| 214 | 0.5 | 1 | 2 | 0.5 | 1 |
| 215 | 0.25 | 0.25 | 0.25 | 1 | <1 |
| 216 | 0.125 | 0.125 | 0.125 | 0.5 | 1 |

TABLE 4

Minimal inhibitory concentrations (MIC) of selected clinical isolates of Escherichia coli, Klebsiella pneumonia and Acintobacter baumannii in Mueller-Hinton II broth

| Ex. | Escherichia coli 926415 MIC [µg/mL] | Klebsiella pneumoniae 968733 MIC [µg/mL] | Acinetobacter baumannii 872842 MIC [µg/mL] |
|---|---|---|---|
| 1 | 1 | 4 | 2 |
| 2 | 2 | 4 | 2 |
| 3 | 0.25 | 1 | 2 |
| 4 | 1 | 8 | 2 |
| 5 | 0.5 | 2 | 1 |
| 6 | 1 | 2 | 2 |
| 7 | 0.25 | 2 | 1 |
| 8 | 1 | 2 | 0.5 |
| 9 | 1 | 2 | 2 |
| 10 | 0.5 | 2 | 1 |
| 12 | 0.125 | 0.5 | 0.125 |
| 13 | 0.5 | 1 | 0.25 |
| 14 | 4 | 8 | 1 |
| 15 | 0.125 | 2 | 0.25 |
| 16 | 0.125 | 0.375 | 0.25 |
| 17 | 1.5 | 0.5 | 0.25 |
| 18 | 0.5 | 0.5 | 1 |
| 19 | 0.25 | 0.75 | 0.75 |
| 20 | 0.25 | 1 | 0.5 |
| 21 | 1 | 2 | 1 |
| 22 | 0.5 | 1 | 0.125 |
| 23 | 0.5 | 2 | 0.5 |
| 25 | 3 | 8 | 1 |
| 26 | 0.25 | 0.5 | 0.125 |
| 27 | 0.5 | 0.5 | 0.125 |
| 28 | 1.5 | 0.375 | 1 |
| 29 | 1 | 1 | 0.25 |
| 30 | 1 | 0.25 | 1 |
| 31 | 1.5 | 0.75 | 1 |
| 32 | 0.5 | 1 | 0.25 |
| 33 | 1 | 0.75 | 0.25 |
| 34 | 0.25 | 1 | 0.125 |
| 35 | 0.5 | 2 | 1 |
| 36 | 0.25 | 0.5 | 0.5 |
| 37 | 0.5 | 2 | 0.5 |
| 38 | 0.125 | 2 | 0.5 |
| 39 | 0.25 | 2 | 0.5 |
| 40 | 0.5 | 4 | 0.125 |
| 41 | 0.5 | 1 | 0.5 |
| 42 | 0.25 | 2 | 0.25 |
| 43 | 1.5 | 0.5 | 1.5 |
| 44 | 0.25 | 2 | 0.5 |
| 45 | 0.25 | 0.25 | 0.25 |
| 46 | 0.5 | 2 | 0.5 |
| 47 | 0.5 | 1 | 0.5 |
| 48 | 0.25 | 1 | 0.5 |
| 49 | 0.5 | 1 | 1 |
| 50 | 0.5 | 2 | 0.5 |
| 51 | 2 | 4 | 4 |
| 52 | 3 | 2 | 4 |
| 53 | 1 | 8 | 2 |
| 54 | 1 | 4 | 1 |
| 57 | 1 | 8 | 4 |
| 58 | 0.25 | 2 | 0.5 |
| 59 | 0.5 | 2 | 2 |
| 60 | 0.25 | 1 | 1 |
| 61 | 2 | 8 | 1 |
| 62 | 1 | 8 | 0.5 |
| 63 | 3 | 8 | 2 |
| 65 | 1 | 2 | 4 |
| 66 | 2 | 2 | 4 |
| 67 | 2 | 2 | 4 |
| 69 | 2 | 2 | 4 |
| 70 | 1 | 8 | 2 |
| 71 | 0.25 | 2 | 1 |
| 72 | 0.5 | 1 | 1 |
| 73 | 0.5 | 0.5 | 0.5 |
| 74 | 1 | 2 | 4 |
| 75 | 1 | 4 | 2 |
| 76 | 0.5 | 2 | 0.5 |
| 77 | 0.5 | 2 | 2 |
| 78 | 0.5 | 0.5 | 1 |
| 79 | 2 | 8 | 2 |
| 80 | 0.25 | 1 | 0.5 |
| 81 | 0.5 | 2 | 2 |
| 82 | 0.5 | 0.5 | 0.5 |
| 83 | 1 | 4 | 1 |
| 84 | 1 | 2 | 2 |
| 85 | 2 | 8 | 1 |
| 86 | 0.25 | 0.5 | 0.5 |
| 87 | 0.125 | 0.25 | 0.5 |
| 88 | 1 | 2 | 1 |
| 89 | 1 | 0.5 | 1 |
| 90 | 0.25 | 0.25 | 0.25 |
| 91 | 0.5 | 1 | 0.5 |
| 92 | 0.5 | 0.5 | 0.5 |
| 93 | 2 | 8 | 1 |
| 94 | 1 | 0.5 | 0.25 |
| 95 | 1 | 1 | 1 |
| 96 | 0.25 | 1 | 1 |
| 98 | 0.5 | 0.5 | 0.25 |
| 99 | 0.25 | 0.5 | 0.25 |
| 100 | 0.5 | 2 | 0.25 |
| 102 | 0.25 | 0.5 | 0.5 |
| 103 | 0.125 | 0.0625 | 0.25 |
| 104 | 0.25 | 1 | 0.25 |
| 105 | 0.125 | 1 | 0.25 |
| 106 | 0.125 | 0.5 | 0.125 |
| 107 | 0.125 | 0.5 | 0.125 |
| 108 | 0.5 | 2 | 1 |
| 109 | 0.5 | 1 | 0.5 |
| 110 | 0.25 | 2 | 0.25 |
| 111 | 0.25 | 1 | 0.25 |
| 112 | 1 | 0.5 | 1 |
| 113 | 0.5 | 4 | 0.25 |
| 114 | 0.0625 | 0.5 | 0.125 |
| 115 | 0.5 | 1 | 0.5 |
| 116 | 0.0625 | 0.5 | 0.125 |
| 117 | 0.25 | 2 | 0.125 |
| 118 | 0.5 | 0.5 | 0.25 |
| 119 | 1 | 4 | 0.5 |
| 120 | 2 | 8 | 0.25 |

TABLE 4-continued

Minimal inhibitory concentrations (MIC) of selected clinical isolates of *Escherichia coli*, *Klebsiella pneumonia* and *Acintobacter baumannii* in Mueller-Hinton II broth

| Ex. | *Escherichia coli* 926415 MIC [µg/mL] | *Klebsiella pneumoniae* 968733 MIC [µg/mL] | *Acinetobacter baumannii* 872842 MIC [µg/mL] |
|---|---|---|---|
| 121 | 0.125 | 0.25 | 0.125 |
| 122 | 0.25 | 1 | 0.03125 |
| 123 | 0.25 | 4 | 0.0625 |
| 124 | 0.125 | 0.5 | 0.25 |
| 125 | 0.25 | 1 | 0.0625 |
| 126 | 0.5 | 0.5 | 0.125 |
| 127 | 2 | 8 | 0.25 |
| 128 | 0.5 | 4 | 0.25 |
| 129 | 0.25 | 2 | 0.0625 |
| 130 | 0.25 | 0.125 | 0.0625 |
| 131 | 0.25 | 0.25 | 0.125 |
| 132 | 0.1255 | 0.125 | 0.0625 |
| 133 | 4 | 8 | 4 |
| 135 | 1 | 8 | 0.5 |
| 136 | 0.5 | 4 | 0.25 |
| 137 | 0.5 | 0.5 | 0.5 |
| 138 | 4 | 2 | 1 |
| 139 | 1 | 4 | 2 |
| 140 | 0.125 | 1 | 0.125 |
| 141 | 0.125 | 2 | 0.125 |
| 142 | 0.25 | 1 | 0.125 |
| 143 | 0.0625 | 0.125 | 0.0625 |
| 144 | 0.5 | 1 | 0.25 |
| 145 | 0.125 | 0.5 | 0.0625 |
| 146 | 4 | 4 | 1 |
| 147 | 0.0625 | 0.5 | 0.0625 |
| 148 | 0.5 | 4 | 0.25 |
| 149 | 0.125 | 0.5 | 0.0625 |
| 150 | 0.5 | 8 | 0.25 |
| 151 | 2 | 8 | 0.5 |
| 152 | 2 | 8 | 0.125 |
| 153 | 0.125 | 0.0625 | 0.03125 |
| 154 | 0.125 | 0.25 | 0.03125 |
| 155 | 0.25 | 0.5 | 0.0625 |
| 156 | 1 | 0.5 | 0.0625 |
| 157 | 0.125 | 1 | 0.03125 |
| 158 | 4 | 8 | 0.25 |
| 159 | 2 | 8 | 0.25 |
| 160 | 2 | 4 | 1 |
| 161 | 0.25 | 2 | 0.5 |
| 162 | 0.25 | 2 | 0.125 |
| 167 | 1 | 2 | 1 |
| 168 | 0.5 | 4 | 1 |
| 169 | 0.5 | 2 | 1 |
| 170 | 0.25 | 0.5 | 0.125 |
| 171 | 2 | 4 | 2 |
| 172 | 0.5 | 0.5 | 0.25 |
| 173 | 0.5 | 1 | 0.25 |
| 175 | 0.5 | 0.5 | 1 |
| 176 | 0.0625 | 0.25 | 0.5 |
| 177 | 2 | 2 | 2 |
| 178 | 1 | 8 | 2 |
| 179 | 0.125 | 0.5 | 0.0625 |
| 184 | 1 | 1 | 1 |
| 185 | 2 | 8 | 1 |
| 186 | 0.25 | 0.5 | 0.0625 |
| 187 | 2 | 1 | 1 |
| 188 | 0.25 | 4 | 1 |
| 189 | 0.5 | 1 | 0.125 |
| 191 | 0.125 | 0.5 | 0.25 |
| 193 | 0.5 | 1 | 1 |
| 194 | 1 | 2 | 2 |
| 196 | 0.125 | 0.5 | 0.5 |
| 197 | 0.25 | 2 | 4 |
| 198 | 0.5 | 1 | 1 |
| 199 | 0.5 | 4 | 0.5 |
| 200 | 0.5 | 1 | 1 |
| 201 | 0.5 | 8 | 0.5 |
| 202 | 0.5 | 2 | 0.5 |
| 203 | 0.25 | 4 | 0.5 |
| 204 | 0.125 | 0.5 | 0.25 |
| 205 | 0.5 | 2 | 0.5 |
| 207 | 0.25 | 0.5 | 1 |
| 208 | 0.5 | 8 | 2 |
| 209 | 0.25 | 0.5 | 0.5 |
| 210 | 0.5 | 4 | 2 |
| 211 | 2 | 8 | 2 |
| 212 | 1 | 4 | 1 |
| 213 | 0.5 | 1 | 0.5 |
| 214 | 2 | 8 | 0.5 |
| 215 | 0.25 | 0.5 | 1 |
| 216 | 0.0625 | 0.25 | 0.5 |
| Colistin[1),3)] | 16 | 16 | 64 |
| Colistin[2),3)] | 8 | >8 | >8 |

[1)]measured in absence of P-80
[2)]measured in presence of P-80
[3)]Colistin (Colistin sulfate salt, Cat-Nr. C4461, Lot-Nr. SLBK0713V) obtained from Sigma Aldrich, Buchs; Switzerland

The invention claimed is:
1. A compound of formula (I) or a pharmaceutically acceptable salt thereof, wherein the compound is selected from the group consisting of Ex. 1 to 216:

| Ex. No. | |
|---|---|
| Ex. 1 | |

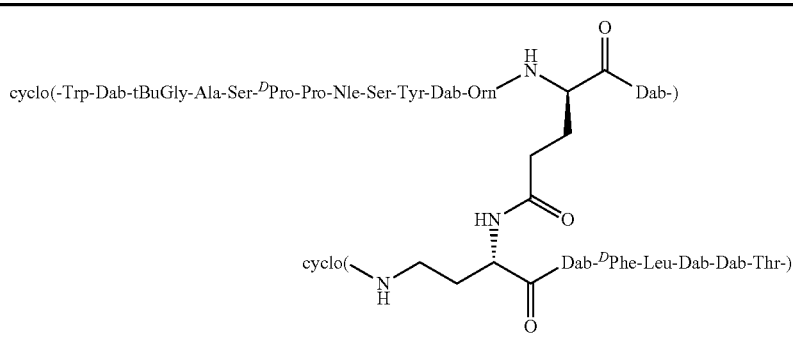

cyclo(-Trp-Dab-tBuGly-Ala-Ser-*D*Pro-Pro-Nle-Ser-Tyr-Dab-Orn—Dab-)

cyclo(—Dab-*D*Phe-Leu-Dab-Dab-Thr-)

| Ex. No. | |
|---|---|
| Ex. 2 | 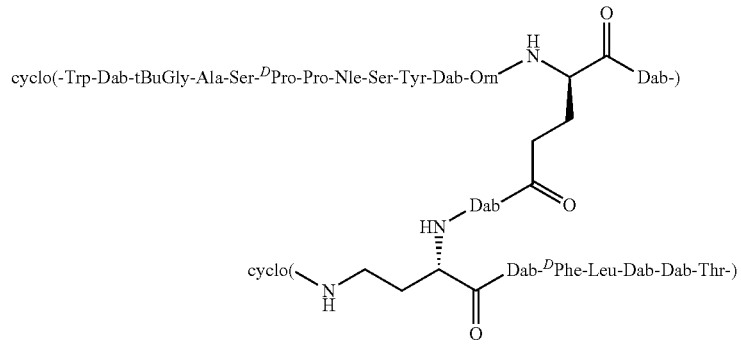 |
| Ex. 3 | 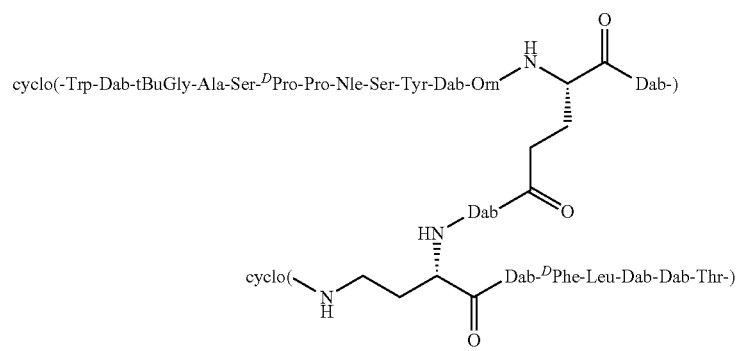 |
| Ex. 4 | 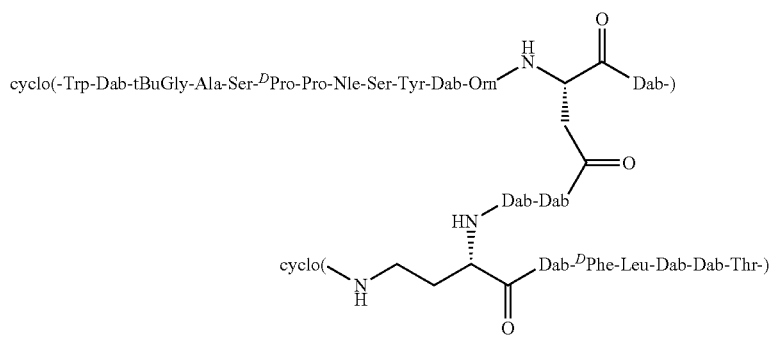 |
| Ex. 5 | 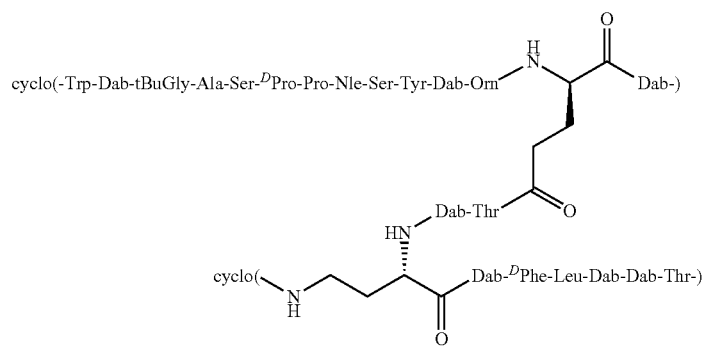 |

| Ex. No. | |
|---|---|
| Ex. 6 | 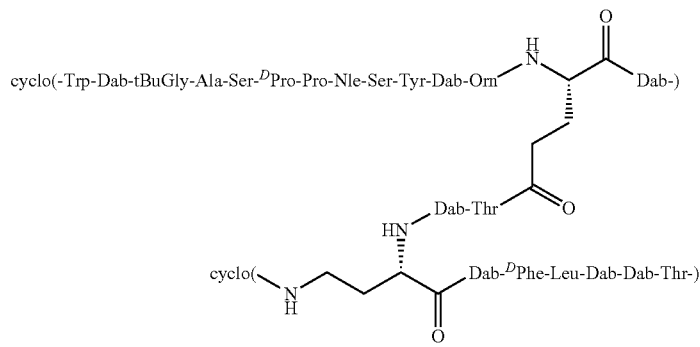 |
| Ex. 7 | 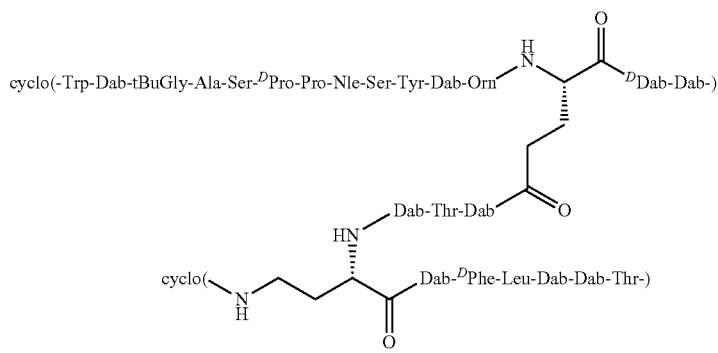 |
| Ex. 8 | 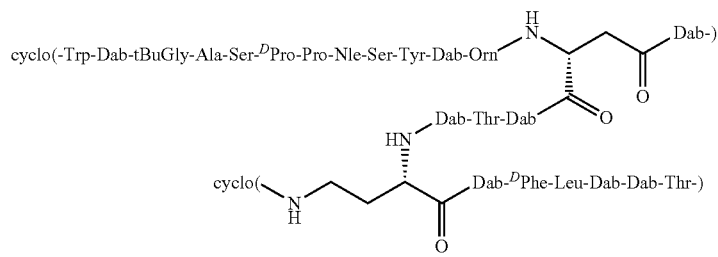 |
| Ex. 9 | 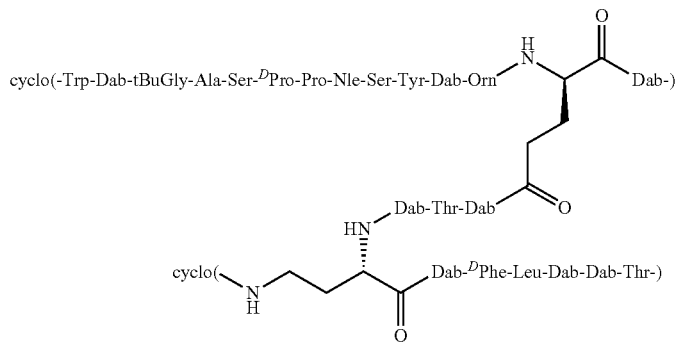 |

| Ex. No. | |
|---|---|
| Ex. 10 | 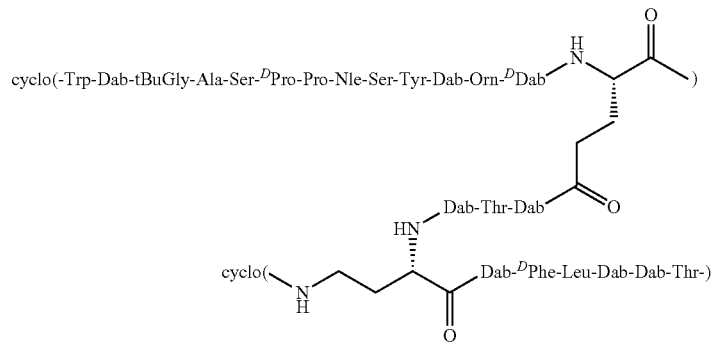 |
| Ex. 11 | 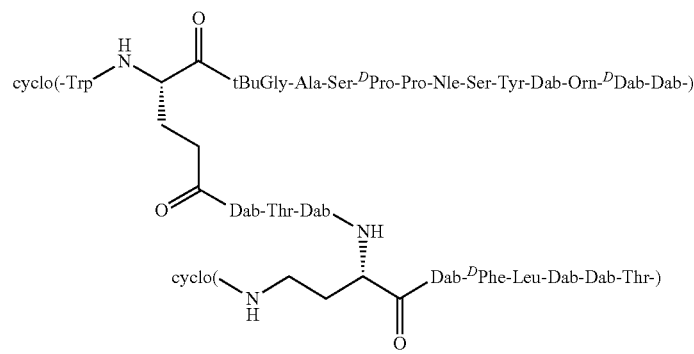 |
| Ex. 12[a)] | 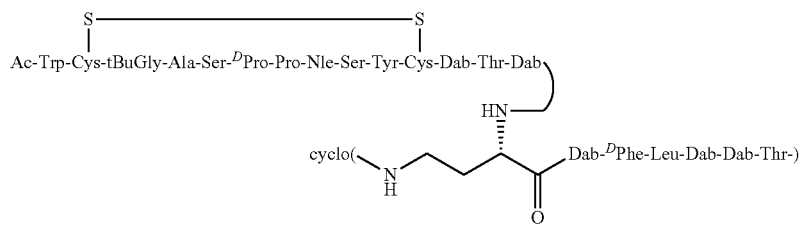 |
| Ex. 13[a)] | 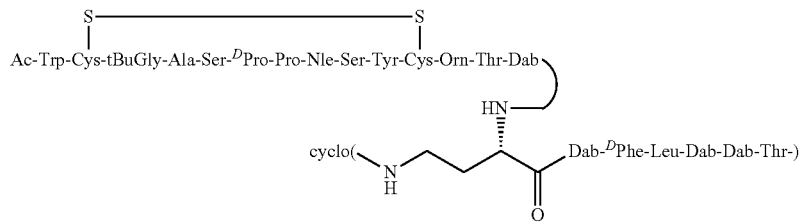 |
| Ex. 14[b)] | 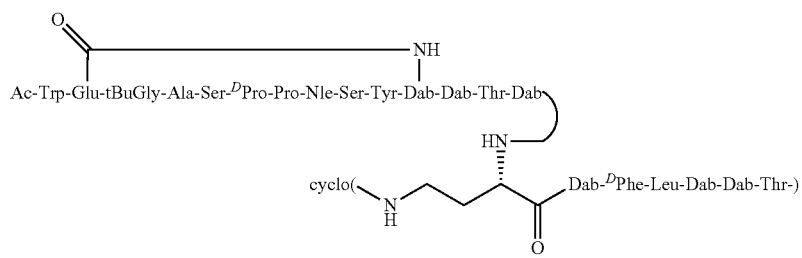 |

| Ex. No. | |
|---|---|
| Ex. 15[a] | 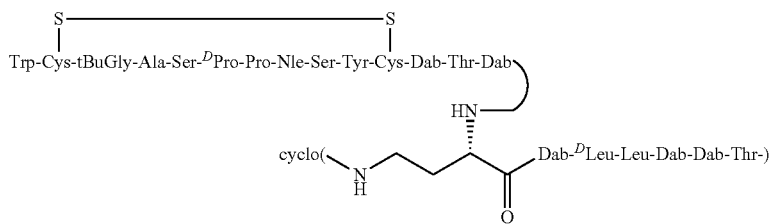 |
| Ex. 16[a] | 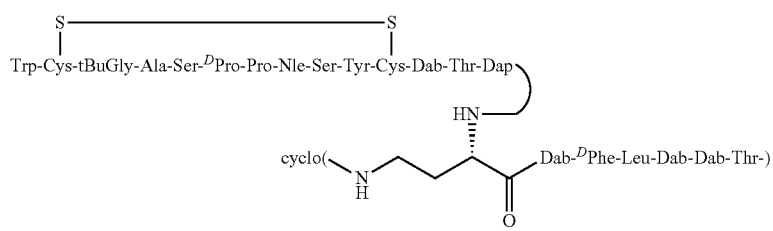 |
| Ex. 17[a] | 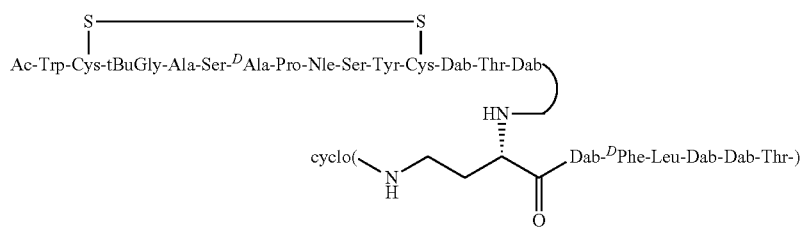 |
| Ex. 18[a] | 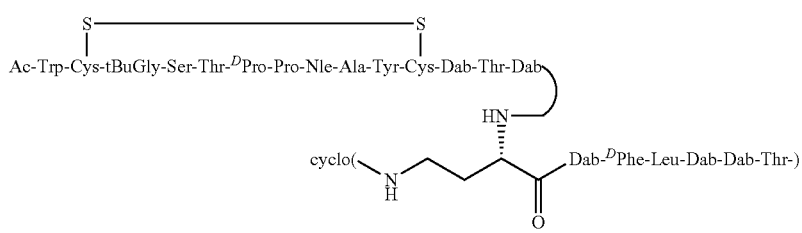 |
| Ex. 19[a] | 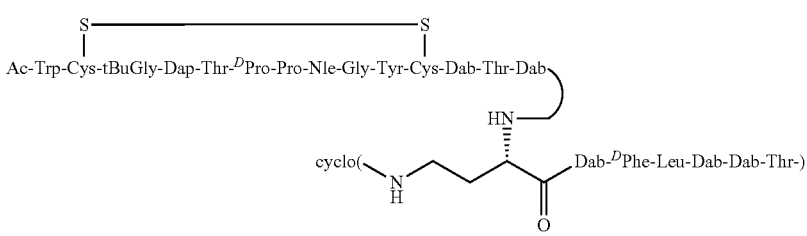 |
| Ex. 20 | 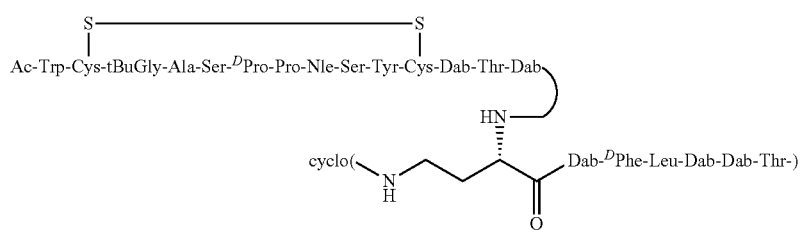 |

-continued
| Ex. No. | |
|---|---|
| Ex. 21[a)] | 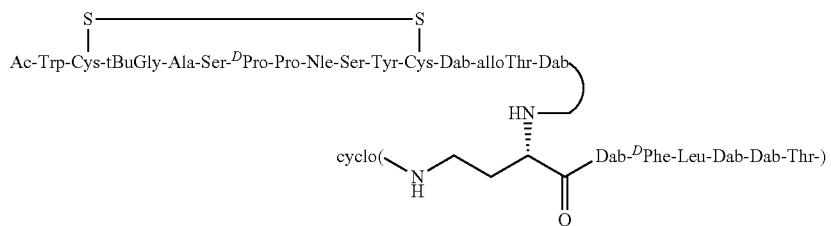 |
| Ex. 22[a)] | 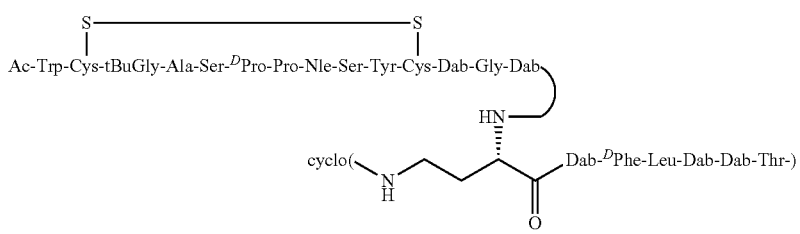 |
| Ex. 23[a)] | 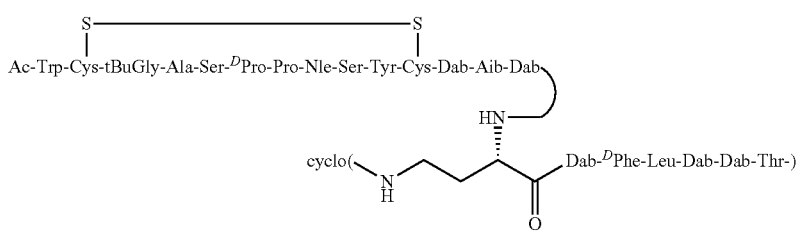 |
| Ex. 24[a) c)] | 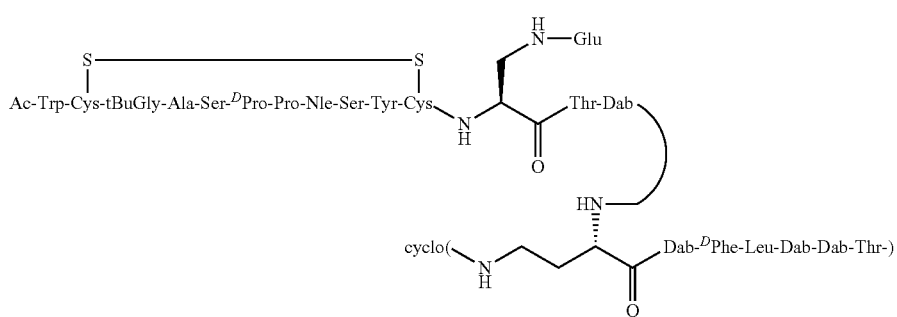 |
| Ex. 25[a) c)] | 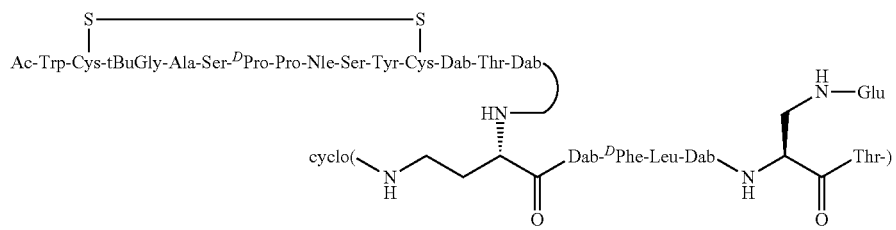 |
| Ex. 26[a)] | 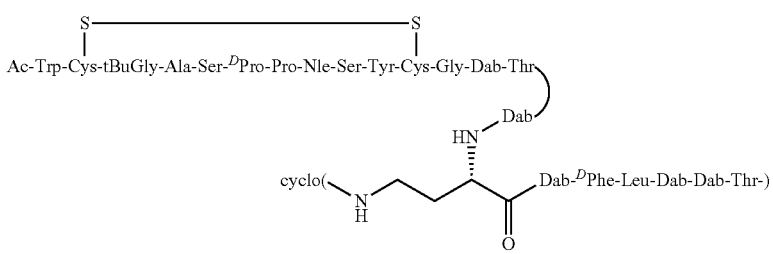 |

| Ex. No. | |
|---|---|
| Ex. 27[a] | 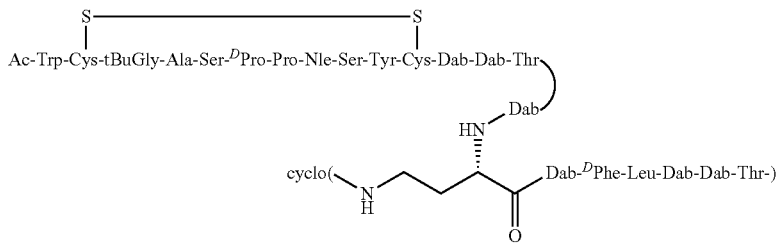 |
| Ex. 28[a] | 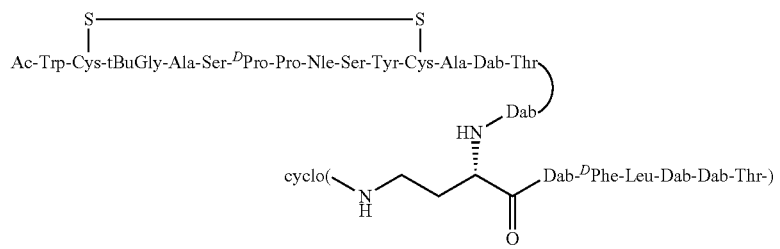 |
| Ex. 29[a] | 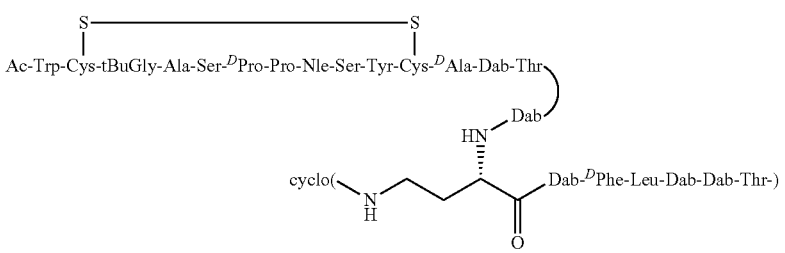 |
| Ex. 30[a] | 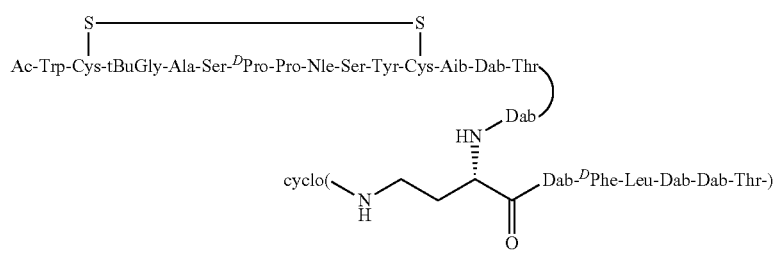 |
| Ex. 31[a] | 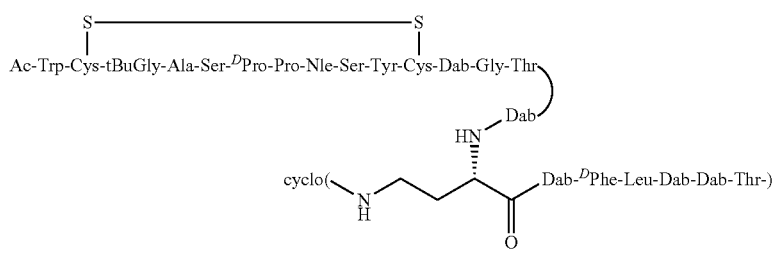 |
| Ex. 32[a] | 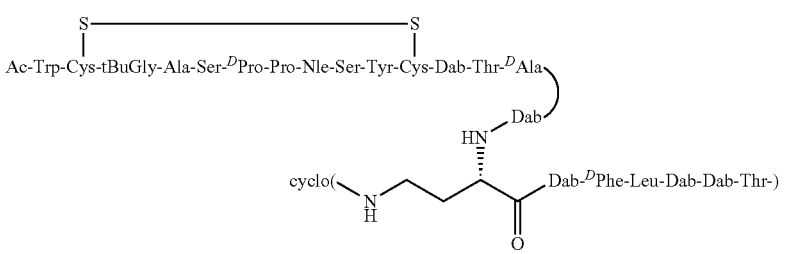 |

| Ex. No. | |
|---|---|
| Ex. 33[a)] | 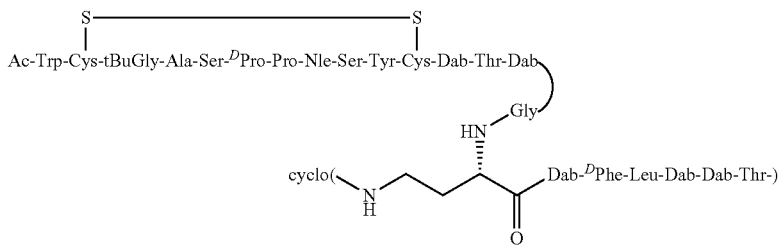 |
| Ex. 34[a)] | 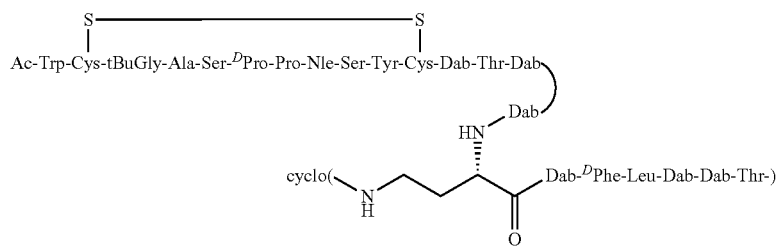 |
| Ex. 35[a)] | 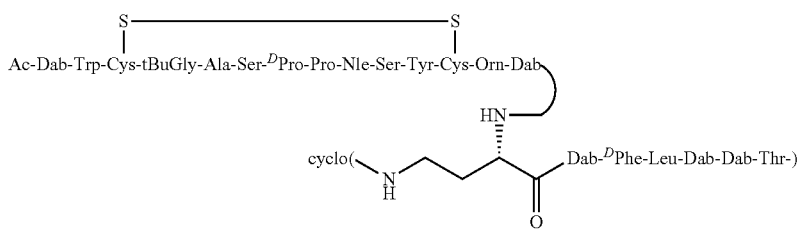 |
| Ex. 36[a)] | 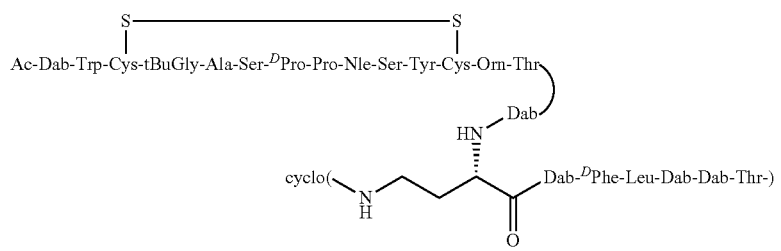 |
| Ex. 37[a)] | 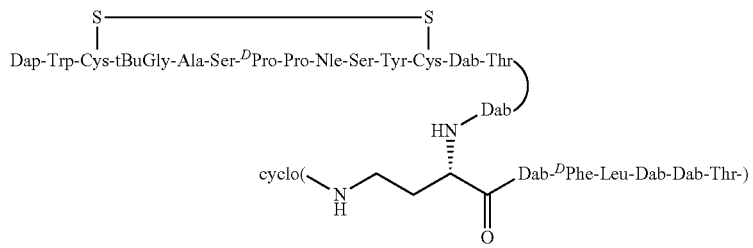 |
| Ex. 38[a)] | 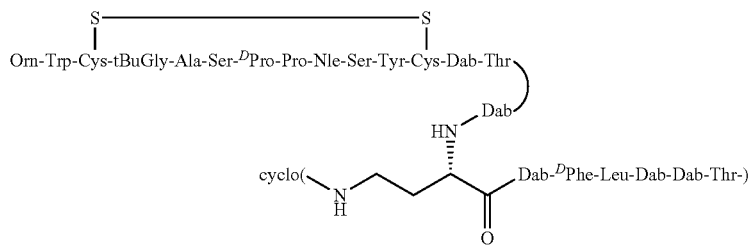 |

| Ex. No. | |
|---|---|
| Ex. 39[a)] | 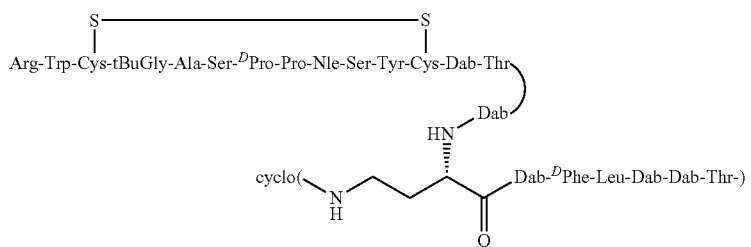 |
| Ex. 40[a)] | 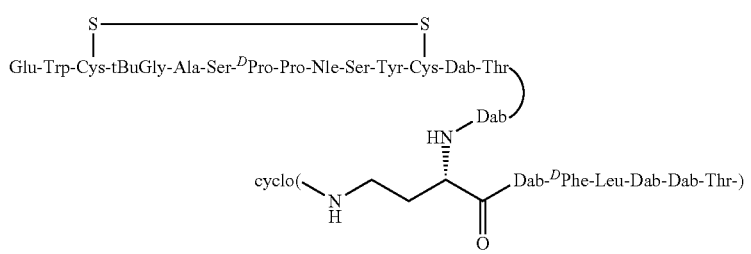 |
| Ex. 41[a)] | 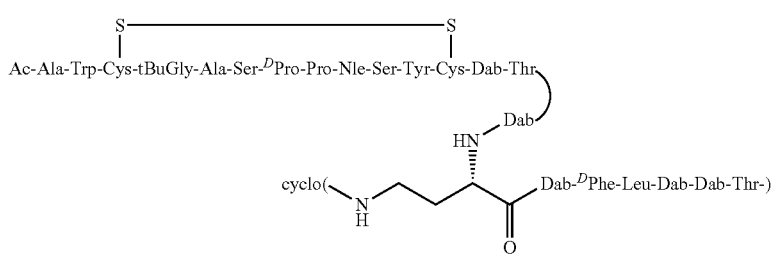 |
| Ex. 42[a)] | 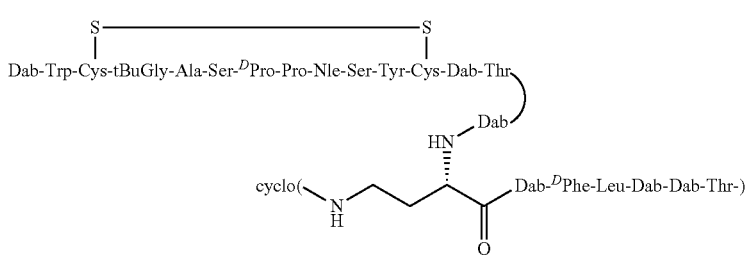 |
| Ex. 43[a)] | 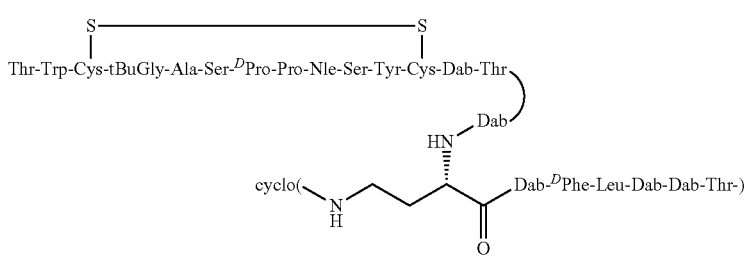 |
| Ex. 44[a)] | 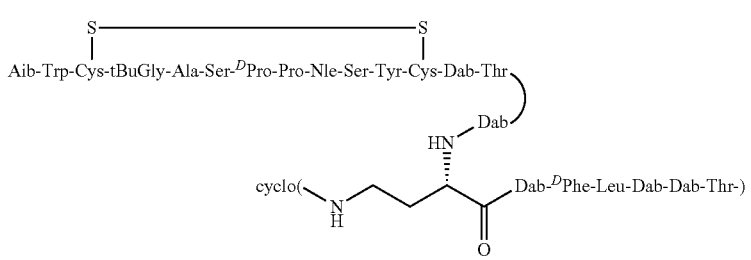 |

| Ex. No. | |
|---|---|
| Ex. 45[a)] | 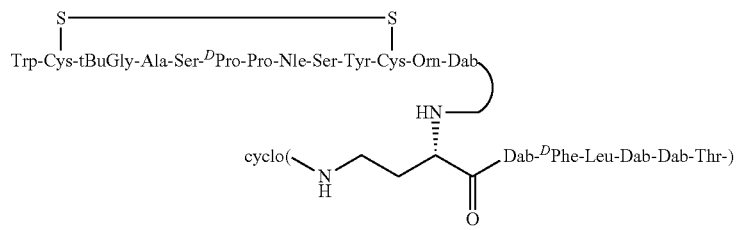 |
| Ex. 46[a)] | 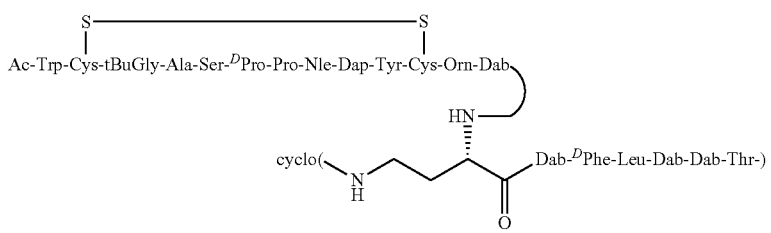 |
| Ex. 47[a)] | 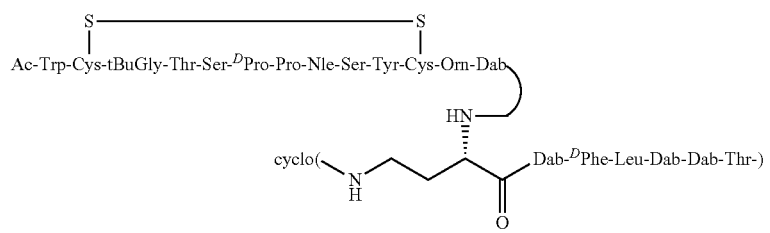 |
| Ex. 48[a)] | 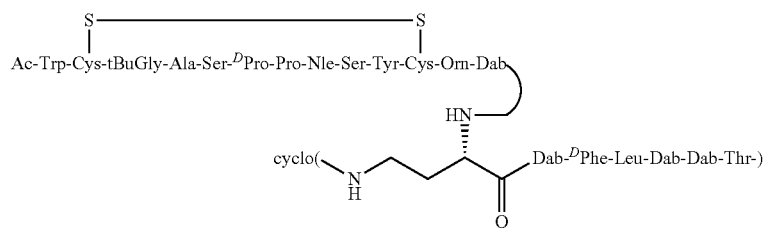 |
| Ex. 49[a)] | 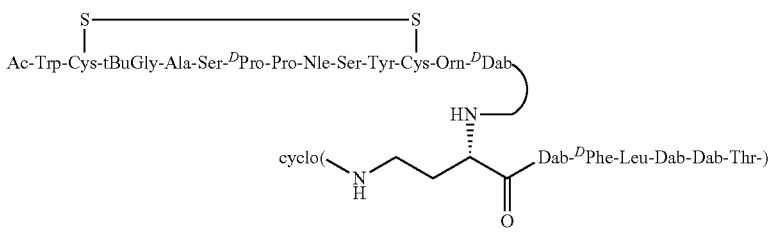 |
| Ex. 50[a)] | 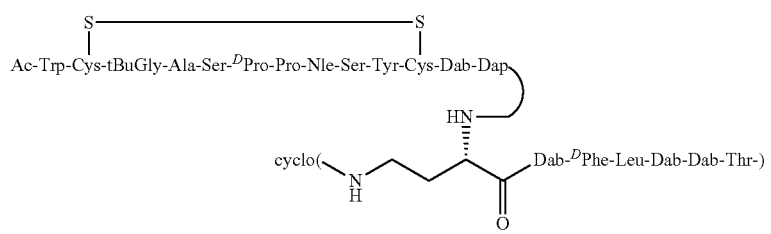 |

| Ex. No. | |
|---|---|
| Ex. 51[a] | 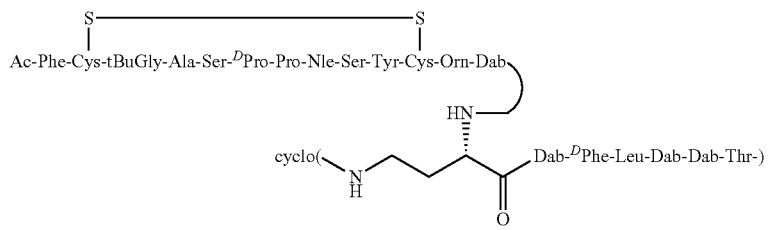 |
| Ex. 52[a] | 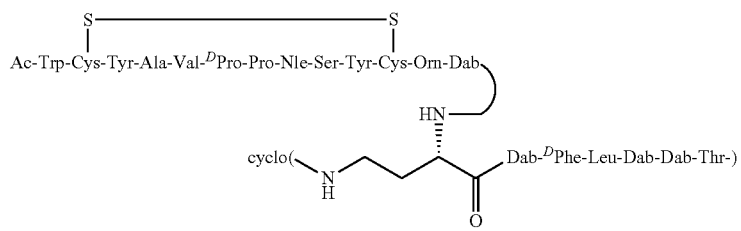 |
| Ex. 53[a] | 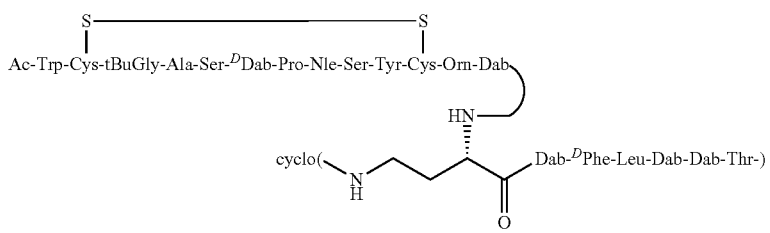 |
| Ex. 54[a] | 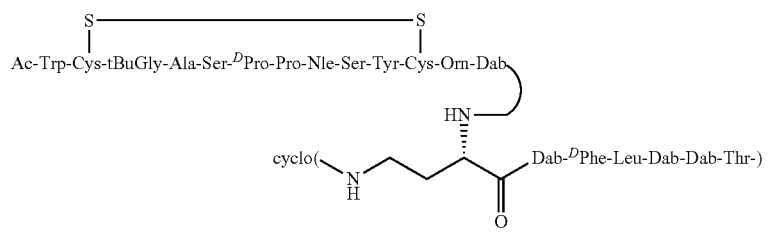 |
| Ex. 55[a] | 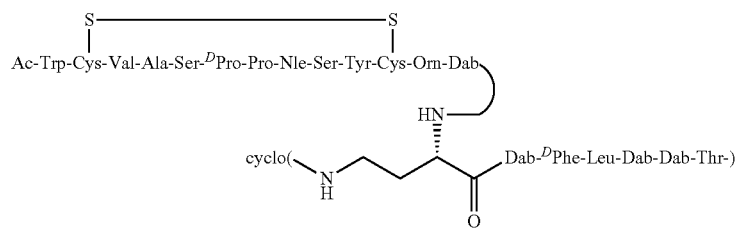 |
| Ex. 56[b] | 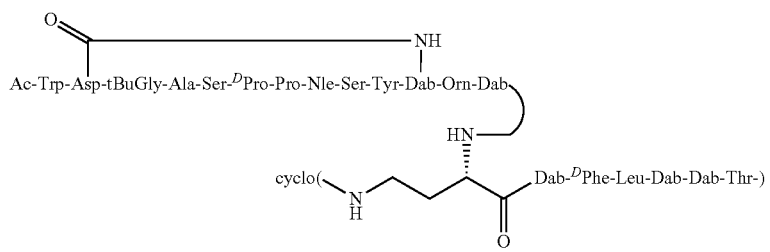 |

| Ex. No. | |
|---|---|
| Ex. 57[a] | 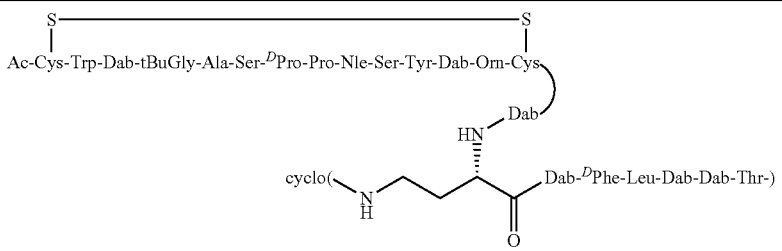 |
| Ex. 58[b] | 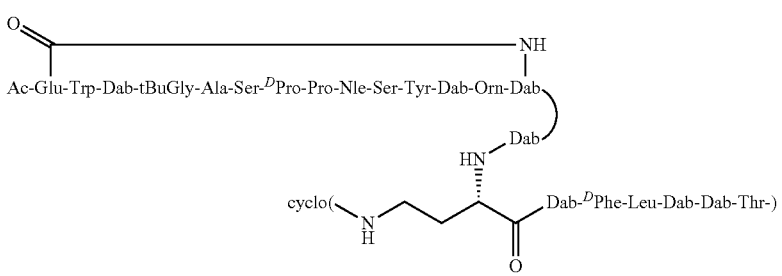 |
| Ex. 59[b] | 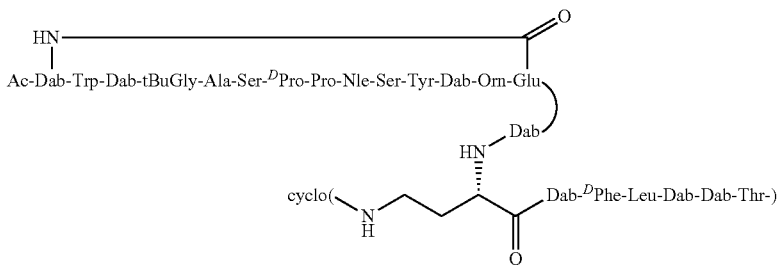 |
| Ex. 60[a] | 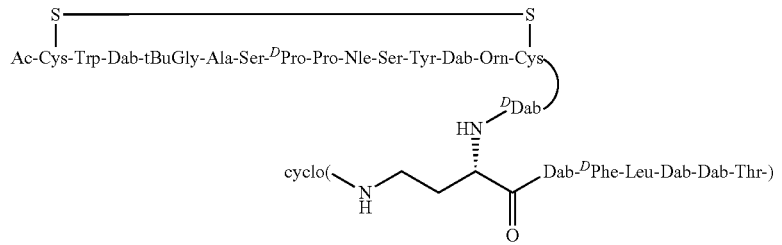 |
| Ex. 61[a] | 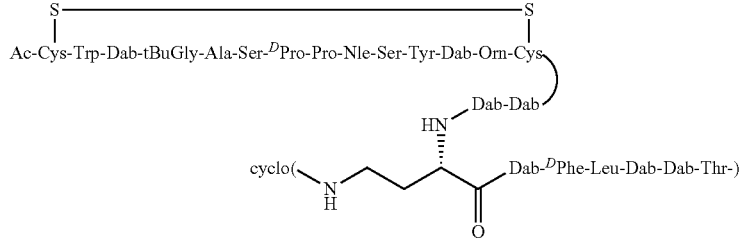 |
| Ex. 62[a] | 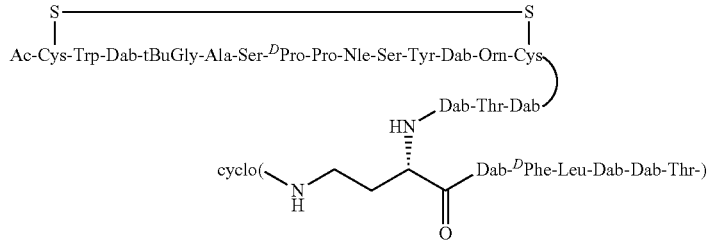 |

| Ex. No. | |
|---|---|
| Ex. 63[a)] | 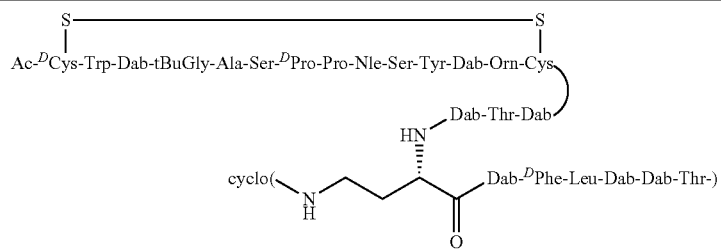 |
| Ex. 64 | 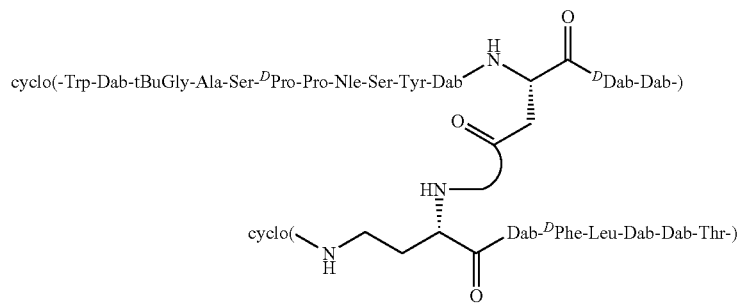 |
| Ex. 65 | 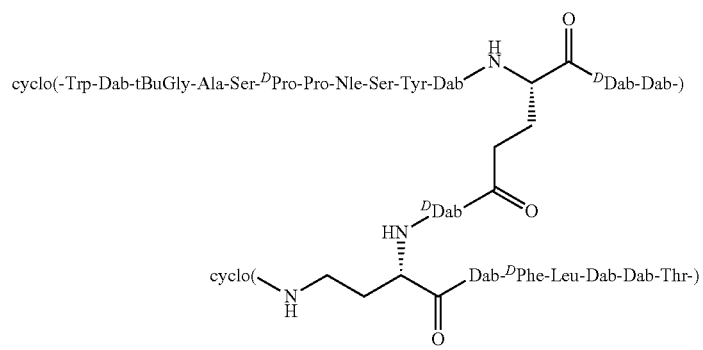 |
| Ex. 66 | 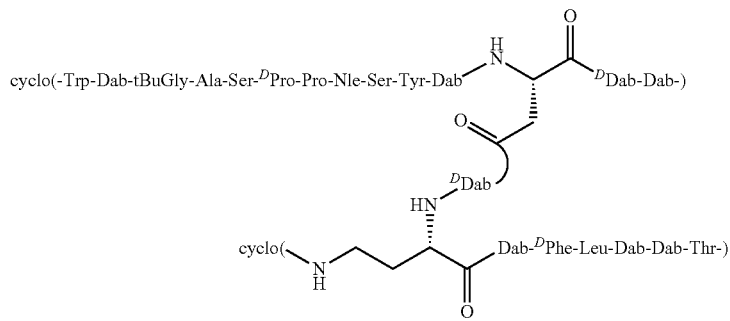 |
| Ex. 67 | 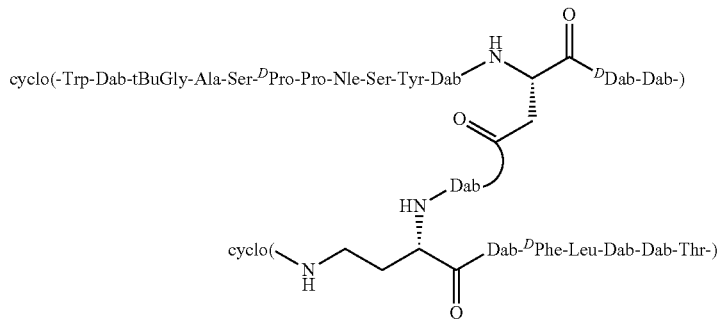 |

| Ex. No. | |
|---|---|
| Ex. 68 | 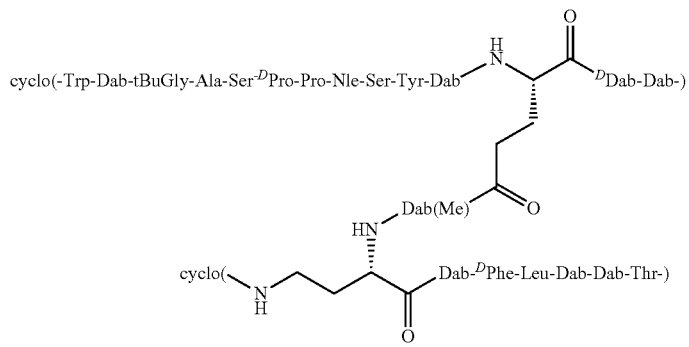 |
| Ex. 69 | 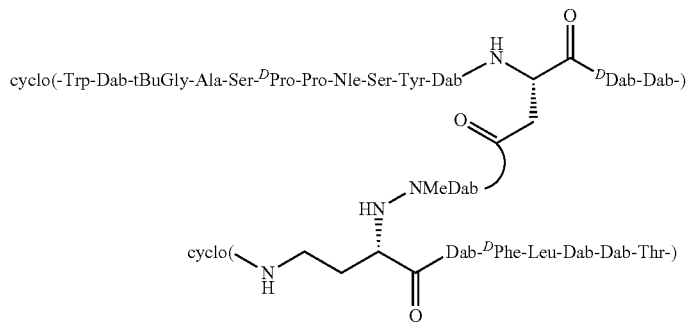 |
| Ex. 70 | 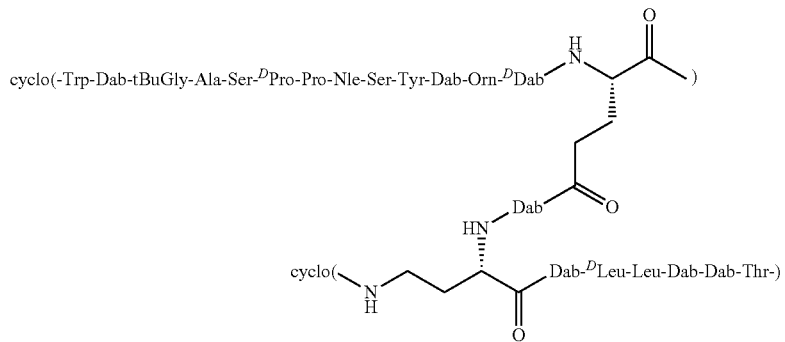 |
| Ex. 71 | 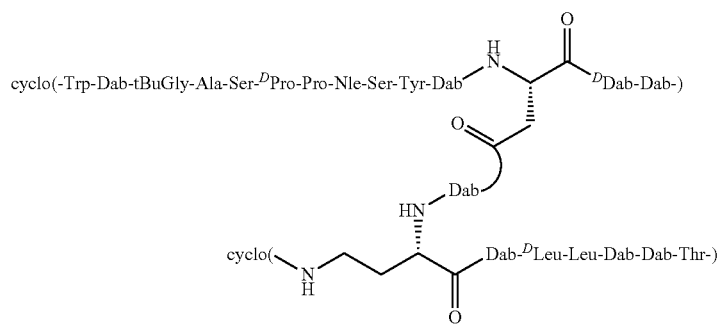 |

| Ex. No. | |
|---|---|
| Ex. 72 | 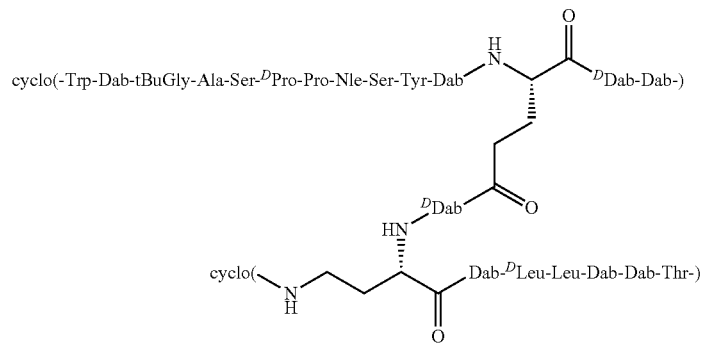 |
| Ex. 73 | 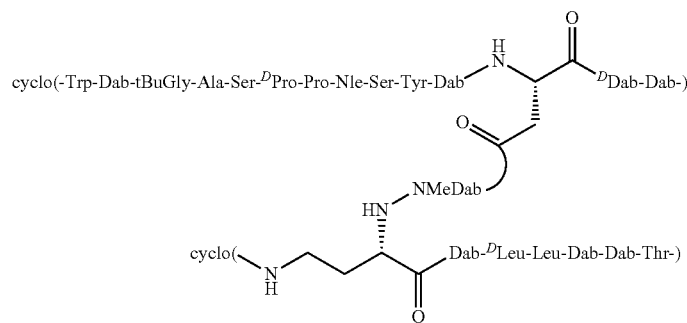 |
| Ex. 74 | 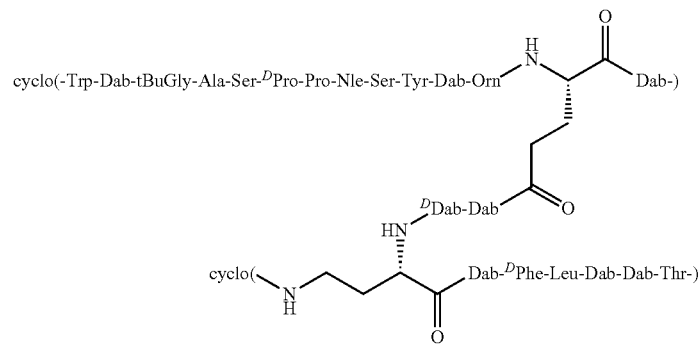 |
| Ex. 75 | 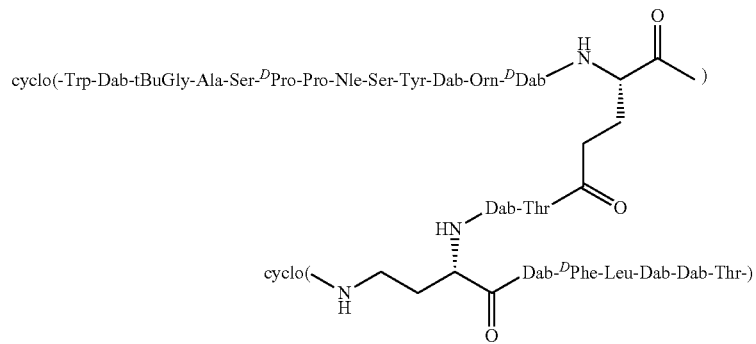 |

| Ex. No. | |
|---|---|
| Ex. 76 | 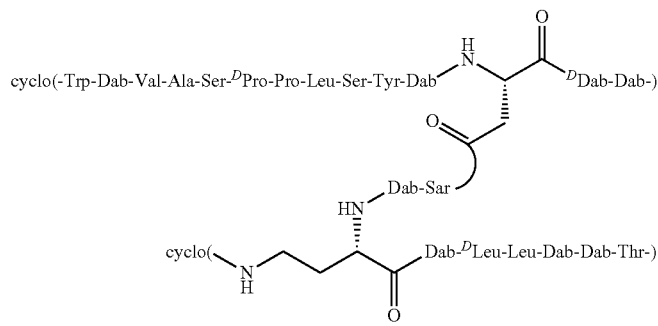 |
| Ex. 77 | 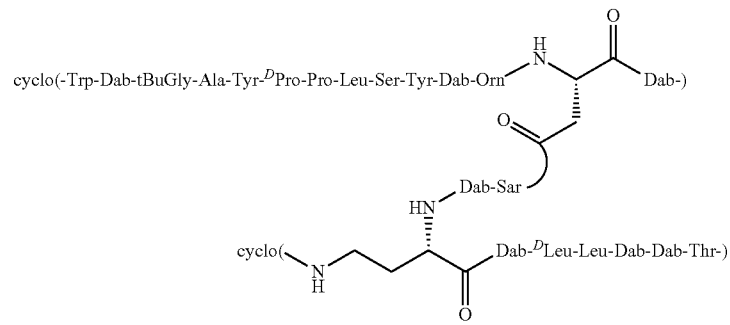 |
| Ex. 78 | 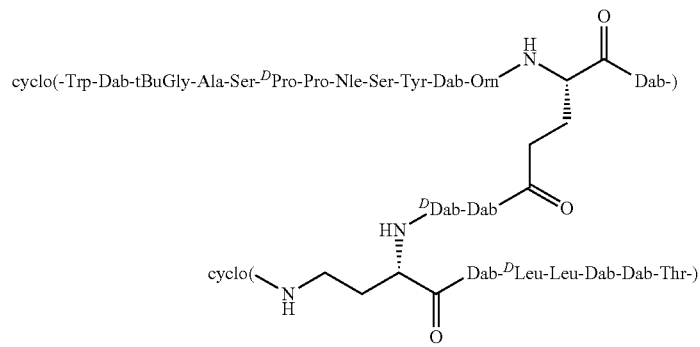 |
| Ex. 79[a)] | 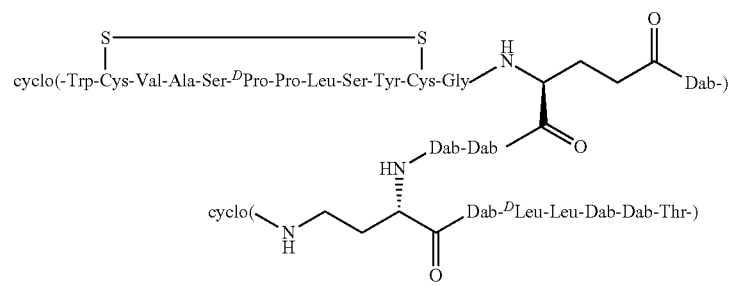 |

| Ex. No. | |
|---|---|
| Ex. 80 | 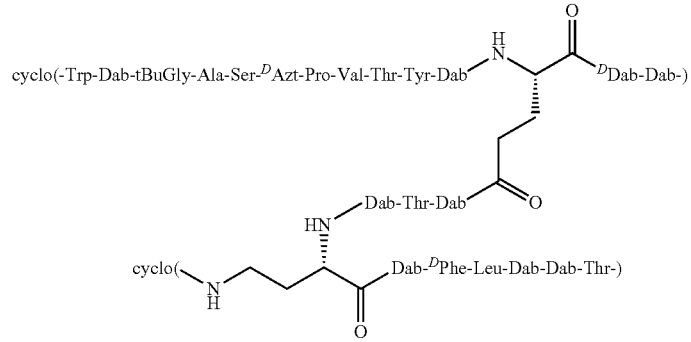 |
| Ex. 81 | 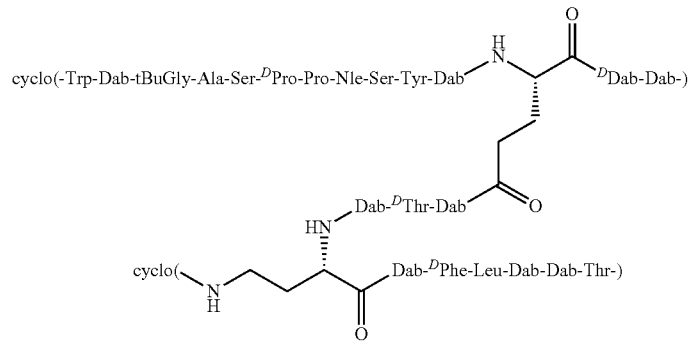 |
| Ex. 82 | 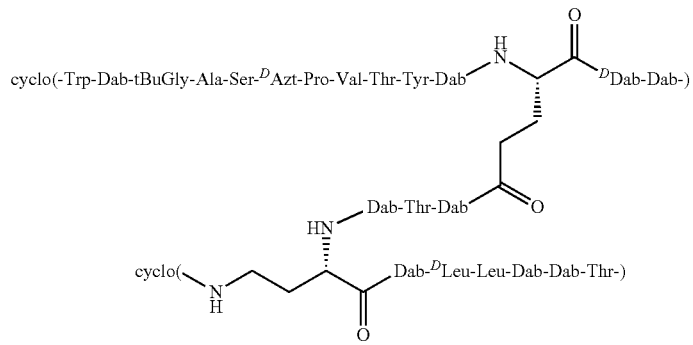 |
| Ex. 83 | 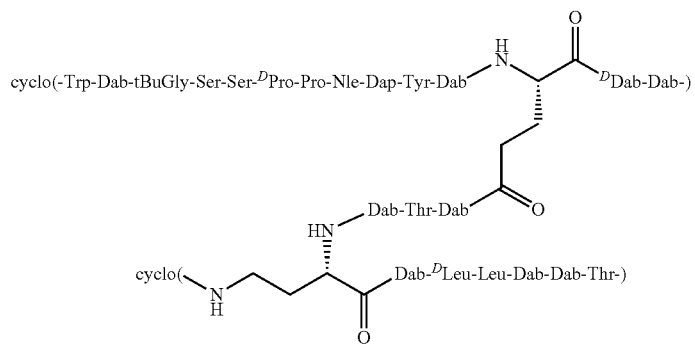 |

-continued
| Ex. No. | |
|---|---|
| Ex. 84 | 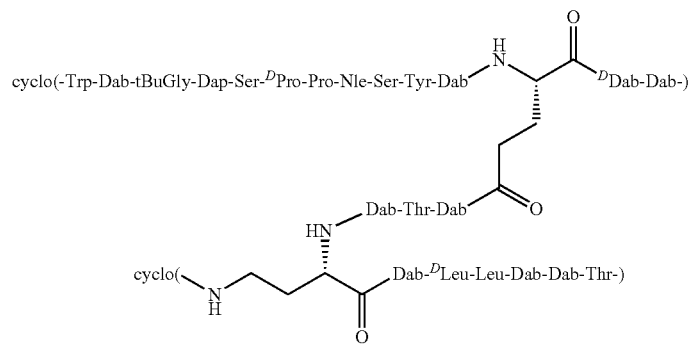 |
| Ex. 85 | 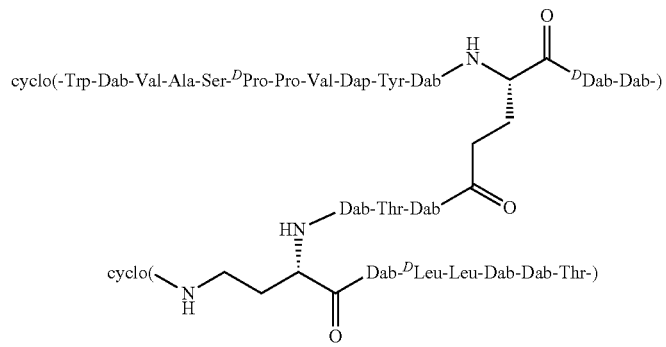 |
| Ex. 86[b)] | 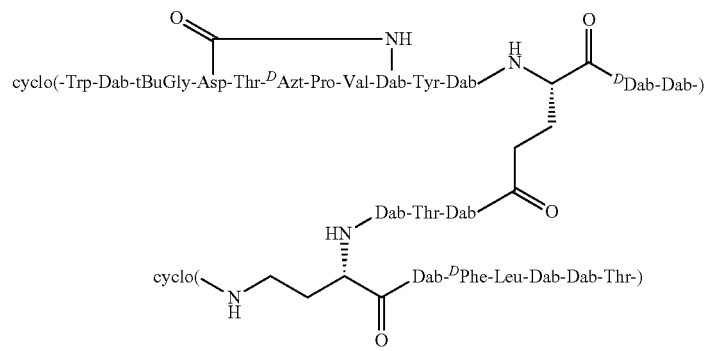 |
| Ex. 87[b)] | 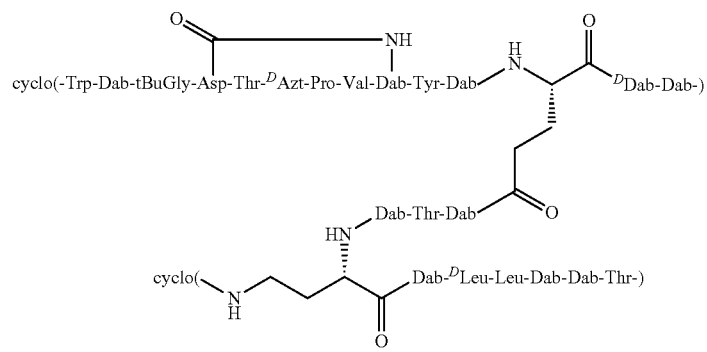 |

| Ex. No. | |
|---|---|
| Ex. 88 | 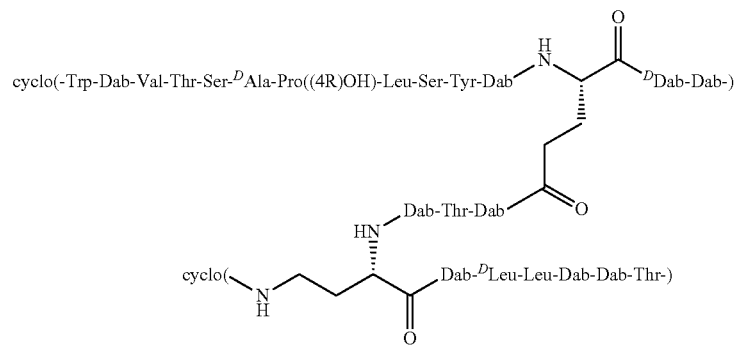 |
| Ex. 89 | 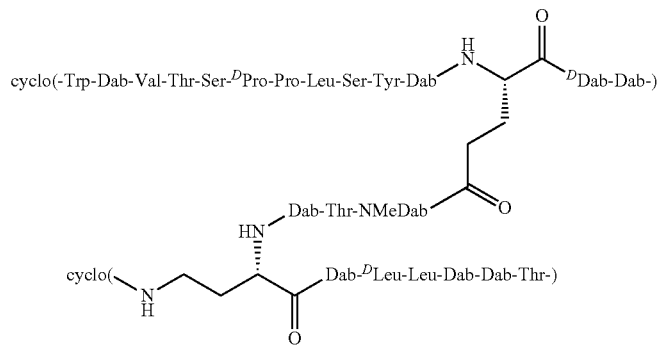 |
| Ex. 90 | 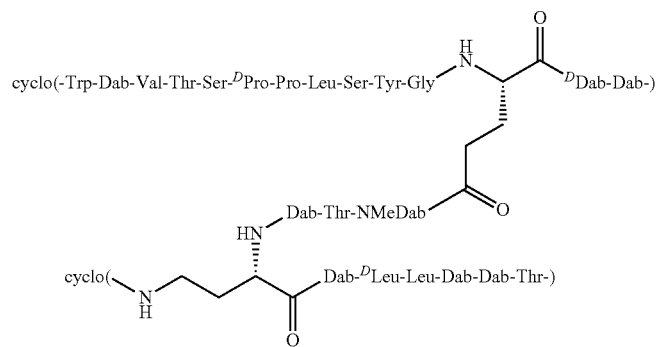 |
| Ex. 91 | 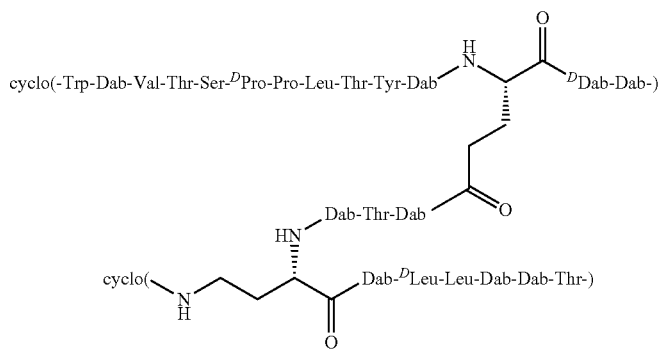 |

| Ex. No. | |
|---|---|
| Ex. 92 | 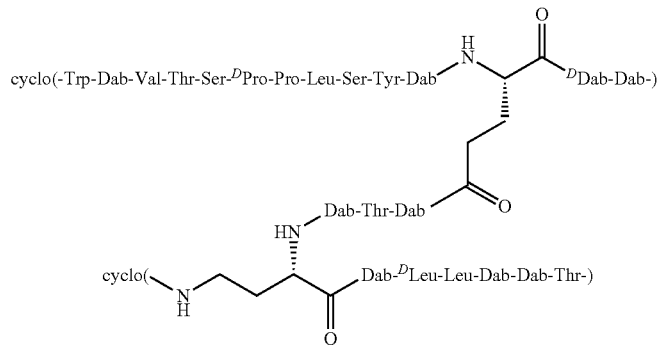 |
| Ex. 93 | 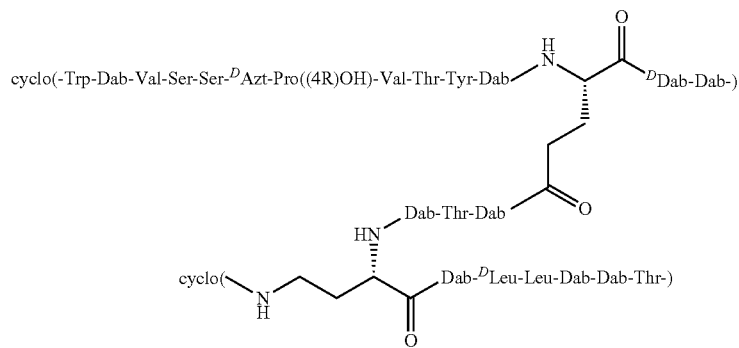 |
| Ex. 94 | 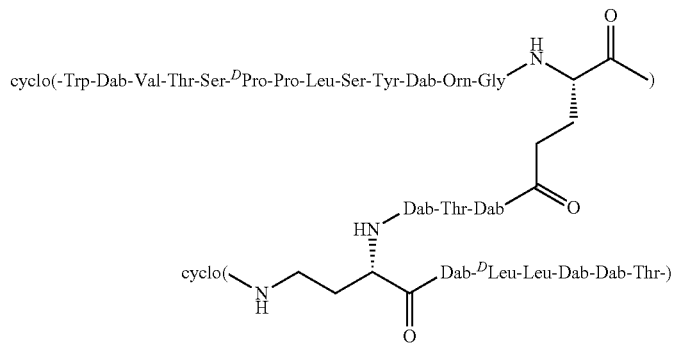 |
| Ex. 95 | 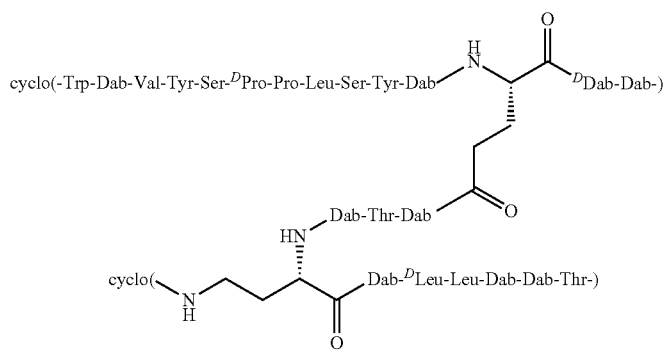 |

| Ex. No. | |
|---|---|
| Ex. 96 | 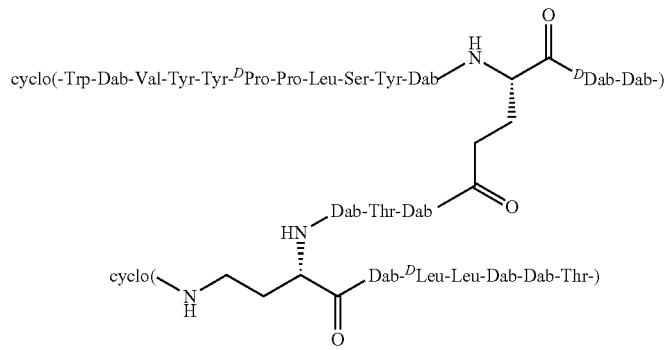 |
| Ex. 97 | 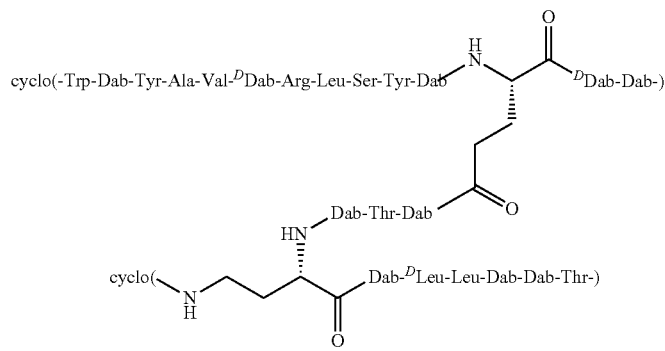 |
| Ex. 98[a)] | 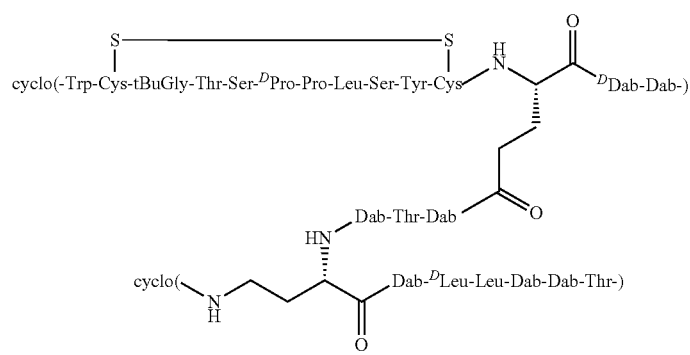 |
| Ex. 99 | 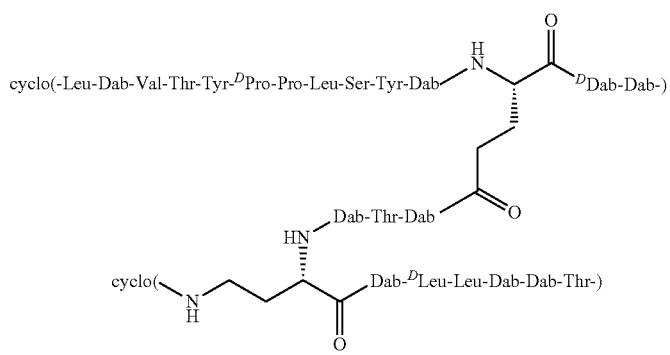 |

| Ex. No. | |
|---|---|
| Ex. 100 | 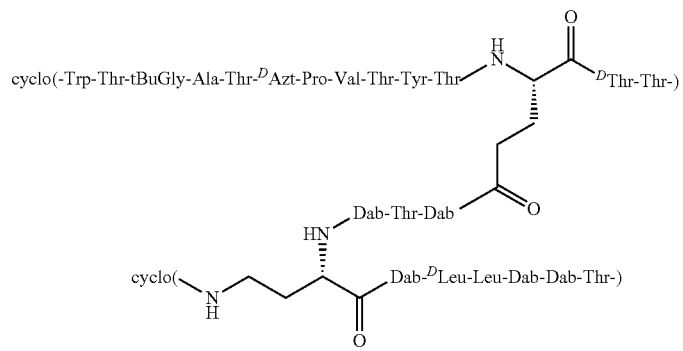 |
| Ex. 101 | 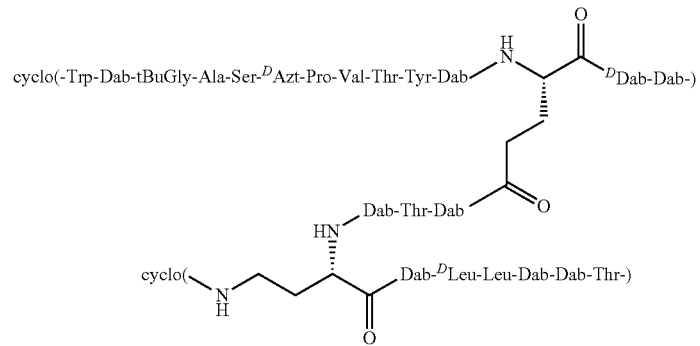 |
| Ex. 102 | 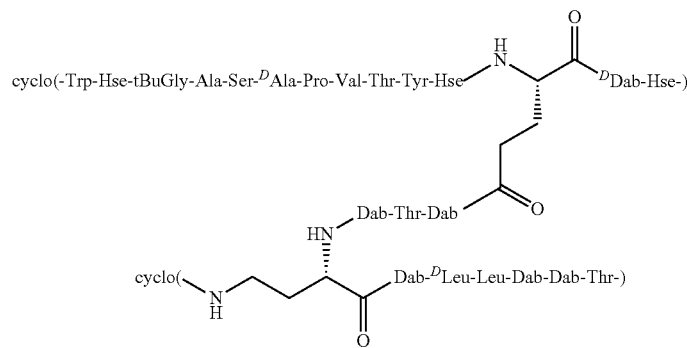 |
| Ex. 103 | 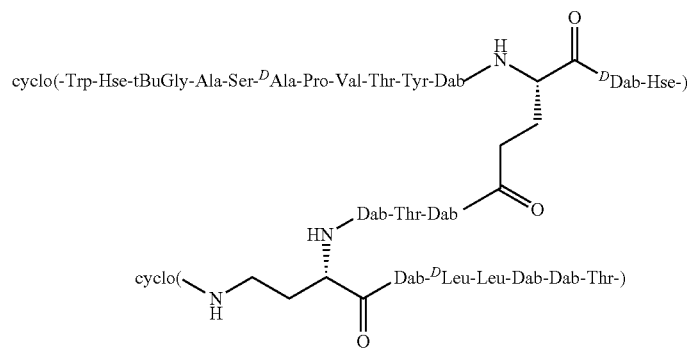 |

| Ex. No. | |
|---|---|
| Ex. 104[a] | 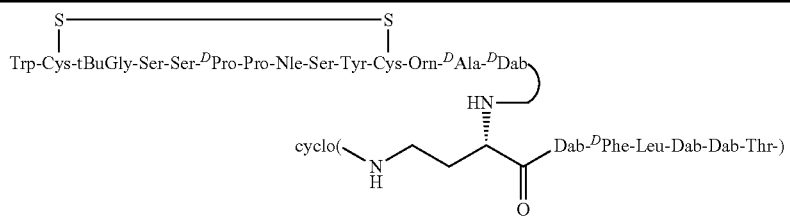 |
| Ex. 105[a] | 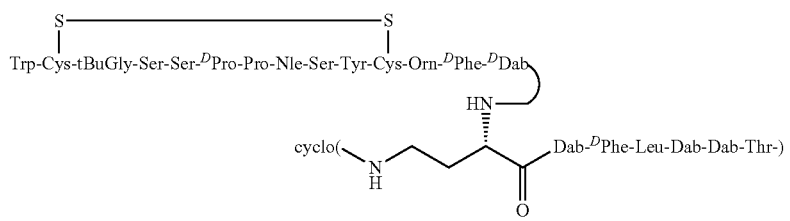 |
| Ex. 106[a] | 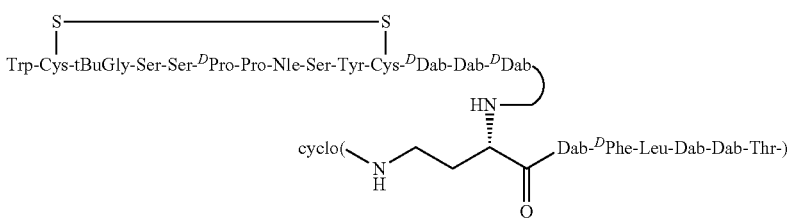 |
| Ex. 107[a] | 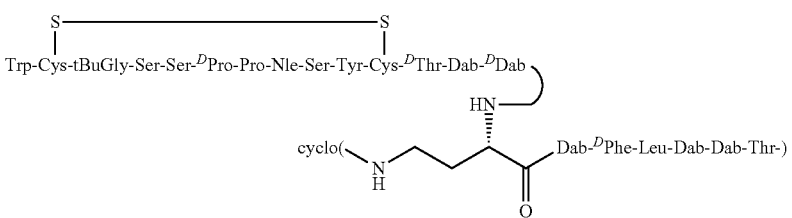 |
| Ex. 108[a] | 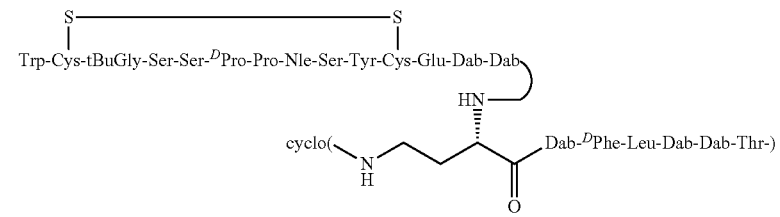 |
| Ex. 109[a] | 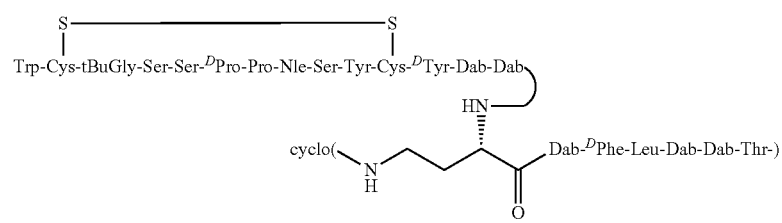 |
| Ex. 110[a] | 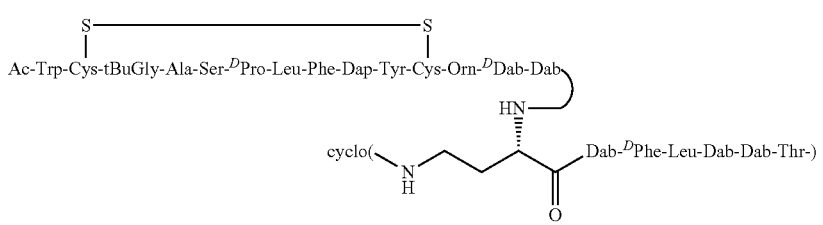 |

| Ex. No. | |
|---|---|
| Ex. 111[a)] | 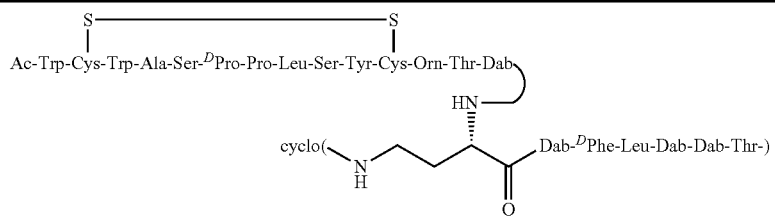 |
| Ex. 112[a)] | 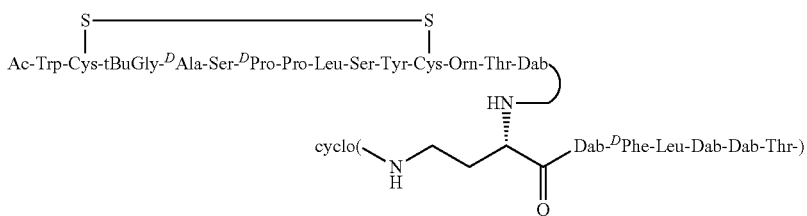 |
| Ex. 113[a)] | 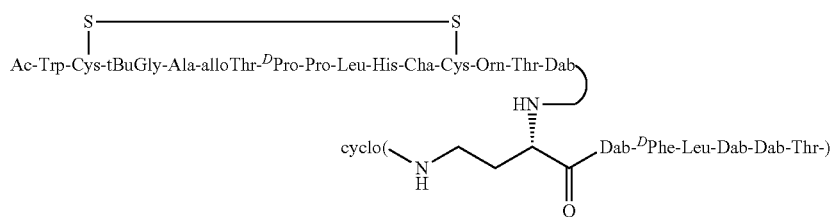 |
| Ex. 114[a)] | 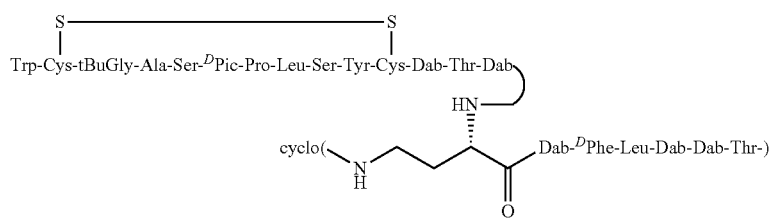 |
| Ex. 115[a)] | 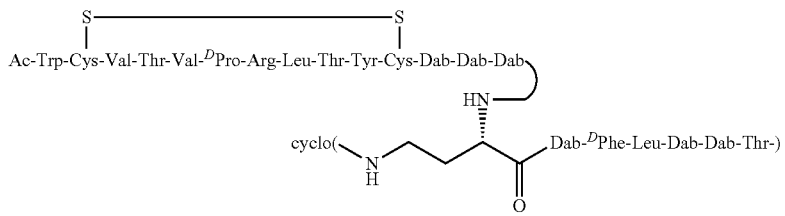 |
| Ex. 116[a)] | 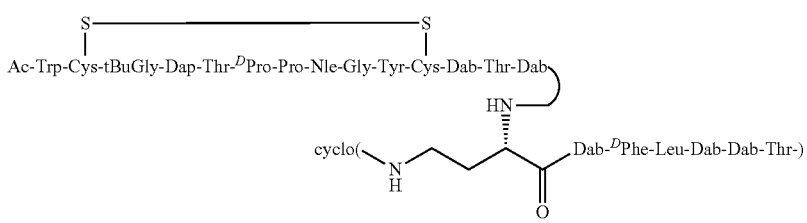 |
| Ex. 117[a)] | 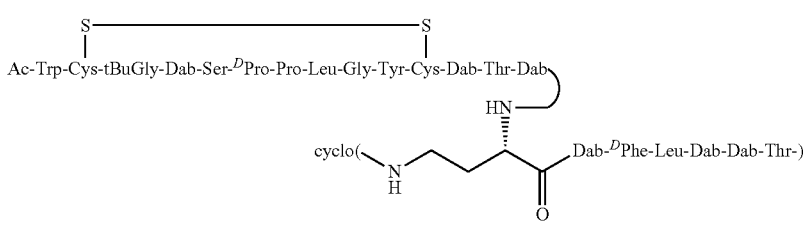 |

| Ex. No. | |
|---|---|
| Ex. 118[a)] | 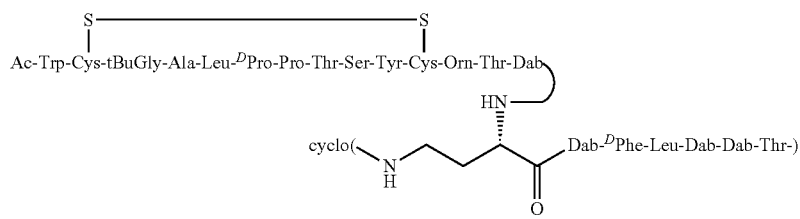 |
| Ex. 119[a)] | 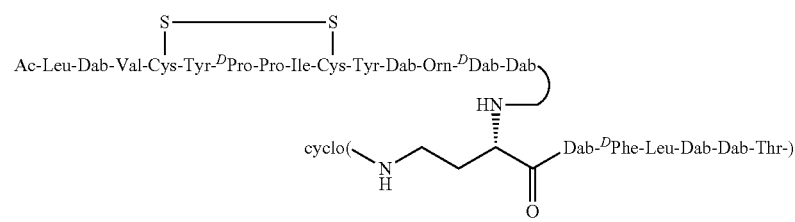 |
| Ex. 120[a)] | 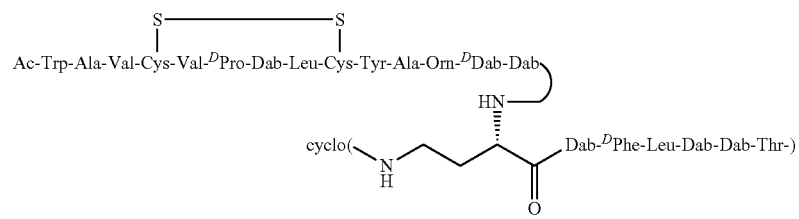 |
| Ex. 121[a)] | 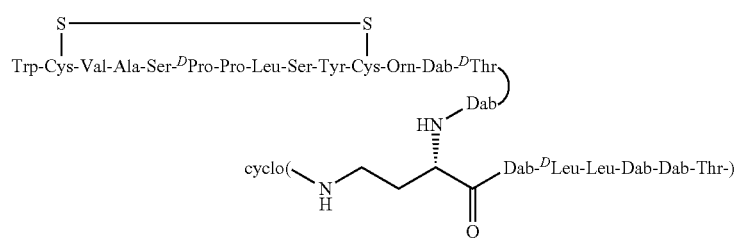 |
| Ex. 122[a)] | 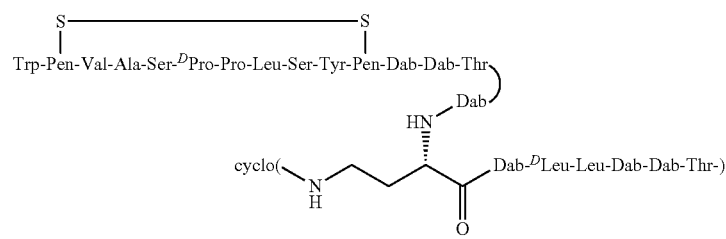 |
| Ex. 123[a)] | 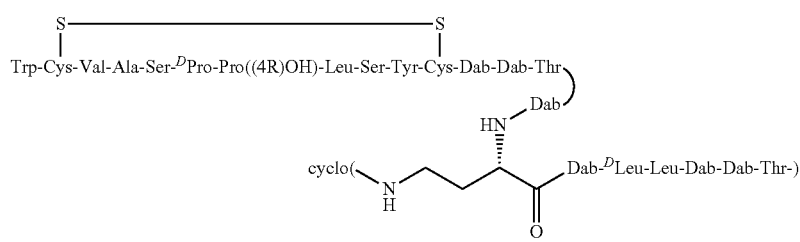 |

| Ex. No. | |
|---|---|
| Ex. 124[a)] | 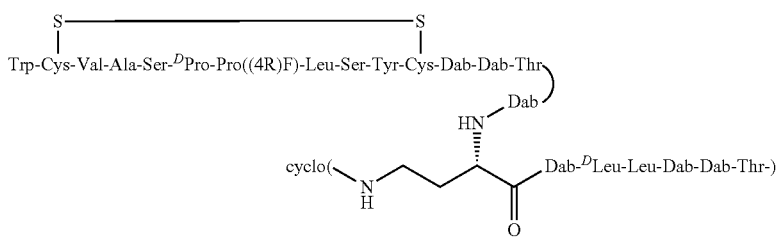 |
| Ex. 125[a)] | 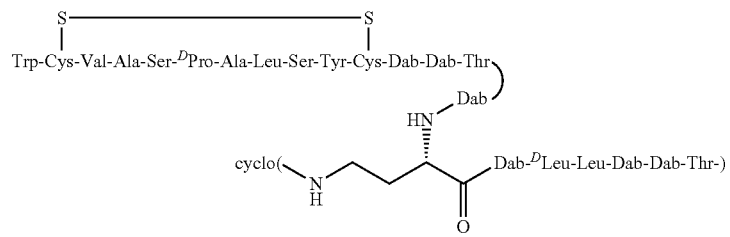 |
| Ex. 126[a)] | 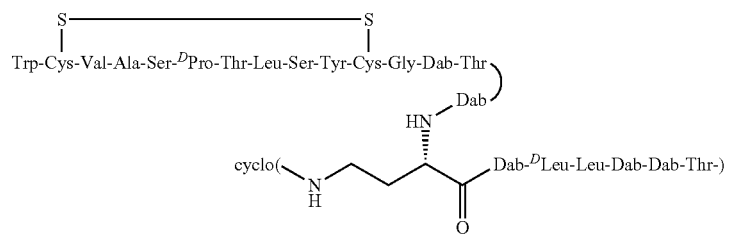 |
| Ex. 127[a)] | 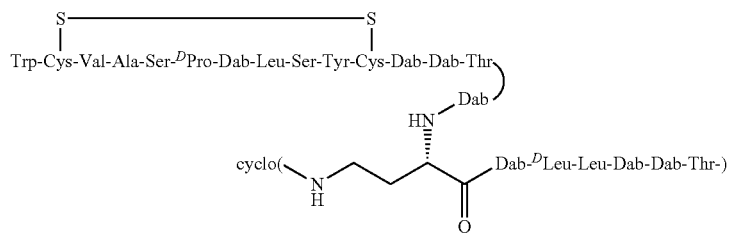 |
| Ex. 128[a)] | 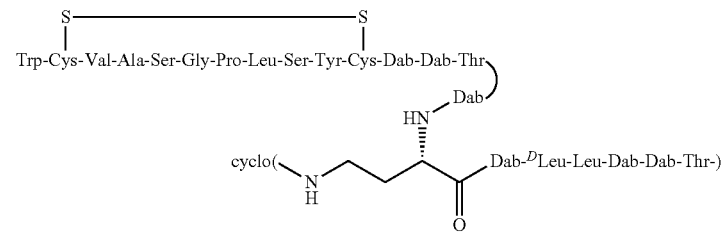 |
| Ex. 129[a)] | 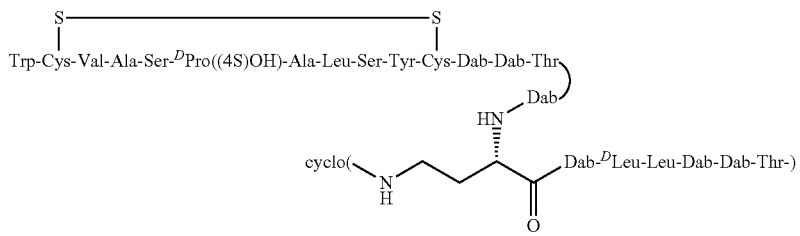 |

-continued
| Ex. No. | |
|---|---|
| Ex. 130[a)] | 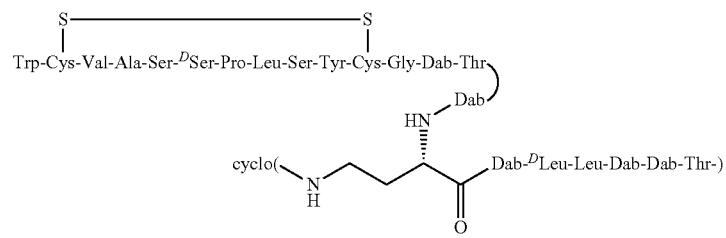 |
| Ex. 131[a)] | 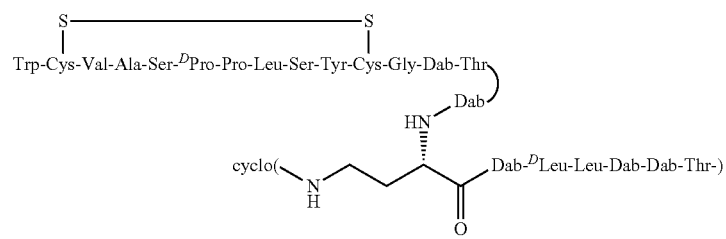 |
| Ex. 132[a)] | 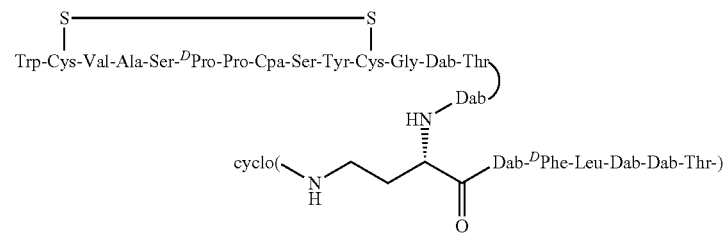 |
| Ex. 133[a) e)] | 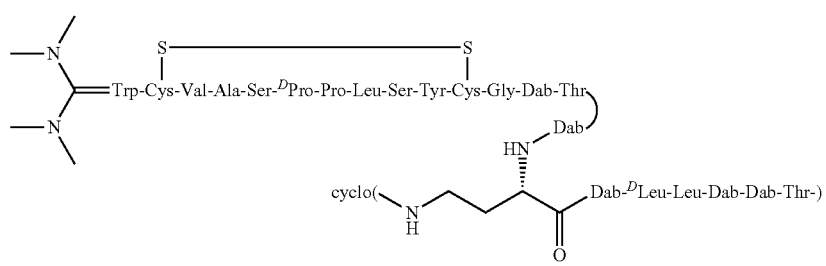 |
| Ex. 134[a)] | 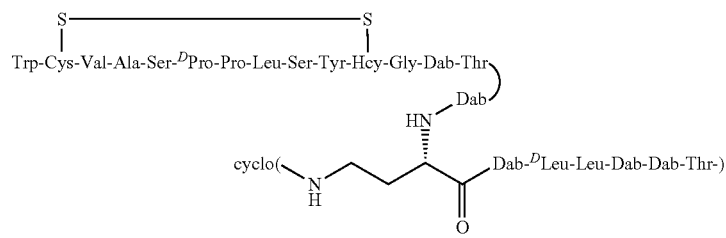 |
| Ex. 135[a) d)] | 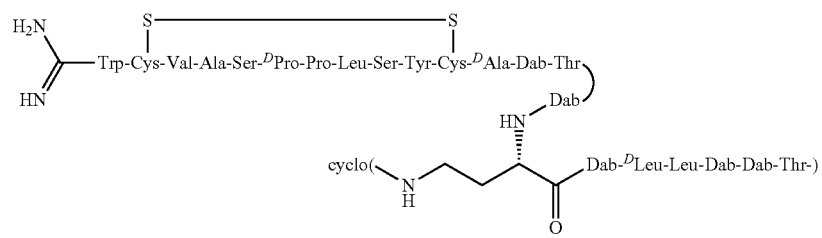 |

-continued
| Ex. No. |  |
|---|---|
| Ex. 136[a)] | 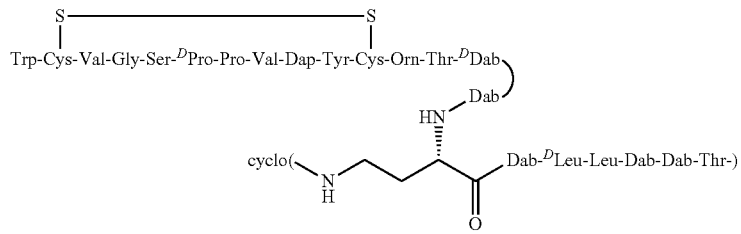 |
| Ex. 137[a)] | 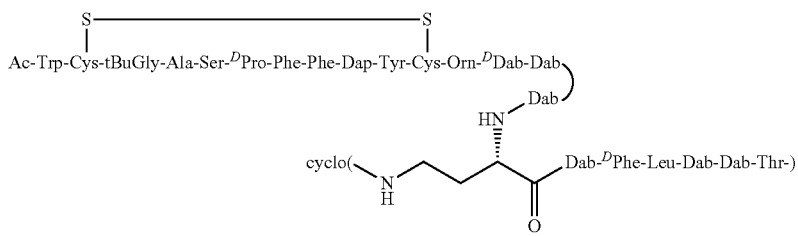 |
| Ex. 138[a)] | 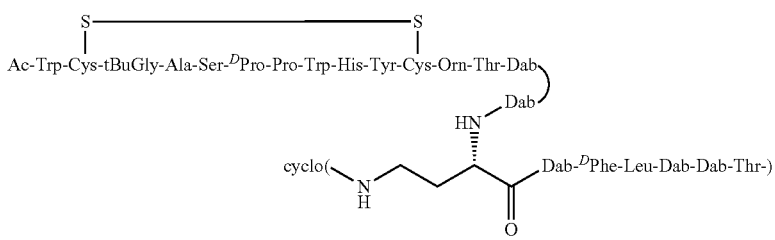 |
| Ex. 139[a)] | 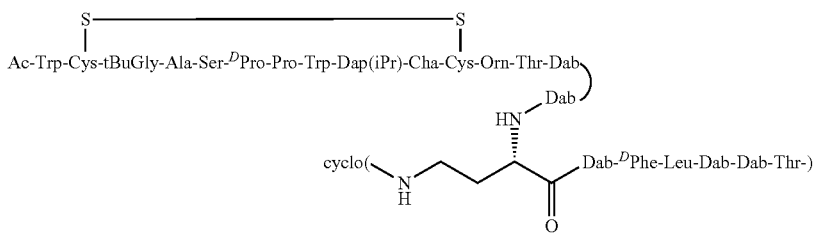 |
| Ex. 140[a)] | 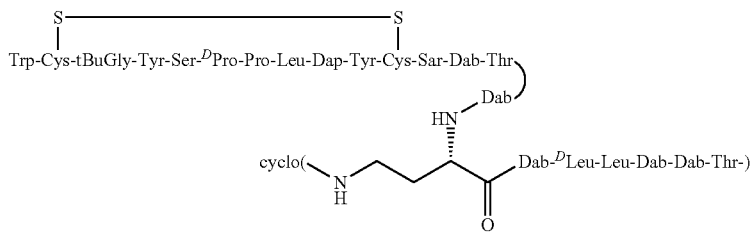 |
| Ex. 141[a)] | 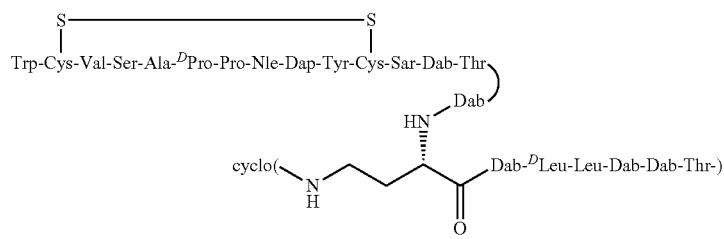 |

| Ex. No. | |
|---|---|
| Ex. 142[a)] | 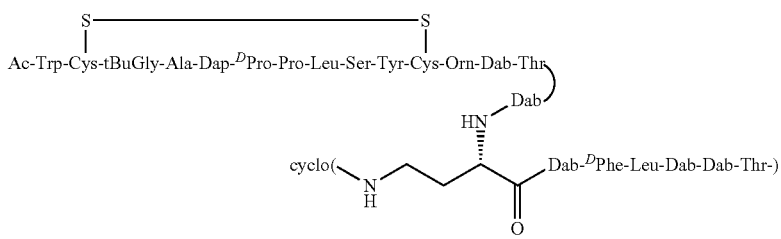 |
| Ex. 143[a)] | 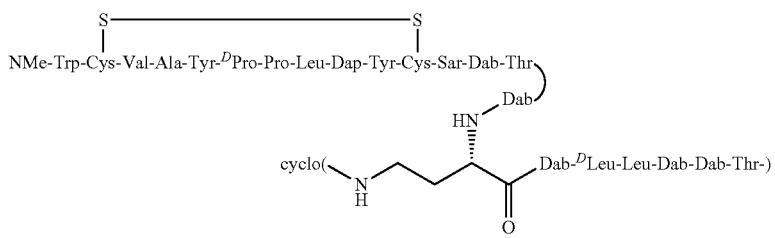 |
| Ex. 144[a)] | 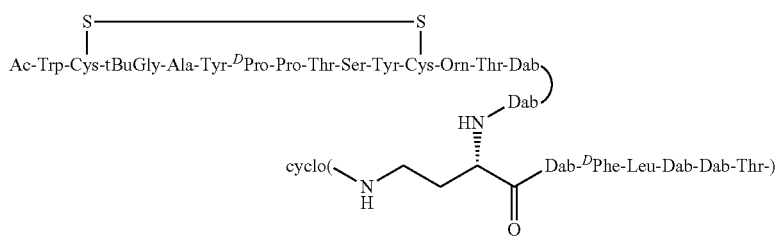 |
| Ex. 145[a)] | 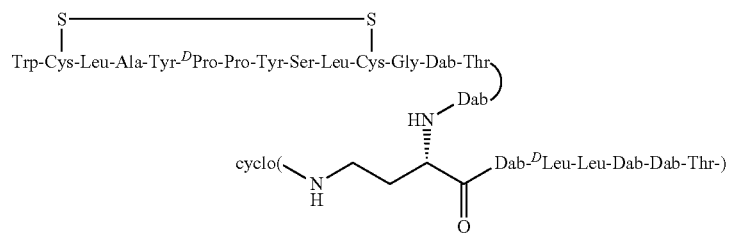 |
| Ex. 146[a)] | 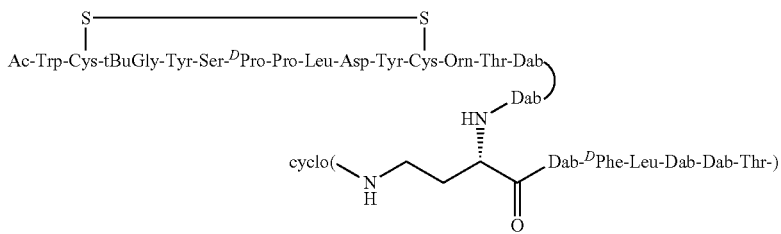 |
| Ex. 147[a)] | 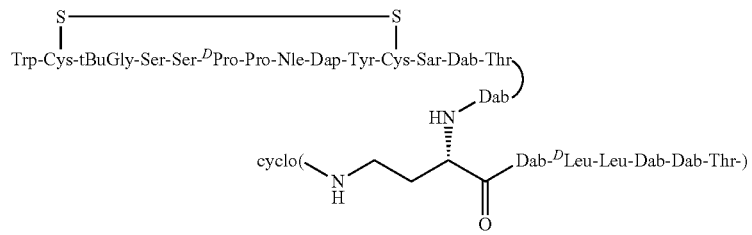 |

| Ex. No. | |
|---|---|
| Ex. 148[a)] | 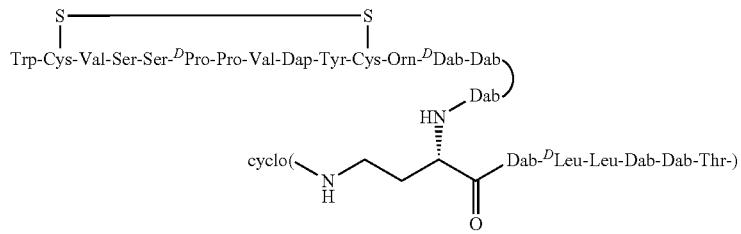 |
| Ex. 149[a)] | 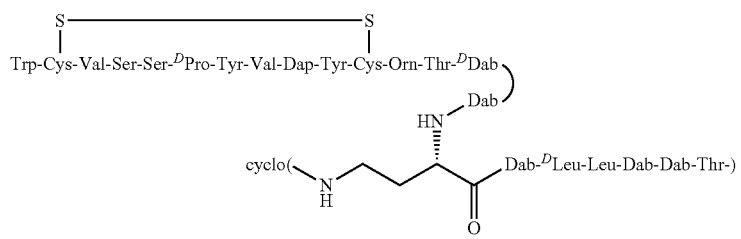 |
| Ex. 150[a)] | 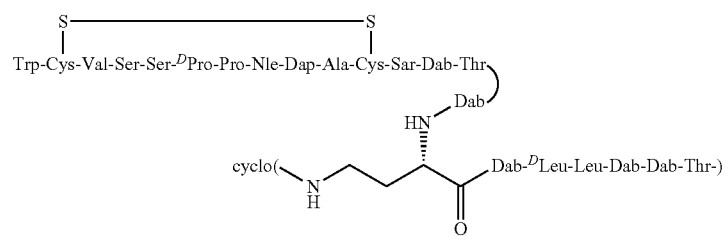 |
| Ex. 151[a)] | 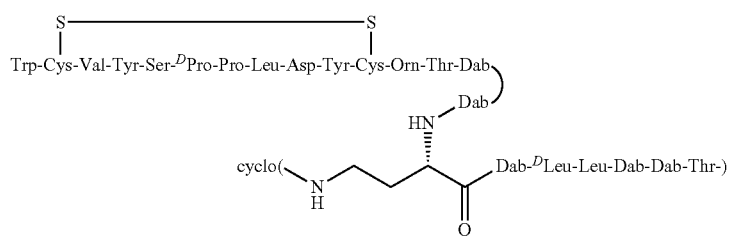 |
| Ex. 152[a)] | 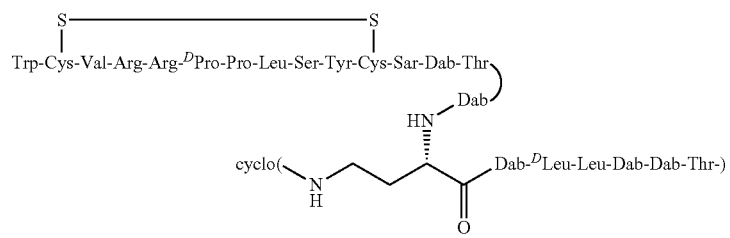 |
| Ex. 153[a)] | 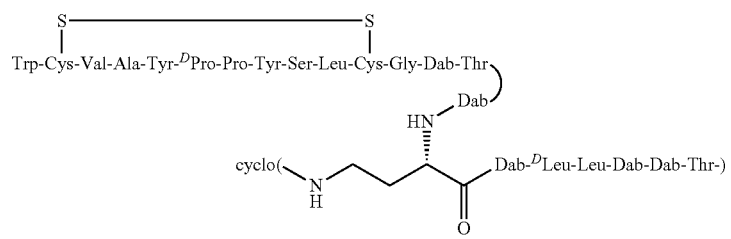 |

| Ex. No. | |
|---|---|
| Ex. 154[a] | 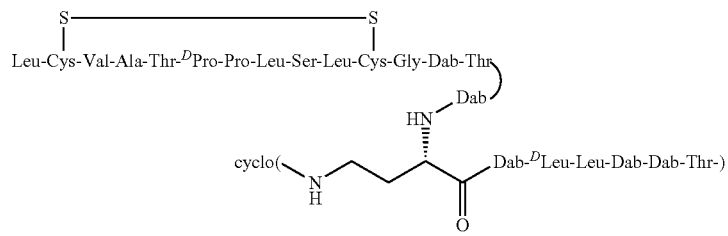 |
| Ex. 155[a] | 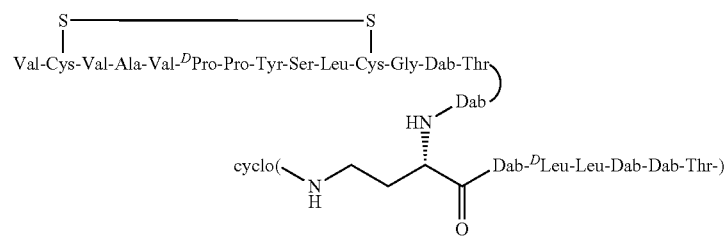 |
| Ex. 156[a] | 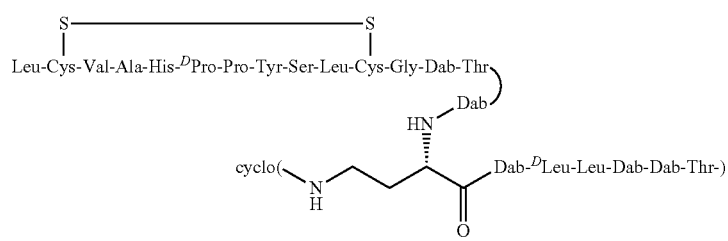 |
| Ex. 157[a] | 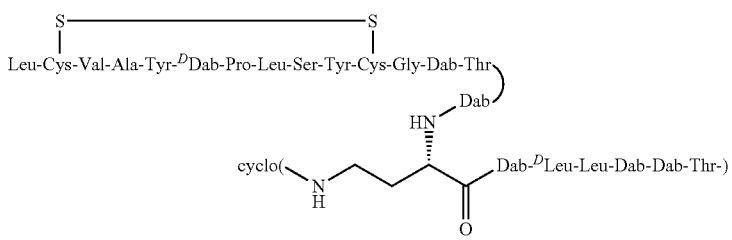 |
| Ex. 158[a] | 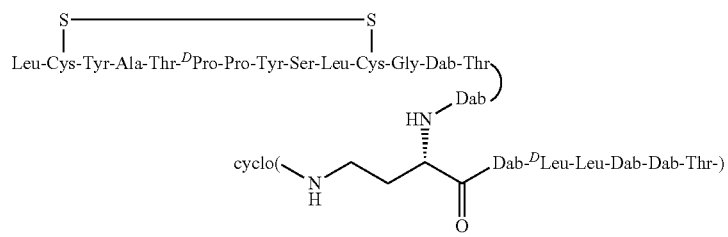 |
| Ex. 159[a] | 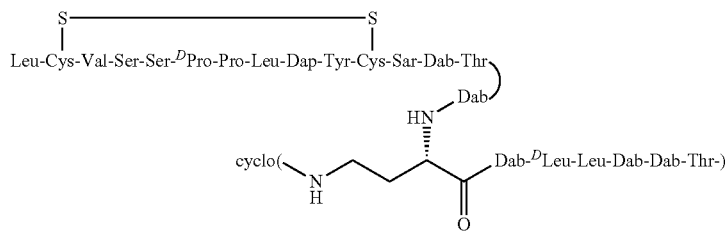 |

| Ex. No. | |
|---|---|
| Ex. 160[a)] | 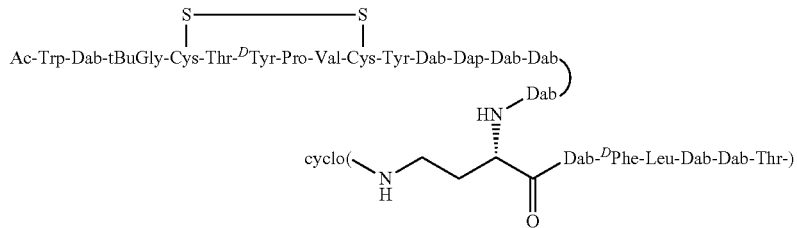 |
| Ex. 161[a)] | 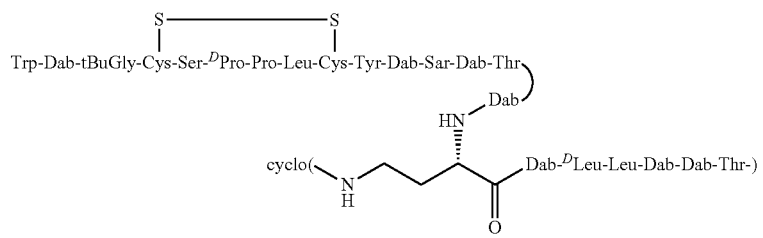 |
| Ex. 162[a)] | 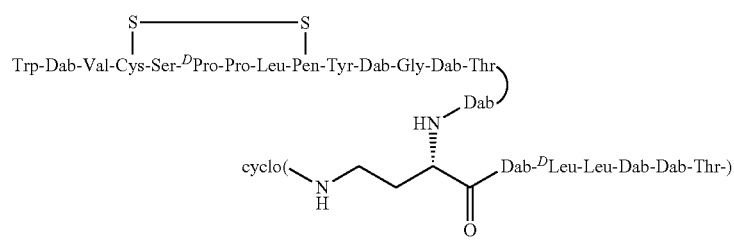 |
| Ex. 163[a)] | 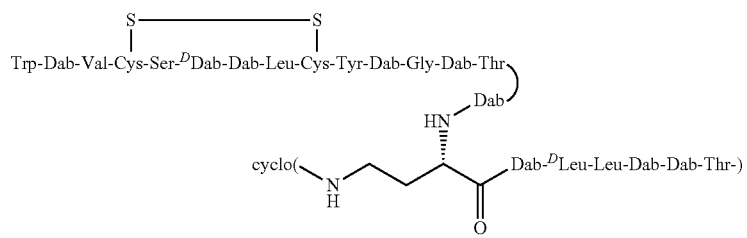 |
| Ex. 164[a)] | 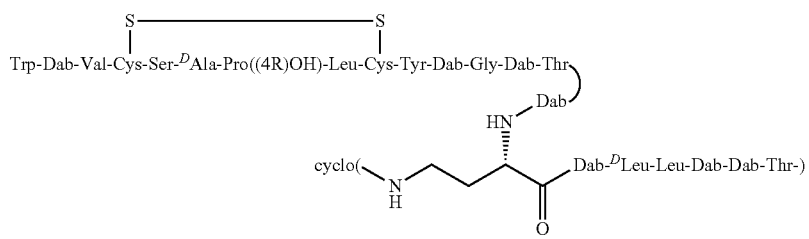 |
| Ex. 165[a)] | 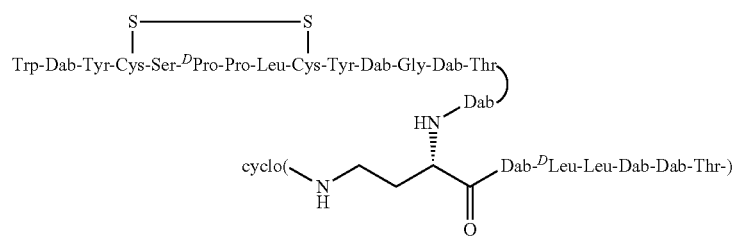 |

-continued
| Ex. No. | |
|---|---|
| Ex. 166[a] | 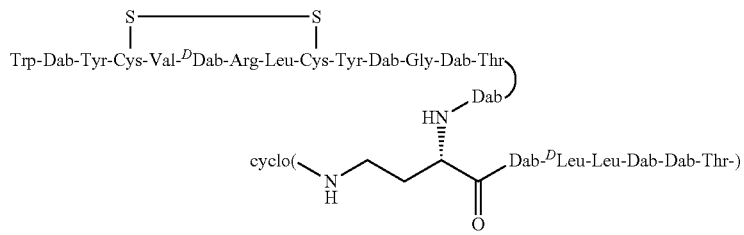 |
| Ex. 167[b] | 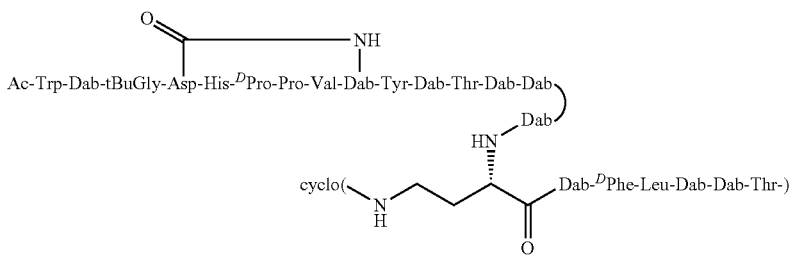 |
| Ex. 168[b] | 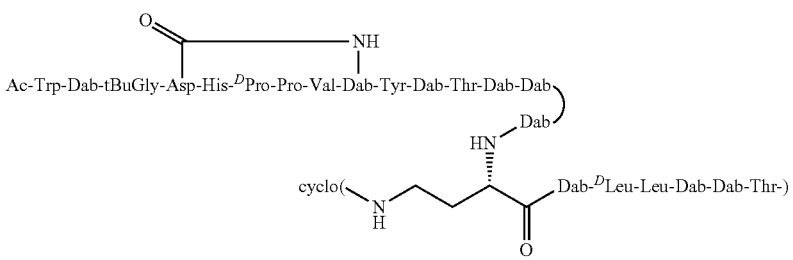 |
| Ex. 169[a] | 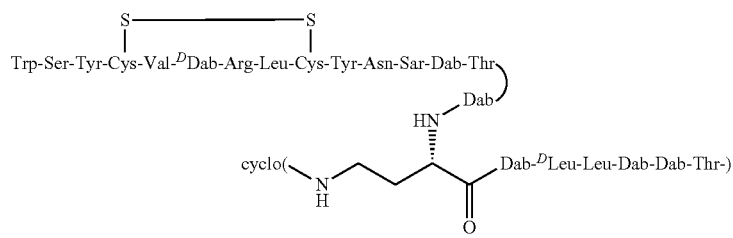 |
| Ex. 170[a] | 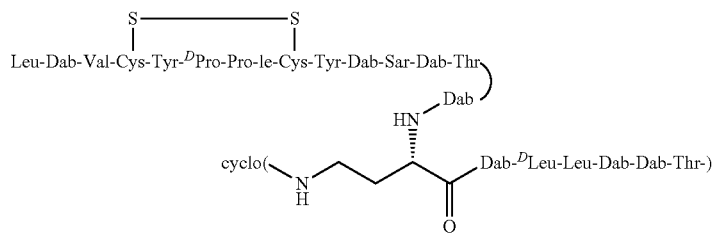 |
| Ex. 171[a] | 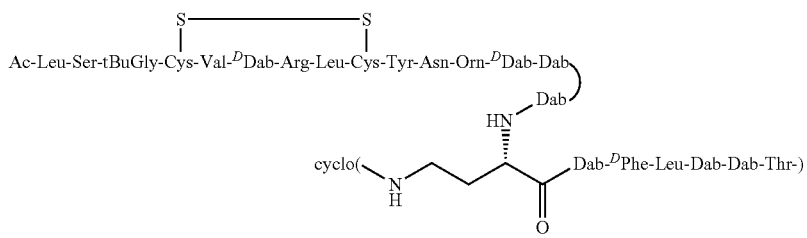 |

| Ex. No. | |
|---|---|
| Ex. 172[b) d)] | 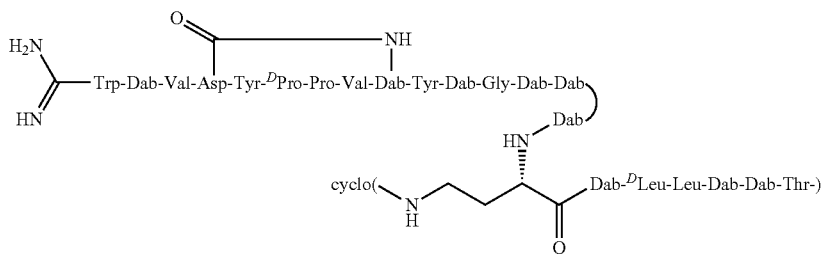 |
| Ex. 173[a) d)] | 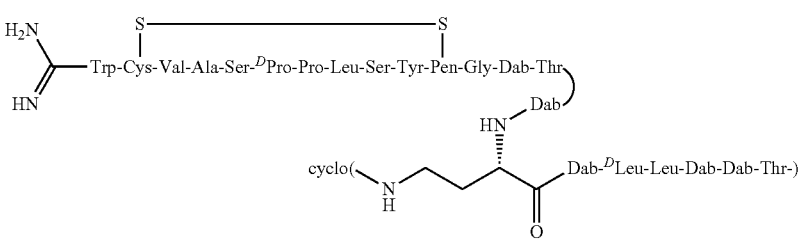 |
| Ex. 174[a) d)] | 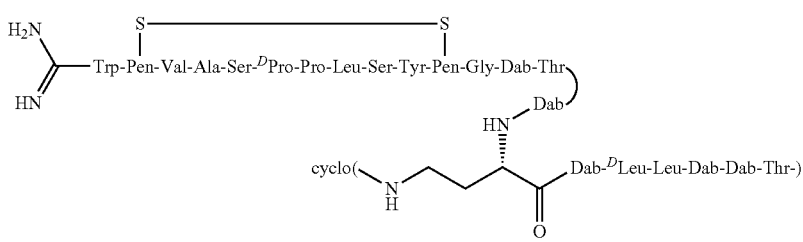 |
| Ex. 175[a)] | 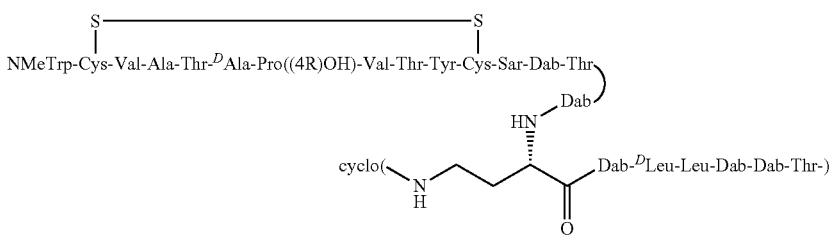 |
| Ex. 176[b)] | 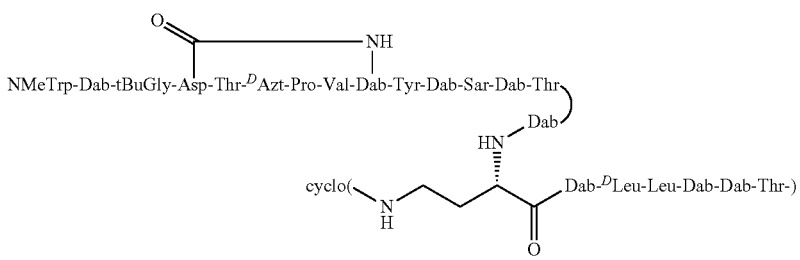 |
| Ex. 177[a) c)] | 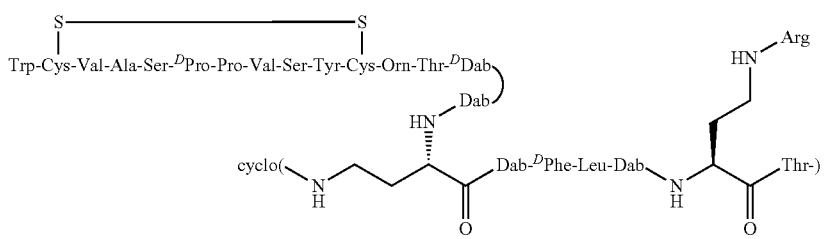 |

| Ex. No. | |
|---|---|
| Ex. 178[a)] | 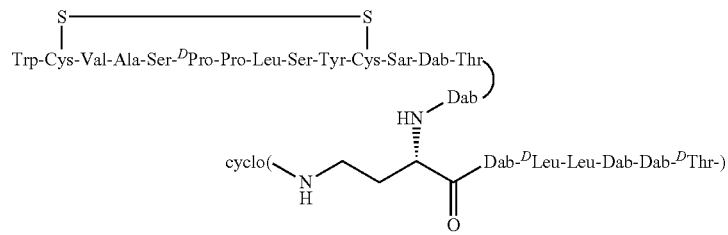 |
| Ex. 179[a)] | 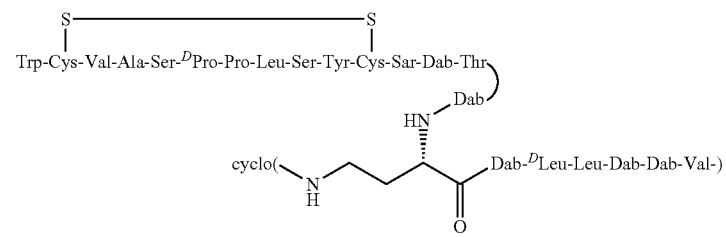 |
| Ex. 180[a)] | 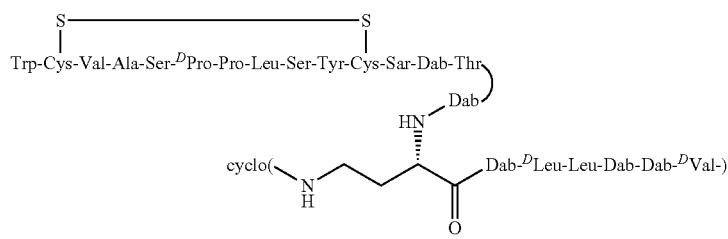 |
| Ex. 181[a)] | 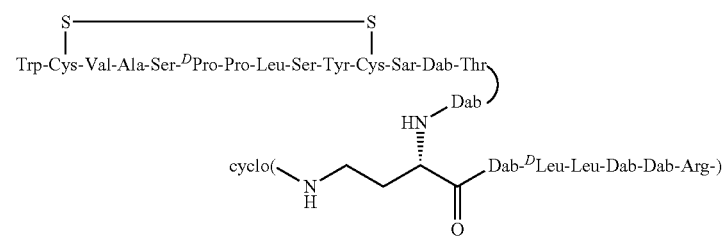 |
| Ex. 182[a)] | 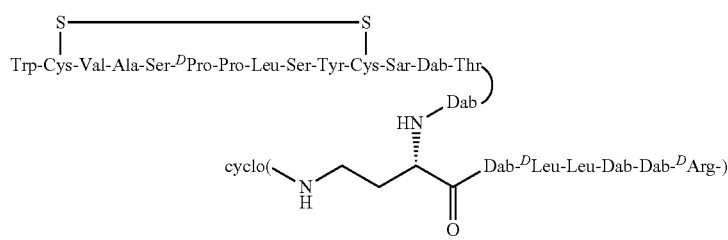 |
| Ex. 183[a)] | 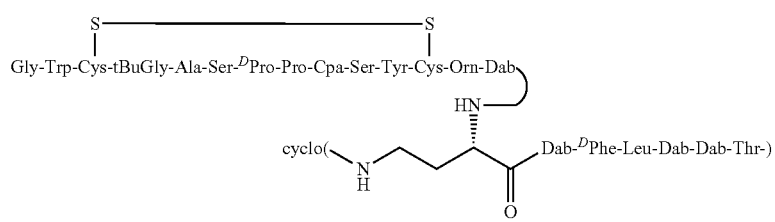 |

| Ex. No. | |
|---|---|
| Ex. 184[a] | 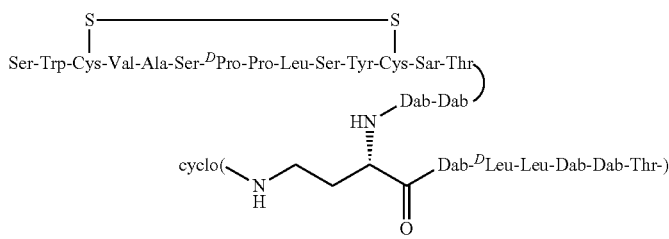 |
| Ex. 185[a] | 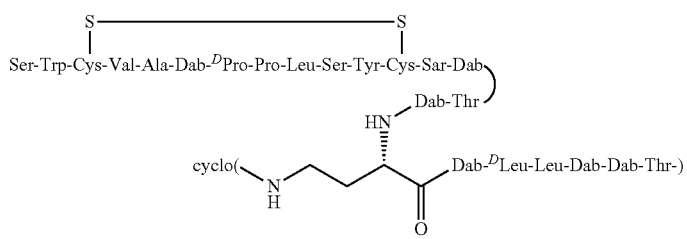 |
| Ex. 186[a] | 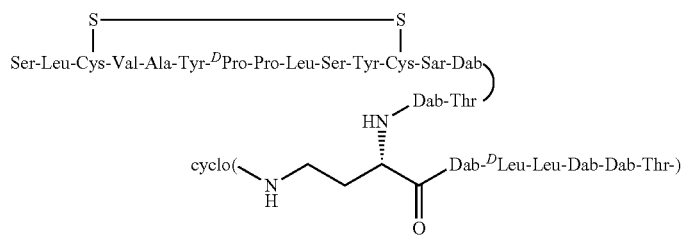 |
| Ex. 187[a) c)] | 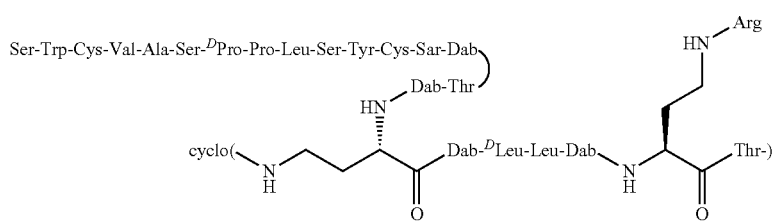 |
| Ex. 188[a] | 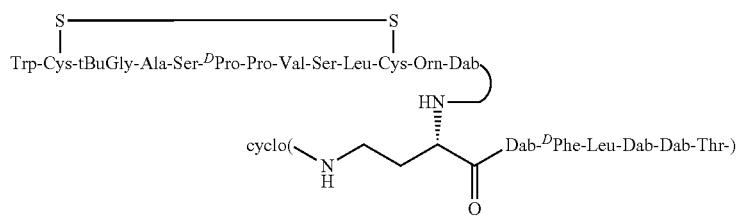 |
| Ex. 189[a] | 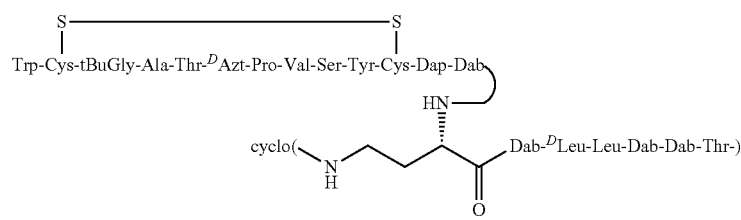 |

-continued
| Ex. No. | |
|---|---|
| Ex. 190[b] | 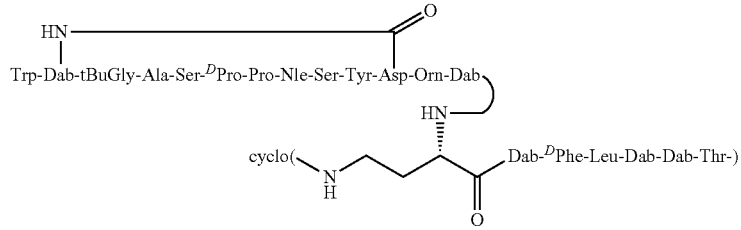 |
| Ex. 191[a) b)] | 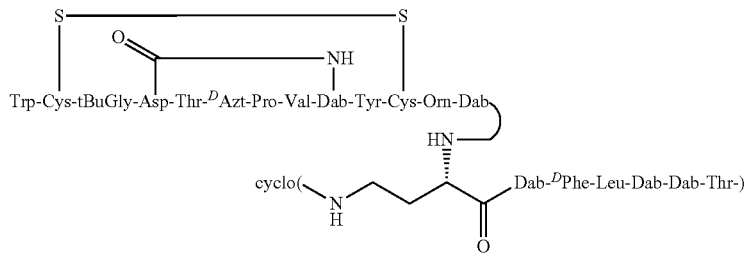 |
| Ex. 192[a)] | 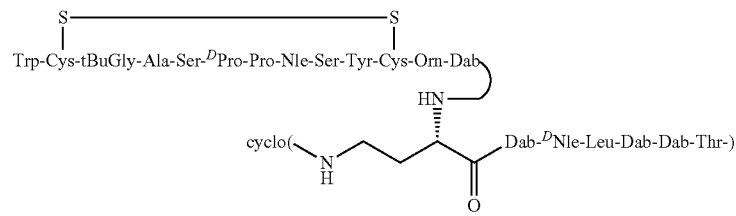 |
| Ex. 193[b)] | 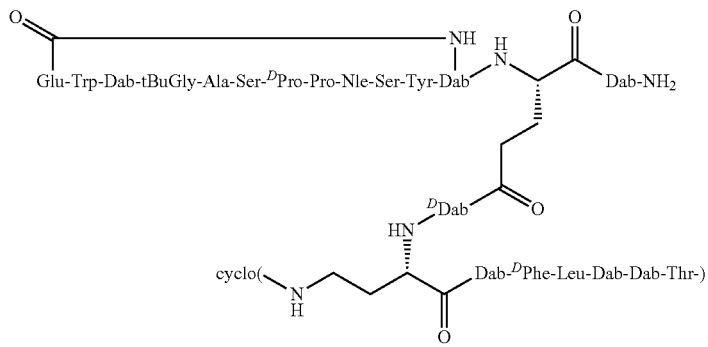 |
| Ex. 194[a)] | 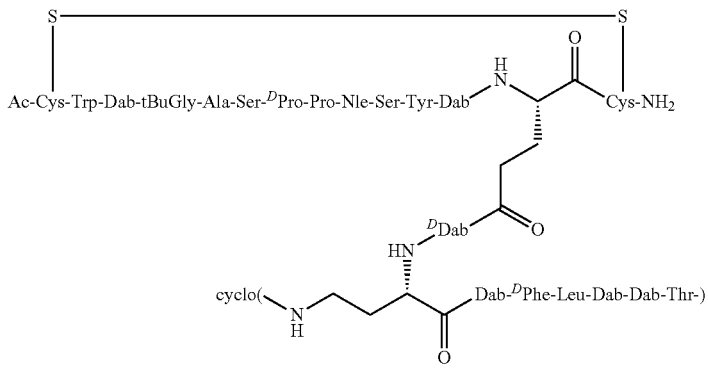 |

| Ex. No. | |
|---|---|
| Ex. 195[a)] | 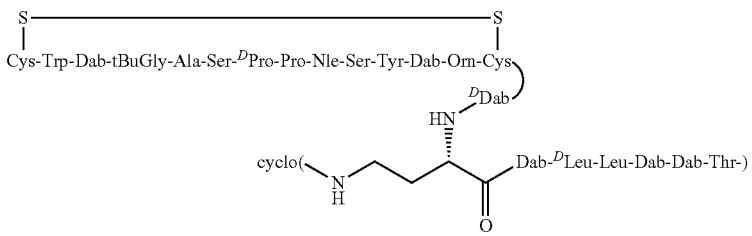 |
| Ex. 196[b)] | 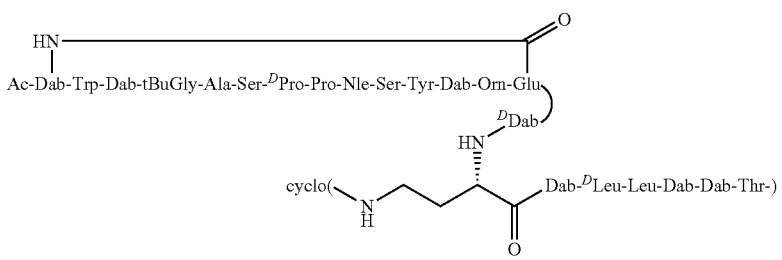 |
| Ex. 197[b)] | 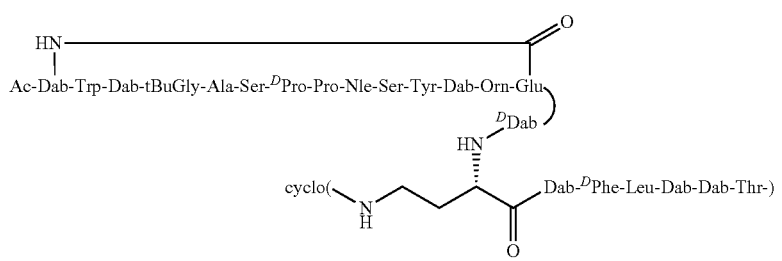 |
| Ex. 198[b)] | 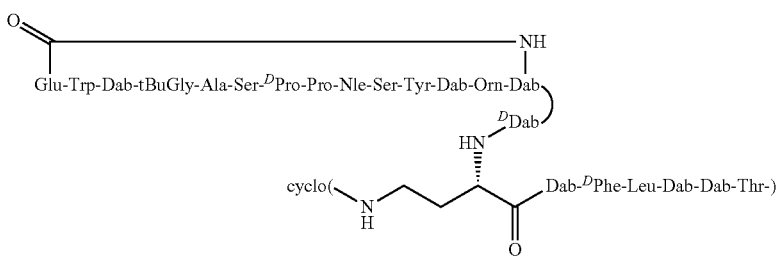 |
| Ex. 199[a)] | 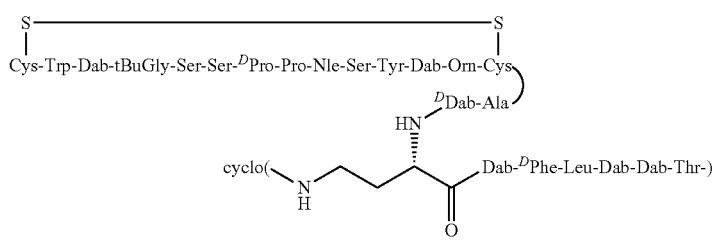 |
| Ex. 200[a)] | 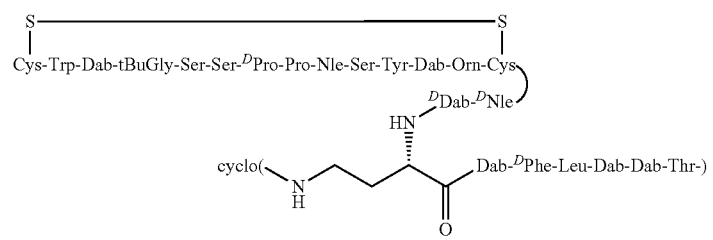 |

| Ex. No. | |
|---|---|
| Ex. 201[a)] | 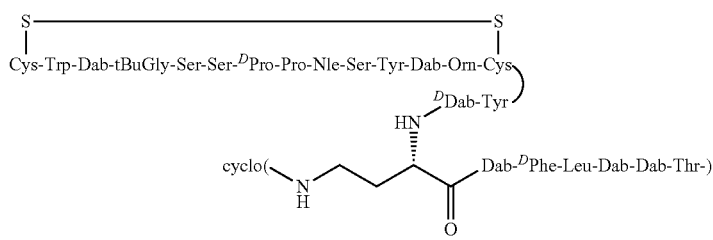 |
| Ex. 202[a)] | 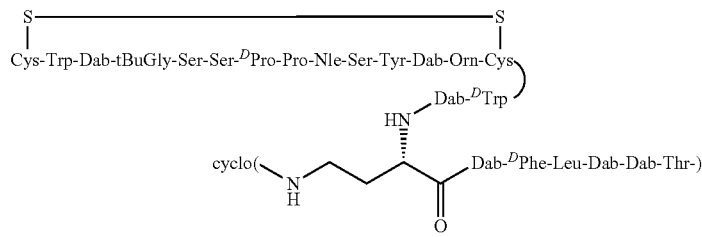 |
| Ex. 203[a)] | 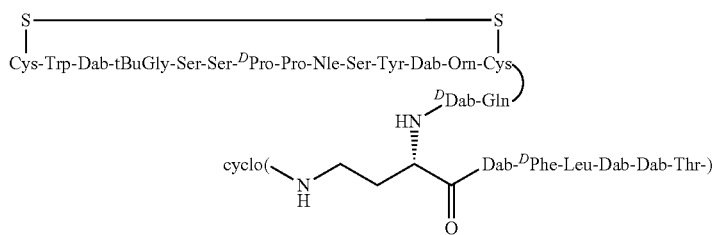 |
| Ex. 204[a)] | 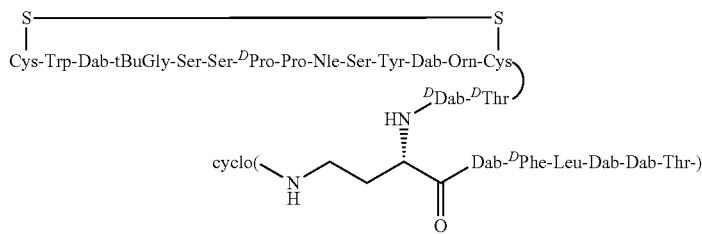 |
| Ex. 205[a)] | 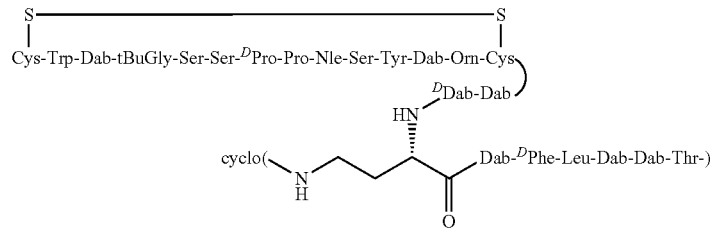 |
| Ex. 206[a)] | 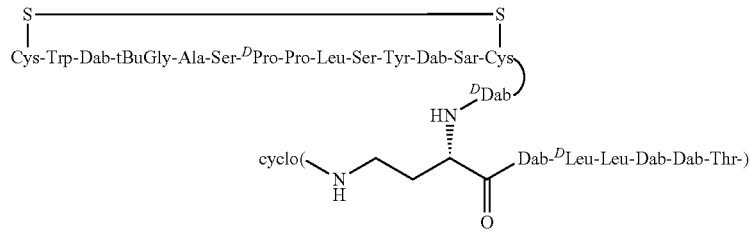 |

| Ex. No. | |
|---|---|
| Ex. 207[a)] | 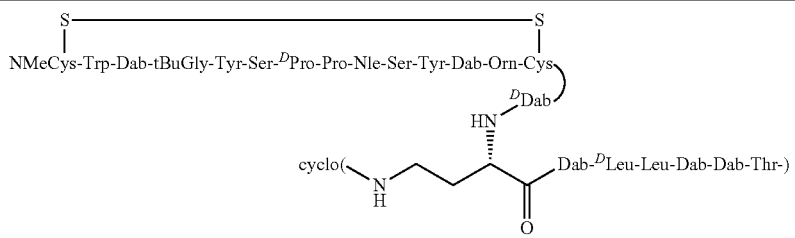 |
| Ex. 208[a)] | 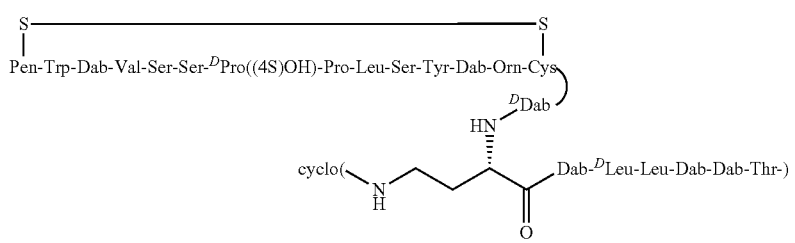 |
| Ex. 209[a)] | 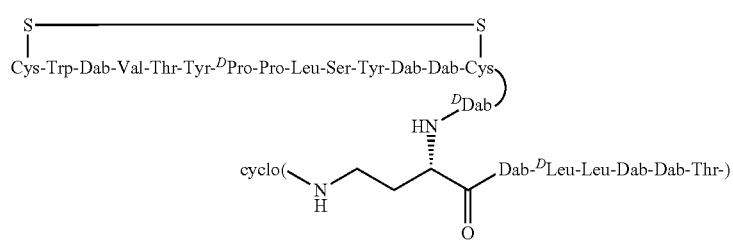 |
| Ex. 210[a) b)] | 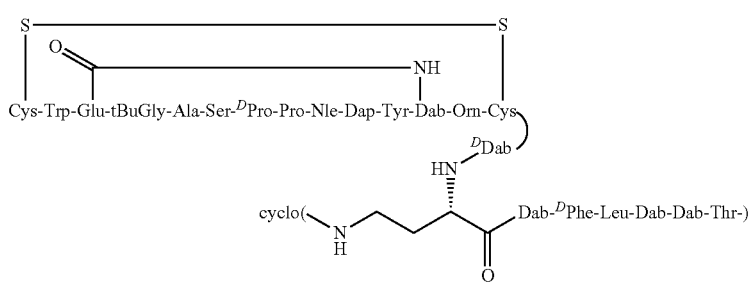 |
| Ex. 211[a)] | 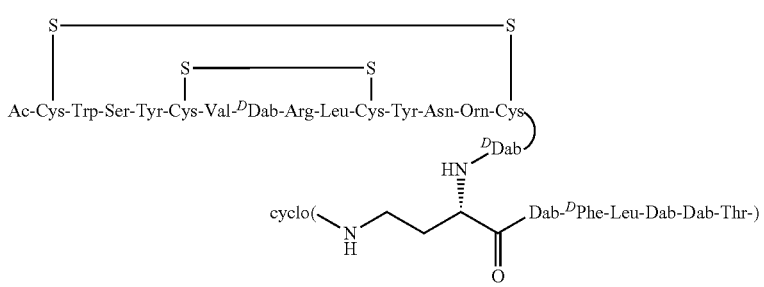 |
| Ex. 212[a)] | 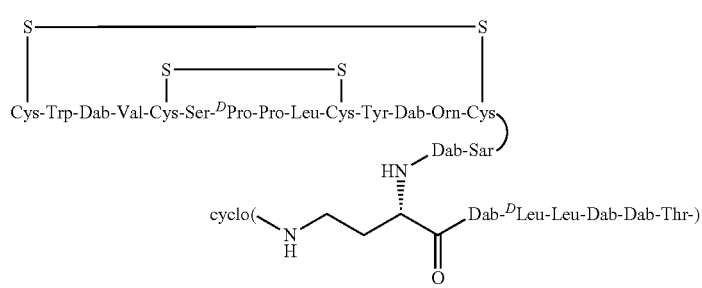 |

| Ex. No. | |
|---|---|
| Ex. 213[a)] | 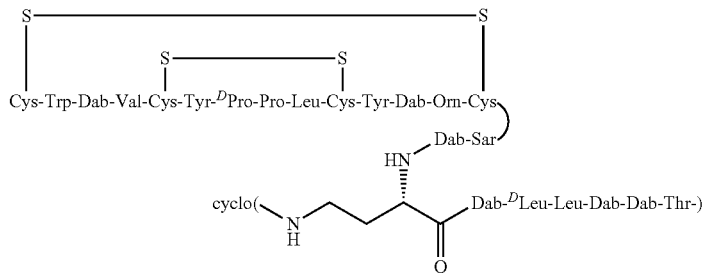 |
| Ex. 214[a)] | 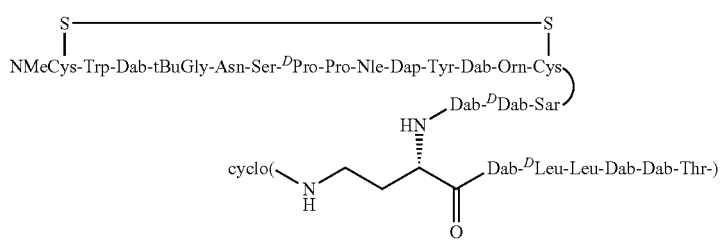 |
| Ex. 215[a)] | 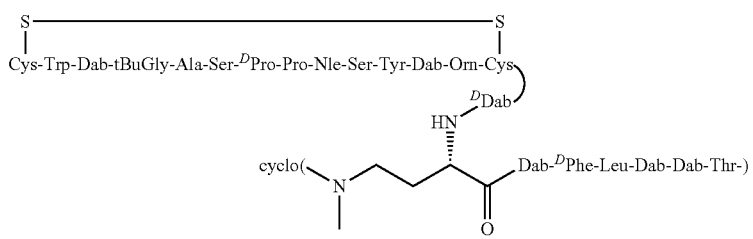 |
| Ex. 216[a)] | 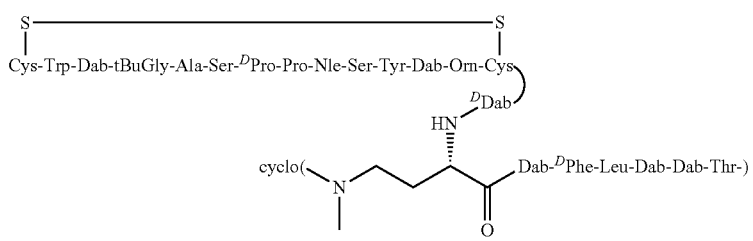 | wherein a) designates compounds comprising one or more disulfide interstrand linkage(s) between indicated amino acid residues, wherein the interstrand linkage(s) comprise at least one disulfide bond(s) between a pair(s) of side-chain thiol groups comprised on the indicated amino acid residues;

wherein b) designates compounds comprising a lactam interstrand linkage between two indicated amino acid residues, wherein the lactam interstrand linkage comprises an amide bond between a side-chain amino group and a side-chain carboxyl group;

wherein c) designates compounds comprising a dipeptidic amino acid residue at indicated position, wherein the dipeptidic amino acid residue comprises an amide bond between a α-carboxyl group of a terminal amino acid residue and a side-chain amino group of a second amino acid residue as specified;

wherein d) designates compounds comprising a guanidine group comprising an amino group of a N-terminal amino acid residue; and wherein e) designates compounds comprising a tetramethylguanidine group comprising an amino group of the N-terminal amino acid residue;

wherein formula (I) is defined as

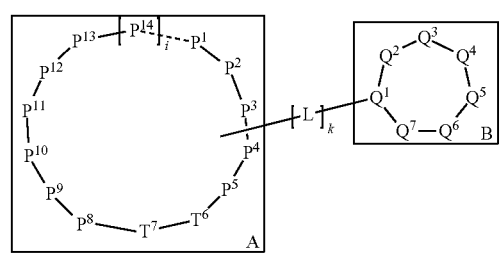

and comprises a module A comprising single elements P or T being connected in either direction from the carbonyl (C=O) point of attachment to the nitrogen (N) of the next element, wherein i is 0 or 1, with the proviso that, if i=1, $P^{13}$ and P$^{14}$; or P$^{1A}$ and P$^{1}$ may not be connected as aforementioned; if i=0, P$^{13}$ and P$^{1}$ are not connected as aforementioned; and wherein, if i=1 and P$^{2}$ and P$^{11}$ taken together and/or P$^{4}$ and P$^{9}$ taken together and/or P$^{13}$ and P$^{14}$ taken together may form naturally or non-naturally cross-linking α-amino acids containing each in total 1 to 12 carbon- and/or heteroatoms in a single side-chain which together are connecting P$^{2}$ and P$^{11}$ and/or P$^{4}$ and P$^{9}$ and/or P$^{13}$ and P$^{14}$ by covalent interaction (inter-strand linkage); then P$^{1}$ is a naturally or non-naturally occurring aromatic L α-amino acid containing 1 to 25 carbon- and/or heteroatoms in a single side-chain; or a naturally or non-naturally occurring aliphatic L α-amino acid containing in total 1 to 25 carbon- and/or heteroatoms in a single side-chain;

P$^{2}$ is a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one amide function; or a naturally or non-naturally occurring alcoholic L α-amino acid containing in total 1 to 25 carbon- and/or heteroatoms in a single side-chain; or a naturally or non-naturally occurring aliphatic L α-amino acid containing in total 1 to 25 carbon- and/or heteroatoms in a single side-chain;

P$^{3}$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

P$^{4}$ is Gly; Sar; or a naturally or non-naturally occurring aliphatic α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function; or a naturally or non-naturally occurring aromatic L α-amino acid containing 1 to 25 carbon- and/or heteroatoms in a single side-chain;

P$^{5}$ is a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring aromatic L α-amino acid containing 1 to 25 carbon- and/or heteroatoms in a single side-chain;

T$^{6}$ is a naturally or non-naturally occurring D α-amino acid containing an optionally substituted side-chain which forms a four-, five- or six-membered hetero-cycle or a bicyclic system comprising the α-carbon and the α-amino atom; or a naturally or non-naturally occurring aliphatic D α-amino acid containing in total 1 to 25 carbon- and/or heteroatoms in a single side-chain; or a naturally or non-naturally occurring basic D α-amino acid containing in total 1 to 25 carbon- and/or heteroatoms in a single side-chain comprising at least one amino function; or a naturally or non-naturally occurring aromatic D α-amino acid containing 1 to 25 carbon- and/or heteroatoms in a single side-chain; or a naturally or non-naturally occurring alcoholic D α-amino acid containing in total 1 to 25 carbon- and/or heteroatoms in a single side-chain;

T$^{7}$ is a naturally or non-naturally occurring L α-amino acid containing an optionally substituted side-chain which forms a five- or six-membered heterocycle or a bicyclic system comprising the α-carbon and the α-amino atom; or a naturally or non-naturally occurring aliphatic L α-amino acid containing in total 1 to 25 carbon- and/or heteroatoms in a single side-chain; or a naturally or non-naturally occurring aromatic L α-amino acid containing 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain;

P$^{8}$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

P$^{9}$ is Gly; Sar; or a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring alcoholic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one amide function; or a naturally or non-naturally occurring aromatic L α-amino acid containing 1 to 25 carbon- and/or heteroatoms in a single side-chain; or a naturally or non-naturally occurring L α-amino acid containing in total 1 to 25 carbon- and/or heteroatoms in a single side-chain comprising at least one urea function, carboxylic acid function, amide function, ester function, sulfone function or ether function;

P$^{10}$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

P$^{11}$ is Gly; Sar; or a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one amide function; or a naturally or non-naturally occurring aliphatic L α-amino acid containing in total 1 to 25 carbon- and/or heteroatoms in a single side-chain; or a naturally or non-naturally occurring alcoholic L α-amino acid containing in total 1 to 25 carbon- and/or heteroatoms in a single side-chain;

$P^{12}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain; or a naturally or non-naturally occurring aromatic α-amino acid containing in total 1 to 25 carbon- and/or heteroatoms in a single side-chain; or a naturally or non-naturally occurring α-amino acid containing in total 1 to 25 carbon- and/or heteroatoms in a single side-chain comprising at least one urea function, carboxylic acid function, amide function, ester function, sulfone function or ether function;

$P^{13}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain; or a naturally or non-naturally occurring aromatic α-amino acid containing 1 to 25 carbon- and/or heteroatoms in a single side-chain; or a naturally or non-naturally occurring α-amino acid containing in total 1 to 25 carbon- and/or heteroatoms in a single side-chain comprising at least one amide function;

$P^{14}$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring α-amino acid containing in total 1 to 25 carbon- and/or heteroatoms in a single side-chain comprising at least one urea function, carboxylic acid function, amide function, ester function, sulfone function or ether function; or a naturally or non-naturally occurring alcoholic α-amino acid containing in total 1 to 25 carbon- and/or heteroatoms in a single side-chain;

with the proviso that,
  if no interstrand linkage is formed, then $P^{13}$ and $P^{14}$, and $P^{14}$ and $P^1$ are connected;
  if $P^{13}$ and $P^{14}$ taken together form an interstrand linkage, as defined above, then $P^{13}$ and $P^{14}$ are not additionally connected;

with the further proviso that,
  if linker L, as defined below, is connected with module A by a carbonyl (C=O) point of attachment of $P^2$; $P^5$; or $P^{12}$; then
  $P^2$; $P^5$; or $P^{12}$; is a naturally or non-naturally occurring α-amino acid
    containing in total 1 to 25 carbon- and/or heteroatoms in a single side-chain comprising at least one carboxyl function;
  if linker L, as defined below, is connected with module A by a carbonyl (C=O) point of attachment of $P^{13}$ and $P^{13}$ and $P^{14}$, and $P^{14}$ and $P^1$ are connected; or
  $P^{14}$ and $P^1$ are not connected; then
  $P^{13}$ is a naturally or non-naturally occurring α-amino acid containing in total 1 to 25 carbon- and/or heteroatoms in a single side-chain comprising at least one carboxyl function;
  if linker L, as defined below, is connected with module A by a carbonyl (C=O) point of attachment of $P^{14}$ and $P^{13}$ and $P^{14}$, and $P^{14}$ and $P^1$ are connected as aforementioned; or
  $P^{13}$ and $P^{14}$ are not connected; then
  $P^{14}$ is a naturally or non-naturally occurring α-amino acid containing in total 1 to 25 carbon- and/or heteroatoms in a single side-chain comprising at least one carboxyl function;

if i=0 and
$P^2$ and $P^{11}$ taken together and/or $P^4$ and $P^9$ taken together form naturally or non-naturally cross-linking α-amino acids containing each in total 1 to 12 carbon- and/or heteroatoms in a single side-chain which together are connecting $P^2$ and $P^{11}$ and/or
$P^4$ and $P^9$ by covalent interaction (interstrand linkage); then $P^1$ to $P^5$; $T^6$; $T^7$; $P^8$ to $P^{13}$ are naturally or non-naturally occurring α-amino acids;

with the proviso that,
  if linker L, as defined below, is connected with module A by a carbonyl (C=O) point of attachment of $P^5$; or $P^{12}$; then
  $P^5$; or $P^{12}$; is a naturally or non-naturally occurring α-amino acid containing in total 1 to 25 carbon- and/or heteroatoms in a single side-chain comprising at least one carboxyl function;

and a module B consisting of single elements Q being connected in either direction from the carbonyl (C=O) point of attachment to the nitrogen (N) of the next element with the proviso that $Q^7$ is connected from the α-carbonyl (C=O) point of attachment to the w-nitrogen (N) of $Q^1$, and wherein $Q^1$ is a naturally or non-naturally occurring basic α-amino acid containing in total 1 to 25 carbon- and/or heteroatoms in a single side-chain comprising at least one amino function;

$Q^2$, $Q^5$, and $Q^6$ are independently
  a naturally or non-naturally occurring basic L α-amino acid containing in total 1 to 25 carbon- and/or heteroatoms in a single side-chain comprising at least one amino function;

$Q^3$ is a naturally or non-naturally occurring aliphatic D α-amino acid containing in total 1 to 25 carbon- and/or heteroatoms in a single side-chain; or or a naturally or non-naturally occurring aromatic D α-amino acid containing in total 1 to 25 carbon- and/or heteroatoms in a single side-chain;

$Q^4$ is a naturally or non-naturally occurring aliphatic L α-amino acid containing in total 1 to 25 carbon- and/or heteroatoms in a single side-chain;

$Q^7$ is a naturally or non-naturally occurring alcoholic α-amino acid containing in total 1 to 25 carbon- and/or heteroatoms in a single side-chain; or a naturally or non-naturally occurring α-amino acid containing in total 1 to 25 carbon- and/or heteroatoms in a single side-chain comprising at least one amide function; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function;

and a linker L consisting of k=0-3 single elements L being connected in either direction from the carbonyl (C=O) point of attachment to the nitrogen (N) of the next element, and wherein, if k=1

L$^1$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain; or a naturally or non-naturally occurring aromatic α-amino acid containing 1 to 25 carbon- and/or heteroatoms in a single side-chain; or a naturally or non-naturally occurring α-amino acid containing in total 1 to 25 carbon- and/or heteroatoms in a single side-chain comprising at least one amide function;

if k=2, the additional element

L$^2$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;

if k=3, the additional element

L$^3$ is Gly; Sar; Aib; or a naturally or non-naturally occurring aliphatic α-amino acid containing in total 1 to 25 carbon- and/or heteroatoms in a single side-chain; or a naturally or non-naturally occurring basic α-amino acid containing in total 1 to 25 carbon- and/or heteroatoms in a single side-chain comprising at least one amino function; or a naturally or non-naturally occurring alcoholic α-amino acid containing in total 1 to 25 carbon- and/or heteroatoms in a single side-chain;

said linker L being connected with module B from the carbonyl (C=O) point of attachment of L$^k$ to the α-nitrogen (N) of Q$^1$ and, if k=1-3 and i=1, being connected with module A from the carbonyl (C=O) point of attachment of P$^2$; P$^5$; P$^{12}$; P$^{13}$; or P$^{14}$; to the nitrogen (N) of L$^1$; or, if k=13 and i=0, being connected with module A from the carbonyl (C=O) point of attachment of P$^5$; P$^{12}$; or P$^{13}$; to the nitrogen (N) of L$^1$; or if k=0 and i=1, then Q$^1$ being directly connected with module A from the carbonyl (C=O) point of attachment of P$^2$; P$^5$; P$^{12}$; P$^{13}$; or P$^{14}$; to the α-nitrogen (N) of Q$^1$; or if k=0 and i=0, then Q$^1$ being directly connected with module A from the carbonyl (C=O) point of attachment of P$^5$; P$^{12}$; or P$^{13}$; to the α-nitrogen (N) of Q$^1$;

the carbonyl (C=O) point of attachment of P$^{13}$; or P$^{14}$; and/or nitrogen (N) of P$^1$; or P$^{14}$; not connected being saturated to form the corresponding naturally or non-naturally occurring terminal α-amino acids optionally having modified carbonyl (C=O) functional groups and/or nitrogen (N) functional groups;

or a tautomer or rotamer thereof; or a salt; or a pharmaceutically acceptable salt; or a hydrate; or a solvate thereof.

2. A diastereomer or epimer of a compound of formula (I) according to claim 1 based on one or more chiral center(s) not explicitly specified in formula (I) or an enantiomer of a compound of formula (I).

3. A pharmaceutical composition comprising a compound or a mixture of compounds according to claim 1 and at least one pharmaceutically inert carrier.

4. A pharmaceutical composition according to claim 3 in a form suitable for oral, topical, transdermal, injection, buccal, transmucosal, rectal, pulmonary or inhalation administration, especially in the form of tablets, dragees, capsules, solutions, liquids, gels, plaster, creams, ointments, syrup, slurries, suspensions, spray, nebulizer or suppositories.

5. A method of treating an infection caused by a Gram-negative bacteria selected from the group consisting of nosocomial infections, catheter-related infections, non-catheter-related infections, urinary tract infections, and bloodstream infections, or a disease or disorder associated with an infection caused by a Gram-negative bacteria, selected from the group consisting of ventilator-associated pneumonia (VAP), hospital-acquired pneumonia (HAP), healthcare-associated pneumonia (HCAP), cystic fibrosis, emphysema, asthma, pneumonia, epidemic diarrhea, necrotizing enterocolitis, typhlitis, gastroenteritis, pancreatitis, keratitis, endophthalmitis, otitis, brain abscess, meningitis, encephalitis, osteochondritis, pericarditis, epididymitis, prostatitis, urethritis, sepsis; surgical wounds, traumatic wounds, and burns, comprising administering to a subject in need thereof a pharmaceutically acceptable amount of a compound or compounds according to claim 1.

6. A process for the preparation of compounds according to claim 1, comprising
(a) coupling a functionalized solid support with an N-protected derivative of that amino acid which in a desired end-product is at position Q$^7$ of module B, any functional group which may be present in said N-protected amino acid derivative being protected;
(b) removing the N-protecting group from the product obtained in step (a);
(c) coupling the product of step (b) with an N-protected derivative of that amino acid which in the desired end-product corresponds to Q$^6$, any functional group which may be present in said N-protected amino acid derivative being protected;
(d) further effecting steps substantially corresponding to steps (b) to (c) using N-protected derivatives of amino acids which in the desired end-product are at positions Q$^5$ to Q$^1$, any functional group(s) which may be present in said N-protected amino acid derivatives being protected;
(e) if coupling to the solid support in step (a) is via a hydroxyl group of the amino acid residue at position Q$^7$, performing the following chemical conversion as described below:
selectively removing an N-protecting group at position Q$^1$ and a carboxyl-protecting group at position Q$^7$; and generating a macrolactam cycle by formation of an amide bond between the thus liberated carboxyl group at position Q$^7$ and the amino group at Q$^1$ of module B;
(f) if L is present (k=1, 2, or 3), effecting steps substantially corresponding to steps (b) to (c) using N-protected derivatives of amino acids which in the desired end-product are at positions L$^k$ to L$^1$, any functional group(s) which may be present in said N-protected amino acid derivatives being protected;
(g) if P$^{14}$ is present in module A (i=1) effecting steps substantially corresponding to steps (b) to (c) using an N-protected derivative of an amino acid which in the desired end-product is at position P$^n$ (n=2, 5, 12, 13, or 14), any functional group(s) which may be present in said N-protected amino acid derivative being protected; and if n=2, further performing steps comprising:
(h1) effecting steps substantially corresponding to steps (b) to (c) using N-protected derivatives of amino acids which in the desired end-product are at positions $P^1$, $P^{14}$, to $P^8$, $T^7$, $T^6$, and $P^5$ to $P^3$, any functional group(s) which may be present in said N-protected amino acid derivatives being protected and optionally following each coupling, selectively deprotecting one or several protected functional group(s) present in the molecule and chemically transforming the reactive group(s) thus liberated to form an interstrand linkage(s); and
(i1) selectively removing a carboxyl-protecting group at position $P^2$ and the N-protecting group at position $P^3$; and generating the macrolactam cycle by formation of an amide bond between the thus liberated carboxyl and amino functions;
if n=5, further performing steps which comprise:
(h2) further effecting steps substantially corresponding to steps (b) to (c) using N-protected derivatives of amino acids which in the desired end-product are at positions $P^4$ to $P^1$, $P^{14}$ to $P^8$, $T^7$, and $T^6$, any functional group(s) which may be present in said N-protected amino acid derivatives being protected and optionally following each coupling, selectively deprotecting one or several protected functional group(s) present in the molecule and chemically transforming the reactive group(s) thus liberated to form an interstrand linkage(s); and
(i2) selectively removing a carboxyl-protecting group at position $P^5$ and the N-protecting group at position $T^6$; and generating the macrolactam cycle by formation of an amide bond between the thus liberated carboxyl and amino functions;
if n=12, further performing steps comprising:
(h3) further effecting steps substantially corresponding to steps (b) to (c) using N-protected derivatives of amino acids which in the desired end-product are at positions $P^{11}$ to $P^8$, $T^7$, $T^6$, $P^5$ to $P^1$, $P^{14}$ and $P^{13}$, any functional group(s) which may be present in said N-protected amino acid derivatives being protected and optionally following each coupling, selectively deprotecting one or several protected functional group(s) present in the molecule and chemically transforming the reactive group(s) thus liberated to form an interstrand linkage(s); and
(i3) selectively removing a carboxyl-protecting group at position $P^{12}$ and the N-protecting group at position $P^{13}$; and generating the macrolactam cycle by formation of an amide bond between the thus liberated carboxyl and amino functions;
if n=13, further performing steps comprising:
(h4) further effecting steps substantially corresponding to steps (b) to (c) using N-protected derivatives of amino acids which in the desired end-product are at positions $P^{12}$ to $P^8$, $T^7$, $T^6$, $P^5$ to $P^1$, and $P^{14}$, any functional group(s) which may be present in said N-protected amino acid derivatives being protected
(i4) selectively removing a carboxyl-protecting group at position $P^{13}$ and an N-protecting group at position $P^{14}$; and generating the macrolactam cycle by formation of an amide bond between the thus liberated carboxyl and amino functions;

if n=14, performing steps comprising:
(h5) further effecting steps substantially corresponding to steps (b) to (d) using N-protected derivatives of amino acids which in the desired end-product are at positions $P^{13}$ to $P^8$, $T^7$, $T^6$, $P^5$ to $P^1$, any functional group(s) which may be present in said N-protected amino acid derivatives being protected
selectively removing a carboxyl-protecting group at position $P^{14}$ and an N-protecting group at position $P^1$; and generating the macrolactam cycle, as defined above, by formation of an amide bond between the thus liberated carboxyl and amino functions;
(i) if coupling to the solid support in step (a) is via a carboxyl group of the amino acid residue at position $Q^7$ of module B, selectively removing an N-protecting group at position $Q^1$ of module B;
(k) detaching the product thus obtained from the solid support;
(l) if coupling to the solid support in step (a) is via a carboxyl group of the amino acid residue at position $Q^7$ of module B, generating the macrolactam cycle by formation of an amide bond between the thus liberated carboxyl group at position $Q^7$ and the amino group at position $Q^1$ of module B;
(m) removing any protecting groups present on functional groups of any members of the chain of amino acid residues and, optionally any protecting group(s) which may in addition be present in the molecule;
(n) optionally converting the product thus obtained into a pharmaceutically acceptable salt or converting a pharmaceutically acceptable, or unacceptable, salt thus obtained into the corresponding free compound of formula (I) or into a different, pharmaceutically acceptable salt.

7. The process according to claim 6, further comprising:
(l1) selectively deprotecting one or more protected functional group(s) present in the molecule and chemically transforming the reactive group(s) thus liberated, wherein (l1) is between steps (l) and (m).

8. The process according to claim 6, further comprising:
(n) implementing additional chemical transformations of one or more reactive group(s) present in the molecule, wherein (n) is after step (m).

9. The process according to claim 6, further comprising:
(o) converting the product thus obtained into a pharmaceutically acceptable salt or converting a pharmaceutically acceptable, or unacceptable, salt thus obtained into the corresponding free compound of formula (I) or into a different, pharmaceutically acceptable salt, wherein (o) is after step (m).

10. The process according to claim 8, further comprising:
(o) converting the product thus obtained into a pharmaceutically acceptable salt or converting a pharmaceutically acceptable, or unacceptable, salt thus obtained into the corresponding free compound of formula (I) or into a different, pharmaceutically acceptable salt, wherein (o) is after step (n).

* * * * *